US010920256B2

(12) United States Patent
Kellmann et al.

(10) Patent No.: US 10,920,256 B2
(45) Date of Patent: Feb. 16, 2021

(54) PROCESS

(71) Applicants: Vestlandets Innovasjonsselskap AS, Bergen (NO); NEWSOUTH INNOVATIONS PTY LIMITED, Sydney (AU)

(72) Inventors: Ralf Kellmann, Bergen (NO); Brett Neilan, Newcastle (AU)

(73) Assignees: Vestlandets Innovasjonsseiskap AS, Bergen (NO); NEWSOUTH INNOVATIONS PTY LIMITED, Sydney (AU)

( * ) Notice: Subject to any disclaimer, the term of this patent is extended or adjusted under 35 U.S.C. 154(b) by 29 days.

(21) Appl. No.: 16/077,281

(22) PCT Filed: Feb. 10, 2017

(86) PCT No.: PCT/EP2017/053077
§ 371 (c)(1),
(2) Date: Aug. 10, 2018

(87) PCT Pub. No.: WO2017/137606
PCT Pub. Date: Aug. 17, 2017

(65) Prior Publication Data

US 2019/0048375 A1 Feb. 14, 2019

(30) Foreign Application Priority Data

Feb. 12, 2016 (GB) .................................. 1602576.9

(51) Int. Cl.

| | |
|---|---|
| ***C12P 17/18*** | (2006.01) |
| ***C12N 15/52*** | (2006.01) |
| ***C12N 15/70*** | (2006.01) |
| ***C12R 1/19*** | (2006.01) |

(52) U.S. Cl.
CPC ............ *C12P 17/182* (2013.01); *C12N 15/52* (2013.01); *C12N 15/70* (2013.01); *C12R 1/19* (2013.01); *C12N 2500/32* (2013.01); *C12N 2500/42* (2013.01)

(58) Field of Classification Search
None
See application file for complete search history.

(56) References Cited

U.S. PATENT DOCUMENTS

| | | | |
|---|---|---|---|
| 6,218,549 | B1 | 4/2001 | Horne et al. |
| 6,326,020 | B1 | 12/2001 | Kohane et al. |
| 7,576,202 | B2 | 8/2009 | Myasoedov et al. |
| 8,952,152 | B2 | 2/2015 | Lagos Gonzalez |
| 9,018,222 | B2 | 4/2015 | Buschmann et al. |
| 9,593,120 | B2 | 3/2017 | Rutman et al. |
| 2003/0100574 | A1 | 5/2003 | Wilson |
| 2003/0148359 | A1 | 8/2003 | Moczydlowski et al. |
| 2004/0029210 | A1 | 2/2004 | Robillot et al. |
| 2006/0057647 | A1 | 3/2006 | Robillot |
| 2010/0048592 | A1 | 2/2010 | Fisher et al. |
| 2010/0144767 | A1 | 6/2010 | Fisher et al. |
| 2010/0284913 | A1 | 11/2010 | Bois et al. |
| 2011/0129842 | A1 | 6/2011 | Neilan et al. |
| 2012/0053344 | A1 | 3/2012 | Lagos Gonzalez |
| 2014/0113301 | A1 | 4/2014 | Neilan et al. |
| 2015/0065528 | A1 | 3/2015 | Rutman et al. |
| 2015/0079159 | A1 | 3/2015 | Shankarappa et al. |
| 2015/0099878 | A1 | 4/2015 | Logas Gonzalez |
| 2015/0099879 | A1 | 4/2015 | Logas Gonzalez |
| 2016/0153030 | A1 | 6/2016 | Neilan et al. |

FOREIGN PATENT DOCUMENTS

| | | | |
|---|---|---|---|
| EP | 1799219 | A1 | 6/2007 |
| EP | 1799220 | A1 | 6/2007 |
| EP | 1844781 | A1 | 10/2007 |
| EP | 1844782 | A1 | 10/2007 |
| EP | 2279265 | A1 | 2/2011 |
| EP | 2412714 | A1 | 2/2012 |
| EP | 2533785 | A1 | 12/2012 |
| JP | H11292880 | A | 10/1999 |
| WO | 2003/006507 | A1 | 1/2003 |
| WO | 2006/084765 | A1 | 8/2006 |
| WO | 2009/129558 | A1 | 10/2009 |
| WO | 2015/157559 | A2 | 10/2015 |

OTHER PUBLICATIONS

Maria Wiese Neurotoxic Alkaloids: Saxitoxin and Its Analogs. Mar. Drugs 2010, 8, 2185-2211 (Year: 2010).*
Combined Search and Examination Report dated Jul. 29, 2019 in corresponding GB Application No. 1903649.0.
D'Agostino et al., "Current knowledge of paralytic shellfish toxin biosynthesis, molecular detection and evlolution", CRC Press, XP002768111, vol. 1, pp. 251-280 (2014).
Tsuchiya et al., "Biosynthetic route towards saxitoxin and shunt pathway", Scientific Reports, vol. 6, pp. 1-8 (Feb. 4, 2016).
Dittmann et al., "Cyanobacterial toxins: biosynthetic routes and evolutionary roots", FEMS Microbiology Reviews, vol. 37, pp. 23-43 (2013).
Soto-Liebe et al., "In silico analysis of putative paralytic shellfish poisoning toxins export proteins in cyanobacteria", PLOS One, vol. 8, pp. 1-10 (2013).
Kellmann et al., "Biosynthetic intermediate analysis and functional homology reveal a saxitoxin gene cluster in cyanobacteria", Applied and Environmental Microbiology, vol. 74, pp. 4044-4053 (2008).
Pearson et al., "The genetics, biosynthesis and regulation of toxic specialized metabolites of cyanobacteria", Harmful Algae, vol. 54, pp. 98-111 (Apr. 2016).
European Search Report dated May 17, 2019 in corresponding EP Application No. 17 706 173.6.
D. Wang et al., "Paralytic shellfish toxin biosynthesis in cyanobacteria and dinoflagellates: A molecular overview", Jornal of Proteomics, vol. 135, pp. 132-140 (2015).

(Continued)

*Primary Examiner* — Kagnew H Gebreyesus
(74) *Attorney, Agent, or Firm* — Mintz Levin Cohn Ferris Glovsky and Popeo, P.C.; Peter F. Corless

(57) ABSTRACT

The present invention relates to processes to make neosaxitoxin, and analogues and variants thereof, and intermediates in the production of neosaxitoxin in recombinant host cells. Neosaxitoxin and the analogues and variants thereof may be used in the production of pharmaceutical compositions.

18 Claims, 22 Drawing Sheets

Specification includes a Sequence Listing.

(56) References Cited

OTHER PUBLICATIONS

R. Orr et al., "Evolution and Distribution of Saxitoxin Biosynthesis in Dinoflagellates", Marine Drugs, vol. 11, pp. 2814-2828 (2013).
IPO Combined Search and Examination Report dated Dec. 4, 2017 in corresponding UK Application No. GB1702275.7.
Examination Report dated Dec. 19, 2018 in corresponding UK Application No. GB1702275.7.
International Search Report dated Mar. 3, 2017 in corresponding PCT Application No. PCT/EP2017/053077.
C. Albermann et al., "A simple and reliable method to conduct and monitor expression cassette integration into the *Escherichia coli* chromosome", Biotechnology Journal, vol. 5, pp. 32-38 (2010).
O. Arakawa et al., "Occurrence of carbamoyl-n-hydroxy derivatives of saxitoxin and neosaxitoxin in a xanthid crab *Zosimus aeneus*", Toxicom, 32(2), pp. 175-183 (1994).
O. Arakawa et al., "A new saxitoxin analogue from a xanthid crab *Atergatis floridus*", Toxicon, 33(12), pp. 1577-1584 (1995).
A.R. Humpage et al., "Application of the neuroblastoma assay for paralytic shellfish poisons to neurotoxic freshwater cyanobacteria: Interlaboratory calibration and comparison with other methods of analysis", Environmental Toxicology and Chemistry, 26(7), pp. 1512-1519 (2007).
D. Jansson et al., "Analysis of paralytic shellfish toxins, potential chemical threat agents, in food using hydrophilic interaction liquid chromatography-mass spectromety", Journal of Chromatography A, 1417, pp. 41-48 (2015).
N. Lagos et al., "The first evidence of paralytic shellfish toxins in the freshwater cyanobacterium *Cylindrospermopsis raciborskii*, isolated from Brazil", Toxicon, vol. 37, pp. 1359-1373 (1999).
A. Negri et al., "Three Novel Hydroxybenzoate Saxitoxin Analogues Isolated from the Dinoflagellate Gymnodinium catenatum", Chem. Res. Toxicol., vol. 16, pp. 1029-1033 (2003).
S.E. Ongley et al., "High-Titer Heterologous Production in *E. coli* of Lyngbyatoxin, a Protein Kinase C Activator from an Uncultured Marine Cyanobacterium", ACS Chemical Biology, vol. 8, pp. 1888-1893 (2013).
H. Onodera et al., "New Saxitoxin Analogues From the Freshwater Filamentous Cyanobacterium *Lyngbya wollei*", Natural Toxins, 5:146-151 (1997).
B.A. Pfeifer et al., "Biosynthesis of Complex Polyketides in a Metabolically Engineered Strain of *E. coli*", Science, vol. 291, pp. 1790-1792 (2001).
Y. Shimizu et al., "Biosynthesis of Saxitoxin Analogues: The Unexpected Pathway", J. Am. Chem. Soc., vol. 106, pp. 6433-6434 (1984).
H. Sletta et al., "The Presence of N-Terminal Secretion Signal Sequences Leads to Strong Stimulation of the Total Expression Levels of Three Texted Medically Important Proteins during High-Cell-Density Cultivations of *Escherichia coli*", Applied and Environmental Microbiology, 73(3), pp. 906-912 (2007).
J.A. Smoker et al., "Rapdi small-scale DNA isolation from filamentous cyanobacteria", FEMS Microbiology Letters, vol. 56, pp. 119-122 (1988).
M. Yotsu-Yamashita et al., "The structure of zetekitoxin AB, a saxitoxin analog from the Panamanian golden frog *Atelopus zeteki*: A potent sodium-channel blocker", PNAS, 101(13), pp. 4346-4351 (2004).
L. Zaman et al., "Occurrence of a methyl derivative of saxitoxin in bangladeshi freshwater puffers", Toxicon, 36(4), pp. 627-630 (1998).
R.J.S. Orr et al., "Evolutionary Acquisition and Loss of Saxitoxin Biosynthesis in Dinoflagellates: the Second "Core" Gene, sxtG", Applied and Environmental Microbiology, 79(7), pp. 2128-2136 (2013).
J.D. Hackett et al., "Evolution of Saxitoxin Synthesis in Cyanobacteria and Dinoflagellates", Mol. Biol. Evol., 30(1), pp. 70-78 (2012).
A. Stuken et al., "Discovery of Nuclear Encoded Genes for Neurotoxin Saxitoxin in Dinoflagellates", PLos One, 6(5), pp. 1-12 (2011).
C. Hoff-Risseti et al., "Cylindrospermopsin and Saxitoxin Synthetase Genes in Clindrospermopsis raciborskii Strains from Brazilian Freshwater", Plos One, 8(8), e74238 (2013).
S.A. Murray et al., "sxtA-Based Quantitative Molecular Assay to Identify Saxitoxin-Producing Harmful Algal Blooms in Marine Water", Applied and Environmental Microbiology, 77(19), pp. 7050-7057 (2011).
A. Ballot et al., "Variability in the sxt Gene Clusters of PSP Toxin Producing Aphanizomenon gracile Strains from Norway, Spain, Germany and North America", Plos One, pp. 1-16 (2016).
Y. Gao et al., "High Specificity of a Quantitative PCR Assay Targeting a Saxitoxin Gene for Monitoring Toxic Algae Associated with Paralytic Shellfish Toxins in the Yellow Sea", Applied and Environmental Microbiology, 81(20), pp. 6973-6981 (2015).
J. Al-Tebrineh et al., "Detection of Saxitoxin-Producing Cyanobacteria and Anabaena circinalis in Environmental Water Blooms by Quantitative PCR", Applied and Environmental Microbiology, 76(23), pp. 7836-7842 (2010).
F. Perini et al., "SxtA and sxtG Gene Expression and Toxin Production in the Mediterranean Alexandrium minutum (Dinophycease)", Marine Drugs, vol. 12, pp. 5258-5276 (2014).
H. Savela et al., "Quantity of the dinoflagellate sxtA4 gene and cell density correlates with paralytic shellfish toxin production in Alexandrium ostenfeldii blooms", Harmful Algae, vol. 52, pp. 1-10 (2016).
K. Soto-Liebe et al, "PSP toxin release from the cyanobacterium *Raphidiopsis brookii* D9 (Nostocales) can be induced by sodium and potassium ions", Toxicon, vol. 60, pp. 1324-1334 (2012).
K. Soto-Liebe et al., "In Silico Analysis of Putative Paralytic Shellfish Poisoning Toxins Export Proteins in Cyanobacteria", Plos One, 8(2), pp. 1-10 (2013).
P. Vico et al., "Influence of nitrogen availability on the expression of genes involved in the biosynthesis of saxitoxin and analogs in Cylindrospermopsis raciborskii", Harmful Algae, vol. 56, pp. 37-43 (2016).
M. Wiese et al., "Gene expression and molecular evolution of sxtA4 in a saxitoxin producing dinoflagellate Alexandrium catenella", Toxicon, vol. 92, pp. 102-112 (2014).
S.A. Murray et al., "Gene duplication, loss and selection in the evolution of saxitoxin biosynthesis in alveolates", Molecular Phylogenetics and Evolution, vol. 92, pp. 165-180 (2015).
Mihali, Troco K., Wayne W. Carmichael, and Brett A. Neilan. "A putative gene cluster from a Lyngbya wollei bloom that encodes paralytic shellfish toxin biosynthesis." PLoS One 6.2 (2011): e14657.
Mihali, Troco K., Ralf Kellmann, and Brett A. Neilan. "Characterisation of the paralytic shellfish toxin biosynthesis gene clusters in Anabaena circinalis AWQC131C and *Aphanizomenon* sp. NH-5." BMC biochemistry 10.1 (2009): 8.
Tsuchiya, Shigeki, et al. "Synthesis of a Tricyclic Bisguanidine Compound Structurally Related to Saxitoxin and its Identification in Paralytic Shellfish Toxin?Producing Microorganisms." Chemistry—A European Journal 21.21 (2015): 7835-7840.
Tsuchiya, Shigeki, et al. "Synthesis and identification of proposed biosynthetic intermediates of saxitoxin in the cyanobacterium *Anabaena circinalis* (TA04) and the dinoflagellate Alexandrium tamarense (Axat-2)." Organic & biomolecular chemistry Dec. 19, 2014: 3016-3020.
Stucken, Karina, et al. "The smallest known genomes of multicellular and toxic cyanobacteria: comparison, minimal gene sets for linked traits and the evolutionary implications." PLoS One 5.2 (2010): e9235.
Murray, Shauna A., Troco K. Mihali, and Brett A. Neilan. "Extraordinary conservation, gene loss, and positive selection in the evolution of an ancient neurotoxin." Molecular biology and evolution 28.3 (2010): 1173-1182.
Soto-Liebe, Katia, et al. "Reassessment of the toxin profile of Cylindrospermopsis raciborskii T3 and function of putative sulfotransferases in synthesis of sulfated and sulfonated PSP toxins." Toxicon 56.8 (2010): 1350-1361.
Office Action dated Apr. 2, 2020 in corresponding Application No. 17706173.6 (6 pages).

* cited by examiner

S-adenosylmethionine acetyl- or malonyl-CoA arginine

R = -H (saxitoxin and its precursors)
or
-OH (neosaxitoxin and its precursors)

Chemical Formula: $C_{10}H_{17}N_7O_5$
Exact Mass: 315.13

SEQUENCE LISTING

<160> NUMBER OF SEQ ID NOS: 101

<210> SEQ ID NO 1
<211> LENGTH: 252
<212> TYPE: PRT
<213> ORGANISM: Cylindrospermopsis raciborskii T3

<400> SEQUENCE: 1

Met Ile Asp Thr Ile Ser Val Leu Leu Arg Glu Trp Thr Val Ile Ser
1 5 10 15

```
Leu Thr Gly Leu Ala Phe Trp Leu Trp Glu Ile Arg Ser Pro Phe His
            20                  25                  30

Gln Ile Glu Tyr Lys Ala Lys Phe Phe Lys Glu Leu Gly Trp Ala Gly
        35                  40                  45

Ile Ser Phe Val Phe Arg Asn Val Tyr Ala Tyr Val Ser Val Ala Ile
    50                  55                  60

Ile Lys Leu Leu Ser Ser Leu Phe Met Gly Glu Ser Ala Asn Phe Ala
65                  70                  75                  80

Gly Val Met Tyr Val Pro Leu Trp Leu Arg Ile Ile Thr Ala Tyr Ile
                85                  90                  95

Leu Gln Asp Leu Thr Asp Tyr Leu Leu His Arg Thr Met His Ser Asn
            100                 105                 110

Gln Phe Leu Trp Leu Thr His Lys Trp His His Ser Thr Lys Gln Ser
        115                 120                 125

Trp Trp Leu Ser Gly Asn Lys Asp Ser Phe Thr Gly Gly Leu Leu Tyr
    130                 135                 140

Thr Val Thr Ala Leu Trp Phe Pro Leu Leu Asp Ile Pro Ser Glu Val
145                 150                 155                 160

Met Ser Val Val Ala Val His Gln Val Ile His Asn Asn Trp Ile His
                165                 170                 175

Leu Asn Val Lys Trp Asn Ser Trp Leu Gly Ile Ile Glu Trp Ile Tyr
            180                 185                 190

Val Thr Pro Arg Ile His Thr Leu His His Leu Asp Thr Gly Gly Arg
        195                 200                 205

Asn Leu Ser Ser Met Phe Thr Phe Ile Asp Arg Leu Phe Gly Thr Tyr
    210                 215                 220

Val Phe Pro Glu Asn Phe Asp Ile Glu Lys Ser Lys Asn Arg Leu Asp
225                 230                 235                 240

Asp Gln Ser Val Thr Val Lys Thr Ile Leu Gly Phe
                245                 250
```

<210> SEQ ID NO 2
<211> LENGTH: 759
<212> TYPE: DNA
<213> ORGANISM: Cylindrospermopsis raciborskii T3

<400> SEQUENCE: 2

```
atgatagata caatatcagt actattaaga gagtggactg taatttttct tacaggttta     60

gccttctggc tttgggaaat tcgctctccc ttgcatcaaa ttgaatacaa agctaaattc    120

ttcaaggaat tgggatgggc gggaatatca ttcgtcttta gaattgttta tgcatatgtt    180

tctgtggcaa ttataaaact attgagttct ctatttatgg gagagtcagc aaattttgca    240

ggagtaatgt atgtgcccct ctggctgagg atcatcactg catatatatt acaggactta    300

actgactatc tattacacag gacaatgcat agtaatcagt ttctttggtt gacgcacaaa    360

tggcatcatt caacaaagca atcatggtgg ctgagtggaa acaaagatag ctttaccggc    420

ggacttttat atactgttac agctttgtgg tttccactgc tggacattcc ctcagaggtt    480

atgtctgtag tggcagtaca tcaagtgatt cataacaatt ggatacacct caatgtaaag    540

tggaactcct ggttaggaat aattgaatgg atttatgtta cgccccgtat tcacactttg    600

catcatcttg atacaggggg aagaaatttg agttctatgt ttactttcat cgaccgatta    660

tttggaacct atgtgtttcc agaaaacttt gatatagaaa aatctaaaaa tagattggat    720

gatcaatcag taacggtgaa gacaattttg ggtttttaa                           759
```

<210> SEQ ID NO 3
<211> LENGTH: 759
<212> TYPE: DNA
<213> ORGANISM: Cylindrospermopsis raciborskii T3

<400> SEQUENCE: 3
atgattgata ccattagcgt tctgctgcgt gaatggaccg ttatttttct gaccggtctg 60
gcattttggc tgtgggaaat tcgtagtccg ctgcatcaga ttgaatacaa agccaaattt 120
ttcaaagaac tgggttgggc aggtatcagc tttgtttttc gtattgttta tgcctatgtt 180
agcgtggcca ttatcaaact gctgagcagc ctgtttatgg gtgaaagcgc aaattttgcc 240
ggtgttatgt atgttccgct gtggctgcgt attattaccg catatattct gcaggatctg 300
accgattatc tgctgcatcg taccatgcat agcaatcagt ttctgtggct gacccataaa 360
tggcatcata gcaccaaaca gagttggtgg ctgagcggta ataaagatag ctttaccggt 420
ggtctgctgt ataccgttac cgcactgtgg tttccgctgc tggatattcc gagcgaagtt 480
atgagcgttg ttgcagttca tcaggtgatt cataacaact ggattcacct gaatgtgaaa 540
tggaatagct ggctgggtat tatcgaatgg atttatgtta caccgcgtat ccataccctg 600
catcatctgg ataccggtgg tcgtaatctg agcagtatgt ttacctttat tgatcgtctg 660
tttggcacct atgtgtttcc ggaaaacttt gatatcgaaa aaagcaaaaa ccgcctggat 720
gatcagagcg ttaccgttaa aaccattctg ggtttctga 759

<210> SEQ ID NO 4
<211> LENGTH: 117
<212> TYPE: PRT
<213> ORGANISM: Cylindrospermopsis raciborskii T3

<400> SEQUENCE: 4

Met Phe Gln Thr Lys Ser Tyr Tyr Ser Val Val Gly Leu Glu Thr Glu
1 5 10 15

Leu Ile Lys Gly Lys Phe Phe Met Ser Asn Glu Leu Thr Asn Glu Gln
20 25 30

Val Phe Lys Leu Val Cys Met Glu Val Ile Glu Lys Met Gly Phe Ala
35 40 45

His Phe Pro Pro Ile Ile Leu Val Tyr Glu Met Thr Asn Ser Gly Phe
50 55 60

Val Asp Trp Cys Glu Gln Met Val Phe Val Asp Asp Lys Gly Lys Leu
65 70 75 80

Asp Glu Gly Glu Lys Phe Leu Leu Asp Trp Met Arg Arg Asn Val Gly
85 90 95

Asn Phe Asp Leu Ile Arg Glu Leu Met Pro Val Ala Glu Arg Leu Glu
100 105 110

Met Lys Met Arg Ser
115

<210> SEQ ID NO 5
<211> LENGTH: 354
<212> TYPE: DNA
<213> ORGANISM: Cylindrospermopsis raciborskii T3

<400> SEQUENCE: 5
atgttccaga ccaagagtta ttactctgtg gtaggattag aaacagaatt gattaaagga 60
aaattcttta tgtctaatga attgacaaac gaacaagtat ttaagctggt ttgtatggaa 120
gtcattgaaa aaatgggatt cgcacacttt cctcccatca ttttagtcta tgagatgact 180
aattccggat ttgtagattg gtgcgagcag atggtttttg ttgatgataa aggtaagcta 240
gatgaaggag aaaaattctt attagactgg atgagacgga acgtaggaaa ctttgatctg 300
atacgtgagt taatgcccgt tgctgaacgt ctagaaatga aaatgaggtc ataa 354

<210> SEQ ID NO 6
<211> LENGTH: 354
<212> TYPE: DNA
<213> ORGANISM: Cylindrospermopsis raciborskii T3

<400> SEQUENCE: 6
atgtttcaga ccaaaagcta ttatagcgtc gttggcctgg aaaccgaact gattaaaggt 60
aaattcttca tgagcaacga actgaccaat gaacaggtgt ttaaactggt gtgcatggaa 120
gtgattgaaa aaatgggttt tgcacacttt ccgcctatta tcctggttta tgaaatgacc 180
aattccggct ttgttgattg gtgcgagcag atggtttttg tggatgataa aggcaaactg 240
gatgagggcg aaaaatttct gctggattgg atgcgtcgta atgtgggtaa ttttgatctg 300
attcgcgaac tgatgccggt ggcagaacgc ctggaaatga aaatgcgtag ctaa 354

<210> SEQ ID NO 7
<211> LENGTH: 318
<212> TYPE: PRT
<213> ORGANISM: Cylindrospermopsis raciborskii T3

<400> SEQUENCE: 7

Met Thr His Val Ala Leu Glu Gln Ala Ile Ala Lys Val Pro Arg Ser
1 5 10 15

Ile Gln Ser Glu Leu Arg Thr Ile Leu Ala Gln His Ala Val Ile Asp
20 25 30

Ser Ser Val Val Ala Ser Trp Ile Asp Arg Leu Gly Thr Asn Ile Ser
35 40 45

Thr Leu Met Ile Gln Leu Leu Pro Val Ala Ala Thr Tyr Ala Arg Val
50 55 60

Pro Ile Ser Gln Phe Tyr Val Gly Ala Ile Ala Leu Gly Lys Pro Gln
65 70 75 80

Ser Lys Asn Gln Leu Gly Ser Gly Thr Leu Tyr Phe Gly Ala Asp Met
85 90 95

Glu Phe Val Gly Gln Ala Leu Ser Phe Ser Val His Ala Glu Gln Ser
100 105 110

Ala Thr Ile Asn Ala Trp Leu His Gly Glu Thr Gly Leu Gln Ala Leu
115 120 125

Ala Ile His Glu Ala Pro Cys Gly Tyr Cys Arg Gln Phe Leu Tyr Glu
130 135 140

Met Ala Thr Val Asn Gln Asn Phe Val Leu Leu Val Lys Ser Asn Glu
145 150 155 160

Ser Gln Pro Glu Gln Thr Tyr Thr Ser Asn Lys Leu Pro His Phe Leu
165 170 175

Pro Glu Pro Phe Gly Pro Ala Asp Leu Gly Leu Thr Gly Gly Leu Met
180 185 190

Gln Thr Val Phe His Asp Leu Glu Thr Tyr Ser Thr Asp Asp Val Val
195 200 205

Leu Ala Ala Leu Ser Ala Ala Asn Gln Ser Tyr Ala Pro Tyr Thr Lys
210 215 220

Asn Phe Ala Gly Val Ala Leu Lys Asp Ser His Gly Asn Ile Phe Thr

-continued

```
225                 230                 235                 240

Gly Arg Tyr Ala Glu Asn Ala Ala Phe Asn Ser Ser Met Ser Pro Met
                245                 250                 255

Glu Ser Ala Leu Thr Phe Met Asn Met Asn Arg Tyr Ser Gln Ser Leu
            260                 265                 270

Phe Asp Ile Cys Asp Ala Val Leu Val Glu Val Glu Thr Gly Ile Ser
        275                 280                 285

Gln Arg Pro Val Thr Glu Ala Phe Leu Ser Ser Ile Ala Pro Lys Val
    290                 295                 300

Lys Leu Arg Tyr Ala Pro Ala Thr Pro Ser Ser Asn Lys Leu
305                 310                 315


<210> SEQ ID NO 8
<211> LENGTH: 957
<212> TYPE: DNA
<213> ORGANISM: Cylindrospermopsis raciborskii T3

<400> SEQUENCE: 8

atgacccatg tagcattaga acaggcgatt gccaaggttc cacgttccat tcaatcagag      60

ttaaggacaa ttcttgccca acatgctgta attgactcaa gtgttgtcgc atcttggatt     120

gatcgacttg gtactaatat tagtacgtta atgattcaat tactacccgt agccgcaact     180

tatgctaggg taccaatatc gcagttttat gtaggggcga tcgctcttgg taaaccacaa     240

tctaagaatc aactgggttc tggaactctt tattttggtg ccgacatgga atttgtagga     300

caggcactta gtttctcagt tcacgcagaa caatccgcca ccataaatgc gtggttgcac     360

ggagaaaccg gtttacaagc attagcaatc cacgaagcac catgtggata ctgccgacaa     420

tttttatacg agatggcaac tgtaaatcaa aattttgttc ttcttgtgaa gtctaatgaa     480

tcacagcctg agcaaactta tacctcaaat aaactcccac attttctacc cgagccattt     540

ggaccagcgg atctaggact cacaggtgga ttaatgcaaa cagtatttca tgatctggag     600

acctattcta ccgatgatgt tgtgcttgct gctctatccg ctgccaatca aagttatgct     660

ccctacacga aaaattttgc aggggtagcg ttaaaagatt cccacgggaa tatatttaca     720

ggtcgatacg ctgaaaacgc tgcctttaat tcatccatgt ctccgatgga atctgctctg     780

actttcatga atatgaatag atattctcaa tcactattcg acatttgtga tgctgtttta     840

gttgaagtgg aaactgggat tagtcaaaga cccgtcactg aagccttcct ttcttctatc     900

gctcccaagg tcaagttaag gtatgcccct gcaactccgt caagtaataa gttatga        957


<210> SEQ ID NO 9
<211> LENGTH: 957
<212> TYPE: DNA
<213> ORGANISM: Cylindrospermopsis raciborskii T3

<400> SEQUENCE: 9

atgacccatg ttgccctgga acaggcaatt gcaaaagttc cgcgtagcat tcagagcgaa      60

ctgcgtacca ttctggcaca gcatgcagtt attgatagca gcgttgtggc aagctggatt     120

gatcgtctgg gcaccaatat tagtaccctg atgatccagc tgctgccggt tgcagcaacc     180

tatgcacgtg ttccgattag ccagttttat gttggtgcca ttgcactggg caaaccgcag     240

agtaaaaatc agctgggtag cggcaccctg tattttggtg cagatatgga atttgttggt     300

caggcactga gctttagcgt tcatgcagaa cagagcgcca ccattaatgc ctggctgcat     360

ggcgaaaccg gactgcaggc actggcaatc catgaagcac cgtgtggtta ttgtcgccag     420
```

-continued

```
tttctgtatg aaatggcaac cgtgaatcag aattttgtgc tgctggtgaa aagcaatgaa    480

agccagccgg aacagaccta taccagcaac aaactgccgc attttctgcc tgaaccgttt    540

ggtccagccg atctgggtct gaccggtggc ctgatgcaga ccgtgtttca cgatctggaa    600

acctatagca ccgatgatgt tgttctggca gcactgagtg cagcaaatca gagttatgca    660

ccgtatacca aaaactttgc cggtgttgca ctgaaagata gtcatggtaa catttttaca    720

ggtcgctatg ccgaaaacgc agcatttaat agcagcatga gcccgatgga aagcgcactg    780

acctttatga atatgaatcg ttattcacag agcctgttcg atatttgtga tgcagttctg    840

gtagaagtgg aaaccggtat tagtcagcgt ccggttaccg aagcctttct gagtagcatt    900

gcaccgaaag tgaaactgcg ctatgcaccg gcaaccccga gcagtaacaa actgtga       957
```

```
<210> SEQ ID NO 10
<211> LENGTH: 1245
<212> TYPE: PRT
<213> ORGANISM: Cylindrospermopsis raciborskii T3

<400> SEQUENCE: 10

Met Leu Gln Lys Ile Asn Arg Tyr Thr His Gly Phe Val Ala Val Pro
1               5                   10                  15

Val Ile Leu Ala Cys Arg Glu Lys Gly Val Phe Glu Leu Leu Ala Asp
            20                  25                  30

Glu Ser Pro Leu Ser Leu Asn Gln Met Val Glu His Leu Gly Ala Asn
        35                  40                  45

Ser Gly His Phe Gln Val Ala Leu Arg Met Leu Glu Ser Leu His Trp
    50                  55                  60

Leu Ser Arg Asn Lys Glu Leu Lys Tyr Ser Leu Thr Ala Glu Ala Ala
65                  70                  75                  80

Ile His Asn Lys Ile Ser Glu Asp Ile Leu Gln Leu Tyr Asn Leu Pro
                85                  90                  95

Ile Gln Ser Tyr Leu Glu Gly Lys Gln Gly Asn Leu Leu Gly Arg Trp
            100                 105                 110

Ile Glu Arg Ser Cys Gln Leu Trp Asn Leu Asp Asn Pro Leu Met Ala
        115                 120                 125

Asp Phe Leu Asp Gly Leu Leu Val Ile Pro Leu Leu Leu Ala Leu His
    130                 135                 140

Lys His Asn Leu Leu Ala Asp Ser Glu Asp Lys Pro Leu Leu Ser Ser
145                 150                 155                 160

Leu Ser Ser Thr Val Gln Glu Glu Leu Gly Lys Leu Phe Leu His Leu
                165                 170                 175

Gly Trp Ala Asp Leu Thr Ala Gly Arg Leu Thr Ile Thr Glu Leu Gly
            180                 185                 190

Arg Phe Met Gly Glu Arg Ala Leu Asn Thr Ala Ile Val Ala Ser Tyr
        195                 200                 205

Thr Pro Met Leu Ser Arg Ile His Asp Val Leu Phe Gly Asn Cys Leu
    210                 215                 220

Ser Val Phe Gln Arg Asp Ala Ser Gly His Glu Arg His Ile Asp Arg
225                 230                 235                 240

Thr Leu Asn Val Ile Gly Ser Gly Phe Gln His Gln Lys Tyr Phe Ala
                245                 250                 255

Asp Leu Glu Glu Ser Ile Leu Ser Val Phe Asn Gln Leu Pro Leu Glu
            260                 265                 270

Glu Gln Pro Lys Tyr Ile Thr Asp Met Gly Cys Gly Asp Gly Thr Leu
        275                 280                 285
```

-continued

```
Leu Lys Arg Val Trp Glu Thr Ile Gln Phe Lys Ser Ala Arg Gly Lys
    290                 295                 300

Ala Leu Glu Gln Tyr Pro Leu Arg Leu Ile Gly Val Asp Tyr Asn Glu
305                 310                 315                 320

Ala Ser Leu Lys Ala Thr Thr Arg Thr Leu Ala Ser Leu Pro His Leu
                325                 330                 335

Val Leu Gln Gly Asp Ile Gly Asn Pro Glu Gln Met Val Arg Ser Leu
            340                 345                 350

Glu Ala His Gly Ile His Asp Pro Glu Asn Ile Leu His Ile Arg Ser
        355                 360                 365

Phe Leu Asp His Asp Arg Leu Phe Ile Pro Pro Gln Lys Arg Asn Glu
    370                 375                 380

Leu Lys Glu Arg Ala His Leu Pro Tyr Gln Ser Val Cys Val Asp Asp
385                 390                 395                 400

Gln Gly Glu Leu Ile Pro Pro His Val Met Val Gln Ser Leu Val Glu
                405                 410                 415

His Leu Glu Arg Trp Ser Gln Val Val Asn Lys His Gly Leu Met Ile
            420                 425                 430

Leu Glu Val His Cys Leu Glu Pro Arg Val Val Tyr Gln Phe Leu Asp
        435                 440                 445

Lys Ser Glu Asn Leu His Phe Asp Ala Phe Gln Gly Phe Ser Gln Gln
    450                 455                 460

Tyr Leu Val Glu Ala Glu Val Phe Leu Met Ser Ala Ala Gln Val Gly
465                 470                 475                 480

Leu Phe Pro Lys Leu Glu Leu Ser Lys Arg Tyr Pro Lys Thr Phe Pro
                485                 490                 495

Phe Thr Arg Ile Thr Leu Asn Tyr Phe Glu Lys Arg Pro Tyr Lys Ile
            500                 505                 510

Ser His Ala Tyr Leu Ser Asp Leu Pro Ala Leu Val Asp Leu Glu Val
        515                 520                 525

Lys Cys Trp Pro Glu Asn Leu Arg Ala Ser Thr His Glu Ile Arg Arg
    530                 535                 540

Arg Leu Glu Leu Asn Pro Gln Gly Asn Leu Val Leu Ile Ile Glu Asp
545                 550                 555                 560

Gln Ile Ile Gly Ala Ile Tyr Ser Gln Thr Ile Thr Ser Thr Glu Ala
                565                 570                 575

Leu Glu Asn Val Lys Tyr Ala Gln Val Pro Thr Leu His Thr Pro Gln
            580                 585                 590

Gly Ser Val Ile Gln Leu Leu Ala Leu Asn Ile Leu Pro Glu Phe Gln
        595                 600                 605

Ala Arg Gly Leu Gly Asn Glu Leu Arg Asp Phe Met Leu Tyr Tyr Cys
    610                 615                 620

Thr Leu Lys Gly Gly Ile Glu Ser Val Val Gly Val Thr Arg Cys Arg
625                 630                 635                 640

Asn Tyr Val Asn Tyr Ser Gln Met Pro Met Met Glu Tyr Leu Lys Leu
                645                 650                 655

His Asn Glu Gln Arg Gln Leu Leu Asp Pro Ile Val Gly Phe His Val
            660                 665                 670

Ser Gly Gly Ala Glu Ile Arg Gly Ile Ile Ala Asn Tyr Arg Pro Glu
        675                 680                 685

Asp Thr Asp Asn Leu Gly Met Gly Ile Leu Ile Glu Tyr Asn Leu Arg
    690                 695                 700
```

-continued

```
Asp Ser Ala Leu His Ser Pro Gly Asp Arg Lys Gly Pro Tyr Ile Asn
705                 710                 715                 720

Ser Ala Ile Gly Ser Leu Val Pro Lys Ala Thr Ser Ala Thr Lys Glu
                725                 730                 735

Asn Lys Thr Val Ala Asp Leu Val Lys Glu Cys Ile Leu Lys Val Met
            740                 745                 750

Gly Ser Gln Arg Gln Ala Ala Tyr Ala Pro Gln Gln Lys Leu Leu Asp
        755                 760                 765

Met Gly Leu Asp Ser Leu Asp Leu Leu Glu Leu Gln Thr Leu Leu Glu
    770                 775                 780

Glu Arg Leu Gly Ile Asn Leu Ser Gly Thr Phe Phe Leu Gln Lys Asn
785                 790                 795                 800

Thr Pro Thr Ala Ile Ile Thr Tyr Phe Gln Asn Gln Val Val Gln Glu
                805                 810                 815

Lys Gln Ser Asp Leu Ala Pro Pro Val Asp Ser Ala Asn Glu Ile Asn
            820                 825                 830

Thr Leu Glu Asn Val Val Asn Gln Gln Lys Ile Pro Gln Val Thr Arg
        835                 840                 845

Val Val Thr Glu Gln Gln Gly Arg Lys Val Leu Ile Asp Gly His Trp
    850                 855                 860

Val Ile Asp Phe Ala Ser Cys Asn Tyr Leu Gly Leu Asp Leu His Pro
865                 870                 875                 880

Lys Val Lys Glu Ala Ile Pro Pro Ala Leu Asp Lys Trp Gly Thr His
                885                 890                 895

Pro Ser Trp Thr Arg Leu Val Ala Ser Pro Ala Ile Tyr Glu Glu Leu
            900                 905                 910

Glu Glu Glu Leu Ser Lys Leu Leu Gly Val Pro Asp Val Leu Val Phe
        915                 920                 925

Pro Ala Val Thr Leu Leu Gln Ile Gly Ile Leu Pro Leu Leu Thr Gly
    930                 935                 940

Asn Asn Gly Val Ile Phe Gly Asp Ile Ala Ala His Arg Cys Ile Tyr
945                 950                 955                 960

Glu Ala Cys Cys Leu Ala Gln His Lys Gly Ala Gln Phe Ile Gln Tyr
                965                 970                 975

Arg His Asn Asp Leu Asn Asp Leu Ala Glu Lys Leu Ala Lys Tyr Pro
            980                 985                 990

Pro Glu Gln Val Lys Ile Ile Val  Ile Asp Gly Val Tyr  Ser Met Ser
        995                 1000                1005

Ala Asp  Phe Pro Asp Leu Pro  Ala Tyr Val His Leu  Ala Lys Glu
    1010                 1015                 1020

Tyr Asn  Ala Leu Ile Tyr Met  Asp Asp Ala His Gly  Phe Gly Ile
    1025                 1030                 1035

Leu Gly  Glu Asn Pro Ser Ser  Asp Met Pro Tyr Gly  Tyr Lys Gly
    1040                 1045                 1050

Asn Gly  Met Val Asn Tyr Phe  Asp Leu Arg Phe Ala  Glu Asp Asn
    1055                 1060                 1065

Ile Ile  Tyr Val Ala Gly Leu  Ser Lys Ala Tyr Ser  Ser Tyr Ala
    1070                 1075                 1080

Ala Phe  Leu Thr Cys Gly Asp  Arg Arg Ile Lys Thr  Asn Phe Arg
    1085                 1090                 1095

Asn Ala  Trp Thr Ala Ile Phe  Ser Gly Pro Ser Pro  Val Ala Ser
    1100                 1105                 1110

Leu Ala  Ser Ala Leu Ala Gly  Leu Gln Val Asn Arg  Gln Glu Gly
```

```
    1115                1120                1125

Glu Gln  Leu Arg Lys Gln Ile  Tyr His Leu Thr His  Lys Leu Val
    1130                1135                1140

Thr Gln  Ala Arg Ala Ile Gly  Phe Glu Val Asp Asn  Tyr Gly Tyr
    1145                1150                1155

Val Pro  Ile Val Gly Val Leu  Val Gly Asp Ala Gln  His Met Ile
    1160                1165                1170

Asp Val  Cys Gln Leu Leu Trp  Glu Tyr Gly Ile Leu  Ile Thr Pro
    1175                1180                1185

Ala Ile  Phe Pro Ile Val Pro  Leu Asn Lys Ser Ala  Leu Arg Phe
    1190                1195                1200

Ser Ile  Thr Ala Ala Asn Thr  Glu Glu Glu Ile Asp  Gln Ala Ile
    1205                1210                1215

Lys Ser  Leu Lys Ala Val Trp  Asp Leu Leu Gln Lys  Arg Lys Ala
    1220                1225                1230

Leu Pro  Cys Lys Gln Glu Glu  Asn Ile Leu Lys His
    1235                1240                1245


<210> SEQ ID NO 11
<211> LENGTH: 3738
<212> TYPE: DNA
<213> ORGANISM: Cylindrospermopsis raciborskii T3

<400> SEQUENCE: 11

atgttacaaa agattaatcg ttatactcac ggctttgtgg cggttcccgt tattcttgcg     60

tgtcgagaaa aaggtgtttt tgaattactc gccgatgaaa gtcctctctc tttaaaccaa    120

atggtggaac atctgggagc taacagcgga cattttcaag ttgctttgag gatgctcgag    180

tctttacatt ggctttcccg aaataaggag cttaaatact ctctaaccgc agaagcagcg    240

attcacaaca aaatttcgga agacattctt caattgtaca acctaccaat tcagtcttat    300

ttagaaggga aacaaggaaa tttgctggga agatggattg agcgttcttg ccaattgtgg    360

aacctggaca atcccctaat ggcagatttt ttagatggat tactggtcat cccactcctg    420

ctggcactgc acaaacacaa cttgcttgca gattcggagg acaaaccttt gctctcctca    480

ttaagctcaa cagtgcaaga agagttgggt aagttatttc tccaccttgg ctgggctgac    540

cttacagcag gtcgtttgac cataaccgaa cttggtcgat ttatgggaga gcgagccttg    600

aatacagcca tagtggcgtc ctacactcct atgttgtccc gcattcatga tgtattgttt    660

ggcaattgtc tctccgtatt ccaaagagat gcttccggtc acgaaaggca cattgatcgc    720

acccttaacg tgatcgggag tggatttcaa caccagaaat attttgccga tttagaagaa    780

agtatcctct cagtattcaa tcagttgcca ttagaagaac aacccaaata cattactgac    840

atggggtgtg gcgatggaac tctcctgaaa cgagtctggg aaaccattca atttaagtct    900

gctaggggaa aagcactcga acagtatccc ctgcgtctta taggtgtaga ttataacgaa    960

gcttctttaa aagctaccac acgcaccctt gctagccttc cccacttagt tttacaggga   1020

gatattggga acccagaaca aatggtgcgt tctttagaag ctcatggcat tcatgatccc   1080

gaaaatatcc tgcacatccg ttcgttcctc gaccatgatc gtctctttat tcctcctcag   1140

aaaagaaacg aattgaaaga acgtgctcac ttaccttacc aatcagtctg tgtcgatgat   1200

caaggagagc ttattcctcc tcatgttatg gtgcaaagtt tggtggaaca cttagaaaga   1260

tggtctcaag tggtcaataa acacggttta atgattttgg aggtccattg tttggaacca   1320

agggtagtct atcagttttt agacaaaagc gaaaacttac atttcgatgc gtttcaggga   1380
```

ttttctcagc agtatcttgt ggaagctgag gtttttctca tgtctgctgc acaagtaggt 1440
ctatttccaa aactagagct ttctaaaaga tacccaaaaa catttccttt tactcgcatt 1500
acgcttaatt acttcgagaa aagaccttac aaaattagtc atgcctattt gtcagattta 1560
cctgccttag ttgacttgga ggtcaagtgt tggccagaaa atttacgggc atctactcat 1620
gaaattcggc gaagacttga gctaaacccg caaggtaatt tagtgctgat tatagaagat 1680
caaattattg gtgcgattta ttcccaaaca attaccagca ctgaggcatt agagaatgta 1740
aaatatgcgc aagtgccgac gttacatact ccccaagggt cagttattca actgctcgca 1800
ctaaatattc tacctgagtt tcaggcgcgg gggttaggaa atgaattgcg ggactttatg 1860
ctttactact gtaccctgaa aggcggcatt gagagcgtgg tgggtgtaac tcgctgtcga 1920
aattatgtca attattccca aatgccgatg atggagtatt taaagctaca caatgagcaa 1980
cgacagcttc tggatccaat tgtgggtttc catgtgtcgg gaggagccga aattagggga 2040
attattgcta attatcgtcc ggaagataca gataatctcg gcatgggtat tttgattgaa 2100
tataacctgc gcgacagtgc tttgcactcg cctggtgatc gcaaaggacc gtatattaac 2160
tcagcaattg gttcattggt accaaaagca acatctgcaa ctaaggaaaa caaaactgta 2220
gcggatctcg ttaaagaatg catcttaaaa gtaatgggtt cccaacgtca ggcagcctac 2280
gctccacaac aaaaactgct ggatatggga ttagattctt tagatttatt agaactgcaa 2340
acgctcctag aggaacgttt agggatcaat ctgtctggaa cgttcttttt acaaaagaac 2400
actccaactg ccatcatcac ttatttccaa aaccaagtgg tacaagagaa acaatctgat 2460
ctagctccac ctgttgactc agccaacgaa atcaacactc tggaaaacgt agttaaccaa 2520
caaaaaattc ctcaagtcac aagagtcgtc acagaacaac aaggtcgcaa ggtgctaatt 2580
gacggacatt gggtgataga ctttgcttct tgcaactatt taggtcttga cttgcatcca 2640
aaagttaagg aagcaattcc accagctttg gataaatggg gcacacatcc aagctggact 2700
cggcttgttg cttccccagc aatttatgag gaattggagg aagaattgtc caaactttta 2760
ggcgtacctg atgttttagt atttccagct gtaacactgc ttcagatagg aattttacca 2820
ctattaactg ggaataatgg tgtcatcttt ggtgacatag ctgcacatcg ttgtatttat 2880
gaagcgtgct gtctggctca gcacaaagga gcccagttca tccaatatcg acataatgat 2940
ttgaacgatt tagccgaaaa actagcaaaa tatccgcctg aacaagtaaa gattattgtc 3000
attgatggcg tgtattccat gtcggcagat tttcccgatc tgccagctta cgtgcatctg 3060
gcaaaagagt acaatgcctt aatttacatg gatgatgctc atggttttgg catttttggc 3120
gaaaatccca gcagcgatat gccttacggt tacaaaggaa acgggatggt gaattatttt 3180
gacctgcggt ttgcagagga taatatcatc tatgtagctg gtttgtccaa agcctattct 3240
tcttacgcag cattcttaac ttgtggcgat cgccggatca aaaccaactt ccgcaacgct 3300
tggactgcca tattttctgg tccttctcct gttgcgagtt tggcaagtgc cttagccgga 3360
ttacaggtga atcgtcagga gggggagcag ttaagaaaac aaatttatca cctaactcac 3420
aaattggtta cacaagcaag agccattgga ttcgaagtgg ataactatgg ttacgttccc 3480
atcgtaggcg tgttagtggg agatgctcaa cacatgattg atgtgtgtca actcctttgg 3540
gaatatggta ttttaattac tcctgctatt tttccaatcg tacctttaaa taaaagtgct 3600
ttaaggtttt cgattacagc cgccaatacc gaagaggaga tagaccaagc aattaaatct 3660
ctcaaagcag tttgggattt gctacaaaaa aggaaagctt tgccttgtaa gcaggaggaa 3720
aacatactca agcattaa 3738

<210> SEQ ID NO 12
<211> LENGTH: 3738
<212> TYPE: DNA
<213> ORGANISM: Cylindrospermopsis raciborskii T3

<400> SEQUENCE: 12
atgctgcaga aaatcaatcg ttatacccat ggttttgttg ccgttccggt tattctggca 60
tgtcgtgaaa aaggtgtttt tgaactgctg gcagatgaaa gtccgctgag cctgaatcag 120
atggttgaac atctgggtgc caatagcggt cattttcagg ttgcactgcg tatgctggaa 180
agtctgcatt ggctgagccg taataaagaa ctgaaatata gcctgaccgc agaagcagca 240
attcataaca aaattagcga agatatcctg cagctgtata atctgccgat tcagagctat 300
ctggaaggta aacagggcaa tctgctgggt cgttggattg aacgtagctg tcagctgtgg 360
aatctggata atccgctgat ggcagatttt ctggatggtc tgctggttat tccgctgctg 420
ctggcactgc ataaacataa cctgctggcc gattctgaag ataaaccgct gctgagcagc 480
ctgagcagta ccgttcaaga agaactgggt aaactgtttc tgcatctggg ttgggcagat 540
ctgacagcag gtcgtctgac cattaccgaa ctgggtcgct ttatgggtga acgtgcactg 600
aataccgcaa ttgttgcaag ctataccccg atgctgagtc gtattcatga tgttctgttt 660
ggtaattgcc tgagcgtttt tcagcgtgat gcaagcggtc atgaacgtca tattgatcgt 720
accctgaatg ttattggtag cggttttcag caccagaaat actttgcaga tctggaagaa 780
agcattctga gcgtgtttaa tcagctgccg ctggaagaac agccgaaata cattaccgat 840
atgggttgtg gtgatggcac cctgctgaaa cgtgtttggg aaaccattca gtttaaaagc 900
gcacgtggta aagcactgga acagtatccg ctgcgtctga ttggtgttga ttataatgaa 960
gcaagcctga aagcaaccac ccgtaccctg gcaagcctgc cgcatctggt tctgcagggt 1020
gatattggta atccggaaca aatggttcgt agcctggaag cacatggcat tcatgatccg 1080
gaaaatattc tgcatattcg cagctttctg gatcacgatc gtctgtttat tccgcctcag 1140
aaacgtaatg aactgaaaga acgtgcccat ctgccgtatc agagtgtttg tgttgatgat 1200
cagggtgaac tgattcctcc gcatgttatg gttcagagcc tggtggaaca cctggaacgt 1260
tggagccagg ttgttaataa acatggtctg atgattctgg aagtgcattg tctggaaccg 1320
cgtgttgttt atcagtttct ggataaaagc gaaaacctgc actttgatgc atttcagggt 1380
tttagccagc agtatctggt tgaagccgaa gtttttctga tgagcgcagc acaggttggt 1440
ctgtttccga aactggaact gagcaaacgt tatccgaaaa cctttccgtt tacccgtatt 1500
accctgaact atttcgaaaa acgtccgtac aaaatcagcc atgcatatct gagcgatctg 1560
cctgcactgg ttgacctgga agttaaatgt tggcctgaga atctgcgtgc aagcacccat 1620
gaaattcgtc gtcgtctgga actgaatccg cagggtaacc tggttctgat tattgaagat 1680
cagattatcg gtgccattta cagccagacc attacaagca ccgaagccct ggaaaatgtt 1740
aaatatgcac aggttccgac cctgcataca ccgcagggtt cagtgattca gctgctggcc 1800
ctgaacattc tgccggaatt tcaggcacgt ggtctgggca atgaactgcg tgattttatg 1860
ctgtattatt gcaccctgaa aggtggtatt gaaagcgttg ttggtgttac ccgttgtcgc 1920
aattatgtga attatagcca gatgccgatg atggaatatc tgaaactgca taatgaacag 1980
cgtcaactgc tggatccgat tgttggtttt catgttagcg gtggtgcaga aattcgtggc 2040
attattgcaa attatcgtcc ggaagataca gataatctgg gtatgggtat tctgatcgaa 2100
tataacctgc gtgatagcgc actgcattca ccgggtgatc gtaaaggtcc gtatatcaat 2160
agcgcaattg gtagcctggt tccgaaagcg accagcgcaa ccaaagaaaa caaaaccgtt 2220
gcggatctgg tgaaagaatg tattctgaaa gtgatgggta gccagcgtca ggcagcatat 2280
gcaccgcagc agaaactgct ggacatgggt ctggatagcc tggatctgct ggaactgcag 2340
accctgctgg aagaacgtct gggtattaat ctgagcggca cctttttct gcaaaaaaac 2400 accccgaccg ccatcattac ctattttcag aatcaggtcg tgcaagagaa acagagtgat 2460
ctggcaccgc ctgttgatag cgccaatgaa atcaatacac tggaaaacgt tgtgaatcag 2520
cagaaaattc cgcaggttac acgtgttgtt accgaacagc agggacgtaa agttctgatt 2580
gatggtcatt gggttattga ttttgccagc tgtaattatc tgggcctgga cctgcatccg 2640
aaagttaaag aagcaattcc tccggcactg gataaatggg gcacccatcc gagctggacc 2700
cgtctggttg caagtccggc aatttatgag gaactggaag aggaactgtc aaaactgctg 2760
ggtgtgccgg atgttctggt ttttccggca gttacactgc tgcagattgg tattctgcct 2820
ctgctgaccg gtaataatgg tgtgattttt ggcgatattg cagcccatcg ttgtatttat 2880
gaagcatgtt gtctggccca gcataaaggt gcacagttta ttcagtatcg tcataacgac 2940
ctgaatgatc tggccgaaaa actggccaaa tatccgcctg aacaggttaa aatcattgtg 3000
atcgatggtg tgtatagcat gagtgccgat ttcccggacc tgcctgcata tgttcatctg 3060
gcaaaagaat ataacgccct gatctatatg gatgatgcac atggctttgg cattctgggt 3120
gaaaatccga gcagcgatat gccgtatggt tataaaggta atggcatggt gaactacttt 3180
gatctgcgtt ttgccgaaga taacatcatt tatgttgcag gtctgagcaa agcctatagc 3240
agctatgcag catttctgac ctgtggtgat cgtcgtatta aaaccaattt tcgtaatgca 3300
tggaccgcga tttttagcgg tccgagtccg gttgcaagcc tggccagcgc actggcaggt 3360
ctgcaggtta atcgtcaaga aggtgaacag ctgcgcaaac aaatctatca tctgacacat 3420
aaactggtta cccaggctcg tgccattggt tttgaagttg ataattatgg ttatgtgccg 3480
attgtgggtg ttctggtggg tgatgcacag catatgattg atgtgtgcca actgctgtgg 3540
gaatatggta tcctgattac ccctgcaatt tttccgattg tgccgctgaa taaatcagca 3600
ctgcgtttta gcattaccgc agcaaatacc gaagaagaaa ttgatcaggc catcaaaagt 3660
ctgaaagcag tttgggacct gctgcaaaaa cgtaaagccc tgccgtgtaa acaagaagaa 3720
aatatcctga aacattga 3738

<210> SEQ ID NO 13
<211> LENGTH: 128
<212> TYPE: PRT
<213> ORGANISM: Cylindrospermopsis raciborskii T3

<400> SEQUENCE: 13

Met Leu Lys Asp Phe Asn Gln Phe Leu Ile Arg Thr Leu Ala Phe Val
1 5 10 15

Phe Ala Phe Gly Ile Phe Leu Thr Thr Gly Val Gly Ile Ala Lys Ala
20 25 30

Asp Tyr Leu Val Lys Gly Gly Lys Ile Thr Asn Val Gln Asn Thr Ser
35 40 45

Ser Asn Gly Asp Asn Tyr Ala Val Ser Ile Ser Gly Gly Phe Gly Pro
50 55 60

Cys Ala Asp Arg Val Ile Ile Leu Pro Thr Ser Gly Val Ile Asn Arg
65 70 75 80

Asp Ile His Met Arg Gly Tyr Glu Ala Ala Leu Thr Ala Leu Ser Asn
85 90 95

Gly Phe Leu Val Asp Ile Tyr Asp Tyr Thr Gly Ser Ser Cys Ser Asn
100 105 110

Gly Gly Gln Leu Thr Ile Thr Asn Gln Leu Gly Lys Leu Ile Ser Asn
115 120 125

<210> SEQ ID NO 14
<211> LENGTH: 387
<212> TYPE: DNA
<213> ORGANISM: Cylindrospermopsis raciborskii T3

<400> SEQUENCE: 14
atgttgaaag atttcaacca gtttttaatc agaacactag cattcgtatt cgcatttggt 60
attttcttaa ccactggagt tggcattgct aaagctgact acctagttaa aggtggaaag 120
attaccaatg ttcaaaatac ttcttctaac ggtgataatt atgccgttag tatcagcggt 180
gggtttggtc cttgcgcaga tagagtgatt atcctaccaa cttcaggagt gataaatcga 240
gacattcata tgcgtggcta tgaagccgca ttaactgcac tatccaatgg ctttttagta 300
gatatttacg actatactgg ctcttcttgc agcaatggtg gccaactaac tattaccaac 360
caattaggta agctaatcag caattag 387

<210> SEQ ID NO 15
<211> LENGTH: 387
<212> TYPE: DNA
<213> ORGANISM: Cylindrospermopsis raciborskii T3

<400> SEQUENCE: 15
atgctgaaag attttaacca gttcctgatt cgtaccctgg catttgtttt tgcctttggc 60
atttttctga caaccggtgt tggtattgca aaagcagatt atctggtgaa aggtggcaaa 120
attaccaatg ttcagaatac cagcagcaac ggtgataatt atgcagttag cattagcggt 180
ggttttggtc cgtgtgcaga tcgtgttatt attctgccga ccagcggtgt tattaatcgt 240
gatattcaca tgcgtggtta tgaagcagca ctgaccgcac tgagcaatgg ttttctggtt 300
gatatctatg attataccgg tagcagctgt agcaatggtg gccagctgac cattaccaat 360
cagctgggta aactgattag caattga 387

<210> SEQ ID NO 16
<211> LENGTH: 471
<212> TYPE: PRT
<213> ORGANISM: Cylindrospermopsis raciborskii T3

<400> SEQUENCE: 16

Met Glu Thr Thr Ser Lys Lys Phe Lys Ser Asp Leu Ile Leu Glu Ala
1 5 10 15

Arg Ala Ser Leu Lys Leu Gly Ile Pro Leu Val Ile Ser Gln Met Cys
20 25 30

Glu Thr Gly Ile Tyr Thr Ala Asn Ala Val Met Met Gly Leu Leu Gly
35 40 45

Thr Gln Val Leu Ala Ala Gly Ala Leu Gly Ala Leu Ala Phe Leu Thr
50 55 60

Leu Leu Phe Ala Cys His Gly Ile Leu Ser Val Gly Gly Ser Leu Ala
65 70 75 80

Ala Glu Ala Phe Gly Ala Asn Lys Ile Asp Glu Val Ser Arg Ile Ala
85 90 95

```
Ser Gly Gln Ile Trp Leu Ala Val Thr Leu Ser Leu Pro Ala Met Leu
            100                 105                 110

Leu Leu Trp His Gly Asp Thr Ile Leu Leu Leu Phe Gly Gln Glu Glu
        115                 120                 125

Ser Asn Val Leu Leu Thr Lys Thr Tyr Leu His Ser Ile Leu Trp Gly
    130                 135                 140

Phe Pro Ala Ala Leu Ser Ile Leu Thr Leu Arg Gly Ile Ala Ser Ala
145                 150                 155                 160

Leu Asn Val Pro Arg Leu Ile Thr Ile Thr Met Leu Thr Gln Leu Ile
                165                 170                 175

Leu Asn Thr Ala Ala Asp Tyr Val Leu Ile Phe Gly Lys Phe Gly Leu
            180                 185                 190

Pro Gln Leu Gly Leu Ala Gly Ile Gly Trp Ala Thr Ala Leu Gly Phe
        195                 200                 205

Trp Val Ser Phe Thr Leu Gly Leu Ile Leu Leu Ile Phe Ser Leu Lys
    210                 215                 220

Val Arg Asp Tyr Lys Leu Phe Arg Tyr Leu His Gln Phe Asp Lys Gln
225                 230                 235                 240

Ile Phe Val Lys Ile Phe Gln Thr Gly Trp Pro Met Gly Phe Gln Trp
                245                 250                 255

Gly Ala Glu Thr Ala Leu Phe Asn Val Thr Ala Trp Val Ala Gly Tyr
            260                 265                 270

Leu Gly Thr Val Thr Leu Ala Ala His Asp Ile Gly Phe Gln Thr Ala
        275                 280                 285

Glu Leu Ala Met Val Ile Pro Leu Gly Val Gly Asn Val Ala Met Thr
    290                 295                 300

Arg Val Gly Gln Ser Ile Gly Glu Lys Asn Pro Leu Gly Ala Arg Arg
305                 310                 315                 320

Val Ala Ser Ile Gly Ile Thr Ile Val Gly Ile Tyr Ala Ser Ile Val
                325                 330                 335

Ala Leu Val Phe Trp Leu Phe Pro Tyr Gln Ile Ala Gly Ile Tyr Leu
            340                 345                 350

Asn Ile Asn Asn Pro Glu Asn Ile Glu Ala Ile Lys Lys Ala Thr Thr
        355                 360                 365

Phe Ile Pro Leu Ala Gly Leu Phe Gln Met Phe Tyr Ser Ile Gln Ile
    370                 375                 380

Ile Ile Val Gly Ala Leu Val Gly Leu Arg Asp Thr Phe Val Pro Val
385                 390                 395                 400

Ser Met Asn Leu Ile Val Trp Gly Leu Gly Leu Ala Gly Ser Tyr Phe
                405                 410                 415

Met Ala Ile Ile Leu Gly Trp Gly Gly Ile Gly Ile Trp Leu Ala Met
            420                 425                 430

Val Leu Ser Pro Leu Leu Ser Ala Val Ile Leu Thr Val Arg Phe Tyr
        435                 440                 445

Arg Val Ile Asp Asn Leu Leu Ala Asn Ser Asp Asp Met Leu Gln Asn
    450                 455                 460

Ala Ser Val Thr Thr Leu Gly
465                 470
```

<210> SEQ ID NO 17
<211> LENGTH: 1416
<212> TYPE: DNA
<213> ORGANISM: Cylindrospermopsis raciborskii T3

<400> SEQUENCE: 17

```
atggaaacaa cctcaaaaaa atttaagtca gatctgatat tagaagcacg agcaagccta     60
aagttgggaa tcccccttagt catttcacaa atgtgcgaaa cgggtattta tacagcgaat   120
gcagtcatga tgggtttact tggtacgcaa gttttggccg ccggtgcttt gggcgcgctc   180
gctttttga ccttattatt tgcctgccat ggtattctct cagtaggagg atcactagca   240
gccgaagctt ttggggcaaa taaaatagat gaagttagtc gtattgcttc cgggcaaata   300
tggctagcag ttaccttgtc tttacctgca atgcttctgc tttggcatgg cgatactatc   360
ttgctgctat tcggtcaaga ggaaagcaat gtgttattga caaaaacgta tttacactca   420
attttatggg gctttcccgc tgcgcttagt attttgacat taagaggcat tgcctctgct   480
ctcaacgttc cccgattgat aactattact atgctcactc agctgatatt gaataccgcc   540
gccgattatg tgttaatatt cggtaaattt ggtcttcctc aacttggttt ggctggaata   600
ggctgggcaa ctgctctggg tttttgggtt agttttacat tggggcttat cttgctgatt   660
ttctccctga aagttagaga ttataaactt ttccgctact tgcatcagtt tgataaacag   720
atctttgtca aaatttttca aactggatgg cccatggggt ttcaatgggg ggcggaaacg   780
gcactattta acgtcaccgc ttgggtagca gggtatttag gaacggtaac attagcagcc   840
catgatattg gcttccaaac ggcagaactg gcgatggtta taccactcgg agtcggcaat   900
gtcgctatga caagagtagg tcagagtata ggagaaaaaa accctttggg tgcaagaagg   960
gtagcatcga ttggaattac aatagttggc atttatgcca gtattgtagc acttgttttc  1020
tggttgtttc catatcaaat tgccggaatt tatttaaata taaacaatcc cgagaatatc  1080
gaagcaatta agaaagcaac tacttttatc cccttggcgg gactattcca aatgttttac  1140
agtattcaaa taattattgt tggggctttg gtcggtctgc gggatacatt tgttccagta  1200
tcaatgaact taattgtctg ggtcttgga ttggcaggaa gctatttcat ggcaatcatt  1260
ttaggatggg gggggatcgg gatttggttg gctatggttt tgagtccact cctctcggca  1320
gttattttaa ctgttcgttt ttatcgagtg attgacaatc ttcttgccaa cagtgatgat  1380
atgttacaga atgcgtctgt tactactcta ggctga                            1416
```

<210> SEQ ID NO 18
<211> LENGTH: 1416
<212> TYPE: DNA
<213> ORGANISM: Cylindrospermopsis raciborskii T3

<400> SEQUENCE: 18

```
atggaaacca cgagcaaaaa attcaaaagc gatctgattc tggaagcacg tgcaagcctg     60
aaactgggta ttccgctggt tattagccag atgtgtgaaa ccggtattta taccgcaaat   120
gcagttatga tgggtctgct gggcacccag gttctggcag ccggtgctct gggtgcactg   180
gcatttctga ccctgctgtt tgcatgtcat ggtattctga gcgttggtgg tagcctggca   240
gcggaagcat ttggtgcaaa caaaattgat gaagttagcc gtattgcaag cggtcagatt   300
tggctggcag ttaccctgag cctgcctgca atgctgctgc tgtggcatgg tgataccatt   360
ctgctgttat ttggtcaaga agaaagcaac gttctgctga ccaaaaccta tctgcatagc   420
attctgtggg gttttccggc agcactgagt attctgacac tgcgtggtat tgccagcgca   480
ctgaatgttc cgcgtctgat taccattacc atgctgaccc agctgattct gaataccgca   540
gcagattatg ttctgatctt tggtaaattt ggtctgccgc agctgggtct ggcaggtatt   600
ggttgggcaa ccgcactggg tttttgggtt agctttaccc tgggtctgat cctgctgatt   660
```

```
tttagcctga aagtgcgtga ttataaactg tttcgttatc tgcaccagtt cgacaagcag    720

atctttgtga aaatctttca gaccggttgg ccgatgggtt ttcagtgggg tgcagaaaca    780

gcactgttta atgttaccgc atgggttgca ggttatctgg gcaccgttac cctggcagca    840

catgatattg gttttcagac agcagaactg gcaatggtta tcccgctggg tgttggtaat    900

gttgcaatga cccgtgttgg tcagagcatt ggtgaaaaaa atccactggg tgcccgtcgt    960

gttgcaagca ttggtattac cattgttggt atttatgcca gcattgttgc cctggttttt   1020

tggctgtttc cgtatcagat tgcaggcatt tatctgaaca ttaataaccc ggaaaacatt   1080

gaagccatca aaaaagccac cacctttatt ccactggcag gtctgtttca gatgttttat   1140

agcattcaga tcattatcgt tggtgcgctg gttggtctgc gtgatacctt tgttccggtt   1200

agcatgaatc tgattgtttg gggtctgggt ttagcaggta gctattttat ggcaattatt   1260

ctgggttggg gtggtattgg tatctggctg gccatggttc tgagtccgct gctgagcgca   1320

gttattctga ccgttcgttt ttatcgcgtg attgataatc tgctggccaa cagtgatgat   1380

atgctgcaga atgcaagcgt taccaccctg ggatga                             1416
```

<210> SEQ ID NO 19
<211> LENGTH: 377
<212> TYPE: PRT
<213> ORGANISM: Cylindrospermopsis raciborskii T3

<400> SEQUENCE: 19

```
Met Thr Asn Gln Asn Asn Gln Glu Leu Glu Asn Asp Leu Pro Ile Ala
1               5                   10                  15

Lys Gln Pro Cys Pro Val Asn Ser Tyr Asn Glu Trp Asp Thr Leu Glu
            20                  25                  30

Glu Val Ile Val Gly Ser Val Glu Gly Ala Met Leu Pro Ala Leu Glu
        35                  40                  45

Pro Ile Asn Lys Trp Thr Phe Pro Phe Glu Glu Leu Glu Ser Ala Gln
    50                  55                  60

Lys Ile Leu Ser Glu Arg Gly Gly Val Pro Tyr Pro Pro Glu Met Ile
65                  70                  75                  80

Thr Leu Ala His Lys Glu Leu Asn Glu Phe Ile His Ile Leu Glu Ala
                85                  90                  95

Glu Gly Val Lys Val Arg Arg Val Lys Pro Val Asp Phe Ser Val Pro
            100                 105                 110

Phe Ser Thr Pro Ala Trp Gln Val Gly Ser Gly Phe Cys Ala Ala Asn
        115                 120                 125

Pro Arg Asp Val Phe Leu Val Ile Gly Asn Glu Ile Ile Glu Ala Pro
    130                 135                 140

Met Ala Asp Arg Asn Arg Tyr Phe Glu Thr Trp Ala Tyr Arg Glu Met
145                 150                 155                 160

Leu Lys Glu Tyr Phe Gln Ala Gly Ala Lys Trp Thr Ala Ala Pro Lys
                165                 170                 175

Pro Gln Leu Phe Asp Ala Gln Tyr Asp Phe Asn Phe Gln Phe Pro Gln
            180                 185                 190

Leu Gly Glu Pro Pro Arg Phe Val Val Thr Glu Phe Glu Pro Thr Phe
        195                 200                 205

Asp Ala Ala Asp Phe Val Arg Cys Gly Arg Asp Ile Phe Gly Gln Lys
    210                 215                 220

Ser His Val Thr Asn Gly Leu Gly Ile Glu Trp Leu Gln Arg His Leu
225                 230                 235                 240
```

```
Glu Asp Glu Tyr Arg Ile His Ile Ile Glu Ser His Cys Pro Glu Ala
                245                 250                 255

Leu His Ile Asp Thr Thr Leu Met Pro Leu Ala Pro Gly Lys Ile Leu
            260                 265                 270

Val Asn Pro Glu Phe Val Asp Val Asn Lys Leu Pro Lys Ile Leu Lys
        275                 280                 285

Ser Trp Asp Ile Leu Val Ala Pro Tyr Pro Asn His Ile Pro Gln Asn
    290                 295                 300

Gln Leu Arg Leu Val Ser Glu Trp Ala Gly Leu Asn Val Leu Met Leu
305                 310                 315                 320

Asp Glu Glu Arg Val Ile Val Glu Lys Asn Gln Glu Gln Met Ile Lys
                325                 330                 335

Ala Leu Lys Asp Trp Gly Phe Lys Pro Ile Val Cys His Phe Glu Ser
            340                 345                 350

Tyr Tyr Pro Phe Leu Gly Ser Phe His Cys Ala Thr Leu Asp Val Arg
        355                 360                 365

Arg Arg Gly Thr Leu Gln Ser Tyr Phe
    370                 375
```

<210> SEQ ID NO 20
<211> LENGTH: 1134
<212> TYPE: DNA
<213> ORGANISM: Cylindrospermopsis raciborskii T3

<400> SEQUENCE: 20

```
atgaccaatc aaaataacca agaattagag aacgatttac caatcgccaa gcagccttgt     60

ccggtcaatt cttataatga gtgggacaca cttgaggagg tcattgttgg tagtgttgaa    120

ggtgcaatgt taccggccct agaaccaatc aacaaatgga cattcccttt tgaagaattg    180

gaatctgccc aaaagatact ctctgagagg ggaggagttc cttatccacc agagatgatt    240

acattagcac acaaagaact aaatgaattt attcacattc ttgaagcaga aggggtcaaa    300

gttcgtcgag ttaaacctgt agatttctct gtccccttct ccacaccagc ttggcaagta    360

ggaagtggtt tttgtgccgc caatcctcgc gatgtttttt tggtgattgg gaatgagatt    420

attgaagcac caatggcaga tcgcaaccgc tattttgaaa cttgggcgta tcgagagatg    480

ctcaaggaat attttcaggc aggagctaag tggactgcag cgccgaagcc acaattattc    540

gacgcacagt atgacttcaa tttccagttt cctcaactgg gggagccgcc gcgtttcgtc    600

gttacagagt ttgaaccgac ttttgatgcg gcagattttg tgcgctgtgg acgagatatt    660

tttggtcaaa aaagtcatgt gactaatggt ttgggcatag aatggttaca acgtcacttg    720

gaagacgaat accgtattca tattattgaa tcgcattgtc cggaagcact gcacatcgat    780

accaccttaa tgcctcttgc acctggcaaa atactagtaa atccagaatt tgtagatgtt    840

aataaattgc caaaaatcct gaaaagctgg gacattttgg ttgcacctta ccccaaccat    900

atacctcaaa accagctgag actggtcagt gaatgggcag gtttgaatgt actgatgtta    960

gatgaagagc gagtcattgt agaaaaaaac caggagcaga tgattaaagc actgaaagat   1020

tggggattta agcctattgt ttgccatttt gaaagctact atccattttt aggatcattt   1080

cactgtgcaa cattagacgt tcgccgacgc ggaactcttc agtcctattt ttaa         1134
```

<210> SEQ ID NO 21
<211> LENGTH: 1134
<212> TYPE: DNA
<213> ORGANISM: Cylindrospermopsis raciborskii T3

<400> SEQUENCE: 21

```
atgaccaatc agaacaacca agagctggaa aatgatctgc cgattgcaaa acagccgtgt     60
ccggttaata gctataatga atgggatacc ctggaagaag ttattgttgg tagcgttgaa    120
ggtgcaatgc tgcctgcact ggaaccgatt aacaaatgga cctttccgtt tgaagaactg    180
gaaagcgcac agaaaattct gagcgaacgt ggtggtgttc cgtatccgcc tgaaatgatt    240
accctggcac ataaagaact gaacgagttt attcatatcc tggaagccga aggtgttaaa    300
gttcgtcgtg ttaaaccggt tgattttagc gttccgttta gcacaccggc atggcaggtt    360
ggtagcggtt tttgtgcagc aaatccgcgt gatgtttttc tggttattgg caacgaaatt    420
atcgaagcac cgatggcaga tcgtaatcgt tattttgaaa cctgggcata tcgcgaaatg    480
ctgaaagaat attttcaggc aggcgcaaaa tggaccgcag caccgaaacc gcagctgttt    540
gatgcacagt atgatttcaa ttttcagttt ccgcagctgg gtgaaccgcc tcgttttgtt    600
gttaccgaat ttgaaccgac ctttgatgca gccgattttg ttcgttgtgg tcgtgatatt    660
tttggccaga aaagccatgt taccaatggt ctgggtattg aatggctgca gcgtcatctg    720
gaagatgaat atcgcattca tatcatcgaa agccattgtc cggaagcact gcatattgat    780
accaccctga tgccgctggc accgggtaaa attctggtta atccggaatt tgtggacgtg    840
aataaactgc cgaaaattct gaaaagctgg gatattctgg ttgcaccgta tccgaatcat    900
attccgcaga atcagctgcg tctggttagc gaatgggcag gtctgaatgt tctgatgctg    960
gatgaagaac gtgtgatcgt ggaaaaaaat caagagcaga tgatcaaagc cctgaaagat   1020
tggggtttta aaccgattgt ttgccacttc gaaagctatt atccgtttct gggtagcttt   1080
cattgtgcaa ccctggatgt tcgtcgtcgt ggcaccctgc agagctattt ttga         1134
```

<210> SEQ ID NO 22
<211> LENGTH: 334
<212> TYPE: PRT
<213> ORGANISM: Cylindrospermopsis raciborskii T3

<400> SEQUENCE: 22

```
Met Thr Thr Ala Asp Leu Ile Leu Ile Asn Asn Trp Tyr Val Val Ala
1               5                   10                  15

Lys Val Glu Asp Cys Lys Pro Gly Ser Ile Thr Thr Ala Leu Leu Leu
            20                  25                  30

Gly Val Lys Leu Val Leu Trp Arg Ser Arg Glu Gln Asn Ser Pro Ile
        35                  40                  45

Gln Ile Trp Gln Asp Tyr Cys Pro His Arg Gly Val Ala Leu Ser Met
    50                  55                  60

Gly Glu Ile Val Asn Asn Thr Leu Val Cys Pro Tyr His Gly Trp Arg
65                  70                  75                  80

Tyr Asn Gln Ala Gly Lys Cys Val His Ile Pro Ala His Pro Asp Met
                85                  90                  95

Thr Pro Pro Ala Ser Ala Gln Ala Lys Ile Tyr His Cys Gln Glu Arg
            100                 105                 110

Tyr Gly Leu Val Trp Val Cys Leu Gly Asp Pro Val Asn Asp Ile Pro
        115                 120                 125

Ser Leu Pro Glu Trp Asp Asp Pro Asn Tyr His Asn Thr Cys Thr Lys
    130                 135                 140

Ser Tyr Phe Ile Gln Ala Ser Ala Phe Arg Val Met Asp Asn Phe Ile
145                 150                 155                 160
```

-continued

```
Asp Val Ser His Phe Pro Phe Val His Asp Gly Gly Leu Gly Asp Arg
                165                 170                 175

Asn His Ala Gln Ile Glu Glu Phe Glu Val Lys Val Asp Lys Asp Gly
            180                 185                 190

Ile Ser Ile Gly Asn Leu Lys Leu Gln Met Pro Arg Phe Asn Ser Ser
        195                 200                 205

Asn Glu Asp Asp Ser Trp Thr Leu Tyr Gln Arg Ile Ser His Pro Leu
    210                 215                 220

Cys Gln Tyr Tyr Ile Thr Glu Ser Ser Glu Ile Arg Thr Ala Asp Leu
225                 230                 235                 240

Met Leu Val Thr Pro Ile Asp Glu Asp Asn Ser Leu Val Arg Met Leu
                245                 250                 255

Val Thr Trp Asn Arg Ser Glu Ile Leu Glu Ser Thr Val Leu Glu Glu
            260                 265                 270

Phe Asp Glu Thr Ile Glu Gln Asp Ile Pro Ile Ile His Ser Gln Gln
        275                 280                 285

Pro Ala Arg Leu Pro Leu Leu Pro Ser Lys Gln Ile Asn Met Gln Trp
    290                 295                 300

Leu Ser Gln Glu Ile His Val Pro Ser Asp Arg Cys Thr Val Ala Tyr
305                 310                 315                 320

Arg Arg Trp Leu Lys Glu Leu Gly Val Thr Tyr Gly Val Cys
                325                 330
```

```
<210> SEQ ID NO 23
<211> LENGTH: 1005
<212> TYPE: DNA
<213> ORGANISM: Cylindrospermopsis raciborskii T3

<400> SEQUENCE: 23

atgacaactg ctgacctaat cttaattaac aactggtacg tagtcgcaaa ggtggaagat      60

tgtaaaccag gaagtatcac cacggctctt ttattgggag ttaagttggt actatggcgc     120

agtcgtgaac agaattcccc catacagata tggcaagact actgccctca ccgaggtgtg     180

gctctgtcta tgggagaaat tgttaataat actttggttt gtccgtatca cggatggaga     240

tataatcaag caggtaaatg cgtacatatc ccggctcacc ctgacatgac acccccagca     300

agtgcccaag ccaagatcta tcattgccag gagcgatacg gattagtatg ggtgtgctta     360

ggtgatcctg tcaatgatat accttcatta cccgaatggg acgatccgaa ttatcataat     420

acttgtacta aatcttattt tattcaagct agtgcgtttc gtgtaatgga taatttcata     480

gatgtatctc attttccttt tgtccacgac ggtgggttag gtgatcgcaa ccacgcacaa     540

attgaagaat ttgaggtaaa agtagacaaa gatggcatta gcataggtaa ccttaaactc     600

cagatgccaa ggtttaacag cagtaacgaa gatgactcat ggactcttta ccaaaggatt     660

agtcatccct tgtgtcaata ctatattact gaatcctctg aaattcggac tgcggatttg     720

atgctggtaa caccgattga tgaagacaac agcttagtgc gaatgttagt aacgtggaac     780

cgctccgaaa tattagagtc aacggtacta gaggaatttg acgaaacaat agaacaagat     840

attccgatta tacactctca acagccagcg cgtttaccac tgttaccttc aaagcagata     900

aacatgcaat ggttgtcaca ggaaatacat gtaccgtcag atcgatgcac agttgcctat     960

cgtcgatggc taaaggaact gggcgttacc tatggtgttt gttaa                    1005

<210> SEQ ID NO 24
<211> LENGTH: 1005
<212> TYPE: DNA
```

-continued

<213> ORGANISM: Cylindrospermopsis raciborskii T3

<400> SEQUENCE: 24
atgacgaccg cagatctgat tctgatcaat aattggtatg ttgtggccaa ggtggaagat 60
tgtaaaccgg gtagcattac caccgcactg ctgctgggtg ttaaactggt tctgtggcgt 120
agccgtgaac agaatagccc gattcagatt tggcaggatt attgtccgca tcgtggtgtt 180
gcactgagca tgggtgaaat tgtgaataat accctggttt gtccgtatca tggttggcgt 240
tataatcagg caggtaaatg tgttcatatt ccggcacatc cggatatgac ccctccggca 300
agcgcacagg caaaaatcta tcattgtcaa gaacgttatg gtctggtttg ggtttgtctg 360
ggtgatccgg ttaatgatat tccgagtctg ccggaatggg atgatccgaa ttatcataat 420
acctgcacca agagctactt tatccaggca agcgcatttc gtgtgatgga taactttatt 480
gatgtgagcc attttccgtt tgtgcatgat ggtggtctgg gcgatcgtaa tcatgcacag 540
attgaagaat ttgaggtgaa agtggataaa gacggtatta gcattggcaa tctgaaactg 600
cagatgcctc gttttaatag cagcaatgaa gatgatagct ggaccctgta tcagcgtatt 660
agccatccgc tgtgtcagta ttatatcacc gaaagcagcg aaattcgtac agcagatctg 720
atgctggtta ccccgattga tgaagataat tcactggttc gtatgctggt gacctggaat 780
cgtagcgaaa ttctggaaag caccgttctg gaagaatttg atgaaaccat tgaacaggat 840
atcccgatta ttcatagcca gcagcctgca cgtctgccgc tgctgccgag caagcagatt 900
aatatgcagt ggctgagcca agaaattcat gttccgagcg atcgttgtac cgttgcatat 960
cgtcgttggc tgaaagaact gggcgttacc tatggtgttt gttga 1005

<210> SEQ ID NO 25
<211> LENGTH: 612
<212> TYPE: PRT
<213> ORGANISM: Cylindrospermopsis raciborskii T3

<400> SEQUENCE: 25

Met Gln Ile Leu Gly Ile Ser Ala Tyr Tyr His Asp Ser Ala Ala Ala
1 5 10 15

Met Val Ile Asp Gly Glu Ile Val Ala Ala Ala Gln Glu Glu Arg Phe
20 25 30

Ser Arg Arg Lys His Asp Ala Gly Phe Pro Thr Gly Ala Ile Thr Tyr
35 40 45

Cys Leu Lys Gln Val Gly Thr Lys Leu Gln Tyr Ile Asp Gln Ile Val
50 55 60

Phe Tyr Asp Lys Pro Leu Val Lys Phe Glu Arg Leu Leu Glu Thr Tyr
65 70 75 80

Leu Ala Tyr Ala Pro Lys Gly Phe Gly Ser Phe Ile Thr Ala Met Pro
85 90 95

Val Trp Leu Lys Glu Lys Leu Tyr Leu Lys Thr Leu Leu Lys Lys Glu
100 105 110

Leu Ala Leu Leu Gly Glu Cys Lys Ala Ser Gln Leu Pro Pro Leu Leu
115 120 125

Phe Thr Ser His His Gln Ala His Ala Ala Ala Ala Phe Phe Pro Ser
130 135 140

Pro Phe Gln Arg Ala Ala Val Leu Cys Leu Asp Gly Val Gly Glu Trp
145 150 155 160

Ala Thr Thr Ser Val Trp Leu Gly Glu Gly Asn Lys Leu Thr Pro Gln
165 170 175

-continued

```
Trp Glu Ile Asp Phe Pro His Ser Leu Gly Leu Leu Tyr Ser Ala Phe
            180                 185                 190

Thr Tyr Tyr Thr Gly Phe Lys Val Asn Ser Gly Glu Tyr Lys Leu Met
        195                 200                 205

Gly Leu Ala Pro Tyr Gly Glu Pro Lys Tyr Val Asp Gln Ile Leu Lys
    210                 215                 220

His Leu Leu Asp Leu Lys Glu Asp Gly Thr Phe Arg Leu Asn Met Asp
225                 230                 235                 240

Tyr Phe Asn Tyr Thr Val Gly Leu Thr Met Thr Asn His Lys Phe His
                245                 250                 255

Ser Met Phe Gly Gly Pro Pro Arg Gln Ala Glu Gly Lys Ile Ser Gln
            260                 265                 270

Arg Asp Met Asp Leu Ala Ser Ser Ile Gln Lys Val Thr Glu Glu Val
        275                 280                 285

Ile Leu Arg Leu Ala Arg Thr Ile Lys Lys Glu Leu Gly Val Glu Tyr
    290                 295                 300

Leu Cys Leu Ala Gly Gly Val Gly Leu Asn Cys Val Ala Asn Gly Arg
305                 310                 315                 320

Ile Leu Arg Glu Ser Asp Phe Lys Asp Ile Trp Ile Gln Pro Ala Ala
                325                 330                 335

Gly Asp Ala Gly Ser Ala Val Gly Ala Ala Leu Ala Ile Trp His Glu
            340                 345                 350

Tyr His Lys Lys Pro Arg Thr Ser Thr Ala Gly Asp Arg Met Lys Gly
        355                 360                 365

Ser Tyr Leu Gly Pro Ser Phe Ser Glu Ala Glu Ile Leu Gln Phe Leu
    370                 375                 380

Asn Ser Val Asn Ile Pro Tyr His Arg Cys Val Asp Asn Glu Leu Met
385                 390                 395                 400

Ala Arg Leu Ala Glu Ile Leu Asp Gln Gly Asn Val Val Gly Trp Phe
                405                 410                 415

Ser Gly Arg Met Glu Phe Gly Pro Arg Ala Leu Gly Gly Arg Ser Ile
            420                 425                 430

Ile Gly Asp Ser Arg Ser Pro Lys Met Gln Ser Val Met Asn Leu Lys
        435                 440                 445

Ile Lys Tyr Arg Glu Ser Phe Arg Pro Phe Ala Pro Ser Val Leu Ala
    450                 455                 460

Glu Arg Val Ser Asp Tyr Phe Asp Leu Asp Arg Pro Ser Pro Tyr Met
465                 470                 475                 480

Leu Leu Val Ala Gln Val Lys Glu Asn Leu His Ile Pro Met Thr Gln
                485                 490                 495

Glu Gln His Glu Leu Phe Gly Ile Glu Lys Leu Asn Val Pro Arg Ser
            500                 505                 510

Gln Ile Pro Ala Val Thr His Val Asp Tyr Ser Ala Arg Ile Gln Thr
        515                 520                 525

Val His Lys Glu Thr Asn Pro Arg Tyr Tyr Glu Leu Ile Arg His Phe
    530                 535                 540

Glu Ala Arg Thr Gly Cys Ala Val Leu Val Asn Thr Ser Phe Asn Val
545                 550                 555                 560

Arg Gly Glu Pro Ile Val Cys Thr Pro Glu Asp Ala Tyr Arg Cys Phe
                565                 570                 575

Met Arg Thr Glu Met Asp Tyr Leu Val Met Glu Asn Phe Leu Leu Val
            580                 585                 590

Lys Ser Glu Gln Pro Arg Gly Asn Ser Asp Glu Ser Trp Gln Lys Glu
```

595 600 605

Phe Glu Leu Asp
610

<210> SEQ ID NO 26
<211> LENGTH: 1839
<212> TYPE: DNA
<213> ORGANISM: Cylindrospermopsis raciborskii T3

<400> SEQUENCE: 26
atgcagatct taggaatttc agcttactac cacgatagtg ctgccgcgat ggttatcgat 60
ggcgaaattg ttgctgcagc tcaggaagaa cgtttctcaa gacgaaagca cgatgctggg 120
tttccgactg gagcgattac ttactgtcta aaacaagtag gaaccaagtt acaatatatc 180
gatcaaattg ttttttacga caagccatta gtcaaatttg agcggttgct agaaacatat 240
ttagcatatg ccccaaaggg atttggctcg tttattactg ctatgcccgt ttggctcaaa 300
gaaaagcttt acctaaaaac acttttaaaa aaagaattgg cgcttttggg ggagtgcaaa 360
gcttctcaat tgcctcctct actgtttacc tcacatcacc aagcccatgc ggccgctgct 420
ttttttccca gtccttttca gcgtgctgcc gttctgtgct tagatggtgt aggagagtgg 480
gcaactactt ctgtctggtt gggagaagga aataaactca caccacaatg ggaaattgat 540
tttccccatt ccctcggttt gctttactca gcgtttacct actacactgg gttcaaagtt 600
aactcaggtg agtacaaact catgggttta gcaccctacg ggaacccaa atatgtggac 660 caaattctca agcatttgtt ggatctcaaa gaagatggta cttttaggtt gaatatggac 720
tacttcaact acacggtggg gctaaccatg accaatcata agttccatag tatgtttgga 780
ggaccaccac gccaggcgga aggaaaaatc tcccaaagag acatggatct ggcaagttcg 840
atccaaaagg tgactgaaga agtcatactg cgtctggcta gaactatcaa aaaagaactg 900
ggtgtagagt atctatgttt agcaggtggt gtcggtctca attgcgtggc taacggacga 960
attctccgag aaagtgattt caaagatatt tggattcaac ccgcagcagg agatgccggt 1020
agtgcagtgg gagcagcttt agcgatttgg catgaatacc ataagaaacc tcgcacttca 1080
acagcaggcg atcgcatgaa aggttcttat ctgggaccta gctttagcga ggcggagatt 1140
ctccagtttc ttaattctgt taacataccc taccatcgat gcgttgataa cgaacttatg 1200
gctcgtcttg cagaaatttt agaccaggga aatgttgtag gctggttttc tggacgaatg 1260
gagtttggtc cgcgtgcttt gggtggccgt tcgattattg gcgattcacg cagtccaaaa 1320
atgcaatcgg tcatgaacct gaaaattaaa tatcgtgagt ccttccgtcc atttgctcct 1380
tcagtcttgg ctgaacgagt ctccgactac ttcgatcttg atcgtcctag tccttatatg 1440
cttttggtag cacaagtcaa agagaatctg cacattccta tgacacaaga gcaacacgag 1500
ctatttggga tcgagaagct gaatgttcct cgttcccaaa ttcccgcagt cactcacgtt 1560
gattactcag ctcgtattca gacagttcac aaagaaacga atcctcgtta ctacgagtta 1620
attcgtcatt ttgaggcacg aactggttgt gctgtcttgg tcaatacttc gtttaatgtc 1680
cgcggcgaac caattgtttg tactcccgaa gacgcttatc gatgctttat gagaactgaa 1740
atggactatt tggttatgga gaatttcttg ttggtcaaat ctgaacagcc acggggaaat 1800
agtgatgagt catggcaaaa agaattcgag ttagattaa 1839

<210> SEQ ID NO 27
<211> LENGTH: 1839
<212> TYPE: DNA

<213> ORGANISM: Cylindrospermopsis raciborskii T3

<400> SEQUENCE: 27
atgcagattc tgggtatcag cgcctattat catgatagcg cagcagcaat ggttattgat 60
ggtgaaattg ttgcagcagc acaagaagaa cgttttagcc gtcgtaaaca tgatgcaggt 120
tttccgaccg gtgcaattac ctattgtctg aaacaggttg gcaccaaact gcagtatatt 180
gatcagatcg tgttctatga taaaccgctg gtgaaatttg aacgtctgct ggaaacctat 240
ctggcctatg caccgaaagg ttttggtagt tttattaccg caatgccggt gtggctgaaa 300
gagaaactgt atctgaaaac cctgctgaaa aaagaactgg cactgctggg tgaatgtaaa 360
gcaagccagc tgcctccgct gctgtttacc agccatcatc aggcacatgc agcagcagca 420
ttttttccga gcccgtttca gcgtgcagca gttctgtgtc tggatggtgt tggtgaatgg 480
gcaaccacca gtgtttggct gggtgaaggt aataaactga caccgcagtg ggaaattgat 540
tttccgcata gcctgggcct gctgtatagc gcatttacct attataccgg ctttaaagtg 600
aacagcggtg agtataaact gatgggtctg gcaccgtatg gtgaaccgaa atatgttgat 660
cagattctga aacatctgct ggatctgaaa gaagatggca cctttcgtct gaacatggat 720
tatttcaatt ataccgttgg tctgaccatg accaaccata aatttcatag catgtttggt 780
ggtccgcctc gtcaggcaga aggtaaaatt agccagcgtg atatggatct ggcaagcagc 840
attcagaaag ttaccgaaga agtgattctg cgtctggcac gtaccattaa gaaagaatta 900
ggtgttgaat acctgtgtct ggcaggcggt gttggtctga attgtgttgc aaatggtcgt 960
attctgcgtg agagcgattt taaagatatt tggattcagc ctgcagccgg tgatgcaggt 1020
agcgcagttg gtgcagcact ggcaatttgg catgaatatc ataaaaaacc gcgtaccagc 1080
accgcaggcg atcgtatgaa aggtagctat ctgggtccga gctttagcga agcagaaatt 1140
ctgcagtttc tgaacagcgt gaatattccg tatcatcgtt gtgtggataa tgaactgatg 1200
gcacgtctgg cggaaattct ggatcagggt aatgttgttg gttggtttag cggtcgtatg 1260
gaatttggtc cgcgtgcact gggtggtcgt agcattattg gtgatagccg tagcccgaaa 1320
atgcagagcg ttatgaatct gaaaatcaaa tatcgcgaaa gcttccgtcc gtttgcaccg 1380
agcgttctgg cagaacgtgt tagcgattat tttgatctgg atcgtccgag cccgtatatg 1440
ctgctggttg cacaggttaa agaaaatctg catattccga tgacccaaga acagcatgaa 1500
ctgtttggta tcgaaaaact gaatgttccg cgtagccaga ttccggcagt tacccatgtt 1560
gattatagcg cacgtattca gaccgttcat aaagaaacca atccgcgtta ttatgaactg 1620
atccgtcatt ttgaagcacg taccggttgt gcagttctgg ttaataccag ctttaatgtt 1680
cgtggtgaac cgattgtgtg tacaccggaa gatgcatatc gttgttttat gcgtaccgag 1740
atggattacc tggtgatgga aaattttctg ctggtgaaaa gcgaacagcc tcgtggtaat 1800
agtgatgaaa gctggcagaa agaatttgag ctggattga 1839

<210> SEQ ID NO 28
<211> LENGTH: 147
<212> TYPE: PRT
<213> ORGANISM: Cylindrospermopsis raciborskii T3

<400> SEQUENCE: 28

Met Ser Glu Phe Phe Pro Gln Lys Ser Gly Lys Leu Lys Met Glu Gln
1 5 10 15

Ile Lys Glu Leu Asp Lys Lys Gly Leu Arg Glu Phe Gly Leu Ile Gly
20 25 30

-continued

Gly Ser Ile Val Ala Val Leu Phe Gly Phe Leu Leu Pro Val Ile Arg
35 40 45

His His Ser Leu Ser Val Ile Pro Trp Val Val Ala Gly Phe Leu Trp
50 55 60

Ile Trp Ala Ile Ile Ala Pro Thr Thr Leu Ser Phe Ile Tyr Gln Ile
65 70 75 80

Trp Met Arg Ile Gly Leu Val Leu Gly Trp Ile Gln Thr Arg Ile Ile
85 90 95

Leu Gly Val Leu Phe Tyr Ile Met Ile Thr Pro Ile Gly Phe Ile Arg
100 105 110

Arg Leu Leu Asn Gln Asp Pro Met Thr Arg Ile Phe Glu Pro Glu Leu
115 120 125

Pro Thr Tyr Arg Gln Leu Ser Lys Ser Arg Thr Thr Gln Ser Met Glu
130 135 140

Lys Pro Phe
145

<210> SEQ ID NO 29
<211> LENGTH: 405
<212> TYPE: DNA
<213> ORGANISM: Cylindrospermopsis raciborskii T3

<400> SEQUENCE: 29
atggaacaga taaaagaact tgacaaaaaa ggattgcgtg agtttggact gattggcggt 60
tctatagtgg cggttttatt cggcttttta ctgccagtta tacgccatca ttccttatca 120
gttatccctt gggttgttgc tggatttctc tggatttggg caataatcgc acctacgact 180
ttaagtttta tttaccaaat atggatgagg attggacttg ttttaggatg gatacaaaca 240
cgaattattt tgggagtttt attttatata atgatcacac caataggatt cataagacgg 300
ctgttgaatc aagatccaat gacgcgaatc ttcgagccag agttgccaac ttatcgccaa 360
ttgagtaagt caagaactac acaaagtatg gagaaaccat tctaa 405

<210> SEQ ID NO 30
<211> LENGTH: 405
<212> TYPE: DNA
<213> ORGANISM: Cylindrospermopsis raciborskii T3

<400> SEQUENCE: 30
atggaacaaa ttaaagaact ggataagaaa ggcctgcgtg aatttggtct gattggtggt 60
agcattgttg ccgttctgtt tggttttctg ctgccggtta ttcgtcatca tagcctgagc 120
gttattccgt gggttgttgc aggttttctg tggatttggg caattattgc accgaccacc 180
ctgagcttta tctatcagat ttggatgcgt attggtctgg tgctgggttg gattcagacc 240
cgtattattc tgggtgttct gttctatatt atgattaccc cgatcggttt tattcgtcgt 300
ctgctgaatc aggatccgat gacccgtatt tttgaaccgg aactgccgac ctatcgtcag 360
ctgagcaaaa gccgtaccac ccagagcatg gaaaaaccgt tctga 405

<210> SEQ ID NO 31
<211> LENGTH: 54
<212> TYPE: PRT
<213> ORGANISM: Cylindrospermopsis raciborskii T3

<400> SEQUENCE: 31

Met Leu Lys Asp Thr Trp Asp Phe Ile Lys Asp Ile Ala Gly Phe Ile
1 5 10 15

```
Lys Glu Gln Lys Asn Tyr Leu Leu Ile Pro Leu Ile Ile Thr Leu Val
            20                  25                  30

Ser Leu Gly Ala Leu Ile Val Phe Ala Gln Ser Ser Ala Ile Ala Pro
        35                  40                  45

Phe Ile Tyr Thr Leu Phe
    50


<210> SEQ ID NO 32
<211> LENGTH: 165
<212> TYPE: DNA
<213> ORGANISM: Cylindrospermopsis raciborskii T3

<400> SEQUENCE: 32

atgctaaaag acacttggga ttttattaaa gacattgccg gatttattaa agaacaaaaa      60

aactatttgt tgattcccct aattatcacc ctggtatcct tgggggcgct gattgtcttt     120

gctcaatctt ctgcgatcgc acctttcatt tacactcttt tttaa                     165


<210> SEQ ID NO 33
<211> LENGTH: 165
<212> TYPE: DNA
<213> ORGANISM: Cylindrospermopsis raciborskii T3

<400> SEQUENCE: 33

atgttaaaag acacctggga ttttatcaag gatatcgcag gctttatcaa agaacagaaa      60

aactatctgc tgattccgct gattattacc ctggttagcc tgggtgcact gattgttttt     120

gcacagagca gcgcaattgc accgtttatc tataccctgt tttga                     165


<210> SEQ ID NO 34
<211> LENGTH: 432
<212> TYPE: PRT
<213> ORGANISM: Cylindrospermopsis raciborskii T3

<400> SEQUENCE: 34

Met Ser Asn Phe Lys Gly Ser Val Lys Ile Ala Leu Met Gly Ile Leu
1               5                   10                  15

Ile Phe Cys Gly Leu Ile Phe Gly Val Ala Phe Val Glu Ile Gly Leu
            20                  25                  30

Arg Ile Ala Gly Ile Glu His Ile Ala Phe His Ser Ile Asp Glu His
        35                  40                  45

Arg Gly Trp Val Gly Arg Pro His Val Ser Gly Trp Tyr Arg Thr Glu
    50                  55                  60

Gly Glu Ala His Ile Gln Met Asn Ser Asp Gly Phe Arg Asp Arg Glu
65                  70                  75                  80

His Ile Lys Val Lys Pro Glu Asn Thr Phe Arg Ile Ala Leu Leu Gly
                85                  90                  95

Asp Ser Phe Val Glu Ser Met Gln Val Pro Leu Glu Gln Asn Leu Ala
            100                 105                 110

Ala Val Ile Glu Gly Glu Ile Ser Ser Cys Ile Ala Leu Ala Gly Arg
        115                 120                 125

Lys Ala Glu Val Ile Asn Phe Gly Val Thr Gly Tyr Gly Thr Asp Gln
    130                 135                 140

Glu Leu Ile Thr Leu Arg Glu Lys Val Trp Asp Tyr Ser Pro Asp Ile
145                 150                 155                 160

Val Val Leu Asp Phe Tyr Thr Gly Asn Asp Ile Val Asp Asn Ser Arg
                165                 170                 175
```

-continued

```
Ala Leu Ser Gln Lys Phe Tyr Pro Asn Glu Leu Gly Ser Leu Lys Pro
            180                 185                 190

Phe Phe Ile Leu Arg Asp Gly Asn Leu Val Val Asp Ala Ser Phe Ile
        195                 200                 205

Asn Thr Asp Asn Tyr Arg Ser Lys Leu Thr Trp Trp Gly Lys Thr Tyr
    210                 215                 220

Met Lys Ile Lys Asp His Ser Arg Ile Leu Gln Val Leu Asn Met Val
225                 230                 235                 240

Arg Asp Ala Leu Asn Asn Ser Ser Arg Gly Phe Ser Ser Gln Ala Ile
                245                 250                 255

Glu Glu Pro Leu Phe Ser Asp Gly Lys Gln Asp Thr Lys Leu Ser Gly
            260                 265                 270

Phe Phe Asp Ile Tyr Lys Pro Pro Thr Asp Pro Glu Trp Gln Gln Ala
        275                 280                 285

Trp Gln Val Thr Glu Lys Leu Ile Ser Ser Met Gln His Glu Val Thr
    290                 295                 300

Ala Lys Lys Ala Asp Phe Leu Val Val Thr Phe Gly Gly Pro Phe Gln
305                 310                 315                 320

Arg Glu Pro Leu Val Arg Gln Lys Glu Met Gln Glu Leu Gly Leu Thr
                325                 330                 335

Asp Trp Phe Tyr Pro Glu Lys Arg Ile Thr Arg Leu Gly Glu Asp Glu
            340                 345                 350

Gly Phe Ser Val Leu Asn Leu Ser Pro Asn Leu Gln Val Tyr Ser Glu
        355                 360                 365

Gln Asn Asn Ala Cys Leu Tyr Gly Phe Asp Asp Thr Gln Gly Cys Val
    370                 375                 380

Gly His Trp Asn Ala Leu Gly His Gln Val Ala Gly Lys Met Ile Ala
385                 390                 395                 400

Ser Lys Ile Cys Gln Gln Gln Met Arg Glu Ser Ile Leu Pro His Lys
                405                 410                 415

His Asp Pro Ser Ser Gln Ser Ser Pro Ile Thr Gln Ser Val Ile Gln
            420                 425                 430
```

<210> SEQ ID NO 35
<211> LENGTH: 1299
<212> TYPE: DNA
<213> ORGANISM: Cylindrospermopsis raciborskii T3

<400> SEQUENCE: 35

```
atgagtaact tcaagggttc ggtaaagata gcattgatgg gaatattgat tttttgtggg      60

ctaatctttg gcgtagcatt tgttgaaatt gggttacgta ttgccgggat cgaacacata     120

gcattccata gcattgatga acacaggggg tgggtagggc gacctcatgt ttccgggtgg     180

tatagaaccg aaggtgaagc tcacatccaa atgaatagtg atggctttcg agatcgagaa     240

cacatcaagg tcaaaccaga aaataccttc aggatagcgc tgttgggaga ttcctttgta     300

gagtccatgc aagtaccgtt ggagcaaaat ttggcagcag ttatagaagg agaaatcagt     360

agttgtatag ctttagctgg acgaaaggcg gaagtgatta attttggagt gactggttat     420

ggaacagacc aagaactaat tactctacgg gagaaagttt gggactattc acctgatata     480

gtagtgctag atttttatac tggcaacgac attgttgata actcccgtgc gctgagtcag     540

aaattctatc ctaatgaact aggttcacta aagccgtttt ttatacttag agatggtaat     600

ctggtggttg atgcttcgtt tatcaatacg gataattatc gctcaaagct gacatggtgg     660

ggcaaaactt atatgaaaat aaaagaccac tcacggattt tacaggtttt aaacatggta     720
```

cgggatgctc ttaacaactc tagtagaggg ttttcttctc aagctataga ggaaccgtta 780
tttagtgatg gaaaacagga tacaaaattg agcgggtttt ttgatatcta caaaccacct 840
actgaccctg aatggcaaca ggcatggcaa gtcacagaga aactgattag ctcaatgcaa 900
cacgaggtga ctgcgaagaa agcagatttt ttagttgtta cttttggcgg tccctttcaa 960
cgagaacctt tagtgcgtca aaaagaaatg caagaattgg gtctgactga ttggttttac 1020
ccagagaagc gaattacacg tttgggtgag gatgaggggt tcagtgtact caatctcagc 1080
ccaaatttgc aggtttattc tgagcagaac aatgcttgcc tatatgggtt tgatgatact 1140
caaggctgtg tagggcattg gaatgcttta ggacatcagg tagcaggaaa aatgattgca 1200
tcgaagattt gtcaacagca gatgagagaa agtatattgc ctcataagca cgacccttca 1260
agccaaagct cacctattac ccaatcagtg atccaataa 1299

<210> SEQ ID NO 36
<211> LENGTH: 1299
<212> TYPE: DNA
<213> ORGANISM: Cylindrospermopsis raciborskii T3

<400> SEQUENCE: 36
atgagcaact tcaaaggcag cgttaaaatt gcactgatgg gcattctgat tttttgcggt 60
ctgatttttg gtgtggcctt tgttgaaatt ggtctgcgta ttgcaggcat tgaacatatt 120
gcctttcata gcattgatga acatcgtggt tgggttggtc gtccgcatgt tagcggttgg 180
tatcgtaccg aaggtgaagc acatattcag atgaatagtg atggttttcg tgatcgcgaa 240
cacattaaag tgaaaccgga aaataccttt cgtattgccc tgctgggtga tagctttgtt 300
gaaagcatgc aggttccgct ggaacagaat ctggcagcag ttattgaagg cgaaattagc 360
agctgtattg cactggcagg tcgtaaagcc gaagttatta actttggtgt taccggttat 420
ggcaccgatc aagaactgat taccctgcgt gaaaaagtgt gggattatag tccggatatt 480
gttgtgctgg atttctatac cggtaacgat attgttgata atagccgtgc actgtcccag 540
aaattctatc cgaatgaact gggtagcctg aaaccgtttt ttatcctgcg tgatggtaat 600
ctggttgttg atgcaagctt tatcaacacc gataactatc gtagcaaact gacctggtgg 660
ggtaaaacct atatgaaaat caaagatcat agccgcattc tgcaggtcct gaatatggtt 720
cgtgatgcac tgaataatag cagccgtggt tttagcagcc aggcaattga agaaccgctg 780
tttagtgatg gtaaacagga taccaaactg agcggcttct tcgatatcta taaaccgcct 840
accgatccgg aatggcagca ggcctggcag gttaccgaaa aactgattag tagcatgcag 900
catgaagtga ccgccaaaaa agccgatttt ctggttgtta cctttggcgg tccgtttcag 960
cgcgaaccgc tggttcgtca gaaagaaatg caagaactgg gtctgaccga ttggttttat 1020
ccggaaaaac gtattacccg tctgggtgaa gatgaaggtt ttagcgtgct gaatctgagc 1080
ccgaatctgc aggtttatag cgaacagaat aatgcctgtc tgtatggttt tgatgatacc 1140
cagggttgtg ttggtcattg gaatgcactg ggtcatcagg ttgcaggtaa aatgattgca 1200
agcaaaattt gtcagcagca gatgcgtgaa agcattctgc cgcataaaca tgatccgagc 1260
agccagagca gcccgattac ccagagcgtt attcagtaa 1299

<210> SEQ ID NO 37
<211> LENGTH: 482
<212> TYPE: PRT
<213> ORGANISM: Cylindrospermopsis raciborskii T3

<400> SEQUENCE: 37

```
Met Thr Asn Thr Glu Arg Gly Leu Ala Glu Ile Thr Ser Thr Gly Tyr
1               5                   10                  15

Lys Ser Glu Leu Arg Ser Glu Ala Arg Val Ser Leu Gln Leu Ala Ile
            20                  25                  30

Pro Leu Val Leu Val Glu Ile Cys Gly Thr Ser Ile Asn Val Val Asp
        35                  40                  45

Val Val Met Met Gly Leu Leu Gly Thr Gln Val Leu Ala Ala Gly Ala
    50                  55                  60

Leu Gly Ala Ile Ala Phe Leu Ser Val Ser Asn Thr Cys Tyr Asn Met
65                  70                  75                  80

Leu Leu Ser Gly Val Ala Lys Ala Ser Glu Ala Phe Gly Ala Asn Lys
                85                  90                  95

Ile Asp Gln Val Ser Arg Ile Ala Ser Gly Gln Ile Trp Leu Ala Leu
            100                 105                 110

Thr Leu Ser Leu Pro Ala Met Leu Leu Leu Trp Tyr Met Asp Thr Ile
        115                 120                 125

Leu Val Leu Phe Gly Gln Val Glu Ser Asn Thr Leu Ile Ala Lys Thr
    130                 135                 140

Tyr Leu His Ser Ile Val Trp Gly Phe Pro Ala Ala Val Gly Ile Leu
145                 150                 155                 160

Ile Leu Arg Gly Ile Ala Ser Ala Val Asn Val Pro Gln Leu Val Thr
                165                 170                 175

Val Thr Met Leu Val Gly Leu Val Leu Asn Ala Pro Ala Asn Tyr Val
            180                 185                 190

Leu Met Phe Gly Lys Phe Gly Leu Pro Glu Leu Gly Leu Ala Gly Ile
        195                 200                 205

Gly Trp Ala Ser Thr Leu Val Phe Trp Ile Ser Phe Leu Val Gly Val
    210                 215                 220

Val Leu Leu Ile Phe Ser Pro Lys Val Arg Asp Tyr Lys Leu Phe Arg
225                 230                 235                 240

Tyr Leu His Gln Phe Asp Arg Gln Thr Val Val Glu Ile Phe Gln Thr
                245                 250                 255

Gly Trp Pro Met Gly Phe Leu Leu Gly Val Glu Ser Val Val Leu Ser
            260                 265                 270

Leu Thr Ala Trp Leu Thr Gly Tyr Leu Gly Thr Val Thr Leu Ala Ala
        275                 280                 285

His Glu Ile Ala Ile Gln Thr Ala Glu Leu Ala Ile Val Ile Pro Leu
    290                 295                 300

Gly Ile Gly Asn Val Ala Val Thr Arg Val Gly Gln Thr Ile Gly Glu
305                 310                 315                 320

Lys Asn Pro Leu Gly Ala Arg Arg Ala Ala Leu Ile Gly Ile Met Ile
                325                 330                 335

Gly Gly Ile Tyr Ala Ser Leu Val Ala Val Ile Phe Trp Leu Phe Pro
            340                 345                 350

Tyr Gln Ile Ala Gly Leu Tyr Leu Lys Ile Asn Asp Pro Glu Ser Met
        355                 360                 365

Glu Ala Val Lys Thr Ala Thr Asn Phe Leu Phe Leu Ala Gly Leu Phe
    370                 375                 380

Gln Phe Phe His Ser Val Gln Ile Ile Val Val Gly Val Leu Ile Gly
385                 390                 395                 400

Leu Gln Asp Thr Phe Ile Pro Leu Leu Met Asn Leu Val Gly Trp Gly
                405                 410                 415
```

```
Leu Gly Leu Ala Val Ser Tyr Tyr Met Gly Ile Ile Leu Cys Trp Gly
            420                 425                 430

Gly Met Gly Ile Trp Leu Gly Leu Val Leu Ser Pro Leu Leu Ser Gly
        435                 440                 445

Leu Ile Leu Met Val Arg Phe Tyr Gln Glu Ile Ala Asn Arg Ile Ala
    450                 455                 460

Asn Ser Asp Asp Gly Gln Glu Ser Ile Ser Ile Asp Asn Val Glu Glu
465                 470                 475                 480

Leu Ser


<210> SEQ ID NO 38
<211> LENGTH: 1449
<212> TYPE: DNA
<213> ORGANISM: Cylindrospermopsis raciborskii T3

<400> SEQUENCE: 38

atgacaaata ccgaaagagg attagcagaa ataacatcaa caggatataa gtcagagctt     60

agatcggagg cacgagttag cctccaactg gcaattccct tagtccttgt cgaaatatgc    120

ggaacgagta ttaatgtggt ggatgtagtc atgatgggct tacttggtac tcaagttttg    180

gctgctggtg ccttgggtgc gatcgctttt ttatctgtat cgaatacttg ttataatatg    240

cttttgtcgg gggtagcaaa ggcatctgag gcttttgggg caaacaaaat agatcaggtt    300

agtcgtattg cttctgggca aatatggctg gcactcacct tgtctttgcc tgcaatgctt    360

ttgctttggt atatggatac tatattggtg ctatttggtc aagttgaaag caacacatta    420

attgcaaaaa cgtatttaca ctcaattgtg tggggatttc cggcggcagt tggtattttg    480

atattaagag gcattgcctc tgctgtgaac gtcccccaat tggtaactgt gacgatgcta    540

gtagggctgg tcttgaatgc cccggccaat tatgtattaa tgttcggtaa atttggtctt    600

cctgaacttg gtttagctgg aataggctgg gcaagtactt tggttttttg gattagtttt    660

ctagtggggg ttgtcttgct gattttctcc ccaaaagtta gagattataa acttttccgc    720

tacttgcatc agtttgatcg acagacggtt gtggaaattt ttcaaactgg atggcctatg    780

ggttttctac tgggagtgga atcagtagta ttgagcctca ccgcttggtt aacaggctat    840

ttgggaacag taacattagc agctcatgag atcgcgatcc aaacagcaga actggcgata    900

gtgataccac tcggaatcgg gaatgttgcc gtcacgagag taggtcagac tataggagaa    960

aaaaaccctt tgggtgctag aagggcagca ttgattggga ttatgattgg tggcatttat   1020

gccagtcttg tggcagtcat tttctggttg tttccatatc agattgcggg actttattta   1080

aaaataaacg atccagagag tatggaagca gttaagacag caactaattt tctcttcttg   1140

gcgggattat tccaattttt tcatagcgtt caaataattg ttgttggggt tttaataggg   1200

ttgcaggata cgtttatccc attgttaatg aatttggtag gctggggtct tggcttggca   1260

gtaagctatt acatgggaat cattttatgt tggggaggta tgggtatctg gttaggtctg   1320

gttttgagtc cactcctgtc cggacttatt ttaatggttc gtttttatca agagattgcc   1380

aataggattg ccaatagtga tgatgggcaa gagagtatat ctattgacaa cgttgaagaa   1440

ctctcctga                                                           1449


<210> SEQ ID NO 39
<211> LENGTH: 1449
<212> TYPE: DNA
<213> ORGANISM: Cylindrospermopsis raciborskii T3
```

-continued

<400> SEQUENCE: 39
atgaccaata ccgaacgtgg tctggccgaa attaccagca ccggttataa aagcgaactg 60
cgtagcgaag cccgtgttag cctgcagctg gcaattcctc tggttctggt tgaaatttgt 120
ggcaccagca ttaatgttgt tgatgttgtg atgatgggtt tactgggtac acaagtgtta 180
gcagcgggtg ccctgggagc aattgccttc ctgagcgtta gcaatacctg ctataatatg 240
ctgctgagtg gtgttgcaaa agcaagcgaa gcctttggag ccaataaaat cgatcaggtt 300
tcacgtattg cctcaggcca gatttggtta gccctgaccc tgtcattacc agccatgctg 360
ttactgtggt atatggatac catcctggtt ctgtttggtc aggttgaaag caataccctg 420
attgcgaaaa catacctgca ttcaattgtg tggggctttc ctgccgcagt tggtatcctg 480
attctgcgtg gcatagcaag tgcagttaac gttcctcagc tggttaccgt gaccatgctg 540
gttggcctgg tgctgaatgc accggctaat tatgtgctga tgttcggcaa attcggttta 600
ccggaattag gcctggctgg cattggctgg gccagcacac tggtgttttg gattagtttt 660
ctggttggtg ttgtgctgct gatattttca ccgaaagttc gcgactacaa actgttccgc 720
tatttacatc agtttgatcg tcagaccgtg gttgagattt ttcagacggg ctggcctatg 780
ggcttcctgc tgggtgtgga aagcgttgtt ctgagcctga ccgcatggct gaccggctat 840
ctgggtacag tgaccttagc agcccatgaa attgcaatcc agactgccga actggcgatt 900
gtgattccgt taggtattgg caatgttgcc gttacccgtg tgggccagac aatcggcgaa 960
aaaaacccgc tgggagcacg ccgtgcagcc ctgattggca ttatgattgg tggcatttat 1020
gcgagcctgg ttgcagtgat tttttggtta ttcccttatc aaatcgcagg cctgtacctg 1080
aaaattaacg atccggaatc aatggaagca gttaaaaccg caacaaactt tctgttttta 1140
gctggcctgt tccagttttt tcatagcgtg cagattattg ttgtgggtgt tctgattggc 1200
ctgcaggata cctttatccc tctgctgatg aatctggtgg gctggggact gggcctggcg 1260
gtttcctatt atatgggtat tatcctgtgc tggggtggca tgggcatctg gttaggtctg 1320
gtactgtcac cgctgctgtc aggcctgatc ctgatggtgc gcttttatca agaaattgcc 1380
aatcgcattg cgaatagcga cgatggccaa gaaagcatta gcattgataa tgttgaagaa 1440
ctgagctaa 1449

<210> SEQ ID NO 40
<211> LENGTH: 276
<212> TYPE: PRT
<213> ORGANISM: Cylindrospermopsis raciborskii T3

<400> SEQUENCE: 40

Met Lys Thr Asn Lys His Ile Ala Met Trp Ala Cys Pro Arg Ser Arg
1 5 10 15

Ser Thr Val Ile Thr Arg Ala Phe Glu Asn Leu Asp Gly Cys Val Val
20 25 30

Tyr Asp Glu Pro Leu Glu Ala Pro Asn Val Leu Met Thr Thr Tyr Thr
35 40 45

Met Ser Asn Ser Arg Thr Leu Ala Glu Glu Asp Leu Lys Gln Leu Ile
50 55 60

Leu Gln Asn Asn Val Glu Thr Asp Leu Lys Lys Val Ile Glu Gln Leu
65 70 75 80

Thr Gly Asp Leu Pro Asp Gly Lys Leu Phe Ser Phe Gln Lys Met Ile
85 90 95

Thr Gly Asp Tyr Arg Ser Glu Phe Gly Ile Asp Trp Ala Lys Lys Leu

```
            100                 105                 110

Thr Asn Phe Phe Leu Ile Arg His Pro Gln Asp Ile Ile Phe Ser Phe
        115                 120                 125

Asp Ile Ala Glu Arg Lys Thr Gly Ile Thr Glu Pro Phe Thr Gln Gln
    130                 135                 140

Asn Leu Gly Met Lys Thr Leu Tyr Glu Val Phe Gln Gln Ile Glu Val
145                 150                 155                 160

Ile Thr Gly Gln Thr Pro Leu Val Ile His Ser Asp Asp Ile Ile Lys
                165                 170                 175

Asn Pro Pro Ser Ala Leu Lys Trp Leu Cys Lys Asn Leu Gly Leu Ala
            180                 185                 190

Phe Asp Glu Lys Met Leu Thr Trp Lys Ala Asn Leu Glu Asp Ser Asn
        195                 200                 205

Leu Lys Tyr Thr Lys Leu Tyr Ala Asn Ser Ala Ser Gly Ser Ser Glu
    210                 215                 220

Pro Trp Phe Glu Thr Leu Arg Ser Thr Lys Thr Phe Leu Ala Tyr Glu
225                 230                 235                 240

Lys Lys Glu Lys Lys Leu Pro Ala Arg Leu Ile Pro Leu Leu Asp Glu
                245                 250                 255

Ser Ile Pro Tyr Tyr Glu Lys Leu Leu Gln His Cys His Ile Phe Glu
            260                 265                 270

Trp Ser Glu His
        275


<210> SEQ ID NO 41
<211> LENGTH: 831
<212> TYPE: DNA
<213> ORGANISM: Cylindrospermopsis raciborskii T3

<400> SEQUENCE: 41

atgaaaacaa acaaacatat agctatgtgg gcttgtccta gaagtcgttc tactgtaatt      60

acccgtgctt ttgagaactt agatgggtgt gttgtttatg atgagcctct agaggctccg     120

aatgtcttga tgacaactta cacgatgagt aacagtcgta cgttagcaga agaagactta     180

aagcaattaa tactgcaaaa taatgtagaa acagacctca agaaagttat agaacaattg     240

actggagatt taccggacgg aaaattattc tcatttcaaa aaatgataac aggtgactat     300

agatctgaat ttggaataga ttgggcaaaa aagctaacta acttcttttt aataaggcat     360

ccccaagata ttattttttc tttcgatata gcggagagaa agacaggtat cacagaacca     420

ttcacacaac aaaatcttgg catgaaaaca ctttatgaag ttttccaaca aattgaagtt     480

attacagggc aaacaccttt agttattcac tcagatgata taattaaaaa ccctccttct     540

gctttgaaat ggctgtgtaa aaacttaggg cttgcatttg atgaaaagat gctgacatgg     600

aaagcaaatc tagaagactc caatttaaag tatacaaaat tatatgctaa ttctgcgtct     660

ggcagttcag aaccttggtt tgaaacttta agatcgacca aaacatttct cgcctatgaa     720

aagaaggaga aaaaattacc agctcggtta atacctctac tagatgaatc tattccttac     780

tatgaaaaac tcttacagca ttgtcatatt tttgaatggt cagaacactg a              831


<210> SEQ ID NO 42
<211> LENGTH: 257
<212> TYPE: PRT
<213> ORGANISM: Cylindrospermopsis raciborskii T3

<400> SEQUENCE: 42
```

```
Met Ser Phe Gln Lys Phe Val Gln Glu Ala Ala Tyr Lys Val Ala Pro
1               5                   10                  15

Phe Lys Pro Asn Arg Phe Ala Lys Ile Ser Glu Arg Glu Asp Lys Cys
            20                  25                  30

Ala Ile Pro Val Pro Ala Trp Arg Ala Leu Leu Ala Asn Arg Asp Leu
        35                  40                  45

Phe Thr Trp Lys Gly Ile Pro Phe Leu Lys Gly Cys Thr Glu Ile Ala
    50                  55                  60

Leu Tyr Ser Met Leu Leu Tyr Glu Leu Arg Pro Lys Thr Ile Ile Glu
65                  70                  75                  80

Ile Gly Ala Leu Ser Gly Gly Ser Ala Ile Trp Leu Ala Asp His Leu
                85                  90                  95

Glu Leu Phe Gln Ile Glu Gly Cys Val Tyr Cys Ile Asp Ile Asp Leu
            100                 105                 110

Ser Leu Leu Asp Glu Lys Ala Lys Thr Asp Ser Arg Val His Phe Leu
        115                 120                 125

Glu Gly Asp Cys Asn Asn Met Gly Ala Ile Met Ser Ser Glu Leu Leu
    130                 135                 140

Ser Gly Leu Ala His Pro Trp Leu Ile Val Glu Asp Ala His Ala Asn
145                 150                 155                 160

Ala Val Gly Val Val Glu Tyr Phe His Glu Asn Gly Leu Lys Ser Gly
                165                 170                 175

Asp Tyr Leu Ile Val Glu Asp Thr Asn Lys Thr Met Trp Glu Leu Asp
            180                 185                 190

Arg Glu Glu Leu Asp Arg Asp Asp Leu Asp Glu Gln Glu Leu Ile Glu
        195                 200                 205

Lys Gly Glu Gln Lys Leu Ala Glu Leu Lys Ser Trp Leu Met Leu His
    210                 215                 220

Glu Asn Glu Tyr Leu Ile Asp Thr Tyr Tyr Gln Asp Met Tyr Gly Tyr
225                 230                 235                 240

Asn Gly Ser Arg Asn Trp Asn Ser Ile Leu Lys Arg Val Glu Lys Asn
                245                 250                 255

Phe
```

<210> SEQ ID NO 43
<211> LENGTH: 774
<212> TYPE: DNA
<213> ORGANISM: Cylindrospermopsis raciborskii T3

<400> SEQUENCE: 43

```
atgagcttcc aaaaatttgt tcaagaagcc gcctataaag ttgcaccttt caaacctaat      60

cggtttgcca aaatttctga aagagaagat aaatgtgcta ttccagtgcc agcttggaga     120

gcgctcttgg caaaccgcga tttgttcact tggaaaggga tacccttcct gaaagggtgc     180

accgaaatag ctctttattc aatgctcctg tatgagcttc gcccgaaaac aataatcgaa     240

ataggagcat taagcggtgg cagcgcgatt tggctagccg atcacttaga actgttccaa     300

atagaaggtt gtgtctactg tatcgatatc gatctttccc tactcgacga gaaagcaaaa     360

actgactctc gcgttcattt tttagagggg gattgtaaca atatgggtgc aataatgtcg     420

tcggaactgc tttctgggct tgctcatccc tggttgatcg tagaagatgc ccatgctaat     480

gcggtgggag tagttgaata ttttcacgaa aacggtctaa aaagtggaga ctacttgatt     540

gtcgaagata ccaacaaaac tatgtgggag ttggacaggg aggagttgga cagggatgat     600

ttggatgagc aagaattaat agaaaaagga gagcagaaat tagcggagtt aaaaagctgg     660
```

ttaatgctcc acgaaaatga gtacctcatc gatacgtact atcaagatat gtacggttac 720
aacggctcta gaaactggaa ttctatcctg aaaagagtag aaaaaaattt ttag 774

<210> SEQ ID NO 44
<211> LENGTH: 774
<212> TYPE: DNA
<213> ORGANISM: Cylindrospermopsis raciborskii T3

<400> SEQUENCE: 44
atgtcatttc agaaatttgt gcaagaagca gcctataaag tcgcaccgtt taaaccgaat 60
cgttttgcca aaattagcga gcgtgaagat aaatgtgcaa ttccggttcc ggcatggcgt 120
gcactgctgg ccaatcgtga cctgtttacc tggaaaggta ttccgtttct gaaaggttgt 180
accgaaattg cactgtatag catgctgctg tatgaactgc gtccgaaaac gattattgaa 240
attggtgcgc tgagcggtgg tagcgcaatt tggctggcag atcatctgga actgtttcag 300
attgaaggtt gcgtgtattg cattgatatt gatctgtctc tgctggacga aaaagcaaaa 360
accgatagcc gtgttcattt tctggaaggt gattgcaata atatgggtgc aattatgtca 420
agcgagctgc tgagtggtct ggcacatcct tggctgattg ttgaagatgc acatgcaaat 480
gccgttggtg tggttgaata ttttcacgaa aacggtctga aagtggcga ttacctgatc 540 gtggaagata ccaataaaac aatgtgggaa ctggatcgcg aagaactgga ccgtgatgac 600
ctggatgaac aagaactgat cgaaaaaggt gagcagaaat tagcagaact gaaaagctgg 660
ctgatgctgc atgagaatga atatctgata gatacctact atcaggatat gtatggctat 720
aatggtagcc gtaattggaa cagcattctg aaacgtgtgg aaaagaactt ttaa 774

<210> SEQ ID NO 45
<211> LENGTH: 108
<212> TYPE: PRT
<213> ORGANISM: Cylindrospermopsis raciborskii T3

<400> SEQUENCE: 45

Met Ile Glu Leu Val Ser His Lys Leu Cys Ile Asn Cys Asn Val Cys
1 5 10 15

Val Gln Val Cys Pro Thr Asn Val Phe Asp Ala Val Pro Asn Gln Pro
20 25 30

Pro Ala Ile Ala Arg Gln Glu Asp Cys Gln Thr Cys Phe Ile Cys Glu
35 40 45

Ala Tyr Cys Pro Ala Asp Ala Leu Tyr Val Ala Pro Gln Ser His Thr
50 55 60

Asn Val Ala Val Asn Glu Asp Asp Leu Ile Asp Ser Gly Ile Met Gly
65 70 75 80

Glu Tyr Arg Arg Ile Leu Gly Trp Gly Tyr Gly Arg Lys Asn Asn Ser
85 90 95

Glu Leu Asp Thr Asp His Lys Leu Arg Leu Phe Glu
100 105

<210> SEQ ID NO 46
<211> LENGTH: 327
<212> TYPE: DNA
<213> ORGANISM: Cylindrospermopsis raciborskii T3

<400> SEQUENCE: 46
atgatcgagc ttgtcagcca taaactctgt attaattgta atgtttgcgt ccaagtatgc 60
cctaccaatg tctttgatgc agttcccaac caaccgcctg cgatcgcccg acaggaagac 120

-continued

```
tgtcaaactt gtttcatctg tgaagcatat tgtcctgcgg atgcgctcta tgttgcgccg    180

caatctcata ccaatgttgc agtcaacgag gatgatttaa ttgacagtgg cattatgggt    240

gaatatcgtc gcatcttagg ttggggatat ggcagaaaaa acaatagcga attggatacc    300

gatcataaac tacggctatt tgaataa                                        327
```

<210> SEQ ID NO 47
<211> LENGTH: 327
<212> TYPE: DNA
<213> ORGANISM: Cylindrospermopsis raciborskii T3

<400> SEQUENCE: 47

```
atgattgaac tggtgagcca taagctgtgc attaattgta atgtttgtgt tcaggtgtgc     60

ccgaccaatg tttttgatgc agtgccgaat cagcctccgg caattgcacg ccaagaagat    120

tgtcagacct gttttatttg tgaagcatat tgtcctgcag atgcgctgta tgttgcaccg    180

cagagccata ccaatgttgc agttaacgaa gatgatttaa tcgacagcgg cattatgggt    240

gaatatcgtc gcattctggg ttggggctat ggtcgtaaaa acaatagcga actggatacc    300

gaccataaac tgcgtctgtt tgaatga                                        327
```

<210> SEQ ID NO 48
<211> LENGTH: 550
<212> TYPE: PRT
<213> ORGANISM: Cylindrospermopsis raciborskii T3

<400> SEQUENCE: 48

```
Met Asn Leu Thr Leu Asn Lys Glu Glu Lys Gln Leu Leu Thr Ala Tyr
1               5                   10                  15

Ser Gly Thr Glu Leu Gln Leu Thr Ala Asp Val Leu Val Ile Gly Gly
            20                  25                  30

Gly Pro Ala Ala Ala Trp Ala Ala Trp Ala Ala Gly Ala Gln Gly Val
        35                  40                  45

Lys Val Ile Ile Val Asp Lys Gly Phe Leu Gly Thr Ser Gly Ala Ala
    50                  55                  60

Ala Ala Ser Gly Asn Ser Val Met Ala Pro Ser Pro Glu Asn Trp Glu
65                  70                  75                  80

Lys Asp Val Ser Glu Cys Tyr Ser Lys Gly Asn Asn Leu Ala Asn Leu
                85                  90                  95

Arg Trp Ile Glu Arg Val Ile Glu Lys Ala Trp Leu Ser Leu Pro Leu
            100                 105                 110

Val Glu Asp Trp Gly Tyr Arg Phe Pro Lys Glu Asn Gly Glu Ser Val
        115                 120                 125

Arg Gln Ser Tyr Tyr Gly Pro Glu Tyr Met Arg Val Leu Arg Lys Asn
    130                 135                 140

Leu Leu Arg Val Gly Val Gln Ile Phe Asp Gln Ser Pro Ala Leu Glu
145                 150                 155                 160

Leu Leu Leu Ala Gln Asp Gly Ser Val Ala Gly Ala Arg Gly Val Gln
                165                 170                 175

Arg Gln Asn His Arg Thr Tyr Thr Val Arg Ala Gly Ala Val Val Leu
            180                 185                 190

Ala Asn Gly Gly Cys Ala Phe Leu Ser Lys Ala Leu Gly Cys Asn Thr
        195                 200                 205

Asn Thr Gly Asp Gly Leu Leu Met Ala Val Glu Ala Gly Gly Glu Leu
    210                 215                 220
```

-continued

```
Ser Ser Met Glu Ala Ser Ser His Tyr Thr Ile Ser Thr Ala Phe Asn
225                 230                 235                 240

Ala Thr Val Thr Arg Ala Ala Pro Phe Tyr Trp Ala Ser Tyr Thr Asp
                245                 250                 255

Glu Ala Gly Asn Asp Leu Gly Gly Tyr Ile Asn Gly Arg Arg Asp Pro
            260                 265                 270

Ser Phe Leu Pro Asn Ala Leu Leu Lys Gly Pro Val Tyr Ala Arg Leu
        275                 280                 285

Asp Arg Ala Thr Pro Glu Ile Gln Ala Leu Val Glu Lys Ser His Phe
    290                 295                 300

Ile Ala Phe Leu Pro Tyr Lys Lys Ala Gly Ile Asp Pro Tyr Thr Glu
305                 310                 315                 320

Arg Val Pro Val Thr Leu Val Leu Glu Gly Thr Val Arg Gly Thr Gly
                325                 330                 335

Gly Ile Arg Ile Val Asn Asp Ser Cys Gly Thr Lys Val Pro Gly Leu
            340                 345                 350

Tyr Ala Ala Gly Asp Ala Ala Ser Arg Glu Phe Leu Ala Gly Ile Ala
        355                 360                 365

Ser Gly Gly Asp Gly Pro Asn Ala Ala Trp Ala Ile Ser Thr Gly Gln
    370                 375                 380

Trp Ala Gly Glu Gly Ala Ala Ala Phe Ala Lys Ser Leu Gly Ala His
385                 390                 395                 400

Val His Glu Arg Val Val Arg Pro Ala Gly Gln Ala Gly Leu Arg Ser
                405                 410                 415

Gln Tyr Pro Gly Ser Glu Thr Phe Asp Ser Glu Ala Val Val Arg Gly
            420                 425                 430

Val Gln Ala Glu Met Phe Pro Leu Glu Lys Asn Tyr Leu Arg Cys Glu
        435                 440                 445

Gln Gly Leu Leu Asp Ser Leu Ala Lys Leu Glu Met Leu Trp Gln Gln
    450                 455                 460

Val Gln Gly Asn Pro Lys Gln Asp Thr Val Arg Asp Leu Glu Phe Ser
465                 470                 475                 480

Arg Arg Ala Ala Ala Leu Val Ser Val Ala Arg Trp Ala Tyr Phe Ser
                485                 490                 495

Ala Leu His Arg Lys Glu Thr Arg Ser Glu His Ile Arg Ile Asp Tyr
            500                 505                 510

Pro Glu Thr Asp Pro Asn Gln Leu Tyr Tyr Gln Ala Thr Gly Gly Leu
        515                 520                 525

Glu Arg Leu Trp Val Arg Arg Asp Trp Val Lys Asp Ala Ser Ala Thr
    530                 535                 540

Pro Pro Val Leu Thr Thr
545                 550
```

<210> SEQ ID NO 49
<211> LENGTH: 1653
<212> TYPE: DNA
<213> ORGANISM: Cylindrospermopsis raciborskii T3

<400> SEQUENCE: 49

```
atgaacttga ctttaaacaa ggaggaaaag caattgctta cagcctatag cggcactgaa      60

ctacaattaa ctgctgacgt gctggtaatt ggtggtggtc ctgccgccgc atgggcagca     120

tgggcggctg gagcccaagg tgtcaaagtc atcattgttg ataaaggttt tctaggtacg     180

agcggtgcag ctgctgccag tggcaatagc gtcatggcac cttctccaga gaattgggag     240
```

```
aaagatgtat ccgaatgtta cagcaaagga aataacctcg ctaacttacg ttggattgaa    300
cgtgtaattg aaaaagcttg gctgagtttg cccttagtgg aagattgggg ctatcgtttc    360
cccaaagaaa atggggaatc cgtgcgccag agttattatg gtccggaata tatgcgggta    420
cttcgcaaga acctgttgcg tgtgggtgtg caaattttcg accaaagtcc ggctctagaa    480
ctgttattag cccaggacgg ctccgtggct ggagctagag gtgtacagag gcaaaatcat    540
cgcacctata ccgttcgcgc tggtgcagta gttctagcga atggcggttg tgcattccta    600
agtaaagctt taggttgcaa taccaataca ggcgatggac tgctgatggc ggtggaagct    660
ggcggcgaac tctccagtat ggaagcttcc agtcactata ccatctcgac cgctttcaat    720
gccacagtga caagggctgc tcccttttac tgggctagtt acaccgatga ggcaggtaac    780
gatcttggtg gctatatcaa tggtcgtcgc gatccatcgt tcctgcccaa tgccctcctg    840
aaaggtcccg tttatgctcg tttggatcga gccacacctg aaatccaagc attggttgaa    900
aagtctcact tcatcgcctt tctaccctat aaaaaagctg gcattgaccc ttatacagaa    960
cgagtacctg taacactggt tttagaaggt acagtccgtg gtacaggtgg aattcggatt   1020
gtgaatgata gttgtggtac aaaagttcct ggactgtatg ccgccggaga tgcagcatcg   1080
cgggagtttt tagctgggat agcttctggg ggtgatggtc ctaatgctgc ttgggcaatc   1140
tctacaggac aatgggcagg ggaaggtgca gccgcctttg ccaagagttt gggcgctcat   1200
gtccatgaac gggttgtgcg tccagcaggt caagccggat tacgttccca gtaccctggt   1260
tccgaaacat tcgatagcga ggcagttgtc cgcggtgtac aagccgagat gttcccatta   1320
gagaagaatt acttgcgctg tgagcaggga cttttggatt ccctcgccaa attagaaatg   1380
ctgtggcagc aagtacaagg gaacccgaaa caagatacag tgcgcgatct ggaattttct   1440
cgtcgagcgg ctgctcttgt gtctgtagca cgatgggcat attttagcgc tttacatcgc   1500
aaggaaacgc gtagcgaaca tattcgcata gactatcctg aaaccgatcc aaatcagctt   1560
tattaccaag ccacgggcgg cttagaaagg ctttgggtga gacgggattg ggtgaaggat   1620
gcgagcgcta caccaccagt attaaccact taa                                1653
```

<210> SEQ ID NO 50
<211> LENGTH: 1653
<212> TYPE: DNA
<213> ORGANISM: Cylindrospermopsis raciborskii T3

<400> SEQUENCE: 50

```
atgaacctga ccctgaacaa agaagaaaaa cagctgctga cggcatatag cggcaccgaa     60
ctgcagctga cagcagatgt tctggttatt ggtggtggtc cggcagccgc atgggcagct    120
tgggcagcag gcgcacaggg tgtgaaagtt attattgtgg ataaaggttt tctgggcacc    180
agcggtgccg cagccgcaag cggtaatagc gttatggcac cgtcaccgga aaattgggaa    240
aaagatgtga gcgaatgtta cagcaaaggt aataatctgg caaatctgcg ttggattgaa    300
cgtgttattg aaaaagcctg gctgtcactg ccgctggttg aagattgggg ttatcgtttt    360
cctaaagaaa atggtgaaag cgtgcgtcag agctattatg gtcctgaata tatgcgtgtt    420
ctgcggaaaa atctgctgcg cgttggtgtt cagatctttg atcagtcacc ggcactggaa    480
ttactgctgg cacaggatgg tagcgttgcc ggtgcacgtg gtgtgcagcg tcagaatcat    540
cgtacatata ccgttcgtgc cggtgccgtt gttctggcca atggtggttg cgcatttctg    600
agtaaagcac tgggttgtaa taccaatacc ggtgatggtc tgttaatggc agttgaagcc    660
ggtggtgaac tgagcagtat ggaagccagc agccattata ccattagcac cgcctttaat    720
```

```
gcaaccgtta cccgtgcagc tccgttttat tgggcaagct ataccgatga agctggcaat    780

gatctgggtg gctatattaa cggtcgtcgt gatccgagct ttctgccgaa cgcactgctg    840

aaaggtccgg tttatgcacg tctggatcgt gcaacaccgg aaattcaggc gctggtagaa    900

aaaagccatt ttattgcatt tctgccgtac aagaaagccg gtattgatcc gtataccgaa    960

cgtgttccgg ttaccctggt gctggaaggc accgtgcgtg gcaccggtgg tattcgcatt   1020

gttaatgatt catgtggcac caaagttccg ggactgtatg cagcgggtga tgcagcaagc   1080

cgtgaatttc tggcaggcat tgccagcggt ggtgatggac cgaatgcagc atgggcaatt   1140

tcaaccggtc agtgggcagg cgaaggtgca gcagcctttg caaaaagtct gggtgcacat   1200

gttcatgaac gcgttgttcg tccggcaggc caggcaggtc tgcgtagtca gtatccgggt   1260

agcgaaacct ttgatagtga agcagttgtt cgtggcgttc aggcagaaat gtttccgctg   1320

gaaaaaaact atctgcgctg tgaacaggga ctgctggata gcctggcaaa actggaaatg   1380

ctgtggcagc aggttcaggg taatccgaaa caggatacag ttcgtgatct ggaattttca   1440

cgtcgtgcgg cagcactggt tagcgtggca cgttgggcat attttagcgc actgcatcgt   1500

aaagaaaccc gtagcgaaca tatccgtatt gattacccgg aaacggatcc gaatcaactg   1560

tattatcagg caaccggtgg cctggaacgt ctgtgggtgc gtcgtgattg ggttaaagat   1620

gcaagcgcca cccctccggt gctgaccacc tga                                1653
```

<210> SEQ ID NO 51
<211> LENGTH: 249
<212> TYPE: PRT
<213> ORGANISM: Cylindrospermopsis raciborskii T3

<400> SEQUENCE: 51

```
Met Ala Gly Lys Leu Asp Gly Lys Val Ala Ile Ile Thr Gly Ala Ser
1               5                   10                  15

Ser Gly Ile Gly Glu Ala Thr Ala Phe Ala Leu Ala Ala Glu Gly Ala
            20                  25                  30

Lys Val Ala Ile Ala Ala Arg Arg Ala Glu Leu Leu His Ala Leu Ala
        35                  40                  45

Lys Arg Ile Glu Ala Ser Gly Gly Gln Ala Leu Pro Ile Val Thr Asp
    50                  55                  60

Ile Thr Asp Glu Ser Gln Val Asn His Leu Val Gln Lys Thr Lys Val
65                  70                  75                  80

Glu Leu Gly His Val Asp Ile Leu Val Asn Asn Ala Gly Ile Gly Val
                85                  90                  95

Phe Gly Ala Ile Asp Thr Gly Asn Pro Ala Asp Trp Arg Arg Ala Phe
            100                 105                 110

Asp Val Asn Val Leu Gly Val Leu Tyr Ala Ile His Ala Val Leu Pro
        115                 120                 125

Leu Leu Lys Ala Gln Lys Ser Gly His Ile Val Asn Ile Ser Ser Val
    130                 135                 140

Asp Gly Arg Ile Ala Gln Ser Gly Ala Val Val Tyr Ser Ala Ala Lys
145                 150                 155                 160

Ser Gly Val Asn Ala Leu Ser Glu Ala Leu Arg Gln Glu Val Ser Leu
                165                 170                 175

Asp Asn Ile Arg Val Thr Ile Ile Glu Pro Gly Leu Val Asp Thr Pro
            180                 185                 190

Phe Asn Asp Leu Ile Ser Asp Pro Ile Thr Lys Gln Leu Ser Lys Glu
        195                 200                 205
```

Gln Leu Ser Thr Ile Thr Pro Leu Gln Ser Glu Asp Ile Ala Arg Ala
    210                 215                 220

Ile Ile Tyr Ala Val Thr Gln Pro Asp His Val Asn Val Asn Glu Ile
225                 230                 235                 240

Leu Ile Arg Pro Thr Ala Glu Asp Asn
                245

<210> SEQ ID NO 52
<211> LENGTH: 750
<212> TYPE: DNA
<213> ORGANISM: Cylindrospermopsis raciborskii T3

<400> SEQUENCE: 52
atggcaggta aattggatgg aaaagtggcg attattactg gagcttcctc tgggattgga 60
gaggctacag catttgcttt agctgcggag gggcaaaag ttgcgatcgc cgcaagacgt 120
gctgagcttt tgcatgcact agcaaaacgg attgaagcca gtggtggtca agcattgcct 180
attgttacag atattacaga cgaatctcaa gtaaatcatc tagtccaaaa gaccaaggtt 240
gagctaggac atgtagatat tttggtgaat aatgcaggaa ttggtgtgtt tggtgcaatt 300
gatactggaa atcccgcaga ctggaggcga gcattcgatg tgaatgttct gggagtttta 360
tatgctatcc acgcagtttt gcctcttctg aaggcccaaa aatccggtca tatagtcaat 420
atatcttctg tcgatggcag gatagcgcag tccggtgcgg tcgtttatag tgctgccaaa 480
tcaggcgtca atgctctttc agaagcatta cgccaggagg tatctttaga caacattcgc 540
gttaccatca ttgagccagg tttagtcgat acgccattta atgacttaat ttctgacccg 600
atcacgaaac agcttagtaa agaacaactt agtacaataa cacctttaca aagtgaggat 660
attgcaagag ctataattta tgcagtgaca caacccgatc atgtaaatgt aaatgaaatt 720
ttgattcgac cgactgcaga agataattaa 750

<210> SEQ ID NO 53
<211> LENGTH: 750
<212> TYPE: DNA
<213> ORGANISM: Cylindrospermopsis raciborskii T3

<400> SEQUENCE: 53
atggcaggta aactggatgg taaggttgca attattaccg gtgcaagcag cggtattggt 60
gaagccaccg catttgcact ggcagcagaa ggtgcaaaag ttgcaattgc agcccgtcgt 120
gcagaactgt tacatgcact ggccaaacgt attgaagcaa gcggtggtca ggcactgccg 180
attgttaccg atatcaccga tgaaagccag gttaatcatc tggttcagaa aaccaaagtt 240
gaactgggtc atgttgatat cctggtgaat aatgcaggta ttggcgtttt tggtgcaatc 300
gataccggta atccggcaga ttggcgtcgt gcatttgatg ttaatgtgct gggtgttctg 360
tatgcaattc atgcagttct gcctttactg aaagcacaga aaagcggtca tattgtgaat 420
attagcagcg tggatggtcg tattgcacag agcggtgcag ttgtttatag cgcagcaaaa 480
agcggtgtta atgccctgag cgaagcactg cgtcaagaag tgagcctgga taatattcgt 540
gtgaccatta ttgaaccggg tctggtagat accccgttta atgatctgat tagtgatccg 600
attaccaaac agctgagcaa agaacagctg tcaaccatta ctccgctgca gagcgaagat 660
attgcacgtg ccattatcta tgcagttacc cagccggatc atgttaacgt taatgaaatt 720
ctgattcgtc cgaccgcaga ggataattga 750

<210> SEQ ID NO 54
<211> LENGTH: 334
<212> TYPE: PRT
<213> ORGANISM: Cylindrospermopsis raciborskii T3

<400> SEQUENCE: 54

```
Met Thr Thr Thr Asp Pro Ile Leu Ile Asn Asn Trp His Val Val Ala
1               5                   10                  15

Asn Val Glu Asp Cys Lys Pro Gly Ser Ile Thr Arg Ser Arg Leu Leu
            20                  25                  30

Gly Val Lys Leu Val Leu Trp Arg Ser Tyr Glu Gln Asn Ser Pro Ile
        35                  40                  45

Gln Val Trp Leu Asp Tyr Cys Pro His Arg Gly Val Pro Leu Ser Met
    50                  55                  60

Gly Glu Ile Thr Asn Asn Thr Leu Val Cys Pro Tyr His Gly Trp Arg
65                  70                  75                  80

Tyr Asn Glu Ala Gly Lys Cys Ile Gln Ile Pro Ala His Pro Gly Met
                85                  90                  95

Val Pro Pro Ala Ser Ala Glu Ala Arg Thr Tyr His Ser Gln Glu Arg
            100                 105                 110

Tyr Gly Leu Val Trp Val Cys Leu Gly Asp Pro Val Asn Asp Ile Pro
        115                 120                 125

Ser Phe Pro Glu Trp Asp Asp Pro Asn Tyr His Lys Thr Tyr Thr Lys
    130                 135                 140

Ser Tyr Leu Ile Lys Ala Ser Ala Phe Arg Val Met Asp Asn Ser Leu
145                 150                 155                 160

Asp Val Ser His Phe Pro Phe Ile His Asp Gly Trp Leu Gly Asp Arg
                165                 170                 175

Asn Tyr Thr Lys Val Glu Glu Phe Glu Val Lys Leu Asp Lys Asp Gly
            180                 185                 190

Leu Thr Met Gly Lys Tyr Gln Phe Gln Thr Ser Arg Ile Val Ser His
        195                 200                 205

Ile Glu Asp Asp Ser Trp Val Asn Trp Phe Arg Leu Ser His Pro Leu
    210                 215                 220

Cys Gln Tyr Cys Val Ser Glu Ser Pro Glu Met Arg Ile Val Asp Leu
225                 230                 235                 240

Met Thr Ile Thr Pro Ile Asp Glu Glu Asn Ser Val Leu Arg Met Leu
                245                 250                 255

Ile Met Trp Asn Gly Tyr Glu Thr Leu Glu Ser Lys Met Leu Thr Glu
            260                 265                 270

Tyr Asp Glu Thr Ile Glu Gln Asp Ile Arg Ile Leu His Ala Gln Gln
        275                 280                 285

Pro Val Arg Leu Pro Leu Leu Thr Pro Lys Gln Ile Asn Thr Gln Leu
    290                 295                 300

Phe Ser His Glu Ile His Val Pro Ser Asp Arg Cys Thr Leu Ala Tyr
305                 310                 315                 320

Arg Arg Trp Leu Lys Gln Leu Gly Val Thr Tyr Gly Val Cys
                325                 330
```

<210> SEQ ID NO 55
<211> LENGTH: 1005
<212> TYPE: DNA
<213> ORGANISM: Cylindrospermopsis raciborskii T3

<400> SEQUENCE: 55

```
atgacaacta ccgacccaat cttaatcaat aactggcacg tagtcgccaa tgtagaagac     60
```

tgtaaacctg gaagtatcac cagatctcgt ttgttgggag tgaagttggt attatggcgc 120
agttatgaac aaaattcacc catacaggta tggcttgact actgccccca ccgaggtgtt 180
cctctgtcta tgggagaaat tacgaataat actttagttt gtccgtatca cggatggaga 240
tacaatgagg ctggtaaatg catacagatc ccagctcacc ctggcatggt accaccggca 300
agtgctgaag ccaggacata tcactcccag gagcgctatg gcttagtgtg ggtgtgcttg 360
ggcgatcctg ttaatgatat accttcattt cctgaatggg atgatccgaa ttatcacaag 420
acttatacca agtcttactt gattaaagct agtgcgtttc gtgtgatgga taattcctta 480
gacgtgtctc attttccttt tatccatgac ggttggttag gtgatcgcaa ttatacaaaa 540
gtggaagaat ttgaggtgaa attagataaa gatggcctta ctatgggtaa gtatcaattc 600
cagacatcaa ggattgtcag ccatatcgaa gatgactctt gggttaattg gttcaggctt 660
agtcatcctt tatgtcaata ctgcgtttca gaatcccctg aaatgaggat tgtggattta 720
atgacgatca caccgattga tgaggaaaat agtgtattgc gtatgttgat aatgtggaac 780
gggtatgaaa cgttagagtc aaagatgcta actgaatatg acgaaacaat agaacaagat 840
attcggatct tacatgcaca acagccggta cgtttaccac tgttaactcc aaagcagata 900
aatacacaat tgttttcaca cgaaatccac gtaccatcag atagatgcac acttgcctat 960
cgtcgatggc taaagcaact aggtgttact tatggggttt gttaa 1005

<210> SEQ ID NO 56
<211> LENGTH: 1005
<212> TYPE: DNA
<213> ORGANISM: Cylindrospermopsis raciborskii T3

<400> SEQUENCE: 56
atgacaacca ccgatccgat cctgattaat aactggcatg ttgtggcaaa tgtcgaggat 60
tgtaaaccgg gtagcattac ccgtagccgt ttactgggtg ttaaactggt tctgtggcgt 120
agctatgaac agaatagccc gattcaggtt tggctggatt attgtccgca tcgtggtgtt 180
ccgctgagca tgggtgaaat taccaataat accctggttt gtccgtatca tggctggcgt 240
tataatgaag caggtaaatg tattcagatt ccggcacatc cgggtatggt tccgcctgca 300
agcgcagaag cacgtaccta tcatagccaa gaacgttatg gtctggtttg ggtttgtctg 360
ggtgatccgg ttaatgatat tccgtcattt ccggaatggg atgatccgaa ttatcacaaa 420
acctacacca aaagctatct gattaaagca agcgcctttc gcgttatgga taattcactg 480
gatgttagcc attttccgtt tattcatgat ggctggctgg gcgatcgtaa ctataccaaa 540
gtggaagaat ttgaagtgaa actggataaa gatggtctga cgatgggcaa atatcagttt 600
cagaccagcc gtattgtgag ccatattgaa gatgatagct gggtgaattg gtttcgtctg 660
agccatccgc tgtgtcagta ttgtgttagc gaaagtccgg aaatgcgtat tgttgatctg 720
atgaccatta cgccgattga tgaagaaaat agcgttctgc gcatgctgat catgtggaat 780
ggttatgaaa ccctggaaag caaaatgctg acagagtatg atgaaacgat cgaacaggat 840
attcgtattc tgcatgccca gcagccggtg cgtctgccgc tgctgacacc gaagcagatt 900
aatacccagc tgtttagcca tgaaattcat gttccgagcg atcgttgtac cctggcatat 960
cgtcgttggc tgaaacaact gggtgtgacc tatggtgttt gttga 1005

<210> SEQ ID NO 57
<211> LENGTH: 241
<212> TYPE: PRT

<213> ORGANISM: Cylindrospermopsis raciborskii T3

<400> SEQUENCE: 57

```
Met Leu Thr Ala Glu Gln Lys Gln Ala Tyr Thr Asn Asp Gly Tyr Phe
1               5                   10                  15

Thr Val Glu Glu Ala Val Pro Lys Ala Leu Ile Glu Glu Ile Arg His
            20                  25                  30

Glu Val Glu Leu Ile Thr Glu Gln Lys Arg Gly Gly Val Leu Ala Gly
        35                  40                  45

Asp Tyr Glu Trp Trp Ser Glu His Thr Ile Pro Asp Pro Val Arg Tyr
    50                  55                  60

Gln Lys Ile Ile Gln Arg Leu Leu Glu Leu Pro Thr Val Met Gly Pro
65                  70                  75                  80

Val Gln Ala Leu Ile Gly Ser Asp Ile Phe Leu Leu Ile Thr Asp Leu
                85                  90                  95

Ala Ile Ile Arg Ala Gly Thr Gly Tyr Ile Ala Trp His Gln Asp His
            100                 105                 110

Gly Tyr Val Val Glu Val Leu Asn Ala Leu Ala Ser Met Ser Lys Asn
        115                 120                 125

Glu Leu Asn Asp Asp Ala Leu Arg Leu Leu Val Pro Val Ala Asn Gln
    130                 135                 140

Ala Met Val Phe Ile Thr Ile Tyr Leu Gln Asp Thr Asp Asn Thr Met
145                 150                 155                 160

Gly Thr Met Arg Val Ile Pro Ser Ser His Gln Trp Glu His Ser Leu
                165                 170                 175

Asp Ser Ser Ser Ala Asn Ser Leu Asn Ala Glu Ile Cys Leu Ser Leu
            180                 185                 190

Pro Gly Gly Ala Ala Met Phe Tyr Thr Pro Thr Val Trp His Thr Ala
        195                 200                 205

Ala Ala Asn Thr Ser Ile Thr Asp Tyr Arg Met Leu Thr Leu Ile Phe
    210                 215                 220

Thr Lys Asn Asn Ile Lys Pro Leu Leu Val Asp Ala Leu Lys Arg Ile
225                 230                 235                 240

Ile
```

<210> SEQ ID NO 58
<211> LENGTH: 726
<212> TYPE: DNA
<213> ORGANISM: Cylindrospermopsis raciborskii T3

<400> SEQUENCE: 58

```
atgctcacag cggaacaaaa acaagcttac acaaatgatg gttatttcac agttgaagaa     60

gctgtaccaa aagcgttaat tgaagaaata cggcatgaag tagaacttat taccgaacaa    120

aaacgtgggg gagtattggc gggtgactat gagtggtggt ctgagcatac tatcccagat    180

ccagttaggt atcaaaagat aattcagagg cttttagagc ttccaactgt gatgggacca    240

gtacaggctc taattgggtc tgatatcttc ctattgatca ccgatctagc cataattcgt    300

gcaggtacag gatacattgc ttggcatcaa gaccatggat atgtagttga agtattgaac    360

gcacttgcat ccatgtcaaa aaacgagtta aatgacgacg cgcttcggtt gttggttcca    420

gtagccaatc aagccatggt attcataact atatacttac aggatacaga taatactatg    480

ggtacaatgc gagttatacc aagtagccac caatgggaac actcattaga ttcatcttct    540

gccaattcac taaatgcaga aatatgtctt tcacttccag gaggggcagc aatgttttat    600
```

acaccaactg tatggcatac cgcagctgcc aacacttcaa ttaccgatta caggatgcta 660
actctgattt ttacaaaaaa caacatcaaa ccactgttgg tggatgcctt gaaaaggata 720
atttag 726

<210> SEQ ID NO 59
<211> LENGTH: 726
<212> TYPE: DNA
<213> ORGANISM: Cylindrospermopsis raciborskii T3

<400> SEQUENCE: 59
atgctgaccg cagaacagaa acaggcatat accaatgatg gctattttac cgtggaagaa 60
gcagttccga aagcactgat tgaagaaatt cgccatgaag tggaactgat caccgagcag 120
aaacgtggtg gtgtgctggc aggcgattat gaatggtggt cagaacacac cattccggat 180
ccggttcgtt atcagaaaat tatccagcgt ctgctggaac tgccgaccgt tatgggtccg 240
gttcaggccc tgattggtag cgatattttt ctgttaatta ccgacctggc aattattcgt 300
gcaggcaccg gttatattgc atggcatcag gatcatggct atgttgttga agttctgaac 360
gccctggcaa gcatgagcaa aaatgagctg aatgatgatg cactgcgcct gctggtgccg 420
gttgcaaatc aggcaatggt gtttattacc atctatctgc aggataccga taacaccatg 480
ggcaccatgc gtgtgattcc gagcagccat cagtgggaac atagtctgga tagcagcagc 540
gccaattcac tgaatgcaga aatttgtctg agcctgcctg gtggtgcagc aatgttttat 600
accccgaccg tttggcatac cgcagcagca aataccagca ttaccgatta tcgtatgctg 660
acgctgatct tcaccaaaaa caacattaaa ccgctgctgg ttgatgccct gaaacgtatt 720
atttga 726

<210> SEQ ID NO 60
<211> LENGTH: 191
<212> TYPE: PRT
<213> ORGANISM: Cylindrospermopsis raciborskii T3

<400> SEQUENCE: 60

Met Ile Asn Ile Glu Gln Phe Arg Gln Glu Ile Glu Asp Trp Ile Ile
1 5 10 15

Asn Val Val Ser Ile Pro Asn Pro Leu Thr Gly Asn Phe Pro Pro Cys
20 25 30

Pro Tyr Ala Lys Ala Ala Trp Leu Asn Asn Arg Val Ser Val Arg Trp
35 40 45

Phe His Gly Pro Glu Leu Pro Glu Leu Leu Met Glu Gln Ile Arg Thr
50 55 60

Trp Asn Asn Asp Phe Glu Met Val Ile Phe Gly Cys Asp Pro Gln Asn
65 70 75 80

Leu Asp Ala Gln Arg Leu Glu Arg Tyr Ile Thr Lys Ala Asn Tyr Val
85 90 95

Leu Pro Glu Tyr Asp Leu Val Ala Leu Gly Ser His Pro Asp Lys Gln
100 105 110

Tyr Val Gly Asp Asp Ala Glu Asn Val Asn Asn Val Ile Ile Thr His
115 120 125

Pro Lys Tyr Val Leu Ala Ser Val Gln Ser Phe Ser Gln Leu Gln Glu
130 135 140

Ala Ser Asp Glu Leu Leu Arg Leu Gly Tyr Phe Gln Tyr Trp Ser Ala
145 150 155 160

Glu Lys Leu Ala Glu Met Lys Ser Glu Arg Ala Ser His Asn Leu Ser 165 170 175

Ser Ile Gln Arg Lys Asn Ser Tyr Arg Ile Ile Pro Thr Asn His
180 185 190

<210> SEQ ID NO 61
<211> LENGTH: 576
<212> TYPE: DNA
<213> ORGANISM: Cylindrospermopsis raciborskii T3

<400> SEQUENCE: 61
atgataaata tcgaacaatt tcgccaagaa atagaggatt ggattatcaa tgttgtcagc 60
attcccaatc ctctaacagg aaattttcca ccctgtcctt acgcgaaggc agcttggtta 120
aataaccgtg ttagtgttcg ttggtttcat ggacctgaac tgccagagct tctaatggaa 180
cagataagaa catggaataa tgactttgaa atggtgattt ttggctgcga ccctcaaaac 240
ctagatgcac agaggttgga aaggtacatt accaaggcga attatgtatt accagaatac 300
gatttggtag ctttaggatc gcatccagac aaacaatatg ttggtgatga cgcggagaat 360
gtgaataacg taatcataac tcaccctaag tatgttttag catcagtaca gtcattcagc 420
cagttacaag aggctagtga tgaattatta agattgggat attttcagta ttggtctgca 480
gaaaaattgg ctgaaatgaa gtcggagcga gcttctcaca acctttcttc tatccagaga 540
aagaacagct ataggataat tcctactaac cattga 576

<210> SEQ ID NO 62
<211> LENGTH: 576
<212> TYPE: DNA
<213> ORGANISM: Cylindrospermopsis raciborskii T3

<400> SEQUENCE: 62
atgatcaaca tcgaacagtt tcgccaagaa atcgaagatt ggattattaa cgttgtcagc 60
attccgaacc cgctgaccgg taattttcct ccgtgtccgt atgcaaaagc agcatggctg 120
aataatcgtg ttagcgtgcg ttggtttcat ggtccggaac tgcctgaact gctgatggaa 180
caaattcgta catggaacaa cgatttcgag atggtgattt ttggttgcga tcctcagaat 240
ctggatgcac agcgtctgga acgttatatc accaaagcaa attatgtgct gcccgaatat 300
gacctggttg cactgggtag ccatccggat aaacagtatg ttggtgatga tgccgaaaat 360
gtgaacaacg tgattattac ccatccgaaa tatgttctgg caagcgttca gagctttagc 420
cagctgcaag aggcaagtga tgagctgctg cgtctgggtt atttccagta ttggtcagca 480
gaaaaactgg ccgaaatgaa aagcgaacgt gcaagccata atctgagcag cattcagcgt 540
aaaaatagct atcgtattat cccgaccaac cattga 576

<210> SEQ ID NO 63
<211> LENGTH: 258
<212> TYPE: PRT
<213> ORGANISM: Cylindrospermopsis raciborskii T3

<400> SEQUENCE: 63

Met Thr Ile Gln Ile Val Gln His Asn Leu Glu Tyr Ser Phe Val Thr
1 5 10 15

Pro Lys Glu Thr Ser Asp Phe Val Glu Arg Thr Met Ser Val Phe Asp
20 25 30

Gln Ala Tyr Pro Lys Phe Leu Ile His Asp Val Trp Ala Asp Pro Ala
35 40 45

Ser Leu Ala Leu Phe Glu Ile Tyr Pro Glu Phe Gln Phe Gly Leu Val

-continued

```
    50                  55                  60

Glu Ala Thr Thr Gln Leu Met Ile Ala Gln Gly Asn Cys Ile Pro Leu
65                  70                  75                  80

Thr Tyr Glu Ser Arg Phe Asp Glu Leu Pro Asp Glu Gly Cys Asp Trp
                85                  90                  95

Ala Leu Ala Lys Trp Leu Glu Asp Arg Glu Gln Asn Arg Leu Pro Asn
            100                 105                 110

Ala Leu Cys Val Val Ser Ile Ser Ile Leu Pro Glu Tyr Gln Gly Lys
        115                 120                 125

Asn Leu Ser Gln Tyr Leu Ile Gly Tyr Met Lys Glu Leu Ala Gln Tyr
    130                 135                 140

His Gly Leu Asn Ser Leu Ile Met Ala Ala Arg Pro Ser Leu Lys Tyr
145                 150                 155                 160

Leu Tyr Pro Leu Ile Pro Ile Glu Arg Tyr Ile Thr Trp Arg Asp Lys
                165                 170                 175

Asn Gly Leu Ile Phe Asp Pro Trp Leu Arg Val Asn Val Lys His Gly
            180                 185                 190

Ala Lys Ile Ala Gly Ile Cys Phe Lys Ser Thr Thr Ile Asn Asp Thr
        195                 200                 205

Ile Asp Gly Trp Glu Asp Arg Val Gly Met Arg Phe Pro Glu Thr Gly
    210                 215                 220

Asp Tyr Ile Ile Pro Lys Gly Leu Val Pro Val Lys Ile Asp Tyr Pro
225                 230                 235                 240

Asn Asn Met Gly Ile Tyr Ile Glu Pro Asn Ile Trp Leu Tyr Tyr Asp
                245                 250                 255

Leu Asp
```

<210> SEQ ID NO 64
<211> LENGTH: 777
<212> TYPE: DNA
<213> ORGANISM: Cylindrospermopsis raciborskii T3

<400> SEQUENCE: 64

```
atgaccattc aaattgtaca gcataattta gagtatagct ttgtaacccc aaaagaaact      60

tctgattttg tggaaaggac gatgagtgtc tttgatcaag catacccaaa atttttgata     120

catgatgtct gggcagatcc agcttcctta gctctatttg aaatttatcc agaattccag     180

tttgggttag tagaagctac cacacagctt atgatagcgc aaggaaactg tatcccttta     240

acttatgaaa gccgttttga tgagttaccg gacgaaggtt gtgactgggc tttagccaag     300

tggcttgaag accgagaaca gaaccgcctg cctaatgcgt tatgtgtagt atcgatttca     360

atcctaccag agtatcaagg caaaaacttg agtcagtatc tgattggata catgaaagaa     420

cttgctcaat accacggtct taattctttg atcatggctg cacgtccaag cctaaaatat     480

ctttacccac ttatacccat agagcggtat attacctggc gagataaaaa tggtcttata     540

tttgaccctt ggttacgagt taatgtcaaa catggggcta aaattgcagg gatctgtttt     600

aaatccacaa caattaatga tactattgac ggttgggaag atagagttgg gatgcgtttt     660

ccagaaactg gtgactatat tattcccaaa ggcttagtac ctgtcaaaat tgactatccc     720

aacaatatgg gaatatacat cgagcctaat atatggttat actatgacct agattaa        777
```

<210> SEQ ID NO 65
<211> LENGTH: 777
<212> TYPE: DNA
<213> ORGANISM: Cylindrospermopsis raciborskii T3

<400> SEQUENCE: 65

```
atgaccatcc agattgtgca gcataacctg gaatatagct ttgtgacccc gaaagaaacc      60
agcgattttg ttgaacgtac catgagcgtt tttgatcagg catatccgaa atttctgatc     120
catgatgttt gggcagatcc ggcaagcctg gccctgtttg aaatttatcc ggaatttcag     180
tttggtctgg tggaagcaac cacccagctg atgattgcac agggtaattg tattccgctg     240
acctatgaaa gccgttttga tgaactgccg gatgaaggtt gtgattgggc actggcaaaa     300
tggctggaag atcgcgaaca gaatcgtctg ccgaatgccc tgtgtgttgt gagcattagc     360
atcctgccgg aatatcaggg taaaaatctg agccagtatc tgatcggcta tatgaaagaa     420
ctggcacagt atcatggtct gaatagcctg attatggcag cacgtccgag cctgaaatat     480
ctgtatccgc tgattccgat tgaacgctat attacctggc gtgataaaaa cggcctgatt     540
tttgatccgt ggctgcgtgt taatgttaaa catggcgcaa aaattgccgg tatctgcttt     600
aaaagcacca ccattaatga taccattgat ggttgggagg atcgtgttgg tatgcgtttt     660
ccggaaaccg gtgattatat cattccgaaa ggtctggttc cggtgaaaat tgattatccg     720
aataacatgg gcatctacat cgaaccgaat atctggctgt attatgatct ggactga        777
```

<210> SEQ ID NO 66
<211> LENGTH: 258
<212> TYPE: PRT
<213> ORGANISM: Cylindrospermopsis raciborskii T3

<400> SEQUENCE: 66

```
Met Val Ile Lys Asn Leu Cys Pro Asp Gly Val Thr Pro Ile Trp Asn
1               5                   10                  15

Lys Ser Gln Met Glu Ser Ser Leu Leu Glu Glu Cys Leu Pro Ala Trp
            20                  25                  30

Val Arg Thr Ser Tyr Ser Thr Phe Val Glu Thr Ile Ser Asp Ser Ala
        35                  40                  45

Phe Pro Cys Phe Trp Gly Thr Ile Gly Glu Gln Lys Gly Met Ile Arg
    50                  55                  60

Tyr Leu Ile Val Ser Ser Leu Thr Asp Pro Ile Leu Val Glu His Thr
65                  70                  75                  80

Leu Glu Gly Ile Tyr Lys Tyr Ile Asp Glu Val Asn Glu Asn Glu Leu
                85                  90                  95

Leu Gln His Glu Asn Ala Asp Leu Leu Thr Leu Val Ile Phe Phe Pro
            100                 105                 110

Pro Glu Pro Thr Val Leu Thr Val Glu Glu Tyr Ala Gly Gln Ala Phe
        115                 120                 125

Asp Phe Leu Asn Ala Leu His Ser Leu Asp Ala Val Ser Cys Pro Cys
    130                 135                 140

His Trp Ser Ala Asp Pro Gln Ser Ala Asn Trp Ser Tyr Ser Leu Gly
145                 150                 155                 160

Gly Cys Ala Leu Phe Val Ser Val Ser Thr Pro Ala Asn Gln Lys Arg
                165                 170                 175

Arg Ser Arg His Leu Gly Ser Gly Met Thr Phe Val Ile Thr Pro Val
            180                 185                 190

Glu Val Leu Leu Asn Lys His Gly Gly Glu Asn Ser Ser Ile Phe Arg
        195                 200                 205

Arg Val Arg Gln Tyr Asp Gly Ile Pro Pro His Pro Asn Leu Leu Ile
    210                 215                 220
```

-continued

```
Met Pro Gly Asn Gly Lys Val Gly Asn Glu Leu Thr Val Gln Val Leu
225                 230                 235                 240

Pro Asp Asn Asn Asp Ser Glu Ile Ser Phe Asp Phe Gln Tyr Lys Phe
                245                 250                 255

Lys Asp
```

<210> SEQ ID NO 67
<211> LENGTH: 777
<212> TYPE: DNA
<213> ORGANISM: Cylindrospermopsis raciborskii T3

<400> SEQUENCE: 67

```
atggtaatca agaatttatg tcctgacgga gttacaccaa tctggaacaa aagccagatg      60

gaatcctctc ttctagagga gtgccttcct gcttgggtac gcactagcta ctcaacattt     120

gttgaaacaa tcagcgattc tgccttccct tgcttctggg gaactatcgg ggaacagaag     180

ggaatgatta gatacctgat agtctcatct ttaactgacc cgatcttggt tgagcatacg     240

cttgagggta tctacaaata cattgatgaa gttaatgaaa acgaattgct tcagcacgaa     300

aatgcggatc ttctgacact tgtcatcttt ttcccacctg aaccaacagt tcttacagta     360

gaggaatatg caggtcaagc atttgatttt ttgaatgcgt tacatagcct tgatgcggtg     420

tcttgtccct gccattggtc tgccgatccg cagtctgcta actggtctta ttctctagga     480

gggtgtgcct tatttgttag tgtttccact ccagcaaatc aaaagcggcg atcgcgccac     540

cttgggtcag gaatgacttt tgtcatcaca ccagttgaag tcctcttgaa taaacatggt     600

ggcgagaatt cgagcatttt tcgccgcgtc cgagagtacg acggcattcc acctcaccct     660

aacttattaa ttatgcctgg gaatgggaaa gtcggtaatg aattgacagt gcaagtactt     720

ccagataata acgatagtga gatctcattt gacttccagt ataaatttaa ggattag        777
```

<210> SEQ ID NO 68
<211> LENGTH: 777
<212> TYPE: DNA
<213> ORGANISM: Cylindrospermopsis raciborskii T3

<400> SEQUENCE: 68

```
atggtgatta aaaacctgtg tccggatggt gttaccccga tttggaataa aagccagatg      60

gaaagcagcc tgctggaaga atgtctgcct gcatgggttc gtaccagcta tagcaccttt     120

gttgaaacca ttagcgatag cgcatttccg tgtttttggg gcaccattgg tgaacagaaa     180

ggtatgattc gttatctgat tgttagcagc ctgaccgatc cgattctggt tgaacatacc     240

ctggaaggta tctacaaata tatcgatgaa gtgaacgaaa acgaactgct gcagcatgaa     300

aatgcagatc tgctgaccct ggttatcttt tttccgcctg aaccgaccgt tctgaccgtt     360

gaagaatatg caggtcaggc atttgatttt ctgaatgcac tgcatagcct ggatgcagtt     420

agctgtccgt gtcattggag cgcagatccg cagagcgcaa attggagcta tagcctgggt     480

ggttgtgcac tgtttgttag cgttagcaca ccggcaaatc agaaacgtcg tagccgtcat     540

ctgggtagcg gtatgacctt tgttattaca ccggttgaag tgctgctgaa taaacatggt     600

ggtgaaaaca gcagcatttt tcgtcgtgtt cgtgaatatg atggtattcc gcctcatccg     660

aatctgctga ttatgcctgg taatggtaaa gtgggtaatg aactgaccgt gcaggttctg     720

ccggataata atgatagcga aatcagcttc gattttcagt ataaattcaa agattga        777
```

<210> SEQ ID NO 69
<211> LENGTH: 408

<212> TYPE: PRT
<213> ORGANISM: Cylindrospermopsis raciborskii T3

<400> SEQUENCE: 69

```
Met Lys Arg Leu Thr Leu Leu Ile Ile Ala Gly Ile Leu Ser Val Ser
1               5                   10                  15

Thr Phe Leu Cys Ile Thr Pro Val Ala Leu Ala Asn Ile Thr Asp Tyr
            20                  25                  30

Tyr Leu Lys Asn Glu Lys Leu Ser Gly Gln Phe Ser Val Pro Val Asn
        35                  40                  45

Leu Ser Val Gly Val Arg Phe Ala His Arg Ser Ser Tyr Ala Thr Ala
    50                  55                  60

Ile Asn Phe Pro Thr Gly Leu Asp Ala Asp Ser Val Ala Val Gly Asp
65                  70                  75                  80

Phe Asn Ser Asp Ser Lys Leu Asp Leu Ala Val Thr Asn Trp Phe Asp
                85                  90                  95

Asn Asn Val Ser Val Leu Leu Gly Asn Gly Asn Gly Ser Phe Gly Ala
            100                 105                 110

Ala Thr Asn Phe Pro Val Gly Thr Asn Pro Val Phe Val Val Thr Gly
        115                 120                 125

Asp Val Asn Gly Asp Ser Lys Leu Asp Leu Ala Val Ala Asn Phe Ser
    130                 135                 140

Ser Asn Asn Val Ser Val Leu Leu Gly Asn Gly Asn Gly Ser Phe Gly
145                 150                 155                 160

Ala Ala Thr Asn Phe Ser Val Gly Thr Asn Pro Tyr Ser Val Ala Ile
                165                 170                 175

Gly Asp Val Asn Asn Asp Ser Glu Leu Asp Leu Ala Phe Thr Asn Trp
            180                 185                 190

Phe Asp Asn Lys Val Leu Val Leu Leu Gly Asn Gly Asn Gly Ser Phe
        195                 200                 205

Gly Ala Ala Ser Ser Phe Pro Val Asp Thr Tyr Ser Ile Ser Val Ala
    210                 215                 220

Ile Ala Asp Phe Asn Ser Asp Ser Lys Leu Asp Leu Ala Ile Thr Asn
225                 230                 235                 240

Trp Val Ser Asn Asn Val Ser Val Leu Leu Gly Asn Gly Asn Gly Ser
                245                 250                 255

Phe Gly Ala Ala Thr Asn Phe Pro Val Gly Thr Asn Pro Ile Phe Val
            260                 265                 270

Ala Thr Gly Asp Val Asn Gly Asp Ser Lys Leu Asp Leu Ala Val Ala
        275                 280                 285

Asn Thr Ser Ser Asn Asn Val Ser Val Leu Leu Gly Asn Gly Asn Gly
    290                 295                 300

Ser Phe Gly Ala Ala Thr Asn Phe Pro Ala Gly Thr Asn Pro Tyr Ser
305                 310                 315                 320

Val Ala Ile Arg Asp Val Asn Gly Asp Ser Lys Leu Asp Leu Ala Val
                325                 330                 335

Thr Asn Tyr Ser Ser Asn Asn Val Ser Val Leu Pro Gly Asn Gly Asn
            340                 345                 350

Gly Ser Phe Gly Ile Ala Thr Asn Phe Pro Val Gly Thr Asn Pro Glu
        355                 360                 365

Ser Ile Ala Ile Ala Asp Phe Asn Gly Asp Ser Lys Leu Asp Leu Ala
    370                 375                 380

Val Thr Asn Ser Gly Asn Asn Asn Val Ser Ile Leu Leu Asn Asn Phe
385                 390                 395                 400
```

-continued

Gln Gly Leu Pro Lys Asn Lys Ile
405

<210> SEQ ID NO 70
<211> LENGTH: 1227
<212> TYPE: DNA
<213> ORGANISM: Cylindrospermopsis raciborskii T3

<400> SEQUENCE: 70
gtgaaaaggc tcactttact aattatagcg gggatattat ctgttagtac atttttatgt 60
ataactcctg ttgcattagc aaatataact gactattatc tgaagaatga aaagctttct 120
gggcaattta gtgttccggt taatttgtcc gtaggagtga gatttgccca caggagtagt 180
tatgctactg ctattaactt cccaactggt cttgatgctg actctgtagc agttggggat 240
ttcaatagcg atagtaagct cgacctggct gttacaaatt ggttcgacaa taacgtctcg 300
gtcttactgg gaaatggtaa tgggtctttt ggcgcagcca ctaactttcc agtcggtact 360
aatcccgtct ttgtagtgac tggggatgta aatggcgaca gcaagcttga cctggctgtt 420
gcaaatttta gtagcaataa cgtctcggtc ttactaggaa atggtaatgg gtcttttggc 480
gcagccacta acttttcagt tggtactaac ccttattctg tagccattgg agatgtgaat 540
aacgatagtg agcttgacct tgcttttaca aattggttcg acaataaggt cttggtttta 600
ctgggaaatg gtaatgggtc ttttggcgca gccagcagct tccctgtcga tacttattcg 660
atttccgtag cgattgcgga ttttaatagc gacagtaagc tcgaccttgc tattacaaat 720
tgggtcagca ataacgtctc ggtcttactg ggaaatggta atgggtcttt tggcgcagcc 780
actaactttc cagtcggtac taatcccata tttgtagcaa ctggggatgt aaatggcgac 840
agcaagcttg acctggctgt tgcaaatact agcagcaata acgtctcggt cttactggga 900
aatggtaatg ggtcttttgg cgcagccact aactttccag ccggtactaa tccctactct 960
gtagcgatta gagatgtgaa tggcgacagt aaacttgacc tggctgttac aaattatagt 1020
agcaataacg tctcggtctt accaggaaat ggtaatgggt cttttggcat agctactaac 1080
tttccagtcg gtactaatcc tgaatctata gcaattgcgg atttcaacgg cgacagcaag 1140
cttgacctgg ctgtcacaaa ttctggcaac aacaacgtct cgatcttgtt gaataatttt 1200
cagggacttc caaaaaataa gatatag 1227

<210> SEQ ID NO 71
<211> LENGTH: 1227
<212> TYPE: DNA
<213> ORGANISM: Cylindrospermopsis raciborskii T3

<400> SEQUENCE: 71
atgaaacgtc tgacgctgct gatcattgca ggtattctgt cagttagcac ctttctgtgt 60
attacaccgg ttgcactggc caatattacc gattattatc tgaaaaacga gaaactgagc 120
ggtcagttta gcgttccggt gaatctgtct gttggtgttc gttttgcaca tcgtagcagc 180
tatgcaaccg caattaactt tccgaccggt ctggatgcag atagcgttgc agttggtgat 240
tttaacagcg atagcaaact ggatctggcc gttaccaatt ggtttgataa caatgttagc 300
gtgctgctgg gtaatggcaa tggcagcttt ggtgcagcaa ccaattttcc ggttggcacc 360
aatccggttt ttgttgttac cggtgatgtt aatggtgaca gtaaactgga tttagccgtg 420
gcaaatttta gcagcaataa tgtttcagtt ctgctgggaa acggtaatgg ttcttttggc 480
gcagccacaa actttagcgt tggtacaaat ccgtatagcg tggccattgg tgatgtgaat 540

```
aatgatagtg aactggacct ggcatttacg aactggttcg ataataaagt tctggtgctg    600

ttaggcaatg gtaatggctc gtttggtgcc gcaagctcat ttccggtgga tacctatagc    660

attagcgttg cgattgcaga tttcaactca gattctaaat tagacctggc gatcaccaat    720

tgggtgtcaa ataatgtgag tgtgttactg gggaatggta acggtagttt tggagctgcg    780

acaaattttc ctgtgggtac aaacccgatt tttgtggcaa ccggtgacgt gaatggcgat    840

tctaagctgg acttagcagt tgcaaatacc agctctaata acgttagcgt tctgttaggt    900

aacgggaacg gctcattcgg tgctgccacg aattttccag caggcaccaa cccgtatagt    960

gttgcaattc gcgacgttaa cggtgatagc aaattagatt tagcggtgac caactatagc   1020

agcaacaacg tgagtgttct gccaggcaac ggtaacggat catttggtat tgcgaccaac   1080

tttccagtag gtacgaatcc ggaaagcatt gcaattgccg attttaatgg ggattccaag   1140

ttagatctgg cagtgacaaa tagcggtaac aataatgtaa gcatactgct gaataacttt   1200

cagggtctgc cgaaaaacaa gatttga                                       1227
```

<210> SEQ ID NO 72
<211> LENGTH: 200
<212> TYPE: PRT
<213> ORGANISM: Cylindrospermopsis raciborskii T3

<400> SEQUENCE: 72

```
Met Lys Ser Thr Asn Ile His Tyr Thr Lys His Leu Ile Ser Pro Tyr
1               5                   10                  15

Asp Arg Tyr Leu Lys Asn Gly His Lys Ser Gly Ile Leu Trp Phe Thr
            20                  25                  30

Gly Leu Ser Gly Ala Gly Lys Thr Thr Leu Ala Leu Lys Leu Glu Gln
        35                  40                  45

Thr Leu Phe Glu Lys Gly Trp Ser Thr Phe Val Leu Asp Gly Asp Ser
    50                  55                  60

Val Arg His Gly Leu Cys Ser Asp Leu Gly Phe Ser Ala Ser Asp Arg
65                  70                  75                  80

Ser Glu Asn Ile Arg Arg Leu Gly Glu Val Ala Lys Leu Phe Ala Glu
                85                  90                  95

Ser Gly Cys Leu Val Ile Thr Ala Phe Ile Ser Pro Tyr Arg Asn Asp
            100                 105                 110

Arg Glu Gln Val Arg Arg Leu Ala Gly Asp Leu Phe His Glu Val Tyr
        115                 120                 125

Ile Ala Thr Pro Leu Glu Leu Cys Glu Gln Arg Asp Pro Lys Gly Leu
    130                 135                 140

Tyr Leu Lys Ala Arg Ser Gly Glu Ile Asp Gly Phe Thr Gly Ile Ser
145                 150                 155                 160

Ala Pro Tyr Glu Pro Pro Asn Ser Pro Asp Leu Trp Val Glu Thr Ser
                165                 170                 175

Glu Leu Thr Val Glu Glu Ser Leu Glu Gln Leu Leu Lys Tyr Val Glu
            180                 185                 190

Asn Lys Phe Thr Ile Phe Lys Gln
        195                 200
```

<210> SEQ ID NO 73
<211> LENGTH: 603
<212> TYPE: DNA
<213> ORGANISM: Cylindrospermopsis raciborskii T3

<400> SEQUENCE: 73

-continued

```
atgaaatcaa ctaatattca ctatacaaaa catcttatat ctccatatga tcgttatcta     60

aagaatggtc ataaaagcgg gattctatgg tttactggac tgtccggggc tggtaaaaca    120

acattggctt taaaattaga gcagactttg ttcgagaaag gatggtctac ctttgtttta    180

gatggtgata gtgttcgtca tggactgtgt tccgatttag gattttctgc tagtgatcgc    240

tcagaaaata tccgtcgttt gggtgaggtt gccaaactct ttgcggagtc aggatgccta    300

gtgatcactg ccttcatctc accctacagg aatgaccgag aacaggtgcg tagactagct    360

ggagatctat ttcatgaagt atacattgca actccactgg aactttgtga gcagcgtgat    420

ccgaaaggtc tttatctaaa agcacgcagt ggggaaatag atggatttac gggaatcagc    480

gccccttatg aaccacccaa tagcccagat ttatgggtgg aaacatccga actcaccgtc    540

gaggaaagcc tagaacaact actcaaatac gtggaaaaca aattcacaat tttcaaacaa    600

tag                                                                  603
```

```
<210> SEQ ID NO 74
<211> LENGTH: 221
<212> TYPE: PRT
<213> ORGANISM: Cylindrospermopsis raciborskii T3

<400> SEQUENCE: 74

Met Lys Ala Val Val Lys Tyr Thr Ile Phe Glu Lys Pro Gln Pro Ile
1               5                   10                  15

Arg Ala Ile Lys Arg Leu Glu Arg Asp Val Leu Arg Met Gly Ala Leu
            20                  25                  30

Val Glu Gln Ser Phe Arg Leu Ser His Gln Ala Leu Phe Asn Arg Asp
        35                  40                  45

Leu Thr Ala Ala Glu Gln Ile Arg Arg Leu Asp Lys Lys Ile Asp Arg
    50                  55                  60

Phe Tyr Arg Gln Ile Glu Val Asp Cys Ala Thr Ile Met Ser Ser Gln
65                  70                  75                  80

Ala Pro Thr Asp Gln Glu Ser Arg Cys Leu Ser Ser Phe Met Gln Leu
                85                  90                  95

Val Arg Asp Leu Glu Arg Ile Gly Asp Tyr Ala Lys Asp Leu Ala Glu
            100                 105                 110

Ile Ala Met Lys Ile Phe Pro Tyr Pro Pro His Pro Thr Leu Gly Glu
        115                 120                 125

Val Ala Ile Met Ser Asp His Ala Gln Ser Met Leu Ala Thr Ser Leu
    130                 135                 140

Val Ala Leu Ala Asp Leu Asp Glu Ile Ser Gly Arg Arg Ile Lys Leu
145                 150                 155                 160

Leu Asp Asp Thr Val Asp Asp Ala Tyr Lys Lys Leu Tyr Arg Asn Leu
                165                 170                 175

Ala Gln Gln Lys Asp Val Pro Gly Val Val Glu Pro Ile Leu Leu Leu
            180                 185                 190

Thr Leu Ala Ile Gln Cys Leu Glu Arg Met Ala Asp His Ala Thr Asn
        195                 200                 205

Ile Gly Gln Arg Val Ala Tyr Ile Val Thr Gly Gln Arg
    210                 215                 220


<210> SEQ ID NO 75
<211> LENGTH: 666
<212> TYPE: DNA
<213> ORGANISM: Cylindrospermopsis raciborskii T3
```

<400> SEQUENCE: 75

```
atgaaagctg ttgtgaaata tacaattttt gaaaaacctc aacctatacg tgccattaaa      60

agactggaac gagatgtttt gcgtatgggt gctttagtag agcagtcatt ccgtctgagt     120

caccaagctc tattcaatcg ggatttaaca gcagctgagc aaatacggag attagacaaa     180

aaaattgatc gcttctacag acaaatagaa gtcgattgtg ccacaattat gagcagtcaa     240

gctcccacag accaagaatc tcggtgttta agctcattca tgcaattagt tagagacttg     300

gaacgtattg gggactatgc caaagatttg gcagaaatag caatgaaaat atttccctat     360

cccccccatc ctactttggg ggaggttgcc attatgtccg atcatgccca atctatgttg     420

gctaccagcc tagtagcttt agcggattta gacgagatta gtggtagaag gattaaatta     480

ttagatgata cagtagatga tgcttacaaa aagttatatc gtaatttggc gcagcagaaa     540

gatgttcccg gggtagtgga gcccatttta ctattaacat tagcaattca gtgtttagag     600

agaatggcag atcatgctac taatattggt caaagggtag catacattgt tacagggcaa     660

agatag                                                                666
```

<210> SEQ ID NO 76
<211> LENGTH: 450
<212> TYPE: PRT
<213> ORGANISM: Cylindrospermopsis raciborskii T3

<400> SEQUENCE: 76

```
Met Phe Leu Leu Gly Phe Leu Leu Gly Leu Ala Val Gly Phe Gly Phe
1               5                   10                  15

Trp Leu Trp Gln Gln Phe Gln Leu Asn Ser His Leu Glu Gln Leu Thr
            20                  25                  30

Gln Pro Leu Asn Pro His Ala Glu Lys Ile Leu Leu Pro Leu Leu Ala
        35                  40                  45

Gly Leu His Arg Lys Ile Ser Thr Val Arg Asp Glu Gln Gln Asn Leu
    50                  55                  60

Arg Leu Ser Leu Lys Ala Tyr Glu Gln Leu Leu Asp Ala Ala Pro Leu
65                  70                  75                  80

Gly Tyr Leu Gln Val Asp Glu Glu Asn Gln Leu Leu Trp Cys Asn Gln
                85                  90                  95

Cys Ala Arg Glu Met Leu Tyr Leu Gln Arg Trp Gln Pro Gly Gln Val
            100                 105                 110

Arg Leu Leu Leu Glu Leu Val Arg Ser Tyr Glu Leu Asp Gln Leu Ile
        115                 120                 125

Glu Gln Thr Arg Asp Trp Gln Lys Pro Gln Met Gln Glu Trp Ile Phe
    130                 135                 140

His Pro Ser Arg Asp His Gly Gln Gly Ile Leu Gly Leu Lys Pro Leu
145                 150                 155                 160

Ser Leu Ala Ala Asn Ser Phe Pro Leu Pro Gly Gly Gln Val Gly Val
                165                 170                 175

Phe Leu Glu Ser His Gln Gln Phe Val Asp Ile His Gln Gln Arg Asp
            180                 185                 190

Arg Ser Phe Ser Asp Leu Ala His Glu Leu Arg Thr Pro Leu Thr Ser
        195                 200                 205

Ile Arg Leu Val Ala Glu Thr Leu Gln Thr Arg Leu Asp Pro Pro Leu
    210                 215                 220

Asn Arg Trp Val Ile Arg Leu Met Gln Glu Val Asp Arg Leu Ile Asn
225                 230                 235                 240
```

```
Leu Val Gln Asn Trp Leu Asp Leu Thr Gln Met Glu Ile Thr Ser Ser
                245                 250                 255

Ile Gln Leu Asn Leu Glu Met Leu Glu Val Arg Ser Leu Ile Phe Ser
            260                 265                 270

Val Trp Glu Asn Leu Glu Pro Leu Ala Ala Asn Gln His Leu Ser Ile
        275                 280                 285

Ser Tyr Ser Gly Pro Glu Lys Val Tyr Ile Cys Ala Asp Lys Ser Arg
    290                 295                 300

Ile Tyr Gln Val Phe Leu Asn Leu Leu Asp Asn Cys Ile Lys Tyr Ser
305                 310                 315                 320

Asn Leu Asn Gly Thr Ile Phe Ile Glu Met Asn Pro Val Cys Gly Glu
                325                 330                 335

Lys Ser Ile Asn Gly Val Asp Pro Glu Ala Asp Thr Ile Leu Asn Gln
            340                 345                 350

Val Ser Asn Gln Ile Leu Glu Ile Asn Ile Ile Asp Ser Gly Val Gly
        355                 360                 365

Phe Ala Pro Met Asp Leu Pro His Val Phe Gln Arg Phe Tyr Arg Gly
    370                 375                 380

Asp Lys Ala Arg His Arg Glu Ser Arg Ser Glu Asn Glu Thr Val Glu
385                 390                 395                 400

Ile Thr Gly Ser Gly Leu Gly Leu Ser Ile Val Arg Gln Ile Ile Ile
                405                 410                 415

Ala His Gly Gly Lys Ile Arg Ala Met Asn His Pro Asp Thr Gly Gly
            420                 425                 430

Ala Trp Ile Gln Ile His Leu Pro Gln Val Val Gln His Asp Gly Gly
        435                 440                 445

Tyr Phe
    450
```

<210> SEQ ID NO 77
<211> LENGTH: 1353
<212> TYPE: DNA
<213> ORGANISM: Cylindrospermopsis raciborskii T3

<400> SEQUENCE: 77

```
atgttcttat tgggatttct tctgggtttg gcagtcggtt ttggtttttg gctttggcaa      60

caatttcaac ttaacagtca tttggagcag ttaacccaac ccttaaaccc tcacgctgaa     120

aagatattat taccccctatt agctggatta catcgtaaaa tatctaccgt tagagatgag     180

caacaaaact tacgcttgtc actcaaagct tatgaacagt tgctggatgc tgcgcctttg     240

ggatatttac aagtagatga agaaaaccaa ctactatggt gtaatcagtg cgcgcgggaa     300

atgctgtatt tacaaagatg gcaaccgggt caagtgcgcc tgctactgga attagtgaga     360

tcctatgagc tggatcagtt aattgagcaa acccgggatt ggcaaaaacc gcaaatgcaa     420

gagtggattt ttcacccttc ccgagatcat ggtcagggta ttttaggatt aaagccattg     480

tctttagcag ctaacagttt tcccctaccg gggggacaag tgggtgtgtt tctagaaagt     540

caccaacaat ttgtagacat tcatcagcaa cgtgaccgct ctttttcaga cctggcccat     600

gaactgagaa cacctctgac ttccattcgt ctggtcgcag aaaccctgca aactcgctta     660

gatcccccctc taaaccgttg ggtcatccgc ttgatgcagg aggttgacag actaattaat     720

ttagtccaaa attggttaga cctgacccag atggaaataa cctcctccat acaactgaat     780

ttggaaatgc tagaagtccg ctccctaatt ttttcagtct gggagaattt agagccccta     840

gccgctaatc agcatcttag tatttcttac tccggcccgg aaaaggtcta tatatgtgct     900
```

```
gataagtcca gaatttatca agtgtttctt aatctgttag ataactgtat taaatacagc    960

aacctgaacg gtactatttt cattgaaatg aatccagttt gtggggagaa gtctattaat   1020

ggggttgatc cagaagcaga tacaatatta aaccaagtat caaatcagat tttagaaatt   1080

aacattattg attccggggt tggatttgct cccatggatc taccccatgt ctttcaaaga   1140

ttttatcggg gggacaaagc tagacaccgc gagtcccgct ctgagaatga aacagtagaa   1200

attactggta gtggtttagg gttatccatt gtccgccaaa taattatagc tcatggtggc   1260

aaaatcaggg ccatgaacca tcctgatacc ggtggtgctt ggatacaaat tcatcttccc   1320

caggtggttc aacatgatgg cggatatttc tga                                1353
```

<210> SEQ ID NO 78
<211> LENGTH: 240
<212> TYPE: PRT
<213> ORGANISM: Cylindrospermopsis raciborskii T3

<400> SEQUENCE: 78

```
Val Asn Gln Ser Ile Val Trp Gln Arg Ala Pro Glu Asn Phe Gln Leu
1               5                   10                  15

Cys Ala Gln Glu Val His Ile Trp Lys Ile Asn Leu Lys Val Ser Pro
            20                  25                  30

Ser Glu Val Glu Leu Cys Arg Arg Ile Leu Ser Gly Asp Glu Ile Ala
        35                  40                  45

Arg Ala Glu Arg Phe Ser Phe Pro Glu His Gln Glu Arg Phe Ile Val
    50                  55                  60

Gly Arg Ala Phe Leu Arg Lys Ile Leu Ser Arg Tyr Leu Asn Val Glu
65                  70                  75                  80

Ala Gln Ala Ile Glu Phe Glu Tyr Glu Glu Arg Gly Lys Pro Leu Leu
                85                  90                  95

Gly Phe Lys Phe Lys Tyr Ser Gly Ile Cys Phe Asn Leu Ser His Ser
            100                 105                 110

Gln Glu Leu Ala Leu Cys Gly Val Thr His Gln Arg Ser Ile Gly Val
        115                 120                 125

Asp Leu Glu Gly Val Arg His Thr Ser Asp Ile Glu Asn Leu Ala Asn
    130                 135                 140

Arg Phe Phe Ser Val Lys Glu Tyr Gly Val Ile Lys Ser Val Pro Pro
145                 150                 155                 160

Glu Gln Gln Gln Gln Val Phe Phe Arg Tyr Trp Thr Cys Lys Glu Ala
                165                 170                 175

Tyr Leu Lys Ala Ile Gly Lys Gly Leu Ser Glu Leu Ser Gln Ile Glu
            180                 185                 190

Ile Glu Leu Thr Pro Asn Lys Ser Ala Arg Leu Arg Val Leu Gly Asp
        195                 200                 205

Trp Gln Leu Lys Glu Leu Val Pro Ala Asp Asn Phe Ala Ala Ala Val
    210                 215                 220

Val Ile Ala Ser His Asn His Leu Asp Arg Phe Glu Phe Trp Glu Pro
225                 230                 235                 240
```

<210> SEQ ID NO 79
<211> LENGTH: 723
<212> TYPE: DNA
<213> ORGANISM: Cylindrospermopsis raciborskii T3

<400> SEQUENCE: 79

```
gtgaatcagt ctattgtttg gcaacgggca cctgaaaatt tccagttgtg cgctcaggaa     60
```

```
gtacatatct ggaagattaa cctgaaagta tcaccatcag aggtggaact ttgtcgcagg    120

attttatctg gtgatgaaat agctcgtgcg gaaagatttt cttttccgga acatcaagag    180

cgttttattg ttggtcgtgc ctttcttaga aaaatactat caagatattt aaacgtagaa    240

gcacaagcaa tagagtttga gtatgaagag agaggaaaac cactgttagg gttcaagttt    300

aagtactctg gaatatgttt taatttatcc cattctcagg aattagcttt atgcggtgtg    360

actcatcaaa gatccattgg agtagatcta gaaggtgttc gtcacacatc agatatagaa    420

aacctagcca accgcttttt ttcagttaaa gaatatgggg taattaaatc agtacccccg    480

gaacaacaac agcaggtatt tttccgttat tggacttgta aagaggccta tttaaaagct    540

attggaaaag gtttgtctga gttatctcaa atagaaatag aattaacgcc aaataaatct    600

gctaggttgc gtgtattggg agattggcag ttaaaagaac tagtaccagc agataatttt    660

gcagcagcag ttgttatagc tagccataat catttagaca ggtttgagtt ttgggaacct    720

taa                                                                  723
```

<210> SEQ ID NO 80
<211> LENGTH: 723
<212> TYPE: DNA
<213> ORGANISM: Cylindrospermopsis raciborskii T3

<400> SEQUENCE: 80

```
atgaatcaat caatcgtgtg gcagcgtgcg ccggaaaact tccaactgtg tgctcaagaa     60

gtgcatatct ggaaaatcaa cctgaaagtg agcccgtctg aagtggaact gtgccgtcgc    120

attctgagtg gcgatgaaat cgcgcgtgcc gaacgctttt ccttcccgga acatcaggaa    180

cgttttattg tgggtcgtgc attcctgcgc aaaatcctga gccgctatct gaacgttgaa    240

gcacaggcta ttgaatttga atacgaagaa cgtggcaaac cgctgctggg tttcaaattc    300

aaatactctg gcatctgctt caatctgagt cattcccagg aactggcgct gtgtggtgtt    360

acccaccaac gttcaattgg cgtcgatctg gaaggtgtgc gccacacgtc ggacatcgaa    420

aacctggcca atcgtttctt tagcgtcaaa gaatacggcg tgattaaaag cgtgccgccg    480

gaacagcaac agcaagtgtt tttccgctat tggacctgta aagaagcgta cctgaaagcc    540

atcggcaaag gtctgtcaga actgtcgcag attgaaatcg aactgacgcc gaacaaatca    600

gcgcgtctgc gcgttctggg tgattggcaa ctgaaagaac tggtcccggc agacaatttt    660

gctgcagcag ttgtcattgc gagtcataat catctggacc gttttgaatt ttgggaaccg    720

tga                                                                  723
```

<210> SEQ ID NO 81
<211> LENGTH: 27
<212> TYPE: DNA
<213> ORGANISM: Artificial Sequence
<220> FEATURE:
<223> OTHER INFORMATION: Primer

<400> SEQUENCE: 81

```
gggctttcat atgttacaaa agattaa                                         27
```

<210> SEQ ID NO 82
<211> LENGTH: 27
<212> TYPE: DNA
<213> ORGANISM: Artificial Sequence
<220> FEATURE:
<223> OTHER INFORMATION: Primer

<400> SEQUENCE: 82
aaagtatgcg gccgcatgct tgagtat 27

<210> SEQ ID NO 83
<211> LENGTH: 26
<212> TYPE: DNA
<213> ORGANISM: Artificial Sequence
<220> FEATURE:
<223> OTHER INFORMATION: Primer

<400> SEQUENCE: 83
ggcatccatg ggcaagattt acggaa 26

<210> SEQ ID NO 84
<211> LENGTH: 27
<212> TYPE: DNA
<213> ORGANISM: Artificial Sequence
<220> FEATURE:
<223> OTHER INFORMATION: Primer

<400> SEQUENCE: 84
ggcatctcga gttataaaag cgcttcg 27

<210> SEQ ID NO 85
<211> LENGTH: 27
<212> TYPE: DNA
<213> ORGANISM: Artificial Sequence
<220> FEATURE:
<223> OTHER INFORMATION: Primer

<400> SEQUENCE: 85
ggttaagatc tgaaattaat acgactc 27

<210> SEQ ID NO 86
<211> LENGTH: 27
<212> TYPE: DNA
<213> ORGANISM: Artificial Sequence
<220> FEATURE:
<223> OTHER INFORMATION: Primer

<400> SEQUENCE: 86
ttttaagatc ttttcagcaa aaaaccc 27

<210> SEQ ID NO 87
<211> LENGTH: 30
<212> TYPE: DNA
<213> ORGANISM: Artificial Sequence
<220> FEATURE:
<223> OTHER INFORMATION: Primer

<400> SEQUENCE: 87
atatccatgg gacctggtga tcgcaaagga 30

<210> SEQ ID NO 88
<211> LENGTH: 29
<212> TYPE: DNA
<213> ORGANISM: Artificial Sequence
<220> FEATURE:
<223> OTHER INFORMATION: Primer

<400> SEQUENCE: 88
tatctcgaga gtgttgattt cgttggctg 29

<210> SEQ ID NO 89
<211> LENGTH: 675

```
<212> TYPE: DNA
<213> ORGANISM: Bacillus subtilis

<400> SEQUENCE: 89

atgaagattt acggaattta tatggaccgc ccgctttcac aggaagaaaa tgaacggttc     60

atgactttca tatcacctga aaaacgggag aaatgccgga gattttatca taaagaagat    120

gctcaccgca ccctgctggg agatgtgctc gttcgctcag tcataagcag gcagtatcag    180

ttggacaaat ccgatatccg ctttagcacg caggaatacg ggaagccgtg catccctgat    240

cttcccgacg ctcatttcaa catttctcac tccggccgct gggtcattgg tgcgtttgat    300

tcacagccga tcggcataga tatcgaaaaa acgaaaccga tcagccttga gatcgccaag    360

cgcttctttt caaaaacaga gtacagcgac cttttagcaa aagacaagga cgagcagaca    420

gactattttt atcatctatg gtcaatgaaa gaaagcttta tcaaacagga aggcaaaggc    480

ttatcgcttc cgcttgattc cttttcagtg cgcctgcatc aggacggaca agtatccatt    540

gagcttccgg acagccattc cccatgctat atcaaaacgt atgaggtcga tcccggctac    600

aaaatggctg tatgcgccgc acaccctgat ttccccgagg atatcacaat ggtctcgtac    660

gaagagcttt tataa                                                      675


<210> SEQ ID NO 90
<211> LENGTH: 224
<212> TYPE: PRT
<213> ORGANISM: Bacillus subtilis

<400> SEQUENCE: 90

Met Lys Ile Tyr Gly Ile Tyr Met Asp Arg Pro Leu Ser Gln Glu Glu
1               5                   10                  15

Asn Glu Arg Phe Met Thr Phe Ile Ser Pro Glu Lys Arg Glu Lys Cys
            20                  25                  30

Arg Arg Phe Tyr His Lys Glu Asp Ala His Arg Thr Leu Leu Gly Asp
        35                  40                  45

Val Leu Val Arg Ser Val Ile Ser Arg Gln Tyr Gln Leu Asp Lys Ser
    50                  55                  60

Asp Ile Arg Phe Ser Thr Gln Glu Tyr Gly Lys Pro Cys Ile Pro Asp
65                  70                  75                  80

Leu Pro Asp Ala His Phe Asn Ile Ser His Ser Gly Arg Trp Val Ile
                85                  90                  95

Gly Ala Phe Asp Ser Gln Pro Ile Gly Ile Asp Ile Glu Lys Thr Lys
            100                 105                 110

Pro Ile Ser Leu Glu Ile Ala Lys Arg Phe Phe Ser Lys Thr Glu Tyr
        115                 120                 125

Ser Asp Leu Leu Ala Lys Asp Lys Asp Glu Gln Thr Asp Tyr Phe Tyr
    130                 135                 140

His Leu Trp Ser Met Lys Glu Ser Phe Ile Lys Gln Glu Gly Lys Gly
145                 150                 155                 160

Leu Ser Leu Pro Leu Asp Ser Phe Ser Val Arg Leu His Gln Asp Gly
                165                 170                 175

Gln Val Ser Ile Glu Leu Pro Asp Ser His Ser Pro Cys Tyr Ile Lys
            180                 185                 190

Thr Tyr Glu Val Asp Pro Gly Tyr Lys Met Ala Val Cys Ala Ala His
        195                 200                 205

Pro Asp Phe Pro Glu Asp Ile Thr Met Val Ser Tyr Glu Glu Leu Leu
    210                 215                 220
```

<210> SEQ ID NO 91
<211> LENGTH: 7035
<212> TYPE: DNA
<213> ORGANISM: Artificial Sequence
<220> FEATURE:
<223> OTHER INFORMATION: Sequence of sxt1 fragment after integration into E. coli lactose operon

<400> SEQUENCE: 91
gtttcatctg tggtgcaacg ggcgctgggt cggttacggc caggacagtc agtggagatg 60
cccaagggca cttcgggtcg aggaacccga cctgcattgg gacgcggcca cggagagcgc 120
gggcaaacgc cggcactata gccagtggag tttgtaaaac gctatttcag agcttggaga 180
gtgtctaaga aagccgggcg atgccaaccc atcccttctt cggctacgtt cgtaatcaag 240
ccacttcctt tttgcattga cgcagggtgt cggaaggcaa ctcgccgaac gcgctcctat 300
agttttcagc gaagcgtccc aaatgtaaga agccgtagtc tagggctatc tcagttatac 360
tacgcacatt ggcactggga tcgttcaagc aggcgcggat gctttcgagc ttgcggttgc 420
ggatgtagtt cttcggcgtg gtgccggcat gcttctcgaa caaattgtag agcgagcgtg 480
gactcatcat cgccagctcc gctaaccgct caaggctgat attccgtttg agattctcct 540
caatgaattg aacgactcgc tcgaaagacg ggttaccttt gctgaaaatt tcacggctga 600
cattgctgcc cagcatttcg agcagcttgg aagcgatgat ccccgcatag tgctcttgga 660
cccgaggcat cgactttgta tgttccgctt cgtcacaaac taacccgagt agattgataa 720
agccatcgag ttgctggaga ttgtgtcgcg cggcgaaacg gataccctcc ctcggcttgt 780
gccaattgtt gtcactgcat gcccgatcaa ggaccactga gggcaattta acgataaatt 840
tctcgcaatc ttctgaatag gtcaggtcgg cttggtcatc cggattgagc agcaatagtt 900
cgcccggcgc aaaatagtgc tcctggccat ggccacgcca caggcaatgg cctttgagta 960
ttatttgcag atgataacag gtctctaatc caggcgagat taccctcacg ctaccgccgt 1020
agctgattcg acacaggtcg aggcatccga agattctgtg gtgcagcctg cctgccgggg 1080
gcccgccctt gggcaggcga atagagtgcg taccgacata ctggttaaca taatcggaga 1140
ctgcataggg ctcggcgtgg acgaagatct gacttttctc gttcaataag caaaaatcca 1200
tagttcacgg ttctcttatt ttaatgtggg ctgcttggtg tgatgtagaa aggcgccaag 1260
tcgatgaaaa tgcaggaatt aattcgcaga tcctggcgga tgagagaaga ttttcagcct 1320
gatacagatt aaatcagaac gcagaagcgg tctgataaaa cagaatttgc ctggcggcag 1380
tagcgcggtg gtcccacctg accccatgcc gaactcagaa gtgaaacgcc gtagcgccga 1440
tggtagtgtg gggtctcccc atgcgagagt agggaactgc caggcatcaa ataaaacgaa 1500
aggctcagtc gaaagactgg gcctttcgtt ttatctgttg tttgtcggtg aacgctctcc 1560
tgagtaggac aaatccgccg ggagcggatt tgaacgttgc gaagcaacgg cccggagggt 1620
ggcgggcagg acgcccgcca taaactgcca ggcatcaaat taagcagaag gccatcctga 1680
cggatggcct ttttgcgtag atcccagcct tgcaagaagc ggatacagga gtgcaaaaaa 1740
tggctatctc tagaaaggcc taccccttag gctttatgca acagaaacaa taataatgga 1800
gtcatgaaca tgctgcagaa aatcaatcgt tatacccatg gttttgttgc cgttccggtt 1860
attctggcat gtcgtgaaaa aggtgttttt gaactgctgg cagatgaaag tccgctgagc 1920
ctgaatcaga tggttgaaca tctgggtgcc aatagcggtc attttcaggt tgcactgcgt 1980
atgctggaaa gtctgcattg gctgagccgt aataaagaac tgaaatatag cctgaccgca 2040

```
gaagcagcaa ttcataacaa aattagcgaa gatatcctgc agctgtataa tctgccgatt   2100
cagagctatc tggaaggtaa acagggcaat ctgctgggtc gttggattga acgtagctgt   2160
cagctgtgga atctggataa tccgctgatg gcagattttc tggatggtct gctggttatt   2220
ccgctgctgc tggcactgca taaacataac ctgctggccg attctgaaga taaaccgctg   2280
ctgagcagcc tgagcagtac cgttcaagaa gaactgggta aactgtttct gcatctgggt   2340
tgggcagatc tgacagcagg tcgtctgacc attaccgaac tgggtcgctt tatgggtgaa   2400
cgtgcactga ataccgcaat tgttgcaagc tataccccga tgctgagtcg tattcatgat   2460
gttctgtttg gtaattgcct gagcgttttt cagcgtgatg caagcggtca tgaacgtcat   2520
attgatcgta ccctgaatgt tattggtagc ggttttcagc accagaaata ctttgcagat   2580
ctggaagaaa gcattctgag cgtgtttaat cagctgccgc tggaagaaca gccgaaatac   2640
attaccgata tgggttgtgg tgatggcacc ctgctgaaac gtgtttggga aaccattcag   2700
tttaaaagcg cacgtggtaa agcactggaa cagtatccgc tgcgtctgat tggtgttgat   2760
tataatgaag caagcctgaa agcaaccacc cgtaccctgg caagcctgcc gcatctggtt   2820
ctgcagggtg atattggtaa tccggaacaa atggttcgta gcctggaagc acatggcatt   2880
catgatccgg aaaatattct gcatattcgc agctttctgg atcacgatcg tctgtttatt   2940
ccgcctcaga aacgtaatga actgaaagaa cgtgcccatc tgccgtatca gagtgtttgt   3000
gttgatgatc agggtgaact gattcctccg catgttatgg ttcagagcct ggtggaacac   3060
ctggaacgtt ggagccaggt tgttaataaa catggtctga tgattctgga agtgcattgt   3120
ctggaaccgc gtgttgttta tcagtttctg gataaaagcg aaaacctgca ctttgatgca   3180
tttcagggtt ttagccagca gtatctggtt gaagccgaag tttttctgat gagcgcagca   3240
caggttggtc tgtttccgaa actggaactg agcaaacgtt atccgaaaac ctttccgttt   3300
acccgtatta ccctgaacta tttcgaaaaa cgtccgtaca aaatcagcca tgcatatctg   3360
agcgatctgc ctgcactggt tgacctggaa gttaaatgtt ggcctgagaa tctgcgtgca   3420
agcacccatg aaattcgtcg tcgtctggaa ctgaatccgc agggtaacct ggttctgatt   3480
attgaagatc agattatcgg tgccatttac agccagacca ttacaagcac cgaagccctg   3540
gaaaatgtta aatatgcaca ggttccgacc ctgcatacac cgcagggttc agtgattcag   3600
ctgctggccc tgaacattct gccggaattt caggcacgtg gtctgggcaa tgaactgcgt   3660
gattttatgc tgtattattg caccctgaaa ggtggtattg aaagcgttgt tggtgttacc   3720
cgttgtcgca attatgtgaa ttatagccag atgccgatga tggaatatct gaaactgcat   3780
aatgaacagc gtcaactgct ggatccgatt gttggttttc atgttagcgg tggtgcagaa   3840
attcgtggca ttattgcaaa ttatcgtccg gaagatacag ataatctggg tatgggtatt   3900
ctgatcgaat ataacctgcg tgatagcgca ctgcattcac cgggtgatcg taaaggtccg   3960
tatatcaata gcgcaattgg tagcctggtt ccgaaagcga ccagcgcaac caaagaaaac   4020
aaaaccgttg cggatctggt gaaagaatgt attctgaaag tgatgggtag ccagcgtcag   4080
gcagcatatg caccgcagca gaaactgctg gacatgggtc tggatagcct ggatctgctg   4140
gaactgcaga ccctgctgga agaacgtctg ggtattaatc tgagcggcac ctttttttctg   4200
caaaaaaaca ccccgaccgc catcattacc tattttcaga atcaggtcgt gcaagagaaa   4260
cagagtgatc tggcaccgcc tgttgatagc gccaatgaaa tcaatacact ggaaaacgtt   4320
gtgaatcagc agaaaattcc gcaggttaca cgtgttgtta ccgaacagca gggacgtaaa   4380
gttctgattg atggtcattg ggttattgat tttgccagct gtaattatct gggcctggac   4440
```

-continued

```
ctgcatccga aagttaaaga agcaattcct ccggcactgg ataaatgggg cacccatccg   4500
agctggaccc gtctggttgc aagtccggca atttatgagg aactggaaga ggaactgtca   4560
aaactgctgg gtgtgccgga tgttctggtt tttccggcag ttacactgct gcagattggt   4620
attctgcctc tgctgaccgg taataatggt gtgatttttg gcgatattgc agcccatcgt   4680
tgtatttatg aagcatgttg tctggcccag cataaaggtg cacagtttat tcagtatcgt   4740
cataacgacc tgaatgatct ggccgaaaaa ctggccaaat atccgcctga acaggttaaa   4800
atcattgtga tcgatggtgt gtatagcatg agtgccgatt tcccggacct gcctgcatat   4860
gttcatctgg caaaagaata taacgccctg atctatatgg atgatgcaca tggctttggc   4920
attctgggtg aaaatccgag cagcgatatg ccgtatggtt ataaaggtaa tggcatggtg   4980
aactactttg atctgcgttt tgccgaagat aacatcattt atgttgcagg tctgagcaaa   5040
gcctatagca gctatgcagc atttctgacc tgtggtgatc gtcgtattaa aaccaatttt   5100
cgtaatgcat ggaccgcgat ttttagcggt ccgagtccgg ttgcaagcct ggccagcgca   5160
ctggcaggtc tgcaggttaa tcgtcaagaa ggtgaacagc tgcgcaaaca aatctatcat   5220
ctgacacata aactggttac ccaggctcgt gccattggtt ttgaagttga taattatggt   5280
tatgtgccga ttgtgggtgt tctggtgggt gatgcacagc atatgattga tgtgtgccaa   5340
ctgctgtggg aatatggtat cctgattacc cctgcaattt ttccgattgt gccgctgaat   5400
aaatcagcac tgcgttttag cattaccgca gcaaataccg aagaagaaat tgatcaggcc   5460
atcaaaagtc tgaaagcagt ttgggacctg ctgcaaaaac gtaaagccct gccgtgtaaa   5520
caagaagaaa atatcctgaa acattgagaa ggagatatac atatgaccca tgttgccctg   5580
gaacaggcaa ttgcaaaagt tccgcgtagc attcagagcg aactgcgtac cattctggca   5640
cagcatgcag ttattgatag cagcgttgtg gcaagctgga ttgatcgtct gggcaccaat   5700
attagtaccc tgatgatcca gctgctgccg gttgcagcaa cctatgcacg tgttccgatt   5760
agccagtttt atgttggtgc cattgcactg ggcaaaccgc agagtaaaaa tcagctgggt   5820
agcggcaccc tgtattttgg tgcagatatg gaatttgttg gtcaggcact gagctttagc   5880
gttcatgcag aacagagcgc caccattaat gcctggctgc atggcgaaac cggactgcag   5940
gcactggcaa tccatgaagc accgtgtggt tattgtcgcc agtttctgta tgaaatggca   6000
accgtgaatc agaattttgt gctgctggtg aaaagcaatg aaagccagcc ggaacagacc   6060
tataccagca acaaactgcc gcattttctg cctgaaccgt ttggtccagc cgatctgggt   6120
ctgaccggtg gcctgatgca gaccgtgttt cacgatctgg aaacctatag caccgatgat   6180
gttgttctgg cagcactgag tgcagcaaat cagagttatg caccgtatac caaaaacttt   6240
gccggtgttg cactgaaaga tagtcatggt aacattttta caggtcgcta tgccgaaaac   6300
gcagcattta atagcagcat gagcccgatg gaaagcgcac tgacctttat gaatatgaat   6360
cgttattcac agagcctgtt cgatatttgt gatgcagttc tggtagaagt ggaaaccggt   6420
attagtcagc gtccggttac cgaagccttt ctgagtagca ttgcaccgaa agtgaaactg   6480
cgctatgcac cggcaacccc gagcagtaac aaactgtgag aaggagatat acatatgttt   6540
cagaccaaaa gctattatag cgtcgttggc ctggaaaccg aactgattaa aggtaaattc   6600
ttcatgagca acgaactgac caatgaacag gtgtttaaac tggtgtgcat ggaagtgatt   6660
gaaaaaatgg gttttgcaca ctttccgcct attatcctgg tttatgaaat gaccaattcc   6720
ggctttgttg attggtgcga gcagatggtt tttgtggatg ataaaggcaa actggatgag   6780
```

-continued

```
ggcgaaaaat ttctgctgga ttggatgcgt cgtaatgtgg gtaattttga tctgattcgc   6840

gaactgatgc cggtggcaga acgcctggaa atgaaaatgc gtagctaact cggtaccaaa   6900

ttccagaaaa gaggcctccc gaaagggggg ccttttttcg ttttggtccc gaagttccta   6960

ttctctagaa agtataggaa cttcgaccgc ctgtctattt ctcttacggt tccaacatcc   7020

atataggccg caatt                                                    7035
```

<210> SEQ ID NO 92
<211> LENGTH: 12758
<212> TYPE: DNA
<213> ORGANISM: Artificial Sequence
<220> FEATURE:
<223> OTHER INFORMATION: Sequence of sxt3 fragment version 1 integrated into the E. coli xylose operon

<400> SEQUENCE: 92

```
ttgcatttcc ttgagcctta tccgacttgt cagtcggata aggcttttta ctttgtctca     60

ggcagttgag ctacgagcct gaagcgttgt tggtgcgttt tatcatgcct ggcgggtagg    120

tcggataagg cgttcacgcc gcatccgaca accacgcagc gttacctgat gtgacgccga    180

caattctcat catcgctaca acatgacctc gctatttaca tcgcgatact cttttggcgt    240

cgtgtcatat gctttttttaa aaacagagta gaaatattgc agcgatggat aaccgcacat    300

ttgcgatatc tcattgatcg acaaggtggt tgaaatcagc agactgcgcg ctttctccag    360

cttctcggca tgaatcatgg catggatggt ttcacccacc tcttctttaa aacgcttctc    420

aagattggag cgcgagatcc cgaccgcatc cagtacctga tccactttaa tccctttaca    480

ggcgtgatta cgaatgtaat gcatggcctg aataacggcg ggatcggtca gcgagcgata    540

atctgttgag cgccgttcaa tgacgcgaac tggtgggacc aaaattcgct gtagcggcat    600

ttcttcttta tctaataatc gatgcaacag ttttgccgcc tgatagccca tttgccgcgc    660

gccctgagcg accgaagaaa gggcgacacg cgacagatag cgggtcagtt cttcgttatc    720

gatgccaatc acgcataatt tttccggtac gggaatatgt agatgttcac atacttgcag    780

aatatgccgc gctcgggcgt cagtaacggc aataatcccg gtttgcggtg gtagcgtttg    840

tagccagtct gccagccgat tttgcgcgtg ttgccagttc tctggcgcgg tttctaaccc    900

ctgataaacc actccgcgat acttttcttc ggcgacaagc tgacgaaatg catattcgcg    960

ctcagtggcc caacgtttgc cgcttgattc cggaagacca taaaaagcaa agcggttaac   1020

gcctttctct tttaaatgca aaaatgcgct ttcaaccagc gcatagttat cggtggcaat   1080

gtaatgaacg ggtgggtaac tttctgcaag gtgatacgag ccgccaaccc caacaatggg   1140

gacgtcgaca tcagccagcg cttgctcgat ctgtttgtcg tcgaagtcgg caatgacgcc   1200

atctcctaac cagtccttga ttttatcaat gcgggcgcgg aaatcttctt caatgaaaat   1260

atcccattcc gattgtgacg cctgtaaata ttcccctacg ccttctacta cctgccggtc   1320

ataggcttta ttggcattga acagtaatgt gatgcggtga cgtttagtaa acatggttct   1380

tttcctgctg aatcatgcaa aaactcaaaa ccggtaatac gtaaccggct ttgagaaaat   1440

ttttatcaaa atcaagaacg gcgtttggtt gcggagtcca tccatactgc cagcaacaga   1500

atcgcacctt taacgatata ctgccagaag gtcggtacat ccatcatact catgccgtta   1560

tccagtgaag ccatgataaa tgcccccatt actgctccgg caacgcttcc cacaccgcca   1620

gccaggctgg tgccgccaat cacgcatgct gcaattgcgt ccagttcggc gatatttccc   1680

gcagaaggtg aaccagcgcc aagtcgagaa ctaaggatta atccggcgat ggctaccatt   1740
```

-continued

```
aatccgttaa tcgcgaacac ggcaagtttg gtgcgttcaa cgttaatccc ggagagacgt   1800

gctgcttcca gattgccgcc gatggcataa atgcgtcgtc caaatgccgt ccgcgtttcc   1860

ataaacattc cgccgagtaa cagcaacgtc agcagcagaa caggagtggg aacgccacgg   1920

taatcattca acagccagat tgcgcctaat acgatgatag cggttaaagc ctggcgaccg   1980

actactgcgg tagaggccgg agactgcaaa cccaaagcct gacggcgcat tcttccgcgc   2040

cattgccaac caacaaaagc cattaagcca agcgcgccaa tgatgaagcc agtgctggca   2100

ggtagatagc tttgcccaat ttgtgacatc gcggcgctgg tgggggaaac agtcgtgccg   2160

ttggtgatgc caatgagtat gccgcgaaat gccaacatgc ccgcgagggt gacaataaat   2220

gaagggactt tgcggtacgc gacccaccat ccgttccagg caccgagaag cagtcccaga   2280

accaacgtca caatgatggt aagtggcaaa ggccagccta accagacgtc acaaatcgcc   2340

gcgacgccac ctaatagccc catcattgag ccgacggaaa ggtcgatttc agcagaaatt   2400

atgacgaaca ccattcctac cgcgaggatg ccggtaatcg cggtctggcg taacaggttg   2460

gagacgttac gggcgcttaa gtaggcacca tcggtggtcc aggtaaagaa cagcatgatt   2520

gcgatgatag ctgcaatcat cacgaagacc tgcaaattca gtgatttcag cccggagaag   2580

ctaccggatg tcggtacggc caatttcact tcagacggat tgcttttcga catgatgttc   2640

gctcctcaat gcggcttcca tcacctgctc ctgagtcagg ttatgattta tcaggttggc   2700

ttttagtttc ccttcatgca tcaccagtac acgatcgcta aggccgagca cttcaggtaa   2760

ttcggaagag atgacaataa cggcaatacc ctgctggacg agttggttaa ttaatttgta   2820

gatctcgtat ttcgcgccaa tatcgatacc cctggtgggt tcatcaagaa tgagaatgcg   2880

cgggttaagt aacagacagc gagcgaggat cgctttttgc tgattgccgc cgctcaaacg   2940

tccaatagca aggtcggggg acgacgtttt aactttgagt tgctggattg attccagaat   3000

acatttttgc tctgccgcgt catcaagctg gctaatgcca ccggtaaatt tattgagtcg   3060

gcgagggtaa tatttttacc aaccgccatt accggaacga tgccgtcgcg ctttctgtct   3120

tcgggtacca tcgcaatccc ctgggcgatg gcttgctgac agttacgaat atctacctgt   3180

ttgccatcaa tataaatttt tccttcccat tgtccgggcc acacgccaaa caggcactga   3240

atggtctcgg tacgtccggc accaacgagt ccggcaatac ccagtatttc gccacgtttc   3300

agggaaaacg agacatcatt aactcgttta atatgacgat tgaccggatg ccatgccgtc   3360

agatgttcaa tacgtaatat ttcatctccg gtggtatgtg gttcattagg gtaaagcgcg   3420

gttaactctc gcccgaccat catggtgata atatcgtctt cactcattcc ggcagcatca   3480

cgcgtaccaa tgtgctgtcc gtcgcgaata acgcaaatcg tatcggaaat cgctttgact   3540

tcgttgagtt tgtgcgaaat ataaatacag gcgataccgt gctgttgtag atcgcgaata   3600

atatccagta aaaccgacgt ttcctgctca gttaatgagg ctgtcggttc atcgagaatt   3660

aacaagcgca cctgtttatt aagtgccttg gcaatttcaa ccagttgttg ttgcccaagc   3720

cctaaatcgc caacgcgggt atcaggtgaa atggataaac tgacctgtgc gagcagcttc   3780

tgacagcgta gcgtcatcag gtcataatcc ataatgccat tgtgggttat ttcgttaccc   3840

aggaagatat tttccagcac ggtcaattct ttcaccaggg ccaattcctg atgaatgatg   3900

gcgatacctt tgcgttcggt atcgcggatg tgactcgcct gaatctcttc tcccgcaaaa   3960

ataatttcgc cttcgtagga gccatgggga taaataccac acagcacttt catcagcgtt   4020

gatttaccag acccattttc cccacaaagt gagacgattt cgccagcatt caaccgcaag   4080

cagacgttat caatcgcctt cacactgccg aaggttttgg taatgttctt catttcaagt   4140
```

```
agataaggca taacgactcc acctaagcca attcattcac gcggcatgga gagaaatcac   4200
gcccccgctc cgcgccgggc gtaacgctta cagctcgctc tctttgtgga atccgtcttt   4260
aattaccgta tctttgatgt tgtttttatt cacatcgatc ggtgtcagga ggcgggaggg   4320
gacatctttc aggccattat tcagtgaggt ccagccttgc aagaagcgga tacaggagtg   4380
caaaaaatgg ctatctctag aaaggcctac cccttaggct ttatgcaaca gaaacaataa   4440
taatggagtc atgaacatat ggtgattaaa aacctgtgtc cggatggtgt taccccgatt   4500
tggaataaaa gccagatgga aagcagcctg ctggaagaat gtctgcctgc atgggttcgt   4560
accagctata gcacctttgt tgaaaccatt agcgatagcg catttccgtg tttttggggc   4620
accattggtg aacagaaagg tatgattcgt tatctgattg ttagcagcct gaccgatccg   4680
attctggttg aacataccct ggaaggtatc tacaaatata tcgatgaagt gaacgaaaac   4740
gaactgctgc agcatgaaaa tgcagatctg ctgaccctgg ttatcttttt tccgcctgaa   4800
ccgaccgttc tgaccgttga agaatatgca ggtcaggcat ttgattttct gaatgcactg   4860
catagcctgg atgcagttag ctgtccgtgt cattggagcg cagatccgca gagcgcaaat   4920
tggagctata gcctgggtgg ttgtgcactg tttgttagcg ttagcacacc ggcaaatcag   4980
aaacgtcgta gccgtcatct gggtagcggt atgacctttg ttattacacc ggttgaagtg   5040
ctgctgaata aacatggtgg tgaaaaacagc agcatttttc gtcgtgttcg tgaatatgat   5100
ggtattccgc ctcatccgaa tctgctgatt atgcctggta atggtaaagt gggtaatgaa   5160
ctgaccgtgc aggttctgcc ggataataat gatagcgaaa tcagcttcga ttttcagtat   5220
aaattcaaag attgagaagg agatatacat atgaccatcc agattgtgca gcataacctg   5280
gaatatagct ttgtgacccc gaaagaaacc agcgattttg ttgaacgtac catgagcgtt   5340
tttgatcagg catatccgaa atttctgatc catgatgttt gggcagatcc ggcaagcctg   5400
gccctgtttg aaatttatcc ggaatttcag tttggtctgg tggaagcaac cacccagctg   5460
atgattgcac agggtaattg tattccgctg acctatgaaa gccgttttga tgaactgccg   5520
gatgaaggtt gtgattgggc actggcaaaa tggctggaag atcgcgaaca gaatcgtctg   5580
ccgaatgccc tgtgtgttgt gagcattagc atcctgccgg aatatcaggg taaaaatctg   5640
agccagtatc tgatcggcta tatgaaagaa ctggcacagt atcatggtct gaatagcctg   5700
attatggcag cacgtccgag cctgaaatat ctgtatccgc tgattccgat tgaacgctat   5760
attacctggc gtgataaaaa cggcctgatt tttgatccgt ggctgcgtgt taatgttaaa   5820
catggcgcaa aaattgccgg tatctgcttt aaaagcacca ccattaatga taccattgat   5880
ggttgggagg atcgtgttgg tatgcgtttt ccggaaaccg gtgattatat cattccgaaa   5940
ggtctggttc cggtgaaaat tgattatccg aataacatgg gcatctacat cgaaccgaat   6000
atctggctgt attatgatct ggactgagaa ggagatatac atatgatcaa catcgaacag   6060
tttcgccaag aaatcgaaga ttggattatt aacgttgtca gcattccgaa cccgctgacc   6120
ggtaattttc ctccgtgtcc gtatgcaaaa gcagcatggc tgaataatcg tgttagcgtg   6180
cgttggtttc atggtccgga actgcctgaa ctgctgatgg aacaaattcg tacatggaac   6240
aacgatttcg agatggtgat ttttggttgc gatcctcaga atctggatgc acagcgtctg   6300
gaacgttata tcaccaaagc aaattatgtg ctgcccgaat atgacctggt tgcactgggt   6360
agccatccgg ataaacagta tgttggtgat gatgccgaaa atgtgaacaa cgtgattatt   6420
acccatccga aatatgttct ggcaagcgtt cagagcttta gccagctgca agaggcaagt   6480
```

gatgagctgc tgcgtctggg ttatttccag tattggtcag cagaaaaact ggccgaaatg 6540
aaaagcgaac gtgcaagcca taatctgagc agcattcagc gtaaaaatag ctatcgtatt 6600
atcccgacca accattgaga aggagatata catatgctga ccgcagaaca gaaacaggca 6660
tataccaatg atggctattt taccgtggaa gaagcagttc cgaaagcact gattgaagaa 6720
attcgccatg aagtggaact gatcaccgag cagaaacgtg gtggtgtgct ggcaggcgat 6780
tatgaatggt ggtcagaaca caccattccg gatccggttc gttatcagaa aattatccag 6840
cgtctgctgg aactgccgac cgttatgggt ccggttcagg ccctgattgg tagcgatatt 6900
tttctgttaa ttaccgacct ggcaattatt cgtgcaggca ccggttatat tgcatggcat 6960
caggatcatg gctatgttgt tgaagttctg aacgccctgg caagcatgag caaaaatgag 7020
ctgaatgatg atgcactgcg cctgctggtg ccggttgcaa atcaggcaat ggtgtttatt 7080
accatctatc tgcaggatac cgataacacc atgggcacca tgcgtgtgat tccgagcagc 7140
catcagtggg aacatagtct ggatagcagc agcgccaatt cactgaatgc agaaatttgt 7200
ctgagcctgc ctggtggtgc agcaatgttt tataccccga ccgtttggca taccgcagca 7260
gcaaatacca gcattaccga ttatcgtatg ctgacgctga tcttcaccaa aaacaacatt 7320
aaaccgctgc tggttgatgc cctgaaacgt attatttgag aaggagatat acatatgaca 7380
accaccgatc cgatcctgat taataactgg catgttgtgg caaatgtcga ggattgtaaa 7440
ccgggtagca ttacccgtag ccgtttactg ggtgttaaac tggttctgtg gcgtagctat 7500
gaacagaata gcccgattca ggtttggctg gattattgtc cgcatcgtgg tgttccgctg 7560
agcatgggtg aaattaccaa taataccctg gtttgtccgt atcatggctg gcgttataat 7620
gaagcaggta aatgtattca gattccggca catccgggta tggttccgcc tgcaagcgca 7680
gaagcacgta cctatcatag ccaagaacgt tatggtctgg tttgggtttg tctgggtgat 7740
ccggttaatg atattccgtc atttccggaa tgggatgatc cgaattatca caaaacctac 7800
accaaaagct atctgattaa agcaagcgcc tttcgcgtta tggataattc actggatgtt 7860
agccatttc cgtttattca tgatggctgg ctgggcgatc gtaactatac caaagtggaa 7920
gaatttgaag tgaaactgga taaagatggt ctgacgatgg gcaaatatca gtttcagacc 7980
agccgtattg tgagccatat tgaagatgat agctgggtga attggtttcg tctgagccat 8040
ccgctgtgtc agtattgtgt tagcgaaagt ccggaaatgc gtattgttga tctgatgacc 8100
attacgccga ttgatgaaga aaatagcgtt ctgcgcatgc tgatcatgtg gaatggttat 8160
gaaaccctgg aaagcaaaat gctgacagag tatgatgaaa cgatcgaaca ggatattcgt 8220
attctgcatg cccagcagcc ggtgcgtctg ccgctgctga caccgaagca gattaatacc 8280
cagctgttta gccatgaaat tcatgttccg agcgatcgtt gtaccctggc atatcgtcgt 8340
tggctgaaac aactgggtgt gacctatggt gtttgttgag aaggagatat acatatggca 8400
ggtaaactgg atggtaaggt tgcaattatt accggtgcaa gcagcggtat tggtgaagcc 8460
accgcatttg cactggcagc agaaggtgca aaagttgcaa ttgcagcccg tcgtgcagaa 8520
ctgttacatg cactggccaa acgtattgaa gcaagcggtg gtcaggcact gccgattgtt 8580
accgatatca ccgatgaaag ccaggttaat catctggttc agaaaaccaa agttgaactg 8640
ggtcatgttg atatcctggt gaataatgca ggtattggcg tttttggtgc aatcgatacc 8700
ggtaatccgg cagattggcg tcgtgcattt gatgttaatg tgctgggtgt tctgtatgca 8760
attcatgcag ttctgccttt actgaaagca cagaaaagcg gtcatattgt gaatattagc 8820
agcgtggatg gtcgtattgc acagagcggt gcagttgttt atagcgcagc aaaaagcggt 8880

-continued

```
gttaatgccc tgagcgaagc actgcgtcaa gaagtgagcc tggataatat tcgtgtgacc   8940
attattgaac cgggtctggt agataccccg tttaatgatc tgattagtga tccgattacc   9000
aaacagctga gcaaagaaca gctgtcaacc attactccgc tgcagagcga agatattgca   9060
cgtgccatta tctatgcagt tacccagccg gatcatgtta acgttaatga aattctgatt   9120
cgtccgaccg cagaggataa ttgagaagga gatatacata tgaacctgac cctgaacaaa   9180
gaagaaaaac agctgctgac ggcatatagc ggcaccgaac tgcagctgac agcagatgtt   9240
ctggttattg gtggtggtcc ggcagccgca tgggcagctt gggcagcagg cgcacagggt   9300
gtgaaagtta ttattgtgga taaaggtttt ctgggcacca gcggtgccgc agccgcaagc   9360
ggtaatagcg ttatggcacc gtcaccggaa aattgggaaa aagatgtgag cgaatgttac   9420
agcaaaggta ataatctggc aaatctgcgt tggattgaac gtgttattga aaaagcctgg   9480
ctgtcactgc cgctggttga agattggggt tatcgttttc ctaaagaaaa tggtgaaagc   9540
gtgcgtcaga gctattatgg tcctgaatat atgcgtgttc tgcggaaaaa tctgctgcgc   9600
gttggtgttc agatctttga tcagtcaccg gcactggaat tactgctggc acaggatggt   9660
agcgttgccg gtgcacgtgg tgtgcagcgt cagaatcatc gtacatatac cgttcgtgcc   9720
ggtgccgttg ttctggccaa tggtggttgc gcatttctga gtaaagcact gggttgtaat   9780
accaataccg gtgatggtct gttaatggca gttgaagccg gtggtgaact gagcagtatg   9840
gaagccagca gccattatac cattagcacc gcctttaatg caaccgttac ccgtgcagct   9900
ccgtttttatt gggcaagcta taccgatgaa gctggcaatg atctgggtgg ctatattaac   9960
ggtcgtcgtg atccgagctt tctgccgaac gcactgctga aaggtccggt ttatgcacgt  10020
ctggatcgtg caacaccgga aattcaggcg ctggtagaaa aaagccattt tattgcattt  10080
ctgccgtaca agaaagccgg tattgatccg tataccgaac gtgttccggt taccctggtg  10140
ctggaaggca ccgtgcgtgg caccggtggt attcgcattg ttaatgattc atgtggcacc  10200
aaagttccgg gactgtatgc agcgggtgat gcagcaagcc gtgaatttct ggcaggcatt  10260
gccagcggtg gtgatggacc gaatgcagca tgggcaattt caaccggtca gtgggcaggc  10320
gaaggtgcag cagcctttgc aaaaagtctg ggtgcacatg ttcatgaacg cgttgttcgt  10380
ccggcaggcc aggcaggtct gcgtagtcag tatccgggta gcgaaacctt tgatagtgaa  10440
gcagttgttc gtggcgttca ggcagaaatg tttccgctgg aaaaaaacta tctgcgctgt  10500
gaacagggac tgctggatag cctggcaaaa ctggaaatgc tgtggcagca ggttcagggt  10560
aatccgaaac aggatacagt tcgtgatctg gaattttcac gtcgtgcggc agcactggtt  10620
agcgtggcac gttgggcata ttttagcgca ctgcatcgta aagaaacccg tagcgaacat  10680
atccgtattg attacccgga aacggatccg aatcaactgt attatcaggc aaccggtggc  10740
ctggaacgtc tgtgggtgcg tcgtgattgg gttaaagatg caagcgccac ccctccggtg  10800
ctgaccacct gagaaggaga tatacatatg attgaactgg tgagccataa gctgtgcatt  10860
aattgtaatg tttgtgttca ggtgtgcccg accaatgttt ttgatgcagt gccgaatcag  10920
cctccggcaa ttgcacgcca agaagattgt cagacctgtt ttatttgtga agcatattgt  10980
cctgcagatg cgctgtatgt tgcaccgcag agccatacca atgttgcagt taacgaagat  11040
gatttaatcg acagcggcat tatgggtgaa tatcgtcgca ttctgggttg gggctatggt  11100
cgtaaaaaca atagcgaact ggataccgac cataaactgc gtctgtttga atgagaagga  11160
gatatacata tgtcatttca gaaatttgtg caagaagcag cctataaagt cgcaccgttt  11220
```

```
aaaccgaatc gttttgccaa aattagcgag cgtgaagata aatgtgcaat tccggttccg  11280

gcatggcgtg cactgctggc caatcgtgac ctgtttacct ggaaaggtat tccgtttctg  11340

aaaggttgta ccgaaattgc actgtatagc atgctgctgt atgaactgcg tccgaaaacg  11400

attattgaaa ttggtgcgct gagcggtggt agcgcaattt ggctggcaga tcatctggaa  11460

ctgtttcaga ttgaaggttg cgtgtattgc attgatattg atctgtctct gctggacgaa  11520

aaagcaaaaa ccgatagccg tgttcatttt ctggaaggtg attgcaataa tatgggtgca  11580

attatgtcaa gcgagctgct gagtggtctg gcacatcctt ggctgattgt tgaagatgca  11640

catgcaaatg ccgttggtgt ggttgaatat tttcacgaaa acggtctgaa aagtggcgat  11700

tacctgatcg tggaagatac caataaaaca atgtgggaac tggatcgcga agaactggac  11760

cgtgatgacc tggatgaaca agaactgatc gaaaaaggtg agcagaaatt agcagaactg  11820

aaaagctggc tgatgctgca tgagaatgaa tatctgatag atacctacta tcaggatatg  11880

tatggctata atggtagccg taattggaac agcattctga aacgtgtgga aaagaacttt  11940

taatctaact aaaaacaccc taacgggtgt tttttctttt ctggtctccc cgaagttcct  12000

attctctaga aagtatagga acttcgctgg attgggccgc gaaattaacc ggcctgagca  12060

atgtcccagc tttaatcgct gcagctcaac aggctgatga aagtgccgag ccagtttggt  12120

ttctgcctta tctttccggc gagcgtacgc cacacaataa tccccaggcg aagggggttt  12180

tctttggttt gactcatcaa catggcccca atgaactggc gcgagcagtg ctggaaggcg  12240

tgggttatgc gctggcagat ggcatggatg tcgtgcatgc ctgcggtatt aaaccgcaaa  12300

gtgttacgtt gattgggggc ggggcgcgta gtgagtactg gcgtcagatg ctggcggata  12360

tcagcggtca gcagctcgat taccgtacgg gaggggatgt ggggccagca ctgggcgcag  12420

caaggctggc gcagatcgcg gcgaatccag agaaatcgct cattgaattg ttgccgcaac  12480

taccgttaga acagtcgcat ctaccagatg cgcagcgtta tgccgcttat cagccacgac  12540

gagaaacgtt ccgtcgcctc tatcagcaac ttctgccatt aatggcgtaa acgttatccc  12600

ctgcctgacc gggtggggga taattcacat ctatatatct cagtaattaa ttaatattta  12660

gtatgaattt attctgaaaa tcatttgtta atggcatttt tcagttttgt ctttcgttgg  12720

ttactcgtaa tgtatcgctg gtagatatgg agatcgtt                          12758
```

<210> SEQ ID NO 93
<211> LENGTH: 7185
<212> TYPE: DNA
<213> ORGANISM: Artificial Sequence
<220> FEATURE:
<223> OTHER INFORMATION: Sequence of sxt3 fragment version 2 integrated into the E. coli xylose operon

<400> SEQUENCE: 93

```
ggtgtcagga ggcgggaggg gacatctttc aggccattat tcagtgaggt ccagccttgc     60

aagaagcgga tacaggagtg caaaaaatgg ctatctctag aaaggcctac cccttaggct    120

ttatgcaaca gaaacaataa taatggagtc atgaacatat ggtgattaaa aacctgtgtc    180

cggatggtgt taccccgatt tggaataaaa gccagatgga aagcagcctg ctggaagaat    240

gtctgcctgc atgggttcgt accagctata gcacctttgt tgaaaccatt agcgatagcg    300

catttccgtg tttttggggc accattggtg aacagaaagg tatgattcgt tatctgattg    360

ttagcagcct gaccgatccg attctggttg aacataccct ggaaggtatc tacaaatata    420

tcgatgaagt gaacgaaaac gaactgctgc agcatgaaaa tgcagatctg ctgaccctgg    480
```

```
ttatcttttt tccgcctgaa ccgaccgttc tgaccgttga agaatatgca ggtcaggcat    540
ttgattttct gaatgcactg catagcctgg atgcagttag ctgtccgtgt cattggagcg    600
cagatccgca gagcgcaaat tggagctata gcctgggtgg ttgtgcactg tttgttagcg    660
ttagcacacc ggcaaatcag aaacgtcgta gccgtcatct gggtagcggt atgacctttg    720
ttattacacc ggttgaagtg ctgctgaata aacatggtgg tgaaaacagc agcatttttc    780
gtcgtgttcg tgaatatgat ggtattccgc ctcatccgaa tctgctgatt atgcctggta    840
atggtaaagt gggtaatgaa ctgaccgtgc aggttctgcc ggataataat gatagcgaaa    900
tcagcttcga ttttcagtat aaattcaaag attgagaagg agatatacat atgaccatcc    960
agattgtgca gcataacctg gaatatagct ttgtgacccc gaaagaaacc agcgattttg   1020
ttgaacgtac catgagcgtt tttgatcagg catatccgaa atttctgatc catgatgttt   1080
gggcagatcc ggcaagcctg gccctgtttg aaatttatcc ggaatttcag tttggtctgg   1140
tggaagcaac cacccagctg atgattgcac agggtaattg tattccgctg acctatgaaa   1200
gccgttttga tgaactgccg gatgaaggtt gtgattgggc actggcaaaa tggctggaag   1260
atcgcgaaca gaatcgtctg ccgaatgccc tgtgtgttgt gagcattagc atcctgccgg   1320
aatatcaggg taaaaatctg agccagtatc tgatcggcta tatgaaagaa ctggcacagt   1380
atcatggtct gaatagcctg attatggcag cacgtccgag cctgaaatat ctgtatccgc   1440
tgattccgat tgaacgctat attacctggc gtgataaaaa cggcctgatt tttgatccgt   1500
ggctgcgtgt taatgttaaa catggcgcaa aaattgccgg tatctgcttt aaaagcacca   1560
ccattaatga taccattgat ggttgggagg atcgtgttgg tatgcgtttt ccggaaaccg   1620
gtgattatat cattccgaaa ggtctggttc cggtgaaaat tgattatccg aataacatgg   1680
gcatctacat cgaaccgaat atctggctgt attatgatct ggactgagaa ggagatatac   1740
atatgctgac cgcagaacag aaacaggcat ataccaatga tggctatttt accgtggaag   1800
aagcagttcc gaaagcactg attgaagaaa ttcgccatga agtggaactg atcaccgagc   1860
agaaacgtgg tggtgtgctg gcaggcgatt atgaatggtg gtcagaacac accattccgg   1920
atccggttcg ttatcagaaa attatccagc gtctgctgga actgccgacc gttatgggtc   1980
cggttcaggc cctgattggt agcgatattt ttctgttaat taccgacctg gcaattattc   2040
gtgcaggcac cggttatatt gcatggcatc aggatcatgg ctatgttgtt gaagttctga   2100
acgccctggc aagcatgagc aaaaatgagc tgaatgatga tgcactgcgc ctgctggtgc   2160
cggttgcaaa tcaggcaatg gtgtttatta ccatctatct gcaggatacc gataacacca   2220
tgggcaccat gcgtgtgatt ccgagcagcc atcagtggga acatagtctg gatagcagca   2280
gcgccaattc actgaatgca gaaatttgtc tgagcctgcc tggtggtgca gcaatgtttt   2340
ataccccgac cgtttggcat accgcagcag caaataccag cattaccgat tatcgtatgc   2400
tgacgctgat cttcaccaaa aacaacatta aaccgctgct ggttgatgcc ctgaaacgta   2460
ttatttgaga aggagatata catatgacaa ccaccgatcc gatcctgatt aataactggc   2520
atgttgtggc aaatgtcgag gattgtaaac cgggtagcat tacccgtagc cgtttactgg   2580
gtgttaaact ggttctgtgg cgtagctatg aacagaatag cccgattcag gtttggctgg   2640
attattgtcc gcatcgtggt gttccgctga gcatgggtga aattaccaat aataccctgg   2700
tttgtccgta tcatggctgg cgttataatg aagcaggtaa atgtattcag attccggcac   2760
atccgggtat ggttccgcct gcaagcgcag aagcacgtac ctatcatagc caagaacgtt   2820
atggtctggt ttgggtttgt ctgggtgatc cggttaatga tattccgtca tttccggaat   2880
```

```
gggatgatcc gaattatcac aaaacctaca ccaaaagcta tctgattaaa gcaagcgcct   2940
ttcgcgttat ggataattca ctggatgtta gccattttcc gtttattcat gatggctggc   3000
tgggcgatcg taactatacc aaagtggaag aatttgaagt gaaactggat aaagatggtc   3060
tgacgatggg caaatatcag tttcagacca gccgtattgt gagccatatt gaagatgata   3120
gctgggtgaa ttggtttcgt ctgagccatc cgctgtgtca gtattgtgtt agcgaaagtc   3180
cggaaatgcg tattgttgat ctgatgacca ttacgccgat tgatgaagaa aatagcgttc   3240
tgcgcatgct gatcatgtgg aatggttatg aaaccctgga aagcaaaatg ctgacagagt   3300
atgatgaaac gatcgaacag gatattcgta ttctgcatgc ccagcagccg gtgcgtctgc   3360
cgctgctgac accgaagcag attaataccc agctgtttag ccatgaaatt catgttccga   3420
gcgatcgttg taccctggca tatcgtcgtt ggctgaaaca actgggtgtg acctatggtg   3480
tttgttgaga aggagatata catatggcag gtaaactgga tggtaaggtt gcaattatta   3540
ccggtgcaag cagcggtatt ggtgaagcca ccgcatttgc actggcagca gaaggtgcaa   3600
aagttgcaat tgcagcccgt cgtgcagaac tgttacatgc actggccaaa cgtattgaag   3660
caagcggtgg tcaggcactg ccgattgtta ccgatatcac cgatgaaagc caggttaatc   3720
atctggttca gaaaaccaaa gttgaactgg gtcatgttga tatcctggtg aataatgcag   3780
gtattggcgt ttttggtgca atcgataccg gtaatccggc agattggcgt cgtgcatttg   3840
atgttaatgt gctgggtgtt ctgtatgcaa ttcatgcagt tctgccttta ctgaaagcac   3900
agaaaagcgg tcatattgtg aatattagca gcgtggatgg tcgtattgca cagagcggtg   3960
cagttgttta tagcgcagca aaaagcggtg ttaatgccct gagcgaagca ctgcgtcaag   4020
aagtgagcct ggataatatt cgtgtgacca ttattgaacc gggtctggta gataccccgt   4080
ttaatgatct gattagtgat ccgattacca aacagctgag caaagaacag ctgtcaacca   4140
ttactccgct gcagagcgaa gatattgcac gtgccattat ctatgcagtt acccagccgg   4200
atcatgttaa cgttaatgaa attctgattc gtccgaccgc agaggataat tgagaaggag   4260
atatacatat gaacctgacc ctgaacaaag aagaaaaaca gctgctgacg gcatatagcg   4320
gcaccgaact gcagctgaca gcagatgttc tggttattgg tggtggtccg gcagccgcat   4380
gggcagcttg ggcagcaggc gcacagggtg tgaaagttat tattgtggat aaaggttttc   4440
tgggcaccag cggtgccgca gccgcaagcg gtaatagcgt tatggcaccg tcaccggaaa   4500
attgggaaaa agatgtgagc gaatgttaca gcaaaggtaa taatctggca aatctgcgtt   4560
ggattgaacg tgttattgaa aaagcctggc tgtcactgcc gctggttgaa gattggggtt   4620
atcgttttcc taaagaaaat ggtgaaagcg tgcgtcagag ctattatggt cctgaatata   4680
tgcgtgttct gcggaaaaat ctgctgcgcg ttggtgttca gatctttgat cagtcaccgg   4740
cactggaatt actgctggca caggatggta gcgttgccgg tgcacgtggt gtgcagcgtc   4800
agaatcatcg tacatatacc gttcgtgccg gtgccgttgt tctggccaat ggtggttgcg   4860
catttctgag taaagcactg ggttgtaata ccaataccgg tgatggtctg ttaatggcag   4920
ttgaagccgg tggtgaactg agcagtatgg aagccagcag ccattatacc attagcaccg   4980
cctttaatgc aaccgttacc cgtgcagctc cgttttattg ggcaagctat accgatgaag   5040
ctggcaatga tctgggtggc tatattaacg gtcgtcgtga tccgagcttt ctgccgaacg   5100
cactgctgaa aggtccggtt tatgcacgtc tggatcgtgc aacaccggaa attcaggcgc   5160
tggtagaaaa aagccatttt attgcatttc tgccgtacaa gaaagccggt attgatccgt   5220
```

ataccgaacg tgttccggtt accctggtgc tggaaggcac cgtgcgtggc accggtggta 5280
ttcgcattgt taatgattca tgtggcacca aagttccggg actgtatgca gcgggtgatg 5340
cagcaagccg tgaatttctg gcaggcattg ccagcggtgg tgatggaccg aatgcagcat 5400
gggcaatttc aaccggtcag tgggcaggcg aaggtgcagc agcctttgca aaaagtctgg 5460
gtgcacatgt tcatgaacgc gttgttcgtc cggcaggcca ggcaggtctg cgtagtcagt 5520
atccgggtag cgaaaccttt gatagtgaag cagttgttcg tggcgttcag gcagaaatgt 5580
ttccgctgga aaaaaactat ctgcgctgtg aacagggact gctggatagc ctggcaaaac 5640
tggaaatgct gtggcagcag gttcagggta atccgaaaca ggatacagtt cgtgatctgg 5700
aattttcacg tcgtgcggca gcactggtta gcgtggcacg ttgggcatat tttagcgcac 5760
tgcatcgtaa agaaacccgt agcgaacata tccgtattga ttacccggaa acggatccga 5820
atcaactgta ttatcaggca accggtggcc tggaacgtct gtgggtgcgt cgtgattggg 5880
ttaaagatgc aagcgccacc cctccggtgc tgaccacctg agaaggagat atacatatga 5940
ttgaactggt gagccataag ctgtgcatta attgtaatgt ttgtgttcag gtgtgcccga 6000
ccaatgtttt tgatgcagtg ccgaatcagc ctccggcaat tgcacgccaa gaagattgtc 6060
agacctgttt tatttgtgaa gcatattgtc ctgcagatgc gctgtatgtt gcaccgcaga 6120
gccataccaa tgttgcagtt aacgaagatg atttaatcga cagcggcatt atgggtgaat 6180
atcgtcgcat tctgggttgg ggctatggtc gtaaaaacaa tagcgaactg gataccgacc 6240
ataaactgcg tctgtttgaa tgagaaggag atatacatat gtcatttcag aaatttgtgc 6300
aagaagcagc ctataaagtc gcaccgttta aaccgaatcg ttttgccaaa attagcgagc 6360
gtgaagataa atgtgcaatt ccggttccgg catggcgtgc actgctggcc aatcgtgacc 6420
tgtttacctg gaaaggtatt ccgtttctga aaggttgtac cgaaattgca ctgtatagca 6480
tgctgctgta tgaactgcgt ccgaaaacga ttattgaaat tggtgcgctg agcggtggta 6540
gcgcaatttg gctggcagat catctggaac tgtttcagat tgaaggttgc gtgtattgca 6600
ttgatattga tctgtctctg ctggacgaaa aagcaaaaac cgatagccgt gttcattttc 6660
tggaaggtga ttgcaataat atgggtgcaa ttatgtcaag cgagctgctg agtggtctgg 6720
cacatccttg gctgattgtt gaagatgcac atgcaaatgc cgttggtgtg gttgaatatt 6780
ttcacgaaaa cggtctgaaa agtggcgatt acctgatcgt ggaagatacc aataaaacaa 6840
tgtgggaact ggatcgcgaa gaactggacc gtgatgacct ggatgaacaa gaactgatcg 6900
aaaaaggtga gcagaaatta gcagaactga aaagctggct gatgctgcat gagaatgaat 6960
atctgataga tacctactat caggatatgt atggctataa tggtagccgt aattggaaca 7020
gcattctgaa acgtgtggaa aagaactttt aatctaacta aaaacaccct aacgggtgtt 7080
ttttcttttc tggtctcccc gaagttccta ttctctagaa agtataggaa cttcgctgga 7140
ttgggccgcg aaattaaccg gcctgagcaa tgtcccagct ttaat 7185

<210> SEQ ID NO 94
<211> LENGTH: 5599
<212> TYPE: DNA
<213> ORGANISM: Artificial Sequence
<220> FEATURE:
<223> OTHER INFORMATION: Sequence of sxt3 fragment version 3 integrated into the E. coli xylose operon

<400> SEQUENCE: 94
ggtgtcagga ggcgggaggg gacatctttc aggccattat tcagtgaggt ccagccttgc 60

-continued

```
aagaagcgga tacaggagtg caaaaaatgg ctatctctag aaaggcctac cccttaggct    120
ttatgcaaca gaaacaataa taatggagtc atgaacatgc tgaccgcaga acagaaacag    180
gcatatacca atgatggcta ttttaccgtg gaagaagcag ttccgaaagc actgattgaa    240
gaaattcgcc atgaagtgga actgatcacc gagcagaaac gtggtggtgt gctggcaggc    300
gattatgaat ggtggtcaga acacaccatt ccggatccgg ttcgttatca gaaaattatc    360
cagcgtctgc tggaactgcc gaccgttatg ggtccggttc aggccctgat tggtagcgat    420
atttttctgt taattaccga cctggcaatt attcgtgcag gcaccggtta tattgcatgg    480
catcaggatc atggctatgt tgttgaagtt ctgaacgccc tggcaagcat gagcaaaaat    540
gagctgaatg atgatgcact gcgcctgctg gtgccggttg caaatcaggc aatggtgttt    600
attaccatct atctgcagga taccgataac accatgggca ccatgcgtgt gattccgagc    660
agccatcagt gggaacatag tctggatagc agcagcgcca attcactgaa tgcagaaatt    720
tgtctgagcc tgcctggtgg tgcagcaatg ttttataccc cgaccgtttg gcataccgca    780
gcagcaaata ccagcattac cgattatcgt atgctgacgc tgatcttcac caaaaacaac    840
attaaaccgc tgctggttga tgccctgaaa cgtattattt gagaaggaga tatacatatg    900
acaaccaccg atccgatcct gattaataac tggcatgttg tggcaaatgt cgaggattgt    960
aaaccgggta gcattacccg tagccgttta ctgggtgtta aactggttct gtggcgtagc   1020
tatgaacaga atagcccgat tcaggtttgg ctggattatt gtccgcatcg tggtgttccg   1080
ctgagcatgg gtgaaattac caataatacc ctggtttgtc cgtatcatgg ctggcgttat   1140
aatgaagcag gtaaatgtat tcagattccg gcacatccgg gtatggttcc gcctgcaagc   1200
gcagaagcac gtacctatca tagccaagaa cgttatggtc tggtttgggt ttgtctgggt   1260
gatccggtta atgatattcc gtcatttccg gaatgggatg atccgaatta tcacaaaacc   1320
tacaccaaaa gctatctgat taaagcaagc gcctttcgcg ttatggataa ttcactggat   1380
gttagccatt ttccgtttat tcatgatggc tggctgggcg atcgtaacta taccaaagtg   1440
gaagaatttg aagtgaaact ggataaagat ggtctgacga tgggcaaata tcagtttcag   1500
accagccgta ttgtgagcca tattgaagat gatagctggg tgaattggtt tcgtctgagc   1560
catccgctgt gtcagtattg tgttagcgaa agtccggaaa tgcgtattgt tgatctgatg   1620
accattacgc cgattgatga agaaaatagc gttctgcgca tgctgatcat gtggaatggt   1680
tatgaaaccc tggaaagcaa aatgctgaca gagtatgatg aaacgatcga acaggatatt   1740
cgtattctgc atgcccagca gccggtgcgt ctgccgctgc tgacaccgaa gcagattaat   1800
acccagctgt ttagccatga aattcatgtt ccgagcgatc gttgtaccct ggcatatcgt   1860
cgttggctga aacaactggg tgtgacctat ggtgtttgtt gagaaggaga tatacatatg   1920
gcaggtaaac tggatggtaa ggttgcaatt attaccggtg caagcagcgg tattggtgaa   1980
gccaccgcat ttgcactggc agcagaaggt gcaaaagttg caattgcagc ccgtcgtgca   2040
gaactgttac atgcactggc caaacgtatt gaagcaagcg gtggtcaggc actgccgatt   2100
gttaccgata tcaccgatga aagccaggtt aatcatctgg ttcagaaaac caaagttgaa   2160
ctgggtcatg ttgatatcct ggtgaataat gcaggtattg gcgtttttgg tgcaatcgat   2220
accggtaatc cggcagattg gcgtcgtgca tttgatgtta atgtgctggg tgttctgtat   2280
gcaattcatg cagttctgcc tttactgaaa gcacagaaaa gcggtcatat tgtgaatatt   2340
agcagcgtgg atggtcgtat tgcacagagc ggtgcagttg tttatagcgc agcaaaaagc   2400
ggtgttaatg ccctgagcga agcactgcgt caagaagtga gcctggataa tattcgtgtg   2460
```

accattattg aaccgggtct ggtagatacc ccgtttaatg atctgattag tgatccgatt 2520
accaaacagc tgagcaaaga acagctgtca accattactc cgctgcagag cgaagatatt 2580
gcacgtgcca ttatctatgc agttacccag ccggatcatg ttaacgttaa tgaaattctg 2640
attcgtccga ccgcagagga taattgagaa ggagatatac atatgaacct gaccctgaac 2700
aaagaagaaa aacagctgct gacggcatat agcggcaccg aactgcagct gacagcagat 2760
gttctggtta ttggtggtgg tccggcagcc gcatgggcag cttgggcagc aggcgcacag 2820
ggtgtgaaag ttattattgt ggataaaggt tttctgggca ccagcggtgc cgcagccgca 2880
agcggtaata gcgttatggc accgtcaccg gaaaattggg aaaaagatgt gagcgaatgt 2940
tacagcaaag gtaataatct ggcaaatctg cgttggattg aacgtgttat tgaaaaagcc 3000
tggctgtcac tgccgctggt tgaagattgg ggttatcgtt ttcctaaaga aaatggtgaa 3060
agcgtgcgtc agagctatta tggtcctgaa tatatgcgtg ttctgcggaa aaatctgctg 3120
cgcgttggtg ttcagatctt tgatcagtca ccggcactgg aattactgct ggcacaggat 3180
ggtagcgttg ccggtgcacg tggtgtgcag cgtcagaatc atcgtacata taccgttcgt 3240
gccggtgccg ttgttctggc caatggtggt tgcgcatttc tgagtaaagc actgggttgt 3300
aataccaata ccggtgatgg tctgttaatg gcagttgaag ccggtggtga actgagcagt 3360
atggaagcca gcagccatta taccattagc accgccttta atgcaaccgt tacccgtgca 3420
gctccgtttt attgggcaag ctataccgat gaagctggca atgatctggg tggctatatt 3480
aacggtcgtc gtgatccgag ctttctgccg aacgcactgc tgaaaggtcc ggtttatgca 3540
cgtctggatc gtgcaacacc ggaaattcag gcgctggtag aaaaaagcca ttttattgca 3600
tttctgccgt acaagaaagc cggtattgat ccgtataccg aacgtgttcc ggttaccctg 3660
gtgctggaag gcaccgtgcg tggcaccggt ggtattcgca ttgttaatga ttcatgtggc 3720
accaaagttc cgggactgta tgcagcgggt gatgcagcaa gccgtgaatt tctggcaggc 3780
attgccagcg gtggtgatgg accgaatgca gcatgggcaa tttcaaccgg tcagtgggca 3840
ggcgaaggtg cagcagcctt tgcaaaaagt ctgggtgcac atgttcatga acgcgttgtt 3900
cgtccggcag gccaggcagg tctgcgtagt cagtatccgg gtagcgaaac ctttgatagt 3960
gaagcagttg ttcgtggcgt tcaggcagaa atgtttccgc tggaaaaaaa ctatctgcgc 4020
tgtgaacagg gactgctgga tagcctggca aaactggaaa tgctgtggca gcaggttcag 4080
ggtaatccga aacaggatac agttcgtgat ctggaatttt cacgtcgtgc ggcagcactg 4140
gttagcgtgg cacgttgggc atattttagc gcactgcatc gtaaagaaac ccgtagcgaa 4200
catatccgta ttgattaccc ggaaacggat ccgaatcaac tgtattatca ggcaaccggt 4260
ggcctggaac gtctgtgggt gcgtcgtgat tgggttaaag atgcaagcgc cacccctccg 4320
gtgctgacca cctgagaagg agatatacat atgattgaac tggtgagcca taagctgtgc 4380
attaattgta atgtttgtgt tcaggtgtgc ccgaccaatg tttttgatgc agtgccgaat 4440
cagcctccgg caattgcacg ccaagaagat tgtcagacct gttttatttg tgaagcatat 4500
tgtcctgcag atgcgctgta tgttgcaccg cagagccata ccaatgttgc agttaacgaa 4560
gatgatttaa tcgacagcgg cattatgggt gaatatcgtc gcattctggg ttggggctat 4620
ggtcgtaaaa acaatagcga actggatacc gaccataaac tgcgtctgtt tgaatgagaa 4680
ggagatatac atatgtcatt tcagaaattt gtgcaagaag cagcctataa agtcgcaccg 4740
tttaaaccga atcgttttgc caaaattagc gagcgtgaag ataaatgtgc aattccggtt 4800

```
ccggcatggc gtgcactgct ggccaatcgt gacctgttta cctggaaagg tattccgttt   4860

ctgaaaggtt gtaccgaaat tgcactgtat agcatgctgc tgtatgaact gcgtccgaaa   4920

acgattattg aaattggtgc gctgagcggt ggtagcgcaa tttggctggc agatcatctg   4980

gaactgtttc agattgaagg ttgcgtgtat tgcattgata ttgatctgtc tctgctggac   5040

gaaaaagcaa aaaccgatag ccgtgttcat tttctggaag gtgattgcaa taatatgggt   5100

gcaattatgt caagcgagct gctgagtggt ctggcacatc cttggctgat tgttgaagat   5160

gcacatgcaa atgccgttgg tgtggttgaa tattttcacg aaaacggtct gaaaagtggc   5220

gattacctga tcgtggaaga taccaataaa acaatgtggg aactggatcg cgaagaactg   5280

gaccgtgatg acctggatga acaagaactg atcgaaaaag gtgagcagaa attagcagaa   5340

ctgaaaagct ggctgatgct gcatgagaat gaatatctga tagataccta ctatcaggat   5400

atgtatggct ataatggtag ccgtaattgg aacagcattc tgaaacgtgt ggaaaagaac   5460

ttttaatcta actaaaaaca ccctaacggg tgtttttct tttctggtct ccccgaagtt   5520

cctattctct agaaagtata ggaacttcgc tggattgggc cgcgaaatta accggcctga   5580

gcaatgtccc agctttaat                                                 5599
```

```
<210> SEQ ID NO 95
<211> LENGTH: 7064
<212> TYPE: DNA
<213> ORGANISM: Artificial Sequence
<220> FEATURE:
<223> OTHER INFORMATION: Sequence of sxt1 fragment, integrated into the
      E. coli lactose operon

<400> SEQUENCE: 95
```

```
atgaccatga ttacggattc actggccgtc gttttacaac gtcgtgactg ggaaaaccct     60

ggcgttaccc aacttaatcg ccttgcagca catcccccctt tcgccagctg gcgtaatagc   120

gaagaggccc gcaccgatcg cccttcccaa cagttgcgca gcctgaatgg cgaatggcgc   180

tttgcctggt ttccggcacc agaagcggtg ccggaaagct ggctggagtg cgatcttcct   240

gaggccgata ctgtcgtcgt cccctcaaac tggcagatgc acggttacga tgcgcccatc   300

tacaccaacg tgacctatcc cattacggtc aatccgccgt ttgttcccac ggagaatccg   360

acgggttgtt actcgctcac atttaatgtt gatgaaagct ggctacagga aggccagacg   420

cgaattattt ttgatggcgt taactcggcg tttcatctgt ggtgcaacgg gcgctgggtc   480

ggttacggcc aggacagtca gtggagatgc ccaagggcac ttcgggtcga ggaacccgac   540

ctgcattggg acgcggccac ggagagcgcg ggcaaacgcc ggcactatag ccagtggagt   600

ttgtaaaacg ctatttcaga gcttggagag tgtctaagaa agccgggcga tgccaaccca   660

tcccttcttc ggctacgttc gtaatcaagc cacttccttt ttgcattgac gcagggtgtc   720

ggaaggcaac tcgccgaacg cgctcctata gttttcagcg aagcgtccca aatgtaagaa   780

gccgtagtct agggctatct cagttatact acgcacattg gcactgggat cgttcaagca   840

ggcgcggatg ctttcgagct tgcggttgcg gatgtagttc ttcggcgtgg tgccggcatg   900

cttctcgaac aaattgtaga gcgagcgtgg actcatcatc gccagctccg ctaaccgctc   960

aaggctgata ttccgtttga gattctcctc aatgaattga acgactcgct cgaaagacgg   1020

gttacctttg ctgaaaattt cacggctgac attgctgccc agcatttcga gcagcttgga   1080

agcgatgatc cccgcatagt gctcttggac ccgaggcatc gactttgtat gttccgcttc   1140

gtcacaaact aacccgagta gattgataaa gccatcgagt tgctggagat tgtgtcgcgc   1200
```

-continued

```
ggcgaaacgg ataccctccc tcggcttgtg ccaattgttg tcactgcatg cccgatcaag   1260
gaccactgag ggcaatttaa cgataaattt ctcgcaatct tctgaatagg tcaggtcggc   1320
ttggtcatcc ggattgagca gcaatagttc gcccggcgca aaatagtgct cctggccatg   1380
gccacgccac aggcaatggc ctttgagtat tatttgcaga tgataacagg tctctaatcc   1440
aggcgagatt accctcacgc taccgccgta gctgattcga cacaggtcga ggcatccgaa   1500
gattctgtgg tgcagcctgc ctgccggggg cccgcccttg ggcaggcgaa tagagtgcgt   1560
accgacatac tggttaacat aatcggagac tgcatagggc tcggcgtgga cgaagatctg   1620
acttttctcg ttcaataagc aaaaatccat agttcacggt tctcttattt taatgtgggc   1680
tgcttggtgt gatgtagaaa ggcgccaagt cgatgaaaat gcaggaatta attcgcagat   1740
cctggcggat gagagaagat tttcagcctg atacagatta aatcagaacg cagaagcggt   1800
ctgataaaac agaatttgcc tggcggcagt agcgcggtgg tcccacctga ccccatgccg   1860
aactcagaag tgaaacgccg tagcgccgat ggtagtgtgg ggtctcccca tgcgagagta   1920
gggaactgcc aggcatcaaa taaaacgaaa ggctcagtcg aaagactggg cctttcgttt   1980
tatctgttgt ttgtcggtga acgctctcct gagtaggaca aatccgccgg gagcggattt   2040
gaacgttgcg aagcaacggc ccggagggtg gcgggcagga cgcccgccat aaactgccag   2100
gcatcaaatt aagcagaagg ccatcctgac ggatggcctt tttgcgtaga tcccagcctt   2160
gcaagaagcg gatacaggag tgcaaaaaat ggctatctct agaaaggcct acccccttagg  2220
ctttatgcaa cagaaacaat aataatggag tcatgaacat gctgcagaaa atcaatcgtt   2280
atacccatgg ttttgttgcc gttccggtta ttctggcatg tcgtgaaaaa ggtgtttttg   2340
aactgctggc agatgaaagt ccgctgagcc tgaatcagat ggttgaacat ctgggtgcca   2400
atagcggtca ttttcaggtt gcactgcgta tgctggaaag tctgcattgg ctgagccgta   2460
ataaagaact gaaatatagc ctgaccgcag aagcagcaat tcataacaaa attagcgaag   2520
atatcctgca gctgtataat ctgccgattc agagctatct ggaaggtaaa cagggcaatc   2580
tgctgggtcg ttggattgaa cgtagctgtc agctgtggaa tctggataat ccgctgatgg   2640
cagattttct ggatggtctg ctggttattc cgctgctgct ggcactgcat aaacataacc   2700
tgctggccga ttctgaagat aaaccgctgc tgagcagcct gagcagtacc gttcaagaag   2760
aactgggtaa actgtttctg catctgggtt gggcagatct gacagcaggt cgtctgacca   2820
ttaccgaact gggtcgcttt atgggtgaac gtgcactgaa taccgcaatt gttgcaagct   2880
ataccccgat gctgagtcgt attcatgatg ttctgtttgg taattgcctg agcgtttttc   2940
agcgtgatgc aagcggtcat gaacgtcata ttgatcgtac cctgaatgtt attggtagcg   3000
gttttcagca ccagaaatac tttgcagatc tggaagaaag cattctgagc gtgtttaatc   3060
agctgccgct ggaagaacag ccgaaataca ttaccgatat gggttgtggt gatggcaccc   3120
tgctgaaacg tgtttgggaa accattcagt ttaaaagcgc acgtggtaaa gcactggaac   3180
agtatccgct gcgtctgatt ggtgttgatt ataatgaagc aagcctgaaa gcaaccaccc   3240
gtaccctggc aagcctgccg catctggttc tgcagggtga tattggtaat ccggaacaaa   3300
tggttcgtag cctggaagca catggcattc atgatccgga aaatattctg catattcgca   3360
gctttctgga tcacgatcgt ctgtttattc cgcctcagaa acgtaatgaa ctgaaagaac   3420
gtgcccatct gccgtatcag agtgtttgtg ttgatgatca gggtgaactg attcctccgc   3480
atgttatggt tcagagcctg gtggaacacc tggaacgttg gagccaggtt gttaataaac   3540
atggtctgat gattctggaa gtgcattgtc tggaaccgcg tgttgtttat cagtttctgg   3600
```

-continued

```
ataaaagcga aaacctgcac tttgatgcat ttcagggttt tagccagcag tatctggttg   3660
aagccgaagt ttttctgatg agcgcagcac aggttggtct gtttccgaaa ctggaactga   3720
gcaaacgtta tccgaaaacc tttccgttta cccgtattac cctgaactat ttcgaaaaac   3780
gtccgtacaa aatcagccat gcatatctga gcgatctgcc tgcactggtt gacctggaag   3840
ttaaatgttg gcctgagaat ctgcgtgcaa gcacccatga aattcgtcgt cgtctggaac   3900
tgaatccgca gggtaacctg gttctgatta ttgaagatca gattatcggt gccatttaca   3960
gccagaccat tacaagcacc gaagccctgg aaaatgttaa atatgcacag gttccgaccc   4020
tgcatacacc gcagggttca gtgattcagc tgctggccct gaacattctg ccggaatttc   4080
aggcacgtgg tctgggcaat gaactgcgtg attttatgct gtattattgc accctgaaag   4140
gtggtattga aagcgttgtt ggtgttaccc gttgtcgcaa ttatgtgaat tatagccaga   4200
tgccgatgat ggaatatctg aaactgcata atgaacagcg tcaactgctg gatccgattg   4260
ttggttttca tgttagcggt ggtgcagaaa ttcgtggcat tattgcaaat tatcgtccgg   4320
aagatacaga taatctgggt atgggtattc tgatcgaata taacctgcgt gatagcgcac   4380
tgcattcacc gggtgatcgt aaaggtccgt atatcaatag cgcaattggt agcctggttc   4440
cgaaagcgac cagcgcaacc aaagaaaaca aaaccgttgc ggatctggtg aaagaatgta   4500
ttctgaaagt gatgggtagc cagcgtcagg cagcatatgc accgcagcag aaactgctgg   4560
acatgggtct ggatagcctg gatctgctgg aactgcagac cctgctggaa gaacgtctgg   4620
gtattaatct gagcggcacc ttttttctgc aaaaaaacac cccgaccgcc atcattacct   4680
attttcagaa tcaggtcgtg caagagaaac agagtgatct ggcaccgcct gttgatagcg   4740
ccaatgaaat caatacactg gaaaacgttg tgaatcagca gaaaattccg caggttacac   4800
gtgttgttac cgaacagcag ggacgtaaag ttctgattga tggtcattgg gttattgatt   4860
ttgccagctg taattatctg ggcctggacc tgcatccgaa agttaaagaa gcaattcctc   4920
cggcactgga taaatggggc acccatccga gctggacccg tctggttgca agtccggcaa   4980
tttatgagga actggaagag gaactgtcaa aactgctggg tgtgccggat gttctggttt   5040
ttccggcagt tacactgctg cagattggta ttctgcctct gctgaccggt aataatggtg   5100
tgatttttgg cgatattgca gcccatcgtt gtatttatga agcatgttgt ctggcccagc   5160
ataaaggtgc acagtttatt cagtatcgtc ataacgacct gaatgatctg gccgaaaaac   5220
tggccaaata tccgcctgaa caggttaaaa tcattgtgat cgatggtgtg tatagcatga   5280
gtgccgattt cccggacctg cctgcatatg ttcatctggc aaaagaatat aacgccctga   5340
tctatatgga tgatgcacat ggctttggca ttctgggtga aaatccgagc agcgatatgc   5400
cgtatggtta taaaggtaat ggcatggtga actactttga tctgcgtttt gccgaagata   5460
acatcattta tgttgcaggt ctgagcaaag cctatagcag ctatgcagca tttctgacct   5520
gtggtgatcg tcgtattaaa accaatttc gtaatgcatg gaccgcgatt tttagcggtc   5580
cgagtccggt tgcaagcctg gccagcgcac tggcaggtct gcaggttaat cgtcaagaag   5640
gtgaacagct gcgcaaacaa atctatcatc tgacacataa actggttacc caggctcgtg   5700
ccattggttt tgaagttgat aattatggtt atgtgccgat tgtgggtgtt ctggtgggtg   5760
atgcacagca tatgattgat gtgtgccaac tgctgtggga atatggtatc ctgattaccc   5820
ctgcaatttt tccgattgtg ccgctgaata aatcagcact gcgttttagc attaccgcag   5880
caaataccga agaagaaatt gatcaggcca tcaaaagtct gaaagcagtt tgggacctgc   5940
```

tgcaaaaacg taaagccctg ccgtgtaaac aagaagaaaa tatcctgaaa cattgagaag 6000
gagatataca tatgacccat gttgccctgg aacaggcaat tgcaaaagtt ccgcgtagca 6060
ttcagagcga actgcgtacc attctggcac agcatgcagt tattgatagc agcgttgtgg 6120
caagctggat tgatcgtctg ggcaccaata ttagtaccct gatgatccag ctgctgccgg 6180
ttgcagcaac ctatgcacgt gttccgatta gccagtttta tgttggtgcc attgcactgg 6240
gcaaaccgca gagtaaaaat cagctgggta gcggcaccct gtattttggt gcagatatgg 6300
aatttgttgg tcaggcactg agctttagcg ttcatgcaga acagagcgcc accattaatg 6360
cctggctgca tggcgaaacc ggactgcagg cactggcaat ccatgaagca ccgtgtggtt 6420
attgtcgcca gtttctgtat gaaatggcaa ccgtgaatca gaattttgtg ctgctggtga 6480
aaagcaatga aagccagccg gaacagacct ataccagcaa caaactgccg cattttctgc 6540
ctgaaccgtt tggtccagcc gatctgggtc tgaccggtgg cctgatgcag accgtgtttc 6600
acgatctgga aacctatagc accgatgatg ttgttctggc agcactgagt gcagcaaatc 6660
agagttatgc accgtatacc aaaaactttg ccggtgttgc actgaaagat agtcatggta 6720
acatttttac aggtcgctat gccgaaaacg cagcatttaa tagcagcatg agcccgatgg 6780
aaagcgcact gacctttatg aatatgaatc gttattcaca gagcctgttc gatatttgtg 6840
atgcagttct ggtagaagtg gaaaccggta ttagtcagcg tccggttacc gaagcctttc 6900
tgagtagcat tgcaccgaaa gtgaaactgc gctatgcacc ggcaaccccg agcagtaaca 6960
aactgtgact cggtaccaaa ttccagaaaa gaggcctccc gaaagggggg cctttttcg 7020 ttttggtccc gaagttccta ttctctagaa agtataggaa cttc 7064

<210> SEQ ID NO 96
<211> LENGTH: 4413
<212> TYPE: DNA
<213> ORGANISM: Artificial Sequence
<220> FEATURE:
<223> OTHER INFORMATION: Sequence of sxt4 fragment integrated into the E. coli melobiose operon

<400> SEQUENCE: 96
aagcctgccg tcagggcaat atcgagaata cttttatcgg tatcgctcag ccagccttgc 60
aagaagcgga tacaggagtg caaaaaatgg ctatctctag aaaggcctac cccttaggct 120
ttatgcaaca gaaacaataa taatggagtc atgaacatat ggaaaccacg agcaaaaaat 180
tcaaaagcga tctgattctg gaagcacgtg caagcctgaa actgggtatt ccgctggtta 240
ttagccagat gtgtgaaacc ggtatttata ccgcaaatgc agttatgatg ggtctgctgg 300
gcacccaggt tctggcagcc ggtgctctgg gtgcactggc atttctgacc ctgctgtttg 360
catgtcatgg tattctgagc gttggtggta gcctggcagc ggaagcattt ggtgcaaaca 420
aaattgatga agttagccgt attgcaagcg gtcagatttg gctggcagtt accctgagcc 480
tgcctgcaat gctgctgctg tggcatggtg ataccattct gctgttattt ggtcaagaag 540
aaagcaacgt tctgctgacc aaaacctatc tgcatagcat tctgtggggt tttccggcag 600
cactgagtat tctgacactg cgtggtattg ccagcgcact gaatgttccg cgtctgatta 660
ccattaccat gctgacccag ctgattctga ataccgcagc agattatgtt ctgatctttg 720
gtaaatttgg tctgccgcag ctgggtctgg caggtattgg ttgggcaacc gcactgggtt 780
tttgggttag ctttaccctg ggtctgatcc tgctgatttt tagcctgaaa gtgcgtgatt 840
ataaactgtt tcgttatctg caccagttcg acaagcagat ctttgtgaaa atctttcaga 900

-continued

```
ccggttggcc gatgggtttt cagtggggtg cagaaacagc actgtttaat gttaccgcat    960
gggttgcagg ttatctgggc accgttaccc tggcagcaca tgatattggt tttcagacag   1020
cagaactggc aatggttatc ccgctgggtg ttggtaatgt tgcaatgacc cgtgttggtc   1080
agagcattgg tgaaaaaaat ccactgggtg cccgtcgtgt tgcaagcatt ggtattacca   1140
ttgttggtat ttatgccagc attgttgccc tggttttttg gctgtttccg tatcagattg   1200
caggcattta tctgaacatt aataacccgg aaaacattga agccatcaaa aaagccacca   1260
cctttattcc actggcaggt ctgtttcaga tgttttatag cattcagatc attatcgttg   1320
gtgcgctggt tggtctgcgt gatacctttg ttccggttag catgaatctg attgtttggg   1380
gtctgggttt agcaggtagc tattttatgg caattattct gggttggggt ggtattggta   1440
tctggctggc catggttctg agtccgctgc tgagcgcagt tattctgacc gttcgttttt   1500
atcgcgtgat tgataatctg ctggccaaca gtgatgatat gctgcagaat gcaagcgtta   1560
ccaccctggg atgagaagga gatatacata tgaaacgtct gacgctgctg atcattgcag   1620
gtattctgtc agttagcacc tttctgtgta ttacaccggt tgcactggcc aatattaccg   1680
attattatct gaaaaacgag aaactgagcg gtcagtttag cgttccggtg aatctgtctg   1740
ttggtgttcg ttttgcacat cgtagcagct atgcaaccgc aattaacttt ccgaccggtc   1800
tggatgcaga tagcgttgca gttggtgatt ttaacagcga tagcaaactg gatctggccg   1860
ttaccaattg gtttgataac aatgttagcg tgctgctggg taatggcaat ggcagctttg   1920
gtgcagcaac caattttccg gttggcacca atccggtttt tgttgttacc ggtgatgtta   1980
atggtgacag taaactggat ttagccgtgg caaattttag cagcaataat gtttcagttc   2040
tgctgggaaa cggtaatggt tcttttggcg cagccacaaa ctttagcgtt ggtacaaatc   2100
cgtatagcgt ggccattggt gatgtgaata atgatagtga actggacctg gcatttacga   2160
actggttcga taataaagtt ctggtgctgt taggcaatgg taatggctcg tttggtgccg   2220
caagctcatt tccggtggat acctatagca ttagcgttgc gattgcagat ttcaactcag   2280
attctaaatt agacctggcg atcaccaatt gggtgtcaaa taatgtgagt gtgttactgg   2340
ggaatggtaa cggtagtttt ggagctgcga caaattttcc tgtgggtaca aacccgattt   2400
ttgtggcaac cggtgacgtg aatggcgatt ctaagctgga cttagcagtt gcaaatacca   2460
gctctaataa cgttagcgtt ctgttaggta acgggaacgg ctcattcggt gctgccacga   2520
attttccagc aggcaccaac ccgtatagtg ttgcaattcg cgacgttaac ggtgatagca   2580
aattagattt agcggtgacc aactatagca gcaacaacgt gagtgttctg ccaggcaacg   2640
gtaacggatc atttggtatt gcgaccaact ttccagtagg tacgaatccg gaaagcattg   2700
caattgccga ttttaatggg gattccaagt tagatctggc agtgacaaat agcggtaaca   2760
ataatgtaag catactgctg aataactttc agggtctgcc gaaaaacaag atttgagaag   2820
gagatataca tatgaccaat accgaacgtg gtctggccga aattaccagc accggttata   2880
aaagcgaact gcgtagcgaa gcccgtgtta gcctgcagct ggcaattcct ctggttctgg   2940
ttgaaatttg tggcaccagc attaatgttg ttgatgttgt gatgatgggt ttactgggta   3000
cacaagtgtt agcagcgggt gccctgggag caattgcctt cctgagcgtt agcaatacct   3060
gctataatat gctgctgagt ggtgttgcaa aagcaagcga agcctttgga gccaataaaa   3120
tcgatcaggt ttcacgtatt gcctcaggcc agatttggtt agccctgacc ctgtcattac   3180
cagccatgct gttactgtgg tatatggata ccatcctggt tctgtttggt caggttgaaa   3240
gcaataccct gattgcgaaa acatacctgc attcaattgt gtggggcttt cctgccgcag   3300
```

```
ttggtatcct gattctgcgt ggcatagcaa gtgcagttaa cgttcctcag ctggttaccg   3360

tgaccatgct ggttggcctg gtgctgaatg caccggctaa ttatgtgctg atgttcggca   3420

aattcggttt accggaatta ggcctggctg gcattggctg ggccagcaca ctggtgtttt   3480

ggattagttt tctggttggt gttgtgctgc tgatattttc accgaaagtt cgcgactaca   3540

aactgttccg ctatttacat cagtttgatc gtcagaccgt ggttgagatt tttcagacgg   3600

gctggcctat gggcttcctg ctgggtgtgg aaagcgttgt tctgagcctg accgcatggc   3660

tgaccggcta tctgggtaca gtgaccttag cagcccatga aattgcaatc cagactgccg   3720

aactggcgat tgtgattccg ttaggtattg gcaatgttgc cgttacccgt gtgggccaga   3780

caatcggcga aaaaaacccg ctgggagcac gccgtgcagc cctgattggc attatgattg   3840

gtggcattta tgcgagcctg gttgcagtga ttttttggtt attcccttat caaatcgcag   3900

gcctgtacct gaaaattaac gatccggaat caatggaagc agttaaaacc gcaacaaact   3960

ttctgttttt agctggcctg ttccagtttt ttcatagcgt gcagattatt gttgtgggtg   4020

ttctgattgg cctgcaggat acctttatcc ctctgctgat gaatctggtg ggctggggac   4080

tgggcctggc ggtttcctat tatatgggta ttatcctgtg ctggggtggc atgggcatct   4140

ggttaggtct ggtactgtca ccgctgctgt caggcctgat cctgatggtg cgcttttatc   4200

aagaaattgc caatcgcatt gcgaatagcg acgatggcca agaaagcatt agcattgata   4260

atgttgaaga actgagctaa tagaccaacc ccttgcggcc tcaatcgggg gggatggggt   4320

tttttgtcga agttcctatt ctctagaaag tataggaact tcgcaaccgt ctgctgaagg   4380

aagccatctg acacttaaag ccatcgttgc gct                                4413
```

<210> SEQ ID NO 97
<211> LENGTH: 7377
<212> TYPE: DNA
<213> ORGANISM: Artificial Sequence
<220> FEATURE:
<223> OTHER INFORMATION: Sequence of sxt2 fragment integrated into the
E. coli maltose operon

<400> SEQUENCE: 97

```
ctgtgaacta aaccgaggtc atgtaaggaa tttcgtgatg ttgcttgcaa ccagccttgc     60

aagaagcgga tacaggagtg caaaaaatgg ctatctctag aaaggcctac cccttaggct    120

ttatgcaaca gaaacaataa taatggagtc atgaacatga ttgataccat tagcgttctg    180

ctgcgtgaat ggaccgttat ttttctgacc ggtctggcat tttggctgtg ggaaattcgt    240

agtccgctgc atcagattga atacaaagcc aaatttttca aagaactggg ttgggcaggt    300

atcagctttg tttttcgtat tgtttatgcc tatgttagcg tggccattat caaactgctg    360

agcagcctgt ttatgggtga aagcgcaaat tttgccggtg ttatgtatgt tccgctgtgg    420

ctgcgtatta ttaccgcata tattctgcag gatctgaccg attatctgct gcatcgtacc    480

atgcatagca atcagtttct gtggctgacc cataaatggc atcatagcac caaacagagt    540

tggtggctga gcggtaataa agatagcttt accggtggtc tgctgtatac cgttaccgca    600

ctgtggtttc cgctgctgga tattccgagc gaagttatga gcgttgttgc agttcatcag    660

gtgattcata acaactggat tcacctgaat gtgaaatgga atagctggct gggtattatc    720

gaatggattt atgttacacc gcgtatccat accctgcatc atctggatac cggtggtcgt    780

aatctgagca gtatgtttac ctttattgat cgtctgtttg gcacctatgt gtttccggaa    840

aactttgata tcgaaaaaag caaaaaccgc ctggatgatc agagcgttac cgttaaaacc    900
```

-continued

```
attctgggtt tctgagaagg agatatacat atgctgaaag attttaacca gttcctgatt    960
cgtaccctgg catttgtttt tgcctttggc atttttctga caaccggtgt tggtattgca   1020
aaagcagatt atctggtgaa aggtggcaaa attaccaatg ttcagaatac cagcagcaac   1080
ggtgataatt atgcagttag cattagcggt ggttttggtc cgtgtgcaga tcgtgttatt   1140
attctgccga ccagcggtgt tattaatcgt gatattcaca tgcgtggtta tgaagcagca   1200
ctgaccgcac tgagcaatgg ttttctggtt gatatctatg attataccgg tagcagctgt   1260
agcaatggtg gccagctgac cattaccaat cagctgggta aactgattag caattgagaa   1320
ggagatatac atatgaccaa tcagaacaac caagagctgg aaaatgatct gccgattgca   1380
aaacagccgt gtccggttaa tagctataat gaatgggata ccctggaaga agttattgtt   1440
ggtagcgttg aaggtgcaat gctgcctgca ctggaaccga ttaacaaatg gacctttccg   1500
tttgaagaac tggaaagcgc acagaaaatt ctgagcgaac gtggtggtgt tccgtatccg   1560
cctgaaatga ttaccctggc acataaagaa ctgaacgagt ttattcatat cctggaagcc   1620
gaaggtgtta aagttcgtcg tgttaaaccg gttgatttta gcgttccgtt tagcacaccg   1680
gcatggcagg ttggtagcgg tttttgtgca gcaaatccgc gtgatgtttt tctggttatt   1740
ggcaacgaaa ttatcgaagc accgatggca gatcgtaatc gttattttga aacctgggca   1800
tatcgcgaaa tgctgaaaga atattttcag gcaggcgcaa aatggaccgc agcaccgaaa   1860
ccgcagctgt ttgatgcaca gtatgatttc aattttcagt ttccgcagct gggtgaaccg   1920
cctcgttttg ttgttaccga atttgaaccg acctttgatg cagccgattt tgttcgttgt   1980
ggtcgtgata tttttggcca gaaaagccat gttaccaatg gtctgggtat tgaatggctg   2040
cagcgtcatc tggaagatga atatcgcatt catatcatcg aaagccattg tccggaagca   2100
ctgcatattg ataccaccct gatgccgctg gcaccgggta aaattctggt taatccggaa   2160
tttgtggacg tgaataaact gccgaaaatt ctgaaaagct gggatattct ggttgcaccg   2220
tatccgaatc atattccgca gaatcagctg cgtctggtta gcgaatgggc aggtctgaat   2280
gttctgatgc tggatgaaga acgtgtgatc gtggaaaaaa atcaagagca gatgatcaaa   2340
gccctgaaag attggggttt taaaccgatt gtttgccact tcgaaagcta ttatccgttt   2400
ctgggtagct ttcattgtgc aaccctggat gttcgtcgtc gtggcaccct gcagagctat   2460
ttttgagaag gagatataca tatgacgacc gcagatctga ttctgatcaa taattggtat   2520
gttgtggcca aggtggaaga ttgtaaaccg ggtagcatta ccaccgcact gctgctgggt   2580
gttaaactgg ttctgtggcg tagccgtgaa cagaatagcc cgattcagat ttggcaggat   2640
tattgtccgc atcgtggtgt tgcactgagc atgggtgaaa ttgtgaataa taccctggtt   2700
tgtccgtatc atggttggcg ttataatcag gcaggtaaat gtgttcatat tccggcacat   2760
ccggatatga cccctccggc aagcgcacag gcaaaaatct atcattgtca agaacgttat   2820
ggtctggttt gggtttgtct gggtgatccg gttaatgata ttccgagtct gccggaatgg   2880
gatgatccga attatcataa tacctgcacc aagagctact ttatccaggc aagcgcattt   2940
cgtgtgatgg ataactttat tgatgtgagc cattttccgt ttgtgcatga tggtggtctg   3000
ggcgatcgta atcatgcaca gattgaagaa tttgaggtga aagtggataa agacggtatt   3060
agcattggca atctgaaact gcagatgcct cgttttaata gcagcaatga agatgatagc   3120
tggaccctgt atcagcgtat tagccatccg ctgtgtcagt attatatcac cgaaagcagc   3180
gaaattcgta cagcagatct gatgctggtt accccgattg atgaagataa ttcactggtt   3240
```

-continued cgtatgctgg tgacctggaa tcgtagcgaa attctggaaa gcaccgttct ggaagaattt 3300
gatgaaacca ttgaacagga tatcccgatt attcatagcc agcagcctgc acgtctgccg 3360
ctgctgccga gcaagcagat taatatgcag tggctgagcc aagaaattca tgttccgagc 3420
gatcgttgta ccgttgcata tcgtcgttgg ctgaaagaac tgggcgttac ctatggtgtt 3480
tgttgagaag gagatataca tatgcagatt ctgggtatca gcgcctatta tcatgatagc 3540
gcagcagcaa tggttattga tggtgaaatt gttgcagcag cacaagaaga acgttttagc 3600
cgtcgtaaac atgatgcagg ttttccgacc ggtgcaatta cctattgtct gaaacaggtt 3660
ggcaccaaac tgcagtatat tgatcagatc gtgttctatg ataaaccgct ggtgaaattt 3720
gaacgtctgc tggaaaccta tctggcctat gcaccgaaag gttttggtag ttttattacc 3780
gcaatgccgg tgtggctgaa agagaaactg tatctgaaaa ccctgctgaa aaaagaactg 3840
gcactgctgg gtgaatgtaa agcaagccag ctgcctccgc tgctgtttac cagccatcat 3900
caggcacatg cagcagcagc attttttccg agcccgtttc agcgtgcagc agttctgtgt 3960
ctggatggtg ttggtgaatg ggcaaccacc agtgtttggc tgggtgaagg taataaactg 4020
acaccgcagt gggaaattga ttttccgcat agcctgggcc tgctgtatag cgcatttacc 4080
tattataccg gctttaaagt gaacagcggt gagtataaac tgatgggtct ggcaccgtat 4140
ggtgaaccga aatatgttga tcagattctg aaacatctgc tggatctgaa agaagatggc 4200
acctttcgtc tgaacatgga ttatttcaat tataccgttg gtctgaccat gaccaaccat 4260
aaatttcata gcatgtttgg tggtccgcct cgtcaggcag aaggtaaaat tagccagcgt 4320
gatatggatc tggcaagcag cattcagaaa gttaccgaag aagtgattct gcgtctggca 4380
cgtaccatta agaaagaatt aggtgttgaa tacctgtgtc tggcaggcgg tgttggtctg 4440
aattgtgttg caaatggtcg tattctgcgt gagagcgatt ttaaagatat ttggattcag 4500
cctgcagccg gtgatgcagg tagcgcagtt ggtgcagcac tggcaatttg gcatgaatat 4560
cataaaaaac cgcgtaccag caccgcaggc gatcgtatga aaggtagcta tctgggtccg 4620
agctttagcg aagcagaaat tctgcagttt ctgaacagcg tgaatattcc gtatcatcgt 4680
tgtgtggata atgaactgat ggcacgtctg gcggaaattc tggatcaggg taatgttgtt 4740
ggttggttta gcggtcgtat ggaatttggt ccgcgtgcac tgggtggtcg tagcattatt 4800
ggtgatagcc gtagcccgaa aatgcagagc gttatgaatc tgaaaatcaa atatcgcgaa 4860
agcttccgtc cgtttgcacc gagcgttctg gcagaacgtg ttagcgatta ttttgatctg 4920
gatcgtccga gcccgtatat gctgctggtt gcacaggtta aagaaaatct gcatattccg 4980
atgacccaag aacagcatga actgtttggt atcgaaaaac tgaatgttcc gcgtagccag 5040
attccggcag ttacccatgt tgattatagc gcacgtattc agaccgttca taaagaaacc 5100
aatccgcgtt attatgaact gatccgtcat tttgaagcac gtaccggttg tgcagttctg 5160
gttaatacca gctttaatgt tcgtggtgaa ccgattgtgt gtacaccgga agatgcatat 5220
cgttgtttta tgcgtaccga gatggattac ctggtgatgg aaaattttct gctggtgaaa 5280
agcgaacagc ctcgtggtaa tagtgatgaa agctggcaga aagaatttga gctggattga 5340
gaaggagata tacatatgga acaaattaaa gaactggata agaaaggcct gcgtgaattt 5400
ggtctgattg gtggtagcat tgttgccgtt ctgtttggtt ttctgctgcc ggttattcgt 5460
catcatagcc tgagcgttat tccgtgggtt gttgcaggtt ttctgtggat ttgggcaatt 5520
attgcaccga ccaccctgag ctttatctat cagatttgga tgcgtattgg tctggtgctg 5580
ggttggattc agacccgtat tattctgggt gttctgttct atattatgat taccccgatc 5640
ggttttattc gtcgtctgct gaatcaggat ccgatgaccc gtatttttga accggaactg 5700
ccgacctatc gtcagctgag caaaagccgt accacccaga gcatggaaaa accgttctga 5760
gaaggagata tacatatgtt aaaagacacc tgggatttta tcaaggatat cgcaggcttt 5820
atcaaagaac agaaaaacta tctgctgatt ccgctgatta ttaccctggt tagcctgggt 5880
gcactgattg tttttgcaca gagcagcgca attgcaccgt ttatctatac cctgttttga 5940
gaaggagata tacatatgag caacttcaaa ggcagcgtta aaattgcact gatgggcatt 6000
ctgatttttt gcggtctgat ttttggtgtg gcctttgttg aaattggtct gcgtattgca 6060
ggcattgaac atattgcctt tcatagcatt gatgaacatc gtggttgggt tggtcgtccg 6120
catgttagcg gttggtatcg taccgaaggt gaagcacata ttcagatgaa tagtgatggt 6180
tttcgtgatc gcgaacacat taaagtgaaa ccggaaaata cctttcgtat tgccctgctg 6240
ggtgatagct ttgttgaaag catgcaggtt ccgctggaac agaatctggc agcagttatt 6300
gaaggcgaaa ttagcagctg tattgcactg gcaggtcgta aagccgaagt tattaacttt 6360
ggtgttaccg gttatggcac cgatcaagaa ctgattaccc tgcgtgaaaa agtgtgggat 6420
tatagtccgg atattgttgt gctggatttc tataccggta acgatattgt tgataatagc 6480
cgtgcactgt cccagaaatt ctatccgaat gaactgggta gcctgaaacc gtttttttatc 6540 ctgcgtgatg gtaatctggt tgttgatgca agctttatca acaccgataa ctatcgtagc 6600
aaactgacct ggtggggtaa aacctatatg aaaatcaaag atcatagccg cattctgcag 6660
gtcctgaata tggttcgtga tgcactgaat aatagcagcc gtggttttag cagccaggca 6720
attgaagaac cgctgtttag tgatggtaaa caggatacca aactgagcgg cttcttcgat 6780
atctataaac cgcctaccga tccggaatgg cagcaggcct ggcaggttac cgaaaaactg 6840
attagtagca tgcagcatga agtgaccgcc aaaaaagccg attttctggt tgttaccttt 6900
ggcggtccgt ttcagcgcga accgctggtt cgtcagaaag aaatgcaaga actgggtctg 6960
accgattggt tttatccgga aaaacgtatt acccgtctgg gtgaagatga aggttttagc 7020
gtgctgaatc tgagcccgaa tctgcaggtt tatagcgaac agaataatgc ctgtctgtat 7080
ggttttgatg atacccaggg ttgtgttggt cattggaatg cactgggtca tcaggttgca 7140
ggtaaaatga ttgcaagcaa aatttgtcag cagcagatgc gtgaaagcat tctgccgcat 7200
aaacatgatc cgagcagcca gagcagcccg attacccaga gcgttattca gtaatactct 7260
aaccccatcg gccgtcttag ggtttttttg tcgaagttcc tattctctag aaagtatagg 7320
aacttcgacc tgtggggtga ctttgccgcc gctgccgtga tgtctgcatt accgatc 7377

<210> SEQ ID NO 98
<211> LENGTH: 6062
<212> TYPE: DNA
<213> ORGANISM: Artificial Sequence
<220> FEATURE:
<223> OTHER INFORMATION: Sequence of sxt2 fragment integrated into the maltose operon after deletetion of sxtL

<400> SEQUENCE: 98
ctgtgaacta aaccgaggtc atgtaaggaa tttcgtgatg ttgcttgcaa ccagccttgc 60
aagaagcgga tacaggagtg caaaaaatgg ctatctctag aaaggcctac cccttaggct 120
ttatgcaaca gaaacaataa taatggagtc atgaacatga ttgataccat tagcgttctg 180
ctgcgtgaat ggaccgttat ttttctgacc ggtctggcat tttggctgtg ggaaattcgt 240
agtccgctgc atcagattga atacaaagcc aaatttttca aagaactggg ttgggcaggt 300

```
atcagctttg tttttcgtat tgtttatgcc tatgttagcg tggccattat caaactgctg    360
agcagcctgt ttatgggtga aagcgcaaat tttgccggtg ttatgtatgt tccgctgtgg    420
ctgcgtatta ttaccgcata tattctgcag gatctgaccg attatctgct gcatcgtacc    480
atgcatagca atcagtttct gtggctgacc cataaatggc atcatagcac caaacagagt    540
tggtggctga gcggtaataa agatagcttt accggtggtc tgctgtatac cgttaccgca    600
ctgtggtttc cgctgctgga tattccgagc gaagttatga gcgttgttgc agttcatcag    660
gtgattcata acaactggat tcacctgaat gtgaaatgga atagctggct gggtattatc    720
gaatggattt atgttacacc gcgtatccat accctgcatc atctggatac cggtggtcgt    780
aatctgagca gtatgtttac ctttattgat cgtctgtttg gcacctatgt gtttccggaa    840
aactttgata tcgaaaaaag caaaaaccgc ctggatgatc agagcgttac cgttaaaacc    900
attctgggtt tctgagaagg agatatacat atgctgaaag attttaacca gttcctgatt    960
cgtaccctgg catttgtttt tgcctttggc atttttctga caaccggtgt tggtattgca   1020
aaagcagatt atctggtgaa aggtggcaaa attaccaatg ttcagaatac cagcagcaac   1080
ggtgataatt atgcagttag cattagcggt ggttttggtc cgtgtgcaga tcgtgttatt   1140
attctgccga ccagcggtgt tattaatcgt gatattcaca tgcgtggtta tgaagcagca   1200
ctgaccgcac tgagcaatgg ttttctggtt gatatctatg attataccgg tagcagctgt   1260
agcaatggtg gccagctgac cattaccaat cagctgggta aactgattag caattgagaa   1320
ggagatatac atatgaccaa tcagaacaac caagagctgg aaaatgatct gccgattgca   1380
aaacagccgt gtccggttaa tagctataat gaatgggata ccctggaaga agttattgtt   1440
ggtagcgttg aaggtgcaat gctgcctgca ctggaaccga ttaacaaatg gacctttccg   1500
tttgaagaac tggaaagcgc acagaaaatt ctgagcgaac gtggtggtgt tccgtatccg   1560
cctgaaatga ttaccctggc acataaagaa ctgaacgagt ttattcatat cctggaagcc   1620
gaaggtgtta aagttcgtcg tgttaaaccg gttgatttta gcgttccgtt tagcacaccg   1680
gcatggcagg ttggtagcgg tttttgtgca gcaaatccgc gtgatgtttt tctggttatt   1740
ggcaacgaaa ttatcgaagc accgatggca gatcgtaatc gttattttga aacctgggca   1800
tatcgcgaaa tgctgaaaga atattttcag gcaggcgcaa aatggaccgc agcaccgaaa   1860
ccgcagctgt ttgatgcaca gtatgatttc aattttcagt ttccgcagct gggtgaaccg   1920
cctcgttttg ttgttaccga atttgaaccg acctttgatg cagccgattt tgttcgttgt   1980
ggtcgtgata tttttggcca gaaaagccat gttaccaatg gtctgggtat tgaatggctg   2040
cagcgtcatc tggaagatga atatcgcatt catatcatcg aaagccattg tccggaagca   2100
ctgcatattg ataccaccct gatgccgctg gcaccgggta aaattctggt taatccggaa   2160
tttgtggacg tgaataaact gccgaaaatt ctgaaaagct gggatattct ggttgcaccg   2220
tatccgaatc atattccgca gaatcagctg cgtctggtta gcgaatgggc aggtctgaat   2280
gttctgatgc tggatgaaga acgtgtgatc gtggaaaaaa atcaagagca gatgatcaaa   2340
gccctgaaag attggggttt taaaccgatt gtttgccact tcgaaagcta ttatccgttt   2400
ctgggtagct ttcattgtgc aaccctggat gttcgtcgtc gtggcaccct gcagagctat   2460
ttttgagaag gagatataca tatgacgacc gcagatctga ttctgatcaa taattggtat   2520
gttgtggcca aggtggaaga ttgtaaaccg ggtagcatta ccaccgcact gctgctgggt   2580
gttaaactgg ttctgtggcg tagccgtgaa cagaatagcc cgattcagat ttggcaggat   2640
```

-continued tattgtccgc atcgtggtgt tgcactgagc atgggtgaaa ttgtgaataa taccctggtt 2700
tgtccgtatc atggttggcg ttataatcag gcaggtaaat gtgttcatat tccggcacat 2760
ccggatatga cccctccggc aagcgcacag gcaaaaatct atcattgtca agaacgttat 2820
ggtctggttt gggtttgtct gggtgatccg gttaatgata ttccgagtct gccggaatgg 2880
gatgatccga attatcataa tacctgcacc aagagctact ttatccaggc aagcgcattt 2940
cgtgtgatgg ataactttat tgatgtgagc cattttccgt ttgtgcatga tggtggtctg 3000
ggcgatcgta atcatgcaca gattgaagaa tttgaggtga aagtggataa agacggtatt 3060
agcattggca atctgaaact gcagatgcct cgttttaata gcagcaatga agatgatagc 3120
tggaccctgt atcagcgtat tagccatccg ctgtgtcagt attatatcac cgaaagcagc 3180
gaaattcgta cagcagatct gatgctggtt accccgattg atgaagataa ttcactggtt 3240
cgtatgctgg tgacctggaa tcgtagcgaa attctggaaa gcaccgttct ggaagaattt 3300
gatgaaacca ttgaacagga tatcccgatt attcatagcc agcagcctgc acgtctgccg 3360
ctgctgccga gcaagcagat taatatgcag tggctgagcc aagaaattca tgttccgagc 3420
gatcgttgta ccgttgcata tcgtcgttgg ctgaaagaac tgggcgttac ctatggtgtt 3480
tgttgagaag gagatataca tatgcagatt ctgggtatca gcgcctatta tcatgatagc 3540
gcagcagcaa tggttattga tggtgaaatt gttgcagcag cacaagaaga acgttttagc 3600
cgtcgtaaac atgatgcagg ttttccgacc ggtgcaatta cctattgtct gaaacaggtt 3660
ggcaccaaac tgcagtatat tgatcagatc gtgttctatg ataaaccgct ggtgaaattt 3720
gaacgtctgc tggaaaccta tctggcctat gcaccgaaag gttttggtag ttttattacc 3780
gcaatgccgg tgtggctgaa agagaaactg tatctgaaaa ccctgctgaa aaaagaactg 3840
gcactgctgg gtgaatgtaa agcaagccag ctgcctccgc tgctgtttac cagccatcat 3900
caggcacatg cagcagcagc atttttttccg agcccgtttc agcgtgcagc agttctgtgt 3960
ctggatggtg ttggtgaatg ggcaaccacc agtgtttggc tgggtgaagg taataaactg 4020
acaccgcagt gggaaattga ttttccgcat agcctgggcc tgctgtatag cgcatttacc 4080
tattataccg gctttaaagt gaacagcggt gagtataaac tgatgggtct ggcaccgtat 4140
ggtgaaccga aatatgttga tcagattctg aaacatctgc tggatctgaa agaagatggc 4200
acctttcgtc tgaacatgga ttatttcaat tataccgttg gtctgaccat gaccaaccat 4260
aaatttcata gcatgtttgg tggtccgcct cgtcaggcag aaggtaaaat tagccagcgt 4320
gatatggatc tggcaagcag cattcagaaa gttaccgaag aagtgattct gcgtctggca 4380
cgtaccatta agaaagaatt aggtgttgaa tacctgtgtc tggcaggcgg tgttggtctg 4440
aattgtgttg caaatggtcg tattctgcgt gagagcgatt ttaaagatat ttggattcag 4500
cctgcagccg gtgatgcagg tagcgcagtt ggtgcagcac tggcaatttg gcatgaatat 4560
cataaaaaac cgcgtaccag caccgcaggc gatcgtatga aaggtagcta tctgggtccg 4620
agctttagcg aagcagaaat tctgcagttt ctgaacagcg tgaatattcc gtatcatcgt 4680
tgtgtggata atgaactgat ggcacgtctg gcggaaattc tggatcaggg taatgttgtt 4740
ggttggttta gcggtcgtat ggaatttggt ccgcgtgcac tgggtggtcg tagcattatt 4800
ggtgatagcc gtagcccgaa aatgcagagc gttatgaatc tgaaaatcaa atatcgcgaa 4860
agcttccgtc cgtttgcacc gagcgttctg gcagaacgtg ttagcgatta ttttgatctg 4920
gatcgtccga gcccgtatat gctgctggtt gcacaggtta aagaaaatct gcatattccg 4980
atgacccaag aacagcatga actgtttggt atcgaaaaac tgaatgttcc gcgtagccag 5040

```
attccggcag ttacccatgt tgattatagc gcacgtattc agaccgttca taaagaaacc   5100

aatccgcgtt attatgaact gatccgtcat tttgaagcac gtaccggttg tgcagttctg   5160

gttaatacca gctttaatgt tcgtggtgaa ccgattgtgt gtacaccgga agatgcatat   5220

cgttgtttta tgcgtaccga gatggattac ctggtgatgg aaaattttct gctggtgaaa   5280

agcgaacagc ctcgtggtaa tagtgatgaa agctggcaga aagaatttga gctggattga   5340

gaaggagata tacatatgga acaaattaaa gaactggata agaaaggcct gcgtgaattt   5400

ggtctgattg gtggtagcat tgttgccgtt ctgtttggtt ttctgctgcc ggttattcgt   5460

catcatagcc tgagcgttat tccgtgggtt gttgcaggtt ttctgtggat ttgggcaatt   5520

attgcaccga ccaccctgag ctttatctat cagatttgga tgcgtattgg tctggtgctg   5580

ggttggattc agacccgtat tattctgggt gttctgttct atattatgat taccccgatc   5640

ggttttattc gtcgtctgct gaatcaggat ccgatgaccc gtatttttga accggaactg   5700

ccgacctatc gtcagctgag caaaagccgt accacccaga gcatggaaaa accgttctga   5760

gaaggagata tacatatgtt aaaagacacc tgggatttta tcaaggatat cgcaggcttt   5820

atcaaagaac agaaaaacta tctgctgatt ccgctgatta ttaccctggt tagcctgggt   5880

gcactgattg tttttgcaca gagcagcgca attgcaccgt ttatctatac cctgttttga   5940

tactctaacc ccatcggccg tcttaggggt tttttgtcga agttcctatt ctctagaaag   6000

tataggaact tcacctgtgg ggtgactttg ccgccgctgc cgtgatgtct gcattaccga   6060

tc                                                                  6062
```

<210> SEQ ID NO 99
<211> LENGTH: 5462
<212> TYPE: DNA
<213> ORGANISM: Artificial Sequence
<220> FEATURE:
<223> OTHER INFORMATION: Sequence of sxt2 fragment integrated into the maltose operon

<400> SEQUENCE: 99

```
ctgtgaacta aaccgaggtc atgtaaggaa tttcgtgatg ttgcttgcaa ccagccttgc     60

aagaagcgga tacaggagtg caaaaaatgg ctatctctag aaaggcctac cccttaggct    120

ttatgcaaca gaaacaataa taatggagtc atgaacatga ttgataccat tagcgttctg    180

ctgcgtgaat ggaccgttat ttttctgacc ggtctggcat tttggctgtg ggaaattcgt    240

agtccgctgc atcagattga atacaaagcc aaatttttca aagaactggg ttgggcaggt    300

atcagctttg tttttcgtat tgtttatgcc tatgttagcg tggccattat caaactgctg    360

agcagcctgt ttatgggtga aagcgcaaat tttgccggtg ttatgtatgt tccgctgtgg    420

ctgcgtatta ttaccgcata tattctgcag gatctgaccg attatctgct gcatcgtacc    480

atgcatagca atcagtttct gtggctgacc cataaatggc atcatagcac caaacagagt    540

tggtggctga gcggtaataa agatagcttt accggtggtc tgctgtatac cgttaccgca    600

ctgtggtttc cgctgctgga tattccgagc gaagttatga gcgttgttgc agttcatcag    660

gtgattcata acaactggat tcacctgaat gtgaaatgga atagctggct gggtattatc    720

gaatggattt atgttacacc gcgtatccat accctgcatc atctggatac cggtggtcgt    780

aatctgagca gtatgtttac ctttattgat cgtctgtttg gcacctatgt gtttccggaa    840

aactttgata tcgaaaaaag caaaaaccgc ctggatgatc agagcgttac cgttaaaacc    900

attctgggtt tctgagaagg agatatacat atgctgaaag attttaacca gttcctgatt    960
```

cgtaccctgg catttgtttt tgcctttggc atttttctga caaccggtgt tggtattgca 1020
aaagcagatt atctggtgaa aggtggcaaa attaccaatg ttcagaatac cagcagcaac 1080
ggtgataatt atgcagttag cattagcggt ggttttggtc cgtgtgcaga tcgtgttatt 1140
attctgccga ccagcggtgt tattaatcgt gatattcaca tgcgtggtta tgaagcagca 1200
ctgaccgcac tgagcaatgg ttttctggtt gatatctatg attataccgg tagcagctgt 1260
agcaatggtg gccagctgac cattaccaat cagctgggta aactgattag caattgagaa 1320
ggagatatac atatgaccaa tcagaacaac caagagctgg aaaatgatct gccgattgca 1380
aaacagccgt gtccggttaa tagctataat gaatgggata ccctggaaga agttattgtt 1440
ggtagcgttg aaggtgcaat gctgcctgca ctggaaccga ttaacaaatg gacctttccg 1500
tttgaagaac tggaaagcgc acagaaaatt ctgagcgaac gtggtggtgt tccgtatccg 1560
cctgaaatga ttaccctggc acataaagaa ctgaacgagt ttattcatat cctggaagcc 1620
gaaggtgtta aagttcgtcg tgttaaaccg gttgatttta gcgttccgtt tagcacaccg 1680
gcatggcagg ttggtagcgg tttttgtgca gcaaatccgc gtgatgtttt tctggttatt 1740
ggcaacgaaa ttatcgaagc accgatggca gatcgtaatc gttattttga aacctgggca 1800
tatcgcgaaa tgctgaaaga atattttcag gcaggcgcaa aatggaccgc agcaccgaaa 1860
ccgcagctgt ttgatgcaca gtatgatttc aattttcagt ttccgcagct gggtgaaccg 1920
cctcgttttg ttgttaccga atttgaaccg acctttgatg cagccgattt tgttcgttgt 1980
ggtcgtgata tttttggcca gaaaagccat gttaccaatg gtctgggtat tgaatggctg 2040
cagcgtcatc tggaagatga atatcgcatt catatcatcg aaagccattg tccggaagca 2100
ctgcatattg ataccaccct gatgccgctg gcaccgggta aaattctggt taatccggaa 2160
tttgtggacg tgaataaact gccgaaaatt ctgaaaagct gggatattct ggttgcaccg 2220
tatccgaatc atattccgca gaatcagctg cgtctggtta gcgaatgggc aggtctgaat 2280
gttctgatgc tggatgaaga acgtgtgatc gtggaaaaaa atcaagagca gatgatcaaa 2340
gccctgaaag attggggttt taaaccgatt gtttgccact tcgaaagcta ttatccgttt 2400
ctgggtagct ttcattgtgc aaccctggat gttcgtcgtc gtggcaccct gcagagctat 2460
ttttgagaag gagatataca tatgacgacc gcagatctga ttctgatcaa taattggtat 2520
gttgtggcca aggtggaaga ttgtaaaccg ggtagcatta ccaccgcact gctgctgggt 2580
gttaaactgg ttctgtggcg tagccgtgaa cagaatagcc cgattcagat ttggcaggat 2640
tattgtccgc atcgtggtgt tgcactgagc atgggtgaaa ttgtgaataa taccctggtt 2700
tgtccgtatc atggttggcg ttataatcag gcaggtaaat gtgttcatat tccggcacat 2760
ccggatatga cccctccggc aagcgcacag gcaaaaatct atcattgtca agaacgttat 2820
ggtctggttt gggtttgtct gggtgatccg gttaatgata ttccgagtct gccggaatgg 2880
gatgatccga attatcataa tacctgcacc aagagctact ttatccaggc aagcgcattt 2940
cgtgtgatgg ataactttat tgatgtgagc cattttccgt ttgtgcatga tggtggtctg 3000
ggcgatcgta atcatgcaca gattgaagaa tttgaggtga aagtggataa agacggtatt 3060
agcattggca atctgaaact gcagatgcct cgttttaata gcagcaatga agatgatagc 3120
tggaccctgt atcagcgtat tagccatccg ctgtgtcagt attatatcac cgaaagcagc 3180
gaaattcgta cagcagatct gatgctggtt accccgattg atgaagataa ttcactggtt 3240
cgtatgctgg tgacctggaa tcgtagcgaa attctggaaa gcaccgttct ggaagaattt 3300

-continued

```
gatgaaacca ttgaacagga tatcccgatt attcatagcc agcagcctgc acgtctgccg   3360
ctgctgccga gcaagcagat taatatgcag tggctgagcc aagaaattca tgttccgagc   3420
gatcgttgta ccgttgcata tcgtcgttgg ctgaaagaac tgggcgttac ctatggtgtt   3480
tgttgagaag gagatataca tatgcagatt ctgggtatca gcgcctatta tcatgatagc   3540
gcagcagcaa tggttattga tggtgaaatt gttgcagcag cacaagaaga acgttttagc   3600
cgtcgtaaac atgatgcagg ttttccgacc ggtgcaatta cctattgtct gaaacaggtt   3660
ggcaccaaac tgcagtatat tgatcagatc gtgttctatg ataaaccgct ggtgaaattt   3720
gaacgtctgc tggaaaccta tctggcctat gcaccgaaag gttttggtag ttttattacc   3780
gcaatgccgg tgtggctgaa agagaaactg tatctgaaaa ccctgctgaa aaaagaactg   3840
gcactgctgg gtgaatgtaa agcaagccag ctgcctccgc tgctgtttac cagccatcat   3900
caggcacatg cagcagcagc attttttccg agcccgtttc agcgtgcagc agttctgtgt   3960
ctggatggtg ttggtgaatg ggcaaccacc agtgtttggc tgggtgaagg taataaactg   4020
acaccgcagt gggaaattga ttttccgcat agcctgggcc tgctgtatag cgcatttacc   4080
tattataccg gctttaaagt gaacagcggt gagtataaac tgatgggtct ggcaccgtat   4140
ggtgaaccga aatatgttga tcagattctg aaacatctgc tggatctgaa agaagatggc   4200
acctttcgtc tgaacatgga ttatttcaat tataccgttg gtctgaccat gaccaaccat   4260
aaatttcata gcatgtttgg tggtccgcct cgtcaggcag aaggtaaaat tagccagcgt   4320
gatatggatc tggcaagcag cattcagaaa gttaccgaag aagtgattct gcgtctggca   4380
cgtaccatta agaaagaatt aggtgttgaa tacctgtgtc tggcaggcgg tgttggtctg   4440
aattgtgttg caaatggtcg tattctgcgt gagagcgatt ttaaagatat ttggattcag   4500
cctgcagccg gtgatgcagg tagcgcagtt ggtgcagcac tggcaatttg gcatgaatat   4560
cataaaaaac cgcgtaccag caccgcaggc gatcgtatga aaggtagcta tctgggtccg   4620
agctttagcg aagcagaaat tctgcagttt ctgaacagcg tgaatattcc gtatcatcgt   4680
tgtgtggata atgaactgat ggcacgtctg gcggaaattc tggatcaggg taatgttgtt   4740
ggttggttta gcggtcgtat ggaatttggt ccgcgtgcac tgggtggtcg tagcattatt   4800
ggtgatagcc gtagcccgaa aatgcagagc gttatgaatc tgaaaatcaa atatcgcgaa   4860
agcttccgtc cgtttgcacc gagcgttctg gcagaacgtg ttagcgatta ttttgatctg   4920
gatcgtccga gcccgtatat gctgctggtt gcacaggtta aagaaaatct gcatattccg   4980
atgacccaag aacagcatga actgtttggt atcgaaaaac tgaatgttcc gcgtagccag   5040
attccggcag ttacccatgt tgattatagc gcacgtattc agaccgttca taaagaaacc   5100
aatccgcgtt attatgaact gatccgtcat tttgaagcac gtaccggttg tgcagttctg   5160
gttaatacca gctttaatgt tcgtggtgaa ccgattgtgt gtacaccgga agatgcatat   5220
cgttgtttta tgcgtaccga gatggattac ctggtgatgg aaaattttct gctggtgaaa   5280
agcgaacagc ctcgtggtaa tagtgatgaa agctggcaga aagaatttga gctggattga   5340
tactctaacc ccatcggccg tcttaggggt tttttgtcga agttcctatt ctctagaaag   5400
tataggaact tcacctgtgg ggtgactttg ccgccgctgc cgtgatgtct gcattaccga   5460
tc                                                                  5462
```

<210> SEQ ID NO 100
<211> LENGTH: 112
<212> TYPE: DNA
<213> ORGANISM: Cylindrospermopsis raciborskii T3

-continued

<400> SEQUENCE: 100
agtccagcct tgcaagaagc ggatacagga gtgcaaaaaa tggctatctc tagaaaggcc 60
taccccttag gctttatgca acagaaacaa taataatgga gtcatgaaca tg 112

<210> SEQ ID NO 101
<211> LENGTH: 114
<212> TYPE: DNA
<213> ORGANISM: Cylindrospermopsis raciborskii T3

<400> SEQUENCE: 101
agtccagcct tgcaagaagc ggatacagga gtgcaaaaaa tggctatctc tagaaaggcc 60
taccccttag gctttatgca acagaaacaa taataatgga gtcatgaaca tatg 114

PROCESS

RELATED APPLICATIONS

This application is the U.S. national stage pursuant to 35 U.S.C. § 371, of International application Ser. No. PCT/EP2017/053077, filed Feb. 10, 2017 and published on Aug. 17, 2017 as publication WO 2017/137606 A1, which claims the benefit of priority of Great Britain Application No. 1602576.9, filed Feb. 12, 2016, which are hereby expressly incorporated by reference in their entirety.

The present invention relates to processes to make neosaxitoxin and analogues thereof, and intermediates in the production of neosaxitoxin in recombinant host cells. Neosaxitoxin may be used in the production of pharmaceutical compositions.

Voltage-gated sodium channels (VGSCs) are integral membrane proteins that form ion channels, conducting sodium ions ($Na^+$) through a cell's plasma membrane. They play an important role in the initiation of action potentials.

It has long been known that blocking such channels may be useful in preventing the transmission of pain impulses; VGSCs are now well-validated targets for the treatment of pain. In particular, a number of VGSC antagonists are currently being investigated in the production of analgesics and anaesthetics.

Saxitoxin and neosaxitoxin both act as specific blockers of VGSCs. These compounds are therefore potentially useful in the treatment of pain. Saxitoxin (SXT), also known as paralytic shellfish toxin (PST), is a neurotoxin produced by many cyanobacteria (e.g. *Anabaena, Aphanizomenon, Cylindrospermopsis, Lyngbya, Planktothrix, Raphidiopsis, Scytonema*) and dinoflagellates (*Alexandrium, Gymnodinium and Pyrodinium*). Saxitoxin is one of the most lethal non-proteinaceous neurotoxins known to date and reversibly binds VGSCs, causing paralysis. It is responsible for many cases of human food poisoning, due to the ingestion of contaminated filter-feeding aquatic animals (e.g. crustaceans, molluscs, shellfish) who bioaccumulate the toxin.

However, there are a number of analogues of SXT, including neosaxitoxin (which is an N1-hydroxylated analogue of SXT), which, although they have high specific toxicities, they have no systemic toxicity when administered in low dosages. They are therefore potentially useful as human therapeutics.

In June 2015, the German drugmaker Grunenthal entered into a collaboration with the Chilean company *Proteus* S.A. and the US-based Boston Children's Hospital to develop the use of neosaxitoxin as a novel anaesthetic for local anaesthesia and post-operative pain management.

There is also a market for other saxitoxin analogues, such as gonyautoxin which has been clinically tested as a muscle relaxant.

*Proteus* S.A. has filed patent applications (e.g. US 2015/0099879) relating to the production and harvesting of neosaxitoxin and saxitoxin from cells which naturally-produce neosaxitoxin and saxitoxin (e.g. cyanobacterial cells).

A biosynthetic pathway for the production of saxitoxin was first proposed by Shimizu et al. (J. Am. Chem. Soc. (1984), 106, 6433-6434). It was not until 2008, however, that the saxitoxin (sxt) gene cluster was first identified; this was in the cyanobacterium *Cylindrospermopsis raciborskii* T3 (Kellmann et al., Appl. Environ. Microbiol. 2008, 74, 4044-4053). The sxt gene cluster consists of 34 genes or open reading frames (ORFs). This lead Kellmann et al. to propose a revised (10-step) biosynthetic pathway for the production of saxitoxin (see FIG. 1 herein) based on the theoretical functions of the Sxt proteins.

Four other sxt gene clusters have since been identified in different genera: *Anabaena circinalis* 131C and *Aphanizomenon* sp. NH-5 (Mihali et al., BMC Biochem. 10, 8 (2009)); *Lyngbya wollei* (Mihali et al., PloS One 6, e14657 (2011)); and *Raphidiopsis brookii* D9 (Stucken, K. et al., PLoS ONE 5, e9235 (2010)). It is notable, however, that there are several differences in these gene clusters, including the absence of some genes and duplications of others. Furthermore, the architecture of the sxt cluster is rearranged in some genomes, resulting in the biosynthesis of saxitoxin analogues. This has made the elucidation of the biosynthetic pathways for the production of saxitoxin and neosaxitoxin particularly difficult, thus preventing the production of saxitoxin and neosaxitoxin by recombinant routes.

In the pathway proposed by Kellmann (2008), it was suggested that the first steps involved the sxtA gene product. The sxtA gene codes for a multi-domain protein related to polyketide synthases (PKS). SxtA was proposed by Kellmann to catalyse the condensation of arginine and one methylated acetate unit to produce a 4-amino-3-oxo-guanidinoheptane (AOGH) intermediate. This process was proposed to occur stepwise, and was catalysed by the four domains of SxtA. The acetyltransferase domain selectively was said to tether acetyl-CoA onto the pantetheinyl arm of the holo-acyl carrier protein. SAM-dependant methylation of the acetyl moiety, catalysed by the first SxA domain, was said to result in the formation of propionate. The final step in AOGH biosynthesis was said to be the condensation of propionate to arginine, catalysed by the class II aminotransferase domain. AOGH was used as a substrate for the biosynthesis of saxitoxin by downstream enzymes encoded by other members of the sxt gene cluster. However, the structure of AOGH was not confirmed due to lack of a chemical standard.

Although Tsuchiya and co-workers have recently elucidated a synthetic route for AOGH (Tsuchiya, S. et al. Org. Biomol. Chem. 12, 3016-3020 (2014); Tsuchiya, S. et al., Chem. Eur. J. 21, 7835-7840 (2015)), this study did not investigate the involvement of SxtA or any other Sxt proteins in the production of AOGH. This step is a key one in the production of saxitoxin and neosaxitoxin.

In summary, therefore, the only commercially-available high-yield route which is currently useable to make saxitoxin and neosaxitoxin is to isolate it from cells (such as cyanobacteria) which naturally produce it.

The current methods for the production of neosaxitoxin are not capable of producing neosaxitoxin in the quantities which are needed to manufacture the desired pharmaceutical compositions. Therefore, there exists a need for improved methods to produce neosaxitoxin.

The biosynthetic pathway for the production of neosaxitoxin has now been elucidated in sufficient detail to enable the production of neosaxitoxin by a recombinant route. In particular, out of the 34 sxt genes or ORFs which were identified by Kellmann (2008), those that are necessary for the production of neosaxitoxin have identified.

It has now been found that the biosynthetic pathway which was proposed by Kellmann (2008) is incorrect and that the Kellmann pathway refers to some genes which are not necessary for the recombinant production of neosaxitoxin; the Kellmann (2008) pathway also fails to refer to some sxt genes which are necessary for the production of neosaxitoxin. Thus the invention provides for the first time a recombinant route for the production of neosaxitoxin and analogues thereof, as well as a recombinant route for the production of various intermediates in the production of neosaxitoxin and analogues thereof.

The invention also facilitates the production of saxitoxin and other analogues thereof, such as gonyautoxin.

In one embodiment, the invention provides a process for producing neosaxitoxin or an analogue thereof, the process comprising the steps:

(A) contacting the substrates:

(i) S-adenosylmethionine, (ii) arginine, (iii) acetyl-CoA, malony-CoA or propionyl-CoA, and (iv) carbamoyl phosphate with Sxt A, B, D, G, H, I, S, T, U, V, W and X polypeptides in a reaction medium, and optionally (B) isolating and/or purifying neosaxitoxin or an analogue thereof from the reaction medium.

Preferably, the process is carried out in a host cell which comprises nucleic acid molecules encoding said Sxt polypeptides.

The invention also provides a process for producing neosaxitoxin or an analogue thereof in a host cell, the process comprising the step:

(A) culturing a host cell which comprises nucleic acid molecules encoding the Sxt polypeptides A, B, D, G, H, I, S, T, U, V, W and X in a culture medium in the presence of the substrates:

(i) S-adenosylmethionine, (ii) arginine, (iii) acetyl-CoA, malony-CoA or propionyl-CoA, and (iv) carbamoyl phosphate preferably under conditions which are suitable for the production of neosaxitoxin or an analogue thereof. Preferably, the host cell additionally comprises a nucleic acid molecule encoding a PPTase.

Preferably, the process additionally comprises the step of isolating and/or purifying neosaxitoxin or an analogue thereof from the host cells or from the culture medium.

As used herein, the term "neosaxitoxin" refers to a compound having the following structure:

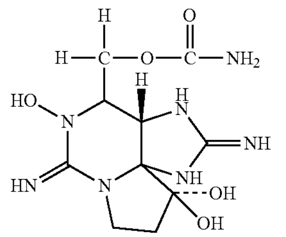

or a stereoisomer thereof.

The host cells may be any cells which are capable of expressing the nucleic acid molecules encoding all of the specified Sxt polypeptides. The host cell is preferably a recombinant host cell.

As used herein, the term "recombinant" refers to the fact that the host cells are not wild-type host cells, e.g. they have been modified by the introduction of one of more nucleic acid molecules encoding one or more of the specified Sxt polypeptides.

The host cells may be prokaryotic or eukaryotic cells. For example, the host cells may be bacterial cells. The bacteria may be a Gram positive or Gram negative bacteria. The Gram positive bacteria may be selected from the group consisting of Actinobacteria, Firmicutes and Tenericutes. The Gram negative bacteria may be selected from the group consisting of Aquificae, Bacteroidetes/Fibrobacteres—Chlorobi (FCB group), Deinococcus-Thermus, Fusobacteria, Gemmatimonadetes, Nitrospirae, Planctomycetes-Verrucomicrobia/Chlamydiae (PVC group), Proteobacteria, Spirochaetes and Synergistetes.

Preferably, the host cell is of the Phylum Proteobacteria; more preferably of the Class Gammaproteobacteria; more preferably of the Family Enterobacteriaceae; and even more preferably of the Genus *Escherichia*. Most preferably, the host cell is of the species *E. coli*. In some embodiments, the host cells are of the genus *Pseudomonas*.

Eukaryotic cells may also be used, e.g. yeast cells and mammalian cells. Since neosaxitoxin is toxic to many eukaryotic cells, the eukaryotic host cells are preferably ones which are not susceptible to neosaxitoxin toxicity. Such cells may be naturally non-susceptible (e.g. yeast cells) or they may be engineered to be non-susceptible (e.g. mammalian cells which co-express a neosaxitoxin antagonist).

Alternatively, the host cells may be ones which do not secrete neosaxitoxin, i.e. any neosaxitoxin which is produced is retained within the cells (thus preventing it from exerting its toxic effect). The host cells may also be plant cells.

In some embodiments, the host cells are heterotrophs. The host cell may be a photoheterotroph or a chemoheterotroph. A heterotroph is an organism that cannot fix carbon and uses organic carbon for growth. Heterotrophs can be further divided based on how they obtain energy: if the heterotroph uses light for energy, then it is a photoheterotroph; if the heterotroph uses chemical energy, it is a chemoheterotroph. In some embodiments, the host cells are not autotrophs. Autotrophs can be photoautotrophs or chemoautotrophs.

Neosaxitoxin is produced naturally by several species of marine dinoflagellates and freshwater cyanobacteria. The invention does not relate to the natural production of neosaxitoxin by such wild-type host cell species. Consequently, in some embodiments of the invention, the host cells are not dinoflagellates or cyanobacteria.

In particular, the host cells are preferably not selected from the group consisting of *Cylindrospermopsis raciborskii, Anphanizomenon flos-aquae, Aphanizomenon* (APh) *issatschenkoi* (usaceb) *Proskina-Lavrenco, Aphanizomenon gracile* (*Lemm*) *Lemm, Anabaena circinalis, Lyngbya wollei* and *Alexandrium tamarens.*

In particular, the host cells are preferably not selected from the group consisting of *Anabaena, Aphanizomenon, Cylindrospermopsis, Lyngbya, Planktothrix, Raphidiopsis, Scytonema* and dinoflagellates (*Alexandrium, Gymnodinium* and *Pyrodinium*).

The host cells may, however, be recombinant dinoflagellates or recombinant cyanobacteria, e.g. dinoflagellates or cyanobacteria which have been modified compared to the wild-type dinoflagellates or cyanobacteria (for example, by addition of one or more genes, preferably by the addition of one or more sxt genes). The host cells comprise and/or express nucleic acid molecules encoding the specified Sxt proteins.

Preferably, the Sxt polypeptide and sxt genes are obtained from a cyanobacteria or a dinoflagellate. More preferably, the Sxt polypeptide and sxt genes are obtained from *Anabaena, Aphanizomenon, Cylindrospermopsis, Lyngbya, Planktothrix, Raphidiopsis, Scytonema, Alexandrium, Gymnodinium* or *Pyrodinium*. Even more preferably, the Sxt polypeptide and sxt genes are obtained from *Cylindrospermopsis raciborskii, Anphanizomenon flos-aquae, Aphanizomenon* (APh) *issatschenkoi* (usaceb) *Proskina-Lavrenco,*

*Aphanizomenon gracile* (*Lemm*) *Lemm, Anabaena circinalis, Lyngbya wollei* or *Alexandrium tamarens. Most preferably, the Sxt polypeptide and sxt genes are obtained from C. raciborskii* T3 strain. In some embodiments, the Sxt polypeptide and sxt genes may be obtained from *Dolichosporum circinale* 134C or *A. minutum.*

The nucleic acid molecules encoding the specified Sxt proteins may be heterologous molecules, i.e. ones that do not occur naturally in the wild-type host cell.

As used herein, the term SxtA preferably refers to a polypeptide having the amino acid sequence given in SEQ ID NO: 10 or a sequence having at least 50% amino acid sequence identity thereto and having the function of a polyketide synthase related protein with four catalytic domains:sxtA1:methyltransferase; sxtA2:GNAT acetyl transferase; sxtA3:acyl carrier protein; and sxtA4:class II aminotransferase.

As used herein, the term sxtA preferably refers to a nucleic acid molecule having the nucleotide sequence given in SEQ ID NO: 11 or 12, or a sequence having at least 50% nucleotide sequence identity thereto and encoding a polyketide synthase related protein with four catalytic domains:sxtA1:methyltransferase; sxtA2:GNAT acetyl transferase; sxtA3:acyl carrier protein; and sxtA4:class II aminotransferase.

As used herein, the term SxtB preferably refers to a polypeptide having the amino acid sequence given in SEQ ID NO: 7 or a sequence having at least 50% amino acid sequence identity thereto and having the function of a cytidine deaminase.

As used herein, the term sxtB preferably refers to a nucleic acid molecule having the nucleotide sequence given in SEQ ID NO: 8 or 9, or a sequence having at least 50% nucleotide sequence identity thereto and encoding a cytidine deaminase. The SxtB polypeptide may also be capable of cyclisation.

As used herein, the term SxtC preferably refers to a polypeptide having the amino acid sequence given in SEQ ID NO: 4 or a sequence having at least 50% amino acid sequence identity thereto and encoding a regulatory subunit. As used herein, the term SxtC preferably refers to a nucleic acid molecule having the nucleotide sequence given in SEQ ID NO: 5 or 6, or a sequence having at least 50% nucleotide sequence identity thereto and encoding a regulatory subunit. The SxtC polypeptide may also be capable of decarbamoylation.

As used herein, the term SxtD preferably refers to a polypeptide having the amino acid sequence given in SEQ ID NO: 1 or a sequence having at least 50% amino acid sequence identity thereto and having the function of a desaturase. As used herein, the term sxtD preferably refers to a nucleic acid molecule having the nucleotide sequence given in SEQ ID NO: 2 or 3, or a sequence having at least 50% nucleotide sequence identity thereto and encoding a desaturase.

As used herein, the term SxtE preferably refers to a polypeptide having the amino acid sequence given in SEQ ID NO: 13 or a sequence having at least 50% amino acid sequence identity thereto and having the function of a chaperone-like protein. As used herein, the term sxtE preferably refers to a nucleic acid molecule having the nucleotide sequence given in SEQ ID NO: 14 or 15, or a sequence having at least 50% nucleotide sequence identity thereto and encoding a chaperone-like protein.

As used herein, the term SxtF preferably refers to a polypeptide having the amino acid sequence given in SEQ ID NO: 16 or a sequence having at least 50% amino acid sequence identity thereto and having the function of a sodium-driven multidrug and toxic compound extrusion protein. As used herein, the term sxtF preferably refers to a nucleic acid molecule having the nucleotide sequence given in SEQ ID NO: 17 or 18, or a sequence having at least 50% nucleotide sequence identity thereto and encoding a sodium-driven multidrug and toxic compound extrusion protein.

As used herein, the term SxtG preferably refers to a polypeptide having the amino acid sequence given in SEQ ID NO: 19 or a sequence having at least 50% amino acid sequence identity thereto and having the function of an amidino transferase. As used herein, the term sxtG preferably refers to a nucleic acid molecule having the nucleotide sequence given in SEQ ID NO: 20 or 21, or a sequence having at least 50% nucleotide sequence identity thereto and encoding an amidino transferase.

As used herein, the term SxtH preferably refers to a polypeptide having the amino acid sequence given in SEQ ID NO: 22 or a sequence having at least 50% amino acid sequence identity thereto and having the function of a dioxygenase. As used herein, the term sxtH preferably refers to a nucleic acid molecule having the nucleotide sequence given in SEQ ID NO: 23 or 24, or a sequence having at least 50% nucleotide sequence identity thereto and encoding a dioxygenase. The SxtH polypeptide may also be capable of C12 hydroxylation.

As used herein, the term SxtI preferably refers to a polypeptide having the amino acid sequence given in SEQ ID NO: 25 or a sequence having at least 50% amino acid sequence identity thereto and having the function of an O-carbamoyl transferase. As used herein, the term sxtl preferably refers to a nucleic acid molecule having the nucleotide sequence given in SEQ ID NO: 26 or 27, or a sequence having at least 50% nucleotide sequence identity thereto and encoding an O-carbamoyl transferase.

As used herein, the term SxtJ preferably refers to a polypeptide having the amino acid sequence given in SEQ ID NO: 28 or a sequence having at least 50% amino acid sequence identity thereto. As used herein, the term sxtJ preferably refers to a nucleic acid molecule having the nucleotide sequence given in SEQ ID NO: 29 or 30, or a sequence having at least 50% nucleotide sequence identity thereto.

As used herein, the term SxtK preferably refers to a polypeptide having the amino acid sequence given in SEQ ID NO: 31 or a sequence having at least 50% amino acid sequence identity thereto. As used herein, the term sxtK preferably refers to a nucleic acid molecule having the nucleotide sequence given in SEQ ID NO: 32 or 33, or a sequence having at least 50% nucleotide sequence identity thereto. sxtJ and sxtK are often associated with 0-carbamoyltransferases. They may be regulatory subunits, and/or mediate binding of SxtI to other proteins or to the membrane.

As used herein, the term SxtL preferably refers to a polypeptide having the amino acid sequence given in SEQ ID NO: 34 or a sequence having at least 50% amino acid sequence identity thereto and having the function of a GDSL-lipase. As used herein, the term sxtL preferably refers to a nucleic acid molecule having the nucleotide sequence given in SEQ ID NO: 35 or 36, or a sequence having at least 50% nucleotide sequence identity thereto and encoding a GDSL-lipase. The SxtL polypeptide may also be capable of decarbamoylation.

As used herein, the term SxtM preferably refers to a polypeptide having the amino acid sequence given in SEQ ID NO: 37 or a sequence having at least 50% amino acid sequence identity thereto and having the function of a sodium-driven multidrug and toxic compound extrusion protein. As used herein, the term sxtM preferably refers to a nucleic acid molecule having the nucleotide sequence given in SEQ ID NO: 38 or 39, or a sequence having at least 50% nucleotide sequence identity thereto and encoding a sodium-driven multidrug and toxic compound extrusion protein.

As used herein, the term SxtN preferably refers to a polypeptide having the amino acid sequence given in SEQ ID NO: 40 or a sequence having at least 50% amino acid sequence identity thereto and having the function of a sulfotransferase. As used herein, the term sxtN preferably refers to a nucleic acid molecule having the nucleotide sequence given in SEQ ID NO: 41 or a sequence having at least 50% nucleotide sequence identity thereto and encoding a sulfotransferase.

As used herein, the term SxtO preferably refers to a polypeptide having the amino acid sequence given in SEQ ID NO: 72 or a sequence having at least 50% amino acid sequence identity thereto and having the function of an adenylylsulfate kinase. As used herein, the term sxtO preferably refers to a nucleic acid molecule having the nucleotide sequence given in SEQ ID NO: 73 or a sequence having at least 50% nucleotide sequence identity thereto and encoding an adenylylsulfate kinase. The SxtO polypeptide may also be capable of PAPS biosynthesis.

As used herein, the term SxtP preferably refers to a polypeptide having the amino acid sequence given in SEQ ID NO: 69 or a sequence having at least 50% amino acid sequence identity thereto and having the function of a putative saxitoxin-binding protein. As used herein, the term sxtP preferably refers to a nucleic acid molecule having the nucleotide sequence given in SEQ ID NO: 70 or 71, or a sequence having at least 50% nucleotide sequence identity thereto and encoding a putative saxitoxin-binding protein.

As used herein, the term SxtQ preferably refers to a polypeptide having the amino acid sequence given in SEQ ID NO: 66 or a sequence having at least 50% amino acid sequence identity thereto. As used herein, the term sxtQ preferably refers to a nucleic acid molecule having the nucleotide sequence given in SEQ ID NO: 67 or 68, or a sequence having at least 50% nucleotide sequence identity thereto.

As used herein, the term SxtR preferably refers to a polypeptide having the amino acid sequence given in SEQ ID NO: 63 or a sequence having at least 50% amino acid sequence identity thereto and having the function of an acyl-CoA N-acyltransferase. As used herein, the term sxtR preferably refers to a nucleic acid molecule having the nucleotide sequence given in SEQ ID NO: 64 or 65, or a sequence having at least 50% nucleotide sequence identity thereto and encoding an acyl-CoA N-acyltransferase.

As used herein, the term SxtS preferably refers to a polypeptide having the amino acid sequence given in SEQ ID NO: 57 or a sequence having at least 50% amino acid sequence identity thereto and capable of epoxidation and ring formation of a neosaxitoxin precursor. As used herein, the term sxtS preferably refers to a nucleic acid molecule having the nucleotide sequence given in SEQ ID NO: 58 or 59, or a sequence having at least 50% nucleotide sequence identity thereto and capable of epoxidation and ring formation of a neosaxitoxin precursor.

As used herein, the term SxtT preferably refers to a polypeptide having the amino acid sequence given in SEQ ID N: 54 or a sequence having at least 50% amino acid sequence identity thereto and capable of C-11 hydroxylation of a neosaxitoxin precursor. As used herein, the term sxtT preferably refers to a nucleic acid molecule having the nucleotide sequence given in SEQ ID NO: 55 or 56, or a sequence having at least 50% nucleotide sequence identity thereto and capable of C-11 hydroxylation of a neosaxitoxin precursor.

As used herein, the term SxtU preferably refers to a polypeptide having the amino acid sequence given in SEQ ID NO: 51 or a sequence having at least 50% amino acid sequence identity thereto and having the function of a short-chain alcohol dehydrogenase. As used herein, the term sxtU preferably refers to a nucleic acid molecule having the nucleotide sequence given in SEQ ID NO: 52 or 53, or a sequence having at least 50% nucleotide sequence identity thereto and encoding a short-chain alcohol dehydrogenase. The SxtU polypeptide may also be capable of C1 reduction.

As used herein, the term SxtV preferably refers to a polypeptide having the amino acid sequence given in SEQ ID NO: 48 or a sequence having at least 50% amino acid sequence identity thereto and having the function of a FAD-dependent succinate dehydrogenase/fumarate reductase. As used herein, the term sxtV preferably refers to a nucleic acid molecule having the nucleotide sequence given in SEQ ID NO: 49 or 50, or a sequence having at least 50% nucleotide sequence identity thereto and encoding a FAD-dependent succinate dehydrogenase/fumarate reductase. The SxtV polypeptide may also encode a dioxygenase reductase.

As used herein, the term SxtW preferably refers to a polypeptide having the amino acid sequence given in SEQ ID NO: 45 or a sequence having at least 50% amino acid sequence identity thereto and having the function of a ferredoxin. As used herein, the term sxtW preferably refers to a nucleic acid molecule having the nucleotide sequence given in SEQ ID NO: 46 or 47, or a sequence having at least 50% nucleotide sequence identity thereto and encoding a ferredoxin. The SxtW polypeptide may also encode an electron carrier.

As used herein, the term SxtX preferably refers to a polypeptide having the amino acid sequence given in SEQ ID NO: 42 or a sequence having at least 50% amino acid sequence identity thereto and capable of the N-1 hydroxylation of neosaxitoxin. As used herein, the term sxtX preferably refers to a nucleic acid molecule having the nucleotide sequence given in SEQ ID NO: 43 or 44, or a sequence having at least 50% nucleotide sequence identity thereto and capable of the N-1 hydroxylation of neosaxitoxin.

As used herein, the term SxtY preferably refers to a polypeptide having the amino acid sequence given in SEQ ID NO: 74 or a sequence having at least 50% amino acid sequence identity thereto and having the function of a phosphate-dependent transcriptional regulator. As used herein, the term sxtY preferably refers to a nucleic acid molecule having the nucleotide sequence given in SEQ ID NO: 75 or a sequence having at least 50% nucleotide sequence identity thereto and encoding a phosphate-dependent transcriptional regulator. The SxtY polypeptide may also be capable of signal transduction.

As used herein, the term SxtZ preferably refers to a polypeptide having the amino acid sequence given in SEQ ID NO: 76 or a sequence having at least 50% amino acid sequence identity thereto and having the function of a histidine kinase. As used herein, the term sxtZ preferably refers to a nucleic acid molecule having the nucleotide sequence given in SEQ ID NO: 77 or a sequence having at least 50% nucleotide sequence identity thereto and encoding a histidine kinase.

The functions and capabilities of some of the sxt genes are further illustrated in FIGS. 2-4, where it can be seen that some are capable of converting Intermediate X to Intermediate Y (where X and Y are the structures of defined intermediates).

As used herein, the term ORF5 preferably refers to a polypeptide having the amino acid sequence given in SEQ ID NO: 60 or a sequence having at least 50% amino acid sequence identity thereto and having the function of a cyanophage S-PM2 protein CAF34141-like protein. ORF 5 is also known in the art as ORF24. As used herein, the term orf5 preferably refers to a nucleic acid molecule having the nucleotide sequence given in SEQ ID NO: 61 or 62, or a sequence having at least 50% nucleotide sequence identity thereto and encoding a cyanophage S-PM2 protein CAF34141-like protein.

Preferably, the host cell additionally comprises and/or expresses a nucleic acid molecule encoding a 4'-phosphopantetheinyl transferase (PPTase). As used herein, the term PPTase preferably refers to a polypeptide having the amino acid sequence given in SEQ ID NO: 78 or 90 or a sequence having at least 50% amino acid sequence identity thereto and having the function of a phosphopantetheinyl transferase. As used herein, the term PPTase gene preferably refers to a nucleic acid molecule having the nucleotide sequence given in SEQ ID NO: 79, 80 or 89, or a sequence having at least 50% nucleotide sequence identity thereto and encoding a phosphopantetheinyl transferase. Preferably, the PPTase is encoded by the *Bacillus subtilis* sfp gene (SEQ ID NO: 89). Most preferably, the PPTase is from *C. raciborskii* T3 strain. In some embodiments, 1-20 (e.g. 20) of the first twenty amino acids of the PPTase may be removed in order to increase the solubility of the PPTase. Additionally, the first V in the amino acid sequence may be changed to M.

Preferably, the nucleotide sequences of the nucleic acid molecules are codon-optimised for the host cell.

The Sxt polypeptides, ORF and PPTases are preferably defined herein as having at least 50% amino acid sequence identity to a reference amino acid sequence. Preferably, the Sxt, ORF and PPTase polypeptides have at least 60%, 70%, 80%, 90%, 95%, 98% or 99% amino acid sequence identity to the specified reference polypeptides. The sxt nucleic acid molecules, orf and PPTase nucleic acid molecules are preferably defined herein as having at least 50% nucleotide sequence identity to a reference nucleotide sequence. Preferably, the sxt, orf and PPTase nucleic acid molecules have at least 60%, 70%, 80%, 90%, 95%, 98% or 99% nucleotide sequence identity to the specified reference nucleic acid molecules.

The nucleic acid molecules may be DNA or RNA. Percentage amino acid sequence identities and nucleotide sequence identities may be obtained using the BLAST methods of alignment (Altschul et al. (1997), "Gapped BLAST and PSI-BLAST: a new generation of protein database search programs", Nucleic Acids Res. 25:3389-3402; and http://www.ncbi.nlm.nih.gov/BLAST). Preferably the standard or default alignment parameters are used. Standard protein-protein BLAST (blastp) may be used for finding similar sequences in protein databases. Like other BLAST programs, blastp is designed to find local regions of similarity. When sequence similarity spans the whole sequence, blastp will also report a global alignment, which is the preferred result for protein identification purposes. Preferably the standard or default alignment parameters are used. In some instances, the "low complexity filter" may be taken off. BLAST protein searches may also be performed with the BLASTX program, score=50, wordlength=3. To obtain gapped alignments for comparison purposes, Gapped BLAST (in BLAST 2.0) can be utilized as described in Altschul et al. (1997) Nucleic Acids Res. 25: 3389. Alternatively, PSI-BLAST (in BLAST 2.0) can be used to perform an iterated search that detects distant relationships between molecules. (See Altschul et al. (1997) supra). When utilizing BLAST, Gapped BLAST, PSI-BLAST, the default parameters of the respective programs may be used. With regard to nucleotide sequence comparisons, MEGABLAST, discontiguous-megablast, and blastn may be used to accomplish this goal. Preferably the standard or default alignment parameters are used. MEGABLAST is specifically designed to efficiently find long alignments between very similar sequences. Discontiguous MEGABLAST may be used to find nucleotide sequences which are similar, but not identical, to the nucleic acids of the invention. The BLAST nucleotide algorithm finds similar sequences by breaking the query into short subsequences called words. The program identifies the exact matches to the query words first (word hits). The BLAST program then extends these word hits in multiple steps to generate the final gapped alignments. In some embodiments, the BLAST nucleotide searches can be performed with the BLASTN program, score=100, wordlength=12. One of the important parameters governing the sensitivity of BLAST searches is the word size. The most important reason that blastn is more sensitive than MEGABLAST is that it uses a shorter default word size (11). Because of this, blastn is better than MEGABLAST at finding alignments to related nucleotide sequences from other organisms. The word size is adjustable in blastn and can be reduced from the default value to a minimum of 7 to increase search sensitivity. A more sensitive search can be achieved by using the newly-introduced discontiguous megablast page. This page uses an algorithm which is similar to that reported by Ma et al. (Bioinformatics. 2002 March; 18(3): 440-5). Rather than requiring exact word matches as seeds for alignment extension, discontiguous megablast uses non-contiguous word within a longer window of template. In coding mode, the third base wobbling is taken into consideration by focusing on finding matches at the first and second codon positions while ignoring the mismatches in the third position. Searching in discontiguous MEGABLAST using the same word size is more sensitive and efficient than standard blastn using the same word size. Parameters unique for discontiguous megablast are: word size: 11 or 12; template: 16, 18, or 21; template type: coding (0), non-coding (1), or both (2).

The Sxt polypeptide sequences of the *Cylindrospermopsis raciborskii* T3 sxt genes are available from GenBank under accession no. DQ787200. The amino acid sequences of the *Cylindrospermopsis raciborskii* T3 Sxt polypeptides are given herein in the attached "SEQUENCES" section. The invention is not, however, limited to the sequences of those polypeptides; the invention encompasses polypeptides from other species which have the same function as the recited *Cylindrospermopsis raciborskii* T3 polypeptides.

In the processes of the invention, the substrates are contacted with the Sxt polypeptides A, B, D, G, H, I, S, T, U, V, W and X, or the host cells comprise one or more nucleic acid molecules coding for such polypeptides. In some embodiments of the invention, the substrates are not contacted with one or more of the Sxt polypeptides A, B, D, G, H, I, S, T, U, V, W and X, or the host cells does not comprise one or more nucleic acid molecules coding for such polypeptides. In some embodiments of the processes of the invention, other Sxt polypeptides or nucleic acid molecules coding for such polypeptides may or may not be used.

If a process of the invention does use a particular Sxt polypeptide, the substrates will be contacted with that Sxt polypeptide and/or the host cells will comprise a nucleic acid molecule coding for such a polypeptide. If a process of the invention does not use a particular Sxt polypeptide, the substrates will not be contacted with that Sxt polypeptide and/or the host cells will not comprise a nucleic acid molecule coding for such a polypeptide.

In some embodiments, the processes of the invention may or may not additionally use one or more Sxt polypeptides independently selected from the group consisting of Sxt C, E, J, K, L, and R, or nucleic acid molecules coding for such polypeptides. Preferably, the processes of the invention do additionally use one or more Sxt polypeptides selected from the group consisting of Sxt C, E, J, K, L, and R (preferably C and/or E), or nucleic acid molecules coding for such polypeptides.

In some embodiments, the process of the invention additionally uses Sxt E or a nucleic acid molecule coding for such polypeptide. In other embodiments, the process of the invention additionally does not use Sxt E or a nucleic acid molecule coding for such polypeptide.

In some embodiments, the processes of the invention may or may not utilise the Sxt Q polypeptide or a nucleic acid molecule coding for such a polypeptide.

In some embodiments, the processes of the invention may or may not utilise the Sxt R polypeptide or a nucleic acid molecule coding for such a polypeptide.

In some embodiments, the processes of the invention may or may not utilise the ORF24 polypeptide or a nucleic acid molecule coding for such a polypeptide.

In other embodiments, the processes of the invention may or may not use one or more Sxt polypeptides independently selected from the group consisting of Sxt F, M, N, O, P, Y, Z, ORF3, ORF4, ORF29, ORF34, OMPR or HISA, or nucleic acid molecules coding for such polypeptides. Preferably, the processes of the invention do not use one or more Sxt polypeptides selected from the group consisting of Sxt F, M, N, O, P, Y, Z, ORF3, ORF4, ORF29, ORF34, OMPR or HISA, or nucleic acid molecules coding for such polypeptides.

In some embodiments of the invention, the processes of the invention may or may not use one or more Sxt polypeptides (or a nucleic acid molecule coding for such a polypeptide) independently selected from the group consisting of:

Sxt ACT C-13 acyltransferase (LWTXs)
Sxt DIOX dioxygenase (C-11)
Sxt N1 N-sulfotransferase
Sxt N2 N-sulfotransferase
Sxt SUL O-sulfotransferase (C-11)
Sxt H1 inactive dioxygenase
Sxt M1 MATE exporter
Sxt M2 MATE exporter
Sxt M3 MATE exporter
Sxt PER drug exporter
Sxt PER2 inactive drug exporter Sxt ACT may be required to make the *Lyngbya wollei*-specific "weird" analogues of saxitoxin (LWTX-1 to -6). These carry a methyl-acetylester side chain instead of a carbamoyl side chain.

Sxt DIOX and Sxt SUL may be required to make C-11 sulfated toxin analogues, such as gonyautoxins 1 to 4 & C-1 to C-4 toxins.

SxtN1 and SxtN2 may be required to make various N-sulfocarbamoyl analogues (C-toxins). SxtN from *C. raciborskii* T3 might be inactive due to a mutation in the catalytic site.

In other embodiments, the processes of the invention may or may not use one or more Sxt polypeptides independently selected from the group consisting of ORF24, P and Q, or nucleic acid molecules coding for such polypeptides. Preferably, the processes of the invention do not use one or more Sxt polypeptides selected from the group consisting of ORF24, P and Q, or nucleic acid molecules coding for such polypeptides.

The host cells of the invention may be produced using standard molecular biology techniques (e.g. Green & Sambrook, "Molecular Cloning: A Laboratory Manual", Fourth Edition, 2012) and with reference to the Examples disclosed herein.

The coding sequences of each of the specified polypeptides will be operably associated with suitable regulatory elements which facilitate the production of the specified polypeptides in the host cells. For example, each coding sequence will be operably associated with a suitable promoter and terminator element. Preferably, these regulatory elements are optimised for use in the host cells. For example, if the host cells are *E. coli*, then *E. coli* regulatory elements (e.g. promoters, terminators, ribosome binding sequences) are preferably used.

One or more of the nucleic acid molecules may be integrated into the genome of the host cells. One or more of the nucleic acid molecules may be present in the host cells in the form of a plasmid or vector. Preferably, all of the specified nucleic acids are integrated into the genomes of the host cells. One or more of the specified nucleic acids may be inserted within a sugar operon within the host cell genome.

The nucleic acid molecules may be present in the form of operons or fragments of gene clusters, i.e. coding for more than one of the desired polypeptides. These may be independently transformed into the host cells. For example, a first nucleic acid molecule may comprise open reading frames encoding sxtA, sxtB and sxtC; a second nucleic acid molecule may comprise open reading frames encoding sxtD, sxtE, sxtG, sxtH, sxtI, sxtJ, sxtK and sxtL; a third nucleic acid molecule may comprise open reading frames encoding sxtQ, sxtR, orf24, sxtS, sxtT, sxtU, sxtV, sxtW and sxtX; and/or a fourth nucleic acid molecule may comprise open reading frames encoding sxtF, sxtP and sxtM. In some embodiments, the third nucleic acid molecule may comprise open reading frames encoding sxtQ, sxtR, sxtS, sxtT, sxtU, sxtV, sxtW and sxtX; or sxtS, sxtT, sxtU, sxtV, sxtW and sxtX.

The nucleic acid molecules may also comprise appropriate selection markers (e.g. genes coding for antibiotic resistance). The nucleic acid molecules may also comprise further control elements such that the expression of one more of the polypeptides is inducible. In some preferred embodiments, the expression of SxtA is inducible.

In some embodiments of the invention, one or more of the nucleic acid molecules or a nucleic acid molecule which encodes a functionally-equivalent polypeptide may already be endogenously present in the host cell (in the host cell genome or in an endogenous plasmid).

The invention also extends to all host cells as defined herein. In particular, the invention provides a host cell which comprises nucleic acid molecules coding for one or more Sxt polypeptides independently selected from the group consisting of A, B, D, G, H, I, S, T, U, V, W and X. The host cell may or may not additionally comprise nucleic acid molecules coding for one or more Sxt polypeptides independently selected from the group consisting of Sxt C, E, J, K, L, and/or R. The host cell may or may not additionally comprise a nucleic acid molecule coding for Sxt Q.

The host cell may or may not additionally comprise one or more nucleic acid molecules coding for one or more or all of the Sxt polypeptides independently selected from the group consisting of Sxt F, M, N, O, P, Y, Z, ORF3, ORF4, ORF29, ORF34, OMPR or HISA. Preferably, the host cell does not comprise nucleic acid molecules coding for one or more or all of the Sxt polypeptides selected from the group consisting of Sxt F, M, N, O, P, Y, Z, ORF3, ORF4, ORF29, ORF34, OMPR or HISA.

The reaction medium and culture medium provide appropriate for the production of neosaxitoxin or an analogue thereof. The conditions will also include appropriate pH and temperature, as can readily be determined by the skilled person. The host cells are cultured in a culture medium under conditions which are suitable for the production of neosaxitoxin or an analogue thereof. Suitable culture media are well known in the art. These will be selected according to the host cells which are being used. Preferably, the culture medium will be an aqueous medium.

The starting substrates for the production of neosaxitoxin or the analogue or variant thereof are:

(i) S-adenosylmethionine, (ii) arginine, (iii) acetyl-CoA, malony-CoA or propionyl-CoA, and (iv) carbamoyl phosphate.

Hence appropriate concentrations of the above substrates need to be available in the reaction medium and culture medium at the start of the process. Appropriate concentrations of the above substrates may readily be determined by the person of skill in the art. Arginine may readily be taken up into the host cells as a substrate from the surrounding culture medium. The other substrates (i.e. S-adenosylmethionine, acetyl-CoA, malony-CoA, propionyl-CoA and carbamoyl phosphate) are unstable. Preferably, these substrates are produced in sufficient amounts within the host cells (they are present in all living cells). The host cells may readily be modified to increase production of these substrates in ways which are routine in the art, if necessary.

In some embodiments of the invention, the process is carried out at a temperature of 14-24° C.; preferably at 16-22° C.; even preferably at about 17, 18, 19, 20 or 21° C.; and most preferably at about 19° C.

Preferably, neosaxitoxin is isolated and/or purified from the reaction or culture medium. Such isolation/purification may be by any suitable means.

In embodiments of the invention wherein the process is carried out in host cells, neosaxitoxin will be produced in the host cells. The host cells may therefore be separated from the culture medium (e.g. by filtration or centrifugation); the host cells may then be lysed; and neosaxitoxin harvested.

Neosaxitoxin may be isolated from the reaction or culture medium by solid phase extraction over a C-18 reverse-phase resin to remove hydrophobic compounds; neosaxitoxin would be present in the flow-through. Solid phase extraction using cation-exchange resin on activated charcoal may also be used. For further purification techniques, reference may be made to US 2015/0099879.

The invention also provides processes to produce various intermediates in the production of neosaxitoxin, as defined below. These processes may be carried out in cell-free media or in host cells which comprise nucleic acid molecules encoding the appropriate Sxt polypeptide.

In other embodiments, the invention provides a process for producing a compound of Formula I [intermediate 4]:

intermediate 4

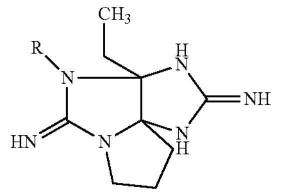

wherein R is OH, the process comprising the steps:

(A) contacting a compound of Formula II [intermediate 3]

intermediate 3

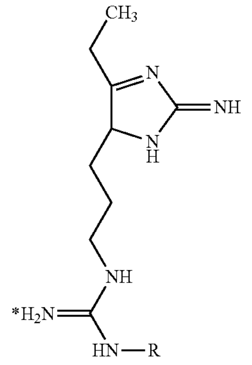

wherein R is OH, with Sxt S, and optionally alpha-ketoglutarate, and optionally molecular oxygen; and (B) isolating or purifying a compound of Formula I from the reaction medium.

The invention also provides a process for producing a compound of Formula I [intermediate 4]:

intermediate 4

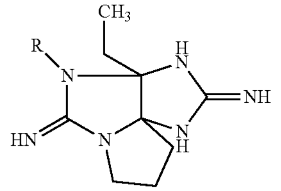

wherein R is OH, the process comprising the steps:

(A) culturing a host cell which comprises a nucleic acid molecule encoding Sxt S in a culture medium in the presence of a compound of Formula II (intermediate 3):

intermediate 3

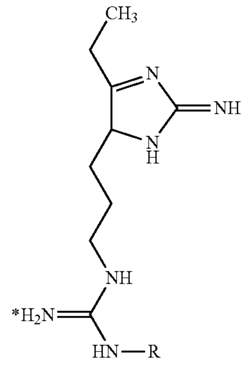

wherein R is OH, under conditions such that Sxt S is produced and Sxt S converts compounds of Formula II to compounds of Formula I.

In other embodiments, the invention provides a process for producing a compound of Formula I [intermediate 4']:

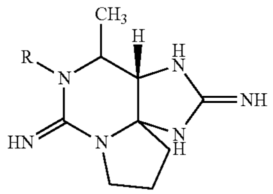

wherein R is OH, the process comprising the steps:

(A) contacting a compound of Formula II [intermediate 3]

intermediate 3

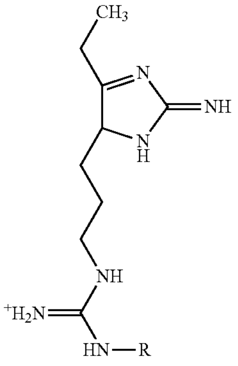

wherein R is OH, with Sxt S, and optionally alpha-ketoglutarate and optionally molecular oxygen;

and (B) isolating or purifying a compound of Formula I from the reaction medium.

The invention also provides a process for producing a compound of Formula I [intermediate 4']:

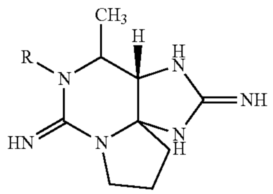

wherein R is OH, the process comprising the steps:

(A) culturing a host cell which comprises a nucleic acid molecule encoding Sxt S in a culture medium in the presence of a compound of Formula II (intermediate 3):

intermediate 3

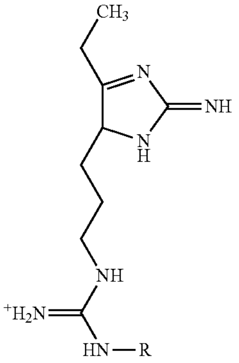

wherein R is OH, under conditions such that Sxt S is produced and Sxt S converts compounds of Formula II to compounds of Formula I.

In other embodiments, the invention provides a process for producing a compound of Formula I [intermediate 5]:

intermediate 5

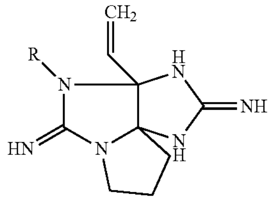

wherein R is OH, the process comprising the steps:

(A) contacting a compound of Formula II [intermediate 4]:

intermediate 4

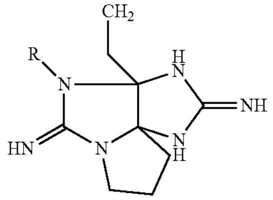

wherein R is OH, with Sxt D, and optionally NADH, and optionally NADPH; and (B) isolating or purifying a compound of Formula I from the reaction medium.

The invention also provides a process for producing a compound of Formula I [intermediate 5]:

intermediate 5

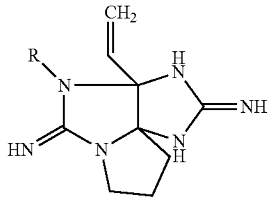

wherein R is OH, the process comprising the steps:

(A) culturing a host cell which comprises a nucleic acid molecule encoding Sxt D in a culture medium in the presence of a compound of Formula II [intermediate 4]:

intermediate 4

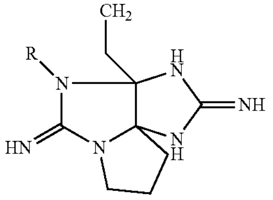

wherein R is OH, under conditions such that Sxt D is produced and Sxt D converts compounds of Formula II to compounds of Formula I.

In other embodiments, the invention provides a process for producing a compound of Formula I [intermediate 5']:

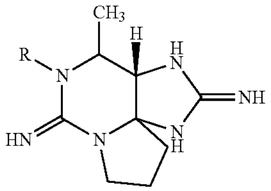

wherein R is OH, the process comprising the steps:

(A) contacting a compound of Formula II [intermediate 4']:

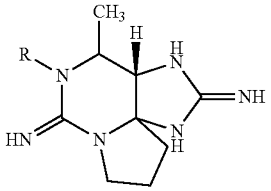

wherein R is OH, with Sxt D, and optionally NADH, and optionally NADPH; and (B) isolating or purifying a compound of Formula I from the reaction medium.

The invention also provides a process for producing a compound of Formula I [intermediate 5']:

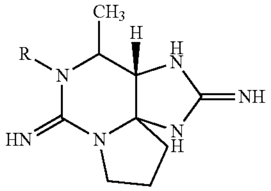

wherein R is OH, the process comprising the steps:

(A) culturing a host cell which comprises a nucleic acid molecule encoding Sxt D in a culture medium in the presence of a compound of Formula II [intermediate 4']:

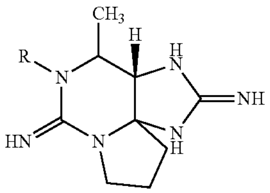

wherein R is OH, under conditions such that Sxt D is produced and Sxt D converts compounds of Formula II to compounds of Formula I.

In other embodiments, the invention provides a process for producing a compound of Formula I [intermediate 6]

intermediate 6

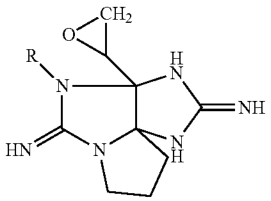

wherein R is OH, the process comprising the steps:

(A) contacting a compound of Formula II [intermediate 5]:

intermediate 5

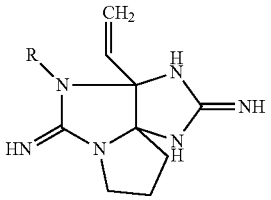

wherein R is OH, with Sxt S, and optionally alpha-ketoglutarate and optionally molecular oxygen; and (B) isolating or purifying a compound of Formula I from the reaction medium.

The invention also provides a process for producing a compound of Formula I [intermediate 6]:

intermediate 6

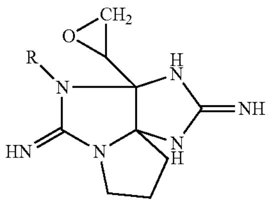

wherein R is OH, the process comprising the steps:

(A) culturing a host cell which comprises a nucleic acid molecule encoding Sxt S in a culture medium in the presence of a compound of Formula II [intermediate 5]:

intermediate 5

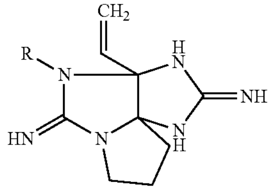

wherein R is OH, under conditions such that Sxt S is produced and Sxt S converts compounds of Formula II to compounds of Formula I.

In other embodiments, the invention provides a process for producing a compound of Formula I [intermediate 6']:

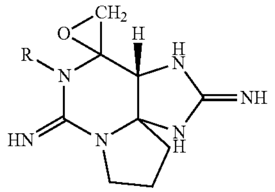

wherein R is OH, the process comprising the steps:

(A) contacting a compound of Formula II [intermediate 5']:

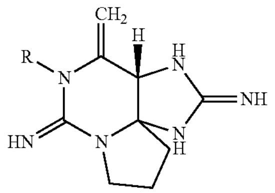

wherein R is OH, with Sxt S, and optionally alpha-ketoglutarate and optionally molecular oxygen; and (B) isolating or purifying a compound of Formula I from the reaction medium.

The invention also provides a process for producing a compound of Formula I [intermediate 6']:

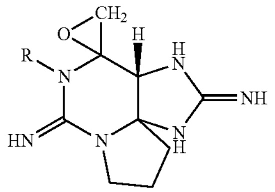

wherein R is OH, the process comprising the steps:

(A) culturing a host cell which comprises a nucleic acid molecule encoding Sxt S in a culture medium in the presence of a compound of Formula II [intermediate 5']:

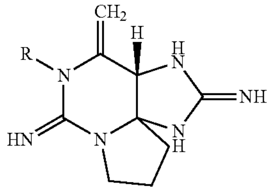

wherein R is OH, under conditions such that Sxt S is produced and Sxt S converts compounds of Formula II to compounds of Formula I.

In other embodiments, the invention provides a process for producing a compound of Formula I [intermediate 7]:

intermediate 7

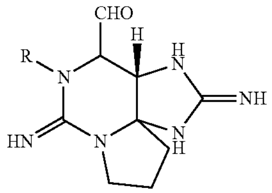

wherein R is OH, the process comprising the steps:

(A) contacting a compound of Formula II [intermediate 6]:

intermediate 6

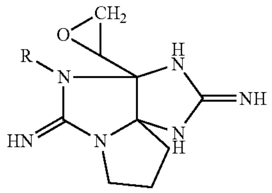

wherein R is OH, with Sxt S, and optionally alpha-ketoglutarate and optionally molecular oxygen;

and (B) isolating or purifying a compound of Formula I from the reaction medium.

The invention also provides a process for producing a compound of Formula I [intermediate 7]:

intermediate 7

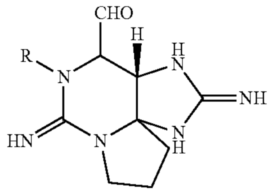

wherein R is OH, the process comprising the steps:

(A) culturing a host cell which comprises a nucleic acid molecule encoding Sxt S in a culture medium in the presence of a compound of Formula II [intermediate 6]:

intermediate 6

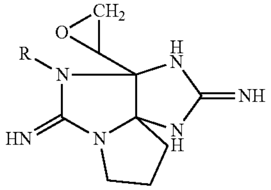

wherein R is OH, under conditions such that Sxt S is produced and Sxt S converts compounds of Formula II to compounds of Formula I.

In other embodiments, the invention provides a process for producing a compound of Formula I [intermediate 7']:

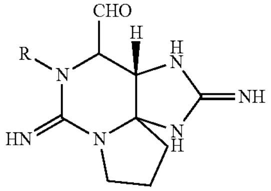

wherein R is OH, the process comprising the steps:

(A) contacting a compound of Formula II [intermediate 6']:

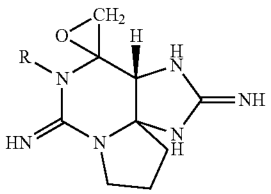

wherein R is OH, with Sxt S, and optionally alpha-ketoglutarate and optionally molecular oxygen;

and (B) isolating or purifying a compound of Formula I from the reaction medium.

The invention also provides a process for producing a compound of Formula I [intermediate 7']:

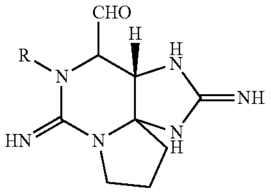

wherein R is OH, the process comprising the steps:

(A) culturing a host cell which comprises a nucleic acid molecule encoding Sxt S in a culture medium in the presence of a compound of Formula II [intermediate 6']:

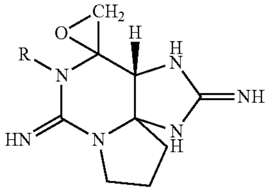

wherein R is OH, under conditions such that Sxt S is produced and Sxt S converts compounds of Formula II to compounds of Formula I.

The invention also encompasses the above processes wherein R is H.

The term "neosaxitoxin analogue" as used herein encompasses analogues and variants of neosaxitoxin, such as those compounds referred to below (preferably saxitoxin).

The elucidation of the saxitoxin and neosaxitoxin biosynthetic pathways as disclosed herein also enables the production of various saxitoxin, neosaxitoxin and gonyautoxin variants, such as the variants shown below (with reference to the structure of saxitoxin):

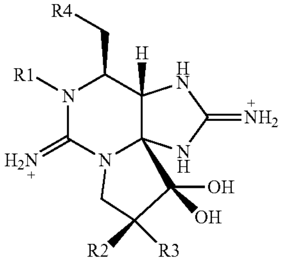

| R1 | R2 | R3 | Carbamate Toxins | Decarbamoyl Toxins | N-sulfocarbamoyl Toxins | Hydroxybenzoate Toxins |
|---|---|---|---|---|---|---|
| H | H | H | STX | dc-STX | B1 | GC3 |
| OH | H | H | NEO | dc-NEO | B2 | |
| OH | H | $OSO_3^-$ | GTX 1 | dc-GTX 1 | C3 | |
| H | H | $OSO_3^-$ | GTX 2 | dc-GTX 2 | C1 | GC1 |
| H | $OSO_3^-$ | H | GTX 3 | dc-GTX 3 | C2 | GC2 |
| OH | $OSO_3^-$ | H | GTX 4 | dc-GTX 4 | C4 | |
| | | | R4: 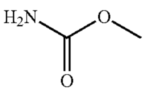 | R4: HO— | R4: 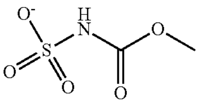 | R4: 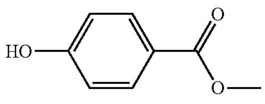 |

The elucidation of the saxitoxin and neosaxitoxin biosynthetic pathways as disclosed herein also enables the production of the following neosaxitoxin analogues and variants (shown below with reference to the structure of saxitoxin):

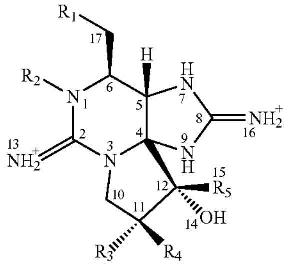

Molecular Structure of Saxitoxin.

Natural Derivatives of Paralytic Shellfish Toxins (Oshima 1995). Abbreviations used are, STX: saxitoxin; GTX: gonyautoxin; C: C-toxin; dc: decarbamoyl; do: deoxy.

| R-1 | R-2 | R3 | R-4 | R-5 | Compound |
|---|---|---|---|---|---|
| Carbamates 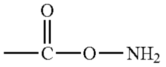 | —H | —H | —H | —OH | STX |
| | —OH | —H | —H | —OH | neoSTX |
| | —OH | $—OSO_3^-$ | —H | —OH | GTX-1 |
| | —H | $—OSO_3^-$ | —H | —OH | GTX-2 |
| | —H | —H | $—OSO_3^-$ | —OH | GTX-3 |
| | —OH | —H | $—OSO_3^-$ | —OH | GTX-4 |

-continued

| R-1 | R-2 | R3 | R-4 | R-5 | Compound |
|---|---|---|---|---|---|
| N-sulfocarbamates 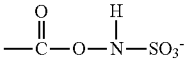 | —H | —H | —H | —OH | GTX-5 |
| | —OH | —H | —H | —OH | GTX-6 |
| | —OH | $—OSO_3^-$ | —H | —OH | C-3 |
| | —H | $—OSO_3^-$ | —H | —OH | C-1 |
| | —H | —H | $—OSO_3^-$ | —OH | C-2 |
| | —OH | —H | $—OSO_3^-$ | —OH | C-4 |
| Decarbamoyl toxins | —H | —H | —H | —OH | dcSTX |
| —OH | —OH | —H | —H | —OH | dcneoSTX |
| | —OH | $—OSO_3^-$ | —H | —OH | dcGTX-1 |
| | —H | $—OSO_3^-$ | —H | —OH | dcGTX-2 |
| | —H | —H | $—OSO_3^-$ | —OH | dcGTX-3 |
| | —OH | —H | $—OSO_3^-$ | —OH | dcGTX-4 |
| Deoxy toxins | —H | —H | —H | —OH | doSTX |
| —H | —OH | $—OSO_3^-$ | —H | —OH | doGTX-2 |
| | —OH | —H | $—OSO_3^-$ | —OH | doGTX-3 |

Substituents of Unusual Saxitoxin Derivatives.

(Abbreviations used are, LTX: *Lyngbya wollei* toxin; GC: *Gymnodinium catenatum* toxin)

| R-1 | R2 | R3 | R4 | R5 | Compound |
|---|---|---|---|---|---|
| 11-STX-ethanoate from xanthid crab *Atergatis floridus*[1] | | | | | |
| 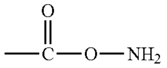 | —H | $—CH_2COO^-$/—H | | —OH | |
| Carbamoyl-N-hydroxy-STX from xanthid crab *Zosimus aenus*[2] | | | | | |
| 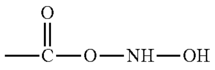 | —H | —H | —H | —OH | |
| | —OH | —H | —H | —OH | |
| Carbamoyl-N-methyl-STX from freshwater puffer *Tetraodon cutcucia*[3] | | | | | |
| 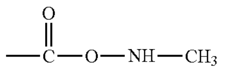 | —H | —H | —H | —OH | |
| De-amino-STX-analogues from *Lyngbya wollei*[4] | | | | | |
| 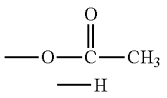 | —H | —H | $—OSO_3^-$ | —H | LTX-1 |
| | —H | —H | $—OSO_3^-$ | —OH | LTX-2 |
| | —H | $—OSO_3^-$ | —H | —OH | LTX-3 |
| | —H | —H | —H | —OH | LTX-5 |
| | —H | —H | —H | —H | LTX-6 |
| | —H | —H | —H | —H | LTX-4 |

-continued

| R-1 | R2 | R3 | R4 | R5 | Compound |
|---|---|---|---|---|---|
| Hydroxybenzoate STX from *Gymnodinium catenatum*[5] | | | | | |
| 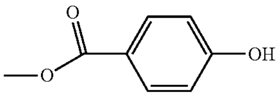 | —H | —H | —$OSO_3^-$ | —OH | GC1 |
| | —H | —$OSO_3^-$ | —H | —OH | GC2 |
| | —H | —H | —H | —OH | GC3 |

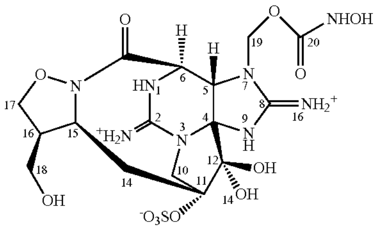

Molecular Structure of *zeteki* toxin AB from the golden frog *Atelopus zeteki* (Yotsu-Yamashita et al. 2004).

Hence, in a further aspect, the invention provides a process for the production of a saxitoxin variant as defined in the above tables, or an intermediate in the production thereof, which comprises a process as disclosed herein for the production of neosaxitoxin or an intermediate in the production of neosaxitoxin, wherein that process has been modified to produce the saxitoxin variant, or an intermediate in the production thereof.

For example, in the production of saxitoxin, the use of a Sxt X polypeptide or sxt X gene may be unnecessary because the Sxt X polypeptide is responsible of the N1-hydroxylation step in the production of neosaxitoxin (and saxitoxin is not N1-hydroxylated).

Prior to sulfonation at C-11 to produce C-11 sulfated toxins, such as GTX-1 to -4, carbon C-11 needs to be hydroxylated. This is putatively carried out by SxtDIOX.

The sulfotransferase, SxtN, putatively catalyses an N-sulfonation to produce N-sulfocarbamoyl toxins, such as GTX5/6 and C1-4 toxins. It is uncertain where in the pathway these reactions occur. However, it is likely that they occur prior to the formation of STX, i.e. on intermediates rather than on the end-product of the pathway.

In a further aspect, there is provided a process of the invention for producing neosaxitoxin or an analogue or variant thereof, wherein the process additionally comprises the step of contacting the neosaxitoxin or the analogue or variant thereof with an SxtN or SxtDIOX polypeptide. For example, the host cell may be one which additionally comprises genes encoding sxtN and/or sxtDIOX.

In such a way, saxitoxin may be converted to GTX-5 by SxtN (by sulphation of the carbamoyl side chain). Similarly, saxitoxin may be converted to 11-hydroxy saxitoxin by SxtDIOX. This step would precede the C-11 sulphation to convert saxitoxin to GTX-2/3 (or neosaxitoxin to GTX-4/1).

There is a strong possibility that the array of toxins produced in a given strain is the result of a combination of each enzyme having different kinetics (reaction speed), and varying relaxed substrate specificities towards intermediate metabolites with various modifications.

Intermediate 8 is converted by 0-carbamoyltransferase SxtI to intermediate 9. Intermediate 8 as well as intermediate 9 may both be the substrate for dioxygenases SxtH and SxtT converting intermediate 8 to dcSTX and intermediate 9 to STX. An analogous pathway is likely for the production of neoSTX and dcneoSTX.

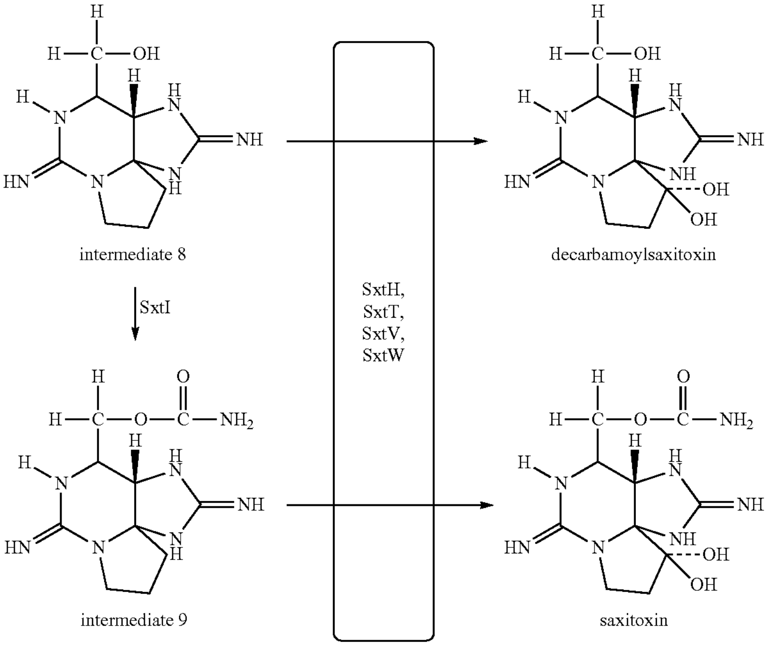

intermediate 8
decarbamoylsaxitoxin
intermediate 9
saxitoxin

Conversions of intermediate 8 to intermediate 9 and decarbamoylsaxitoxin, and intermediate 9 to saxitoxin.

well known in the art. The pharmaceutically acceptable carriers, adjuvants and/or excipients may be a preservative.

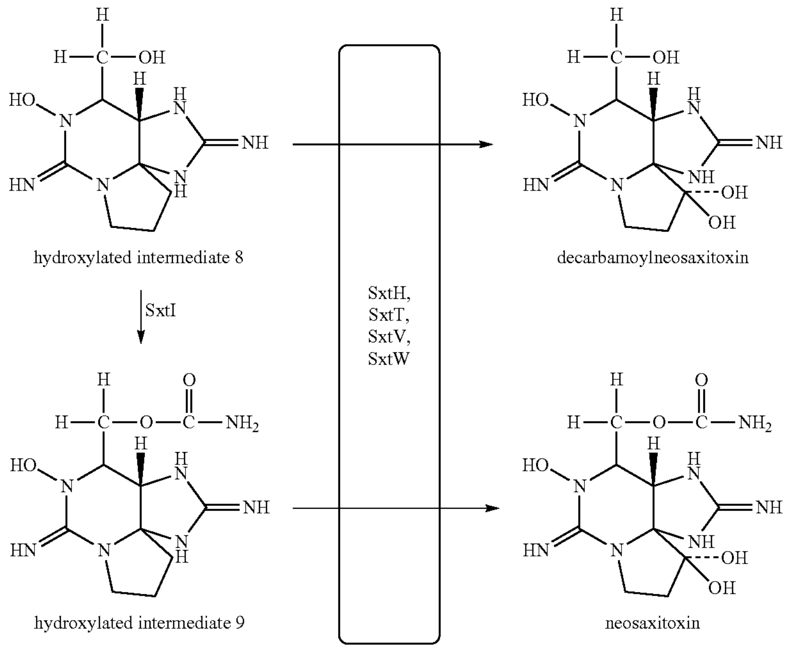

hydroxylated intermediate 8 decarbamoylneosaxitoxin hydroxylated intermediate 9 neosaxitoxin

Conversion of hydroxylated intermediate 8 to hydroxylated intermediate 9 and decarbamoylneosaxitoxin, and hydroxylated intermediate 9 to neosaxitoxin.

In yet a further embodiment, the invention provides neosaxitoxin or an analogue thereof which is produced by a process of the invention. The neosaxitoxin or analogue thereof which is produced by a process of the invention may further be converted into a salt, particularly into a pharmaceutically-acceptable salt thereof with an inorganic or organic acid or base.

Acids which may be used for this purpose include hydrochloric acid, hydrobromic acid, sulphuric acid, sulphonic acid, methanesulphonic acid, phosphoric acid, fumaric acid, succinic acid, lactic acid, citric acid, tartaric acid, maleic acid, acetic acid, trifluoroacetic acid and ascorbic acid. Bases which may be suitable for this purpose include alkali and alkaline earth metal hydroxides, e.g. sodium hydroxide, potassium hydroxide or caesium hydroxide, ammonia and organic amines such as diethylamine, triethylamine, ethanolamine, diethanolamine, cyclohexylamine and dicyclohexylamine. Procedures for salt formation are conventional in the art.

The neosaxitoxin or analogue thereof which is produced by a process of the invention or a salt thereof may further be formulated for use in a pharmaceutical composition. Hence, in a further aspect, there is provided a process of the invention for producing neosaxitoxin or analogue thereof or a salt thereof which additionally comprises the step of formulating the isolated or purified neosaxitoxin, or a salt thereof, in a pharmaceutical composition. Preferably, the step comprises combining isolated or purified neosaxitoxin or analogue thereof or a salt thereof with one or more pharmaceutically acceptable carriers, adjuvants and/or excipients.

In particular, neosaxitoxin or an analogue thereof or a salt thereof may be formulated with one or more conventional carriers, diluents and/or excipients according to techniques The compositions may be adapted for oral administration or for parenteral administration, for example by intradermal, subcutaneous, intraperitoneal, intravenous, or intramuscular injection. Suitable pharmaceutical forms thus include plain or coated tablets, capsules, suspensions and solutions containing the active component optionally together with one or more conventional inert carriers and/or diluents, such as corn starch, lactose, sucrose, microcrystalline cellulose, magnesium stearate, polyvinylpyrrolidone, citric acid, tartaric acid, water, water/ethanol, water/glycerol, water/sorbitol, water/polyethyleneglycol, propylene glycol, stearylalcohol, carboxymethylcellulose or fatty substances such as hard fat or suitable mixtures of any of the above.

Alternatively, neosaxitoxin or a salt thereof may be formulated for topical administration, e.g. in the form of a gel, cream, emulsion, paste, etc., e.g. comprising neosaxitoxin or a salt thereof together with a conventional diluent, carrier or excipient.

In other embodiments, neosaxitoxin or a salt thereof may be formulated for transdermal administration.

BRIEF DESCRIPTION OF THE FIGURES

In FIG. 2, the pathway involves the use of a 6-5-5-membered ring intermediate.

In FIG. 3, the pathway involves the use of a 5-5-5-membered ring intermediate which gets converted to a 6-5-5-ring system.

EXAMPLES

Figure 1:
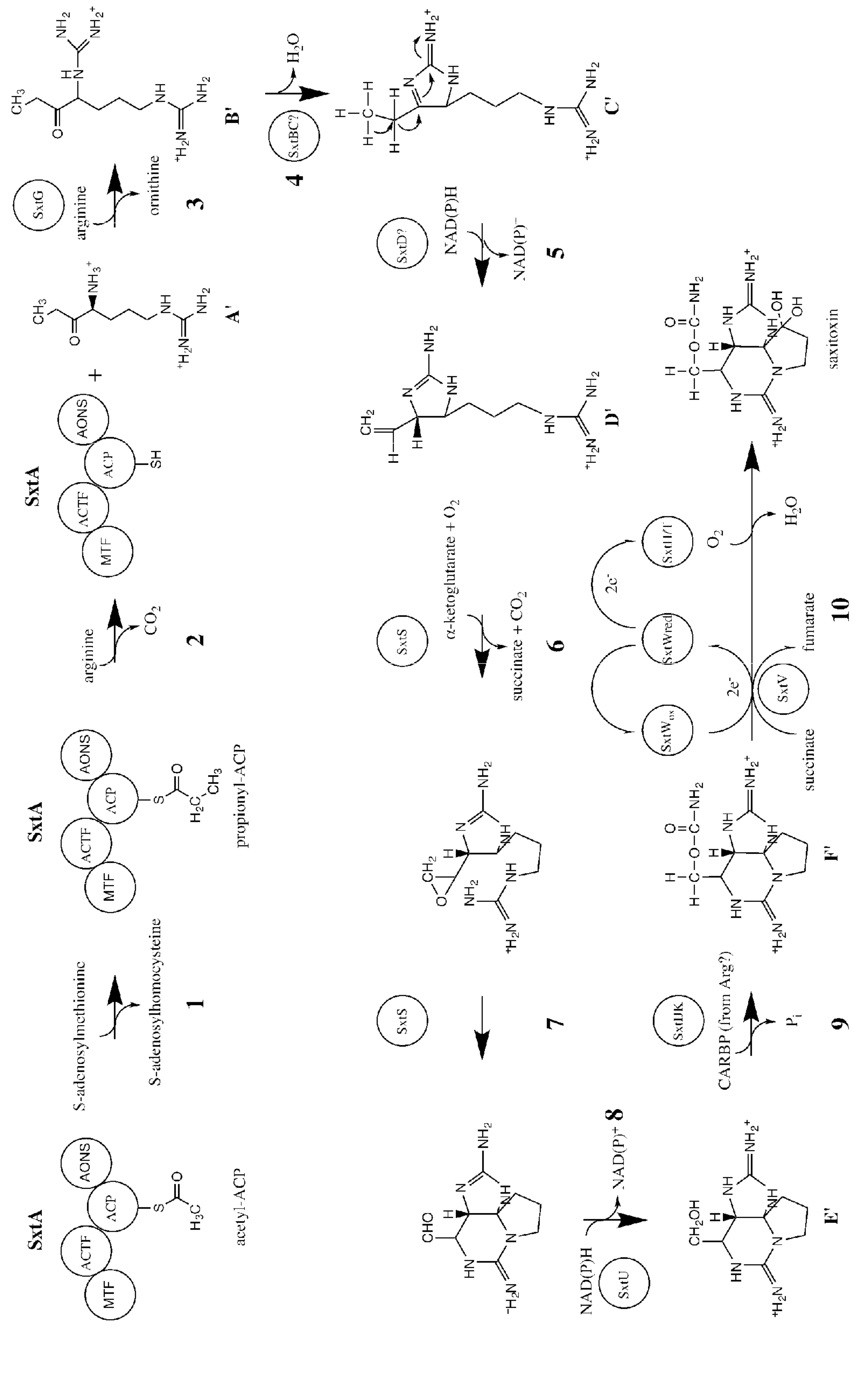
FIG. 1: Previous biochemical pathway for the production of saxitoxin which was proposed by Kellmann (2008).
Figure 2:
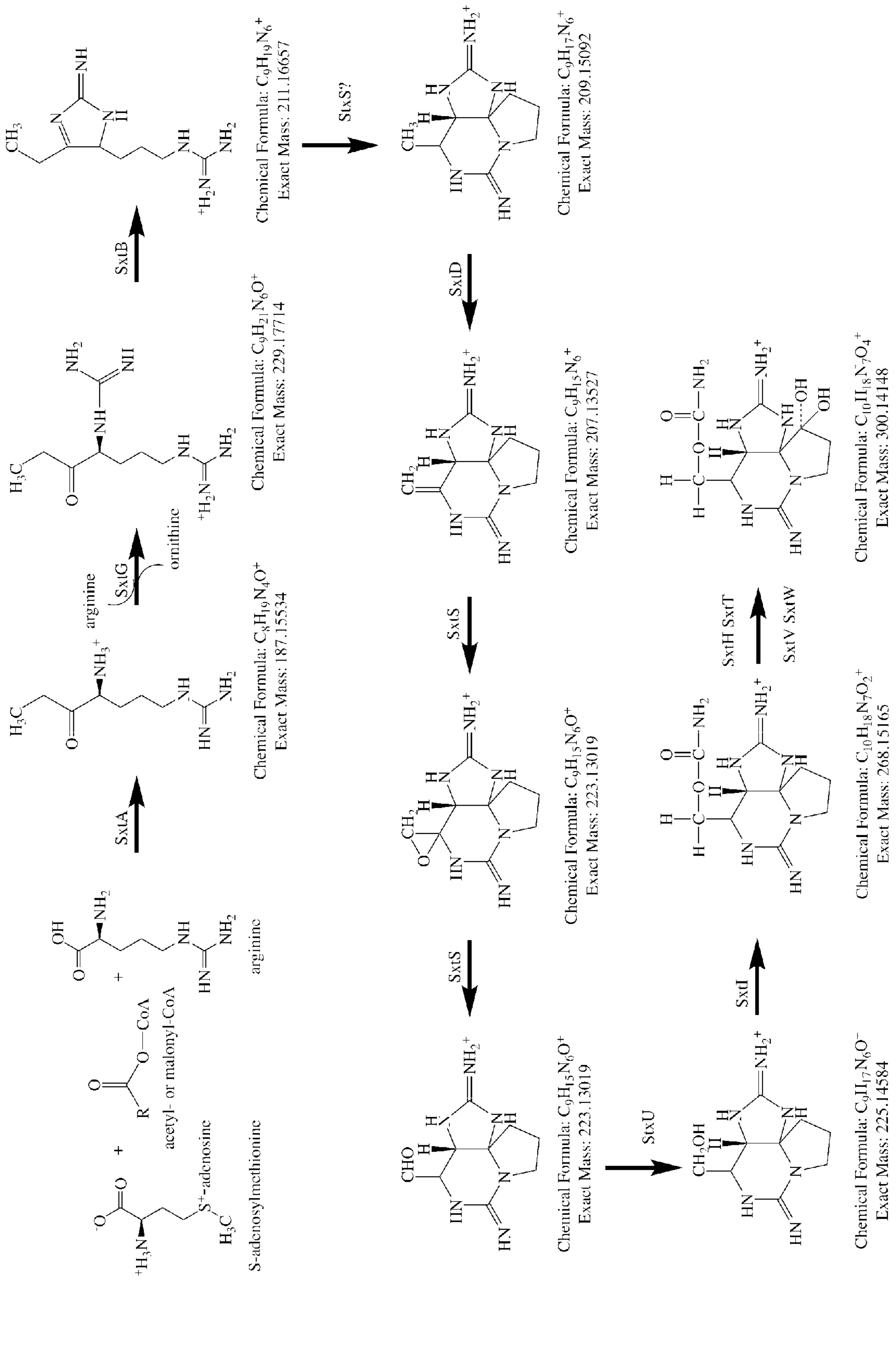
FIGS. 2-3: Two revised biochemical pathways for the production of neosaxitoxin.
Figure 3:
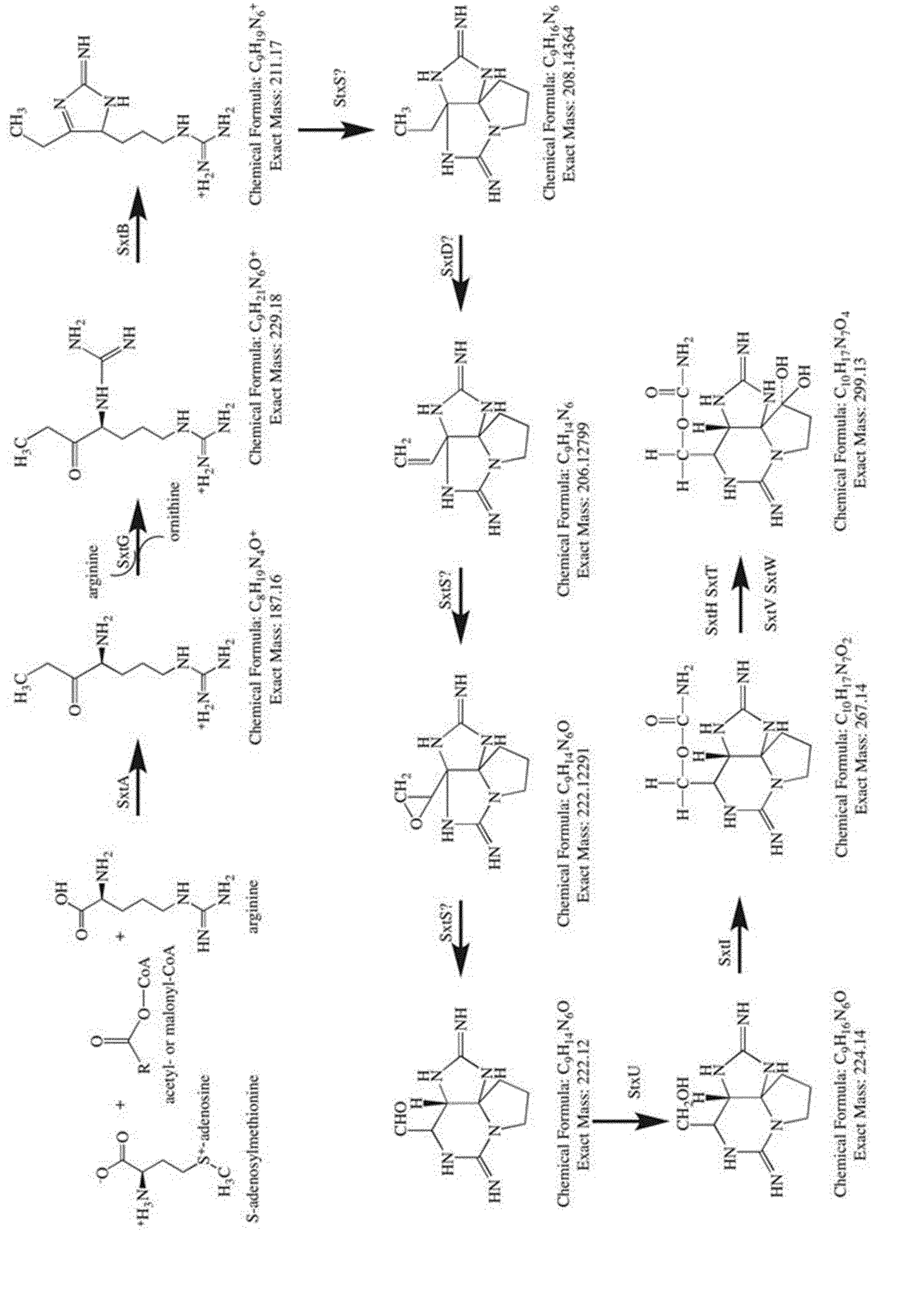
Figure 4A:
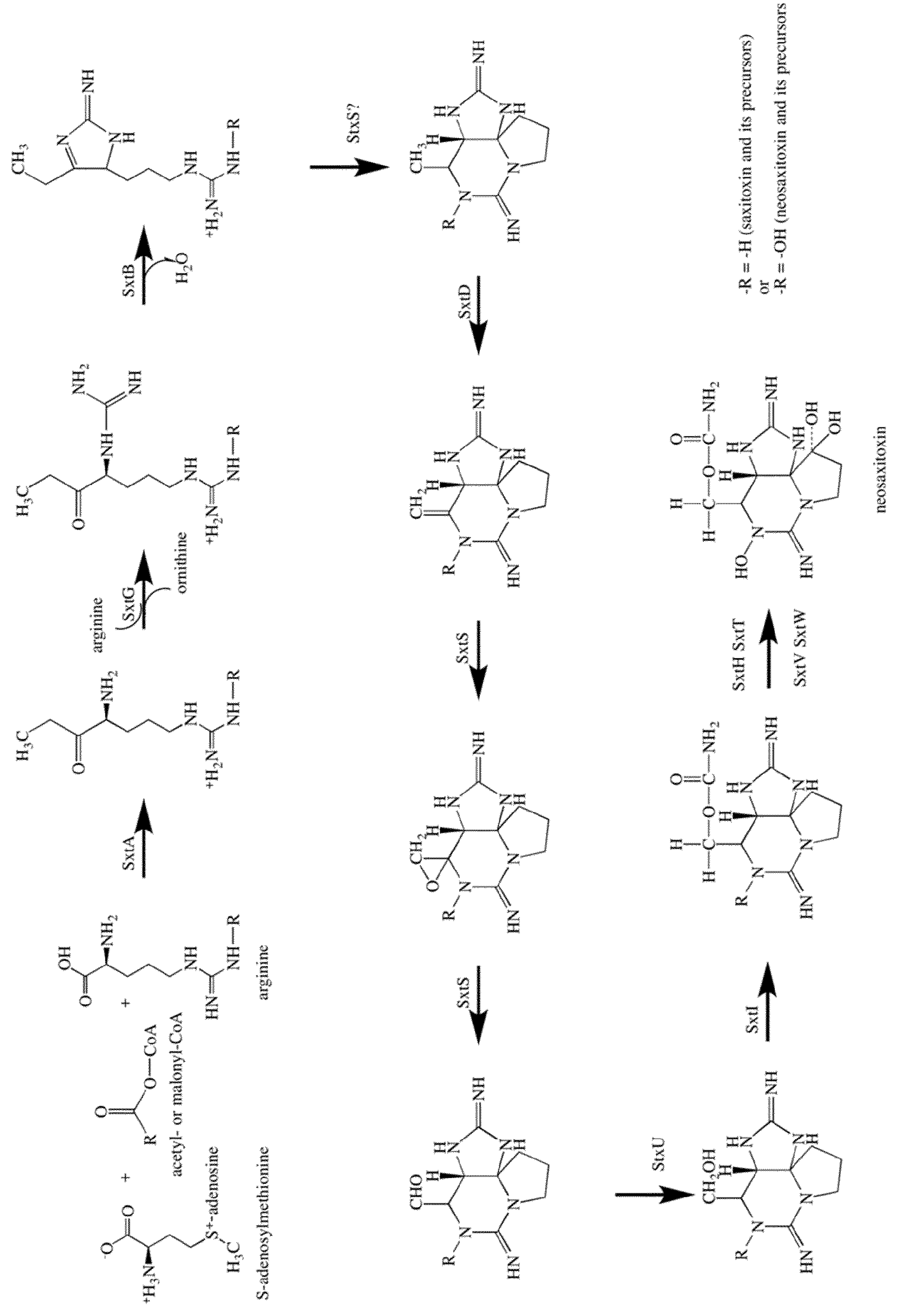
FIGS. 4A-B: Proposed biochemical pathways showing where in the pathways the N-1 hydroxyl group is introduced in the production of neosaxitoxin. The —R group indicates where the hydroxylation may occur.
Figure 4B:
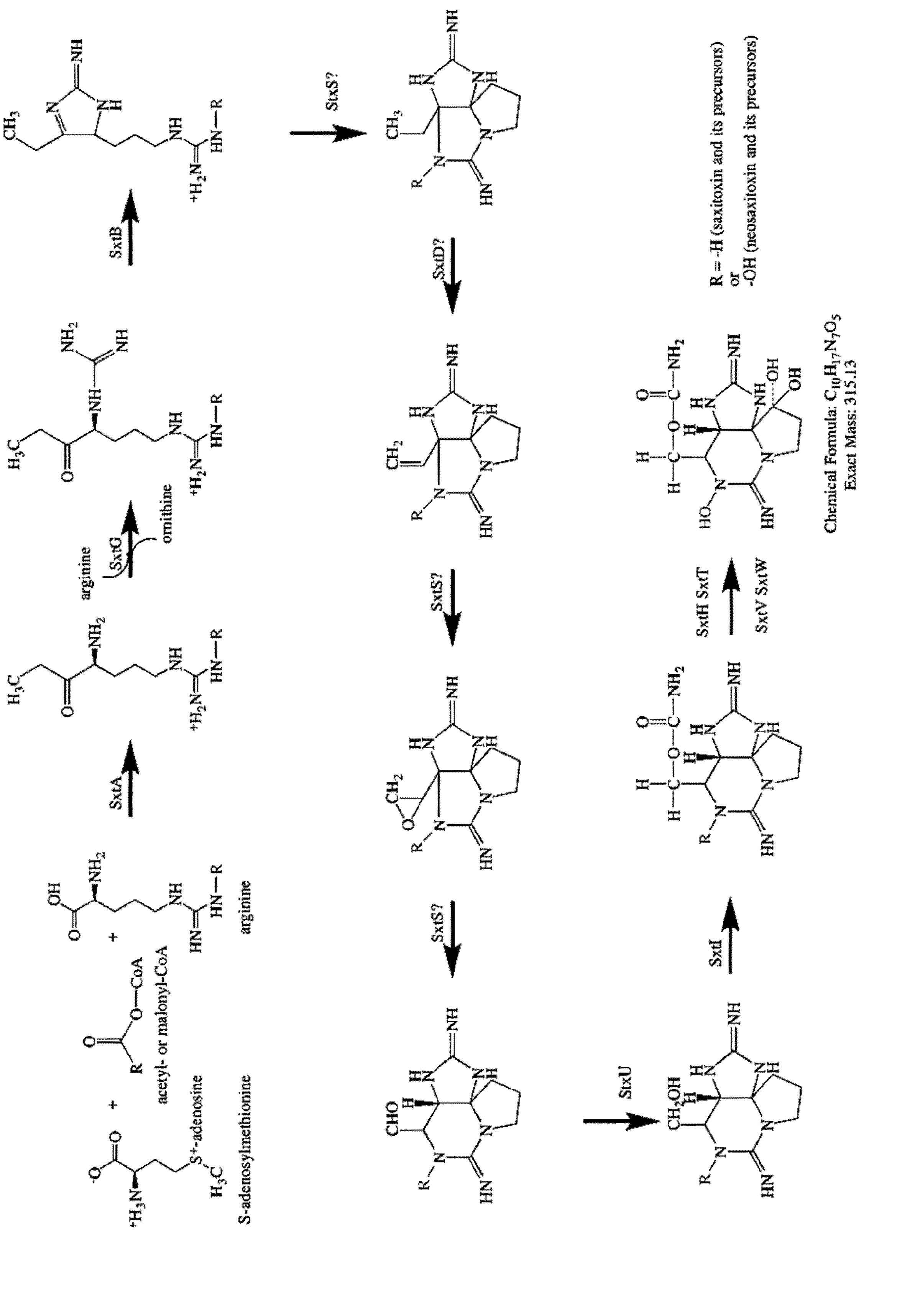

The present invention is further illustrated by the following Examples, in which parts and percentages are by weight and degrees are Celsius, unless otherwise stated. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions. Thus, various modifications of the invention in addition to those shown and described herein will be apparent to those skilled in the art from the foregoing description. Such modifications are also intended to fall within the scope of the appended claims.

The disclosure of each reference set forth herein is incorporated herein by reference in its entirety.

Example 1: Production of SxtA

Subcloning of sxtA and Sfp in pET28b

PCR amplifications of sxtA from *Cylindrospermopsis raciborskii* T3 and sfp from *Bacillus subtilis* were performed from genomic DNA using Velocity polymerase (Bioline). The manufacturer's protocols were followed, with an annealing temperature of 55° C. and extension times of 4 min and 1 min for sxtA and sfp, respectively (sxtA primers: forward, 5'-GGGCTTTCATATGTTACAAAAGATTAA-3' (SEQ ID NO: 81) and reverse, 5'-AAAGTATGCGGCCG-CATGCTTGAGTAT-3' (SEQ ID NO: 82); sfp primers: forward 5'-GGCATCCATGGGCAAGATTTACGGAA-3' (SEQ ID NO: 83) and reverse, 5'-GGCATCTCGAGT-TATAAAAGCGCTTCG-3' (SEQ ID NO: 84)). PCR amplicons were purified (DNA clean and concentrator 5X kit, ZymoResearch) and digested with NdeI/NotI (sxtA) or NcoI/XhoI (sfp; New England Biolabs). Digested products were purified and ligated into pET-28b (Novagen), cut with the same enzymes, and purified via agarose gel electrophoresis (DNA recovery kit, ZymoResearch). After transformation in electrocompetent *Escherichia coli* GB2005 cells, positive clones were screened by PCR of the purified plasmid (PureLink Miniprep, Invitrogen) with the universal primers T7 promoter and T7 terminator. The inserts were sequenced (Ramaciotti Center at UNSW, Australia) for verification.

For co-expression with sxtA, the sfp gene was amplified from pET28b::sfp using Velocity polymerase (Bioline) with primers for the T7 promoter and T7 terminator (5'-GGTTAAGATCTGAAATTAATACGACTC-3' (SEQ ID NO: 85), 5'-TTTTAAGATCTTTTCAGCAAAAAACCC-3' (SEQ ID NO: 86)). The manufacturer's protocols were followed with an annealing temperature of 55° C. and an extension time of 1 min. Amplicons were purified (DNA clean and concentrator 5X kit, ZymoResearch) and digested with BglII (New England Biolabs). Digested products were purified and ligated into a pET28b::sxtA cut with the same enzyme, and purified as described previously. After transformation in electrocompetent *Escherichia coli* GB2005 cells, the positive clones were screened by PCR of the purified plasmid (PureLink Miniprep, Invitrogen). The insert was sequenced (Ramaciotti Center at UNSW, Australia) for verification.

Expression of sxtA with Sfp and Purification of Holo-SxtA

For expression of sxtA, 0.5 mL of overnight *E. coli* BL21 (DE3) transformants containing pET28b::sxtA,sfp and pRARE plasmids (Invitrogen) was subcultured in 50 mL Lysogeny Broth (LB) medium supplemented with 50 $\mu g \cdot mL^{-1}$ kanamycin and 30 $\mu g \cdot mL^{-1}$ chloramphenicol and incubated at 30° C. under agitation (200 rpm) until an optical density of 0.8-1.0 at 600 nm. Cultures were then induced with 200 μM isopropyl β-D-thiogalactoside (IPTG) and incubated overnight at 18° C. with agitation and pelleted by centrifugation (4000 rpm, at 4° C. for 20 min, Hitachi CR22GIII centrifuge, R10A5 rotor). The cell pellet was frozen until further purification.

Pelleted cells were resuspended in 10 mL of lysis buffer (20 mM sodium phosphate buffer, pH 7.4, 500 mM NaCl, 20 mM imadazole), and lysed by sonication (Branson Digital Sonifier M450, 3 mm probe, 30% of amplitude, 3 min at 4° C. with cycles of 15 s power on and 59 s off). The resulting suspension was centrifuged (20 000 rpm, at 4° C. for 60 min, Hitachi CR22GIII centrifuge, R20A2 rotor), and the supernatant was loaded on a Ni-affinity column (1 mL HiTrap column, fitted on an AKTApurifier, GE Healthcare), equilibrated with 20 mM sodium phosphate buffer, pH 7.4, 500 mM NaCl, 20 mM imidazole (butter A). After injection, the column was washed (35 mL of buffer A, 1 $mL \cdot min^{-1}$) and the proteins were eluted using 20 mM sodium phosphate buffer, pH 7.4, 500 mM NaCl, 500 mM imidazole (buffer B) and a stepwise gradient of 0% to 20% buffer B in 20 min, followed by 10 min at 20%, then a linear gradient from 20% to 100% in 20 min, and a final wash at 100% for 10 min. The collected fractions (1 mL, detection at 280 nm) were analyzed by 10% polyacrylamide gel electrophoresis under denaturing conditions (SDS-PAGE), and the fractions containing the pure protein were pooled. The protein solution was desalted and concentrated via centrifugal filter (Amicon Ultra-4 centrifugal filter unit 100k) with 50 mM HEPES-150 mM NaCl pH7.4 and then glycerol was added to a final concentration of 10% (w/v). Protein concentration was determined by using protein assay kit (Bio-Rad) and stored at −80° C.

Cloning of the Acyl Carrier Protein Domain of sxtA for Expression Alone and with Sfp The acyl carrier protein of sxtA (sxtA-ACP) coding gene was amplified using Velocity polymerase (Bioline) (primers: forward 5'-ATATCCATGGGACCTGGTGATCGCAAAGGA-3' (SEQ ID NO: 87) and reverse 5'-TATCTCGAGAGTGTTGATTTCGTTGGCTG-3' (SEQ ID NO: 88)). Manufacturer protocols were followed with an annealing temperature of 54° C. and an extension time of 1.5 min. PCR amplicons were purified, digested, and ligated into pET-28b using the same method as described for sfp. After transformation in electrocompetent *Escherichia coli* GB2005 cells, the positive clones were screened by with universal primers T7 promoter and T7 terminator and sequenced as described previously. For co-expression with sfp, the gene was cloned in pET28b::sxtA-ACP plasmid, as described previously.

Expression and Purification of Apo- and Holo-sxtA-ACP

For expression of sxtA-ACP, 10 mL of overnight *E. coli* BL21 (DE3) transformants containing pET28b::sxtA-ACP and pET28b::sxtA-ACP, sfp plasmids were grown in 1 L Lysogeny broth (LB) supplemented with 50 $\mu g \cdot mL^{-1}$ kanamycin and 30 $\mu g \cdot mL^{-1}$ chloramphenicol and incubated at 37° C. under agitation (200 rpm) until the induction with 100 μM IPTG, as described above. Cells were collected by centrifugation (4000 rpm, at 4° C. for 20 min, Hitachi CR22GIII centrifuge, R10A5), resuspended in 15 mL of Lysis buffer, and disrupted by sonication (Branson Digital Sonifier M450, 3 mm probe, 30% of amplitude, 3 min at 4° C. with cycles of 1 s power on followed by 4 s off). The resulting suspension was centrifuged (20 000 g, at 4° C. for 60 min, Hitachi CR22GIII centrifuge, R20A2 rotor), and the supernatant was loaded on a Ni-affinity column (1 mL HiTrap column, fitted on an AKTApurifier, GE Healthcare) previously equilibrated with 20 mM sodium phosphate buffer, pH 7.4, 500 mM NaCl, 20 mM imidazole (buffer A). After injection, the column was washed (35 mL of buffer A, 1 $mL \cdot min^{-1}$) and the proteins were eluted using 20 mM sodium phosphate buffer, pH 7.4, 500 mM NaCl, 500 mM imidazole (buffer B) and a linear gradient from 0% to 20% B in 20 min, then 10 min at 20%, then a linear gradient from 20% to 100% in 20 min, and a final wash at 100% for 20 min. The collected fractions (1 mL, detection at 280 nm) were analyzed by 15% polyacrylamide gel electrophoresis under denaturing conditions (SDS-PAGE), and fractions containing the pure protein were pooled together. The protein solution was desalted and concentrated using centrifucation filtration (Amicon Ultra-15 centrifugal filter unit 3k) with 50 mM HEPES-150 mM NaCl, pH 7.4, freezed in liquid nitrogen and stored at −80° C. Protein concentration was determined by using protein assay kit (Bio-Rad).

Figure 5:
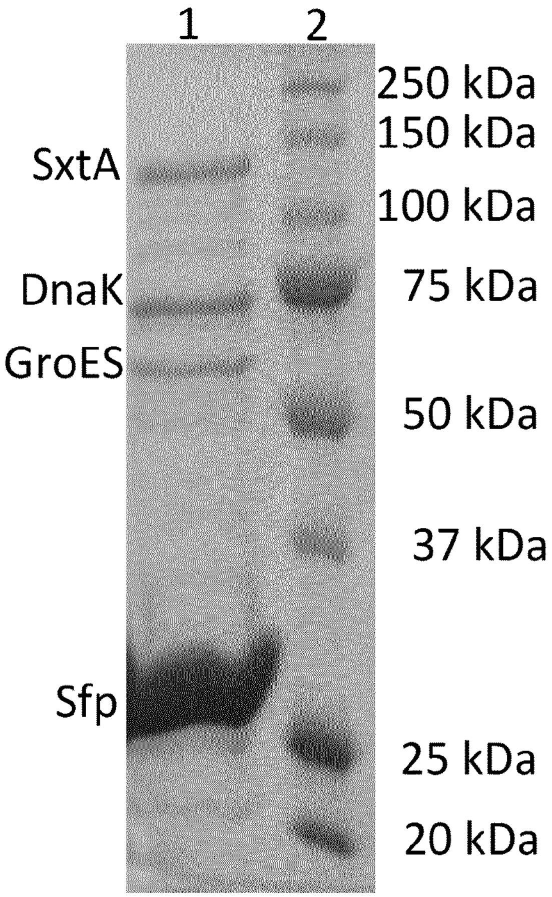
FIG. 5: SDS-PAGE of SxtA after IMAC. Lane 1: protein solution containing SxtA (147 kDa); the chaperons, DnaK and GroES, (70 kDa and 60 kDa, respectively); Sfp, (27 kDa). Lane 2: Ladder Precision Plus Protein Standards Dual Color (BioRad).

SxtA was successfully detected after purification on IMAC and SDS-PAGE (FIG. 5). A protein at the expected size of 143 kDa was purified with a yield of 0.5 mg·L-1 of culture, and the identity was confirmed to be SxtA by trypsinolysis.

MALDI-TOF-TOF Mass Spectrometry Analysis of Apo- and Holo-sxtA-ACP

Figure 6:
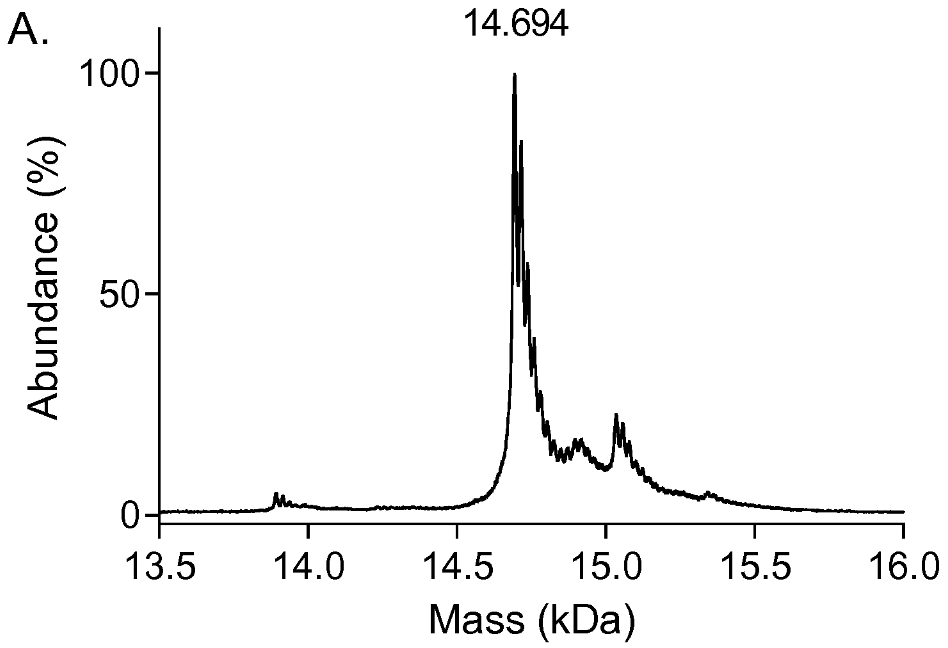
FIG. 6: MALDI-TOF-TOF analysis of phosphopantetheinylation of the SxtA-ACP domain. Purified SxtA (a) and SxtA co-expressed with Sfp(b) were analysed by MALDI-TOF-TOF with respective masses of 14,694 Da and 15,034 Da. The difference of 340 Da corresponds to the attachment of a phosphopantetheinyl arm.
Figure 6:
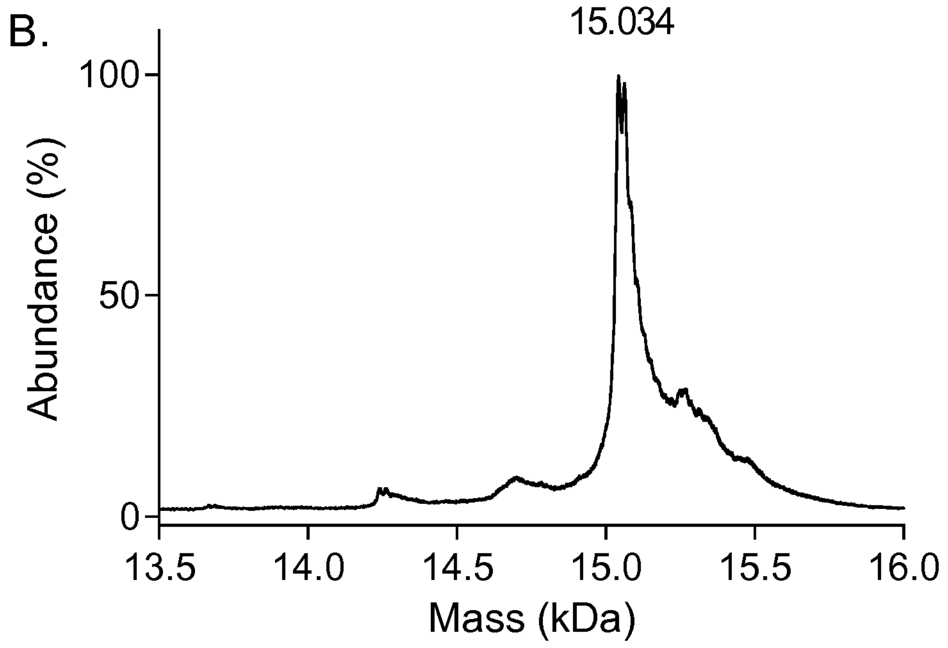
Figure 7:
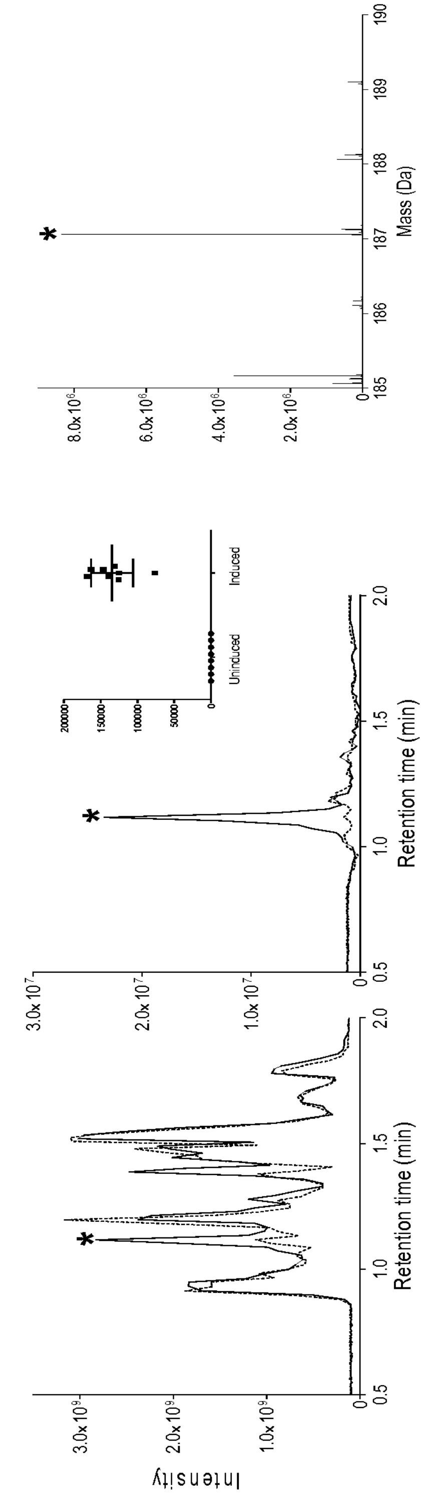
FIG. 7: Liquid chromatography-mass spectroscopy of *E. coli* transformant methanolic extracts. a) Total ion current chromatograms of both induced (dashed line) and non-induced (solid line) extracts. b) Extracted ion chromatograms for m/z=187.06 of both induced (dashed line) and non-induced (solid line) extracts. c) ProgenesisQI statistical analysis comparing the expression of the molecular ion at m/z 187.06 between induced (square) and non-induced (circle) extracts. d) Mass spectrum of induced extract.

Protein mass was detected by MALDI-TOF-TOF mass spectrometry. For matrix preparation, 10 mg of 3 5-dimethoxy-4-hydroxyl cinnamic acid was added into 1 mL 80% acetonitrile with 0.1% TFA, and 1 mL of matrix was mixed with 1 μl of protein sample on the surface of a MALDI target plate, followed by analysis by Bruker ultrafleXtreme MALDI-TOF/TOF with a YAG laser. Data acquisition was performed in the positive ion mode and the instrument calibrated immediately prior to each analysis. Analysis was performed in the linear delayed extraction mode acquiring 100 averaged spectra. The results are shown in FIG. 6.

Extraction of the 4-Amino-3-Oxo-Guanidinoheptane

BL21 (DE3) transformants containing pRARE and pET28b::sxtA,sfp were resuspended in methanol acidified with 0.1% of acid acetic. The cells were disrupted by sonication (Branson Digital Sonifier M450, 3 mm probe, 30% of amplitude, 2 min at 4° C. with cycles of 5 s power on and 15 s off). The resulting suspension was centrifuged (20,000 rpm, at 4° C. for 30 min, Hitachi CR22GIII centrifuge, R20A2 rotor). The supernatant was dried under rotary evaporation and store at −20° C. until further analysis.

Mass Spectroscopy Analyses of 4-Amino-3-Oxo-Guanidinoheptane

To determine the biosynthetic products of SxtA, intracellular metabolites of *E. coli* cells containing pET28b::sxtA, sfp and pRARE were chemically extracted and analysed by LC-MS.

Samples were resuspended in 95:5 acetonitrile:water (typically 1 mL) and transferred to HPLC vials for mass spectrometric analysis. LC-MS analysis was performed on 10 μL of sample using a Dionex U3000 UHPLC interfaced to a Q-Exactive Plus (ThermoFisher Scientific) via a heated electrospray interface. Ionisation was performed in positive mode under default source conditions (as suggested by the manufacturer's Tune software). Samples were injected onto a Waters BEH HILIC column (2.1×100 mm, 1.9 μm). Chromatographic conditions were as in Turner et al. with no modifications.

The mass spectrometer was run in data dependant analysis mode, with six MS/MS spectra being collected after every full scan mass spectrum. Inclusion lists of toxins and metabolites from the literature where used to prioritise their detections.

Comparison of the mass spectra between induced cells and non-induced controls showed the presence of a molecular ion at 1.1 min of m/z 187.06 [M+H]+, corresponding to theprotonated mass of the AOGH($C_8H_{18}N_4O$). Secondary ion fragmentation of this molecular ion resulted in a fragmentation pattern closely resembling that of AOGH. The experiment was realised in eight replicates and mass data were analysed by Progenesis QI to quantify the difference of expression between induced and non-induced extraction. The putative AOGH compound was observed to be overexpressed in the induced cells, compared to non-induced controls (Figure),with a maximum fold change equal to infinity (entirely absent in negative controls) and an ANOVA p-value of $1.1\times10^{-16}$.

The compound at 187.06 Da mass was purified and analysed NMR confirmed the structure of the AOGH.

Example 2: Sxt1 Fragment

The following three open reading frames (ORFs) from *C. raciborskii* T3 were placed in a nucleotide fragment labelled "sxtl": sxtA, sxtB and sxtC. Each ORF was codon optimised for expression in *E. coli* by Life Technology using GeneArt software.

EcoRI restriction sites were added at both ends of the fragment. In addition, homologous regions of 50 bp to the lacZ (H1) and lacA (H2) genes were added to the 5'- and 3'-end, respectively, for integration by RED ET mediated recombination into the *E. coli* genome. Downstream of H1, a terminator was added to prevent readthrough, followed by the transcription factor gene xylS and its Ps2 promoter. (XylS is the transcription factor that is required for transcription from the Pm promoter, after binding to its inducer, toluic acid.) This was followed by a terminator and then Pm promoter for the transcription of the downstream sxt genes. Upstream of each ORF, a ribosomal binding site (RBS) was added. Finally, a kanamycin resistance marker with two flanking FRT sites for excision by flippase-recombinase (GeneBridges), and homology arm H2 were added, including a terminal EcoRI site.

Example 3: sxt2 Fragment

The following sxt genes were included in the "sxt2" fragment: sxtD, sxtE, sxtG, sxtH, sxtl, sxtJ, sxtK, sxtL. Each ORF was codon optimised for expression in *E. coli* by Life Technology using GeneArt software.

The sxt2 fragment was designed to have terminal EcoRI sites, homology arms for recombination with the malE (H1) and malG (H2) genes of *E. coli*, and a Pm promoter upstream of the sxt genes. This fragment also contained the kanR resistance cassette with FRT sites like fragment sxt1.

Example 4: sxt3 Fragment

Three variants of sxt3 fragment were designed. The following sxt genes were included in the "sxt3" fragment, variant 1: sxtQ, sxtR, orf24, sxtS, sxtT, sxtU, sxtV, sxtW, sxtX. The following sxt genes were included in the "sxt3" fragment, variant 2: sxtQ, sxtR, sxtS, sxtT, sxtU, sxtV, sxtW, sxtX. The following sxt genes were included in the "sxt3" fragment, variant 3: sxtS, sxtT, sxtU, sxtV, sxtW, sxtX. Each ORF was codon optimised for expression in *E. coli* by Life Technology using GeneArt software.

Each variant of the sxt3 fragment was designed to have terminal EcoRI sites, homology arms for recombination with the xylF (H1) and xylB (H2) genes of *E. coli*, and a Pm promoter upstream of the sxt genes. Each variant of this fragment also contained the kanR resistance cassette with FRT sites like fragment sxt1.

Example 5: sxt4 Fragment

The following sxt genes were included in the "sxt4" fragment: sxtF, sxtP, sxtM. Each ORF was codon optimised for expression in *E. coli* by Life Technology using GeneArt software.

The sxt4 fragment was designed to have terminal EcoRI sites, homology arms for recombination with the melR (H1) and melB (H2) genes of *E. coli*, and a Pm promoter upstream of sxt genes. This fragment also contained the kanR resistance cassette with FRT sites like fragment sxt1.

Example 6: Creation of *E. coli* BL21(DE3) PPTase

It is desirable to use a phosphopantetheinyl transferase (PPTase) to convert the apo-form of the polyketide synthase, SxtA, into its holo-form.

The entire genomes of *Raphidiopsis brooki* D9 and *Cylindrospermopsis racoborskii* CS-505 have been sequenced and the sequences deposited in GenBank. Each of these strains only contain a single PPTase gene. Specific PCR primers were designed based on the D9 and CS-505 PPTase genes to PCR amplify and sequence the PPTase gene from *C. raciborskii* T3.

A synthetic gene construct was designed for integratation of the *C. raciborskii* T3 PPTase gene into the maltose operon of *E. coli* BL21(DE3). The PPTase gene was codon optimised for expression in *E. coli* and the construct was fitted with a T7 promoter and a beta-lactamase gene for selection for ampicillin resistance. The start codon was also changed to ATG.

Figure 8:
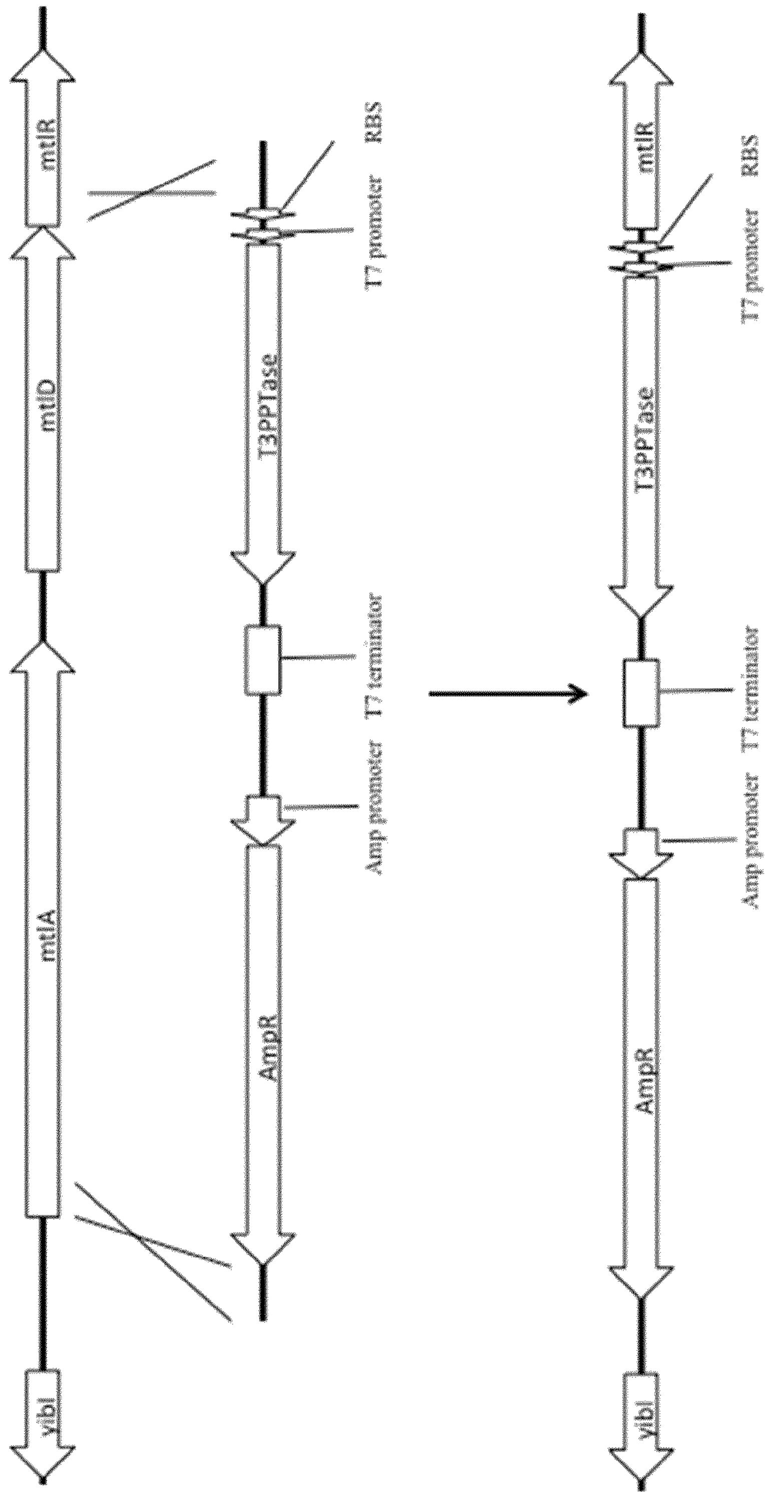
FIG. 8: Scheme for the insertion of the PPTase gene construct into the mannitol operon of *E. coli*.

The gene construct was then integrated into the maltose operon of *E. coli* BL21(DE3) (Life Technology) using the Quick & Easy *E. coli* Gene Deletion Kit following the manufacturer's instructions (Gene Bridges, catalog No. K006), and as depicted in FIG. 8. Correct integration and absence of unintended mutations was verified by sequencing.

Example 7: Production of 4-Amino-3-Oxo-Guanidinoheptane by *E. coli* BL21(DE3) PPTase pSxt1

The sxtl fragment was produced by Life Technology inside a pMA-RQ (ampR) plasmid backbone. This plasmid will be called pSxt1 herein. The pSxt1 plasmid was transformed into E. co/i BL21(DE3) PPTase, which carries the phosphopantetheinyl transferase from *Cylindrospermopsis raciborskii* T3 in its genome. The PPTase gene is under T7 promoter control (IPTG-inducible), and the sxtA, B, and C genes on pSxt1 are under Pm promoter control (m-toluoic acid inducible).

The goal of this experiment was to measure the expression and activity of the sxtA gene in *E. coli* at three different temperatures, 5° C., 19° C., and 30° C., at constant inducer concentrations (IPTG (0.5 mM) and m-toluic acid (1 mM)). The experimental strain was *E. coli* BL21(DE3) PPTase pSxt1, and the negative control was *E. coli* BL21 (DE3) (parent strain). Enzymatic product of only SxtA was expected, as the substrates for SxtB and SxtC are the enzymatic products of other enzymes, such as SxtG, which are not encoded on pSxt1.

Seed-cultures of BL21(DE3) (parent strain) and BL21 (DE3) PPTase pSxt1 were grown overnight at 37° C. in, respectively, LB and LB 50 μg/ml ampicillin and kanamycin. The following day, triplicates volumes of 200 ml LB medium with kanamycin 50 μg/ml were inoculated each with 2 ml seed culture of *E. coli* BL21(DE3) PPTase pSxt1, and incubated at 30° C. until the culture reached an $OD_{600}$ of ~0.6.

For the negative control, triplicate volumes of 200-ml LB without antibiotics were inoculate each with 2 ml seed culture from *E. coli* BL21(DE3) and incubated at 30° C. to an $OD_{600}$ of ~0.6. All cultures were then transferred to the corresponding temperature, and acclimatised for 30 minutes. Subsequently, IPTG (0.5 mM final concentration) and m-toluic acid (1 mM final concentration) was added to each culture, which were then incubated for 48 hours at 5° C., and for 18 hours at 19° C., and at 30° C.

Samples for SDS-PAGE as well as for RT-PCR were taken before induction, and at the end of the experiment. After 18 hours induction, the cultures were harvested by centrifugation 7.500 rpm for 12 min. The cell pellets were frozen until extraction for LC-MS analysis Extraction The cell pellets were resuspended in 1 ml water and sonicated on ice (output control 4, duty cycle 50%, 7 minutes in total in cycles of 2-3 minutes). After sonication, 4 ml acetonitrile was added, the samples were vortexed, and centrifuged to remove cell debris and other particulates.

LC-MS/MS Analysis

LC-MS analysis was carried out at the Hormonelaboratory, Haukeland University Hospital on a Waters Xevo TQ-S coupled to an iclass Acquity UPLC that was fitted with a 50×2.1 mm Acquity BEH amide column. Mobile phase A consisted of 10 mM ammonium formate pH 3.0 and mobile phase B consisted of 95% acetonitrile with 10 mM ammonium formate pH 3.0. The flow-rate was 0.4 ml per min, and the column temperature was held at 40° C. A gradient over 3 min was applied from 85% B to 70% B. The injection volume was always 1 μl.

Analytes were ionised in positive mode by electrospray ionisation. The following mrm transitions were measured. Arginine 175.05→60.00, 175→70.02, 4-amino-3-oxo-guanidinoheptane: 187.1→170.1, 187.1→128.1, 187.1→110.1, 187.1→72.08, 187.1→60.05, according to Tsuchiya et a/. (2014) and Tsuchiya et a/. (2015).

A large arginine peak was detected in all culture treatments, as well as for pure arginine solution (data not shown), whereas a 4-amino-3-oxo-guanidinoheptane signal was absent from the arginine solution and all controls. Furthermore, a 4-amino-3-oxo-guanidinoheptane signal was absent from all *E. coli* BL21(DE3) PPTase pSxt1 cultures, apart from the culture induced at 19° C.

This experiment demonstrated that SxtA could be expressed in a catalytically-active form in *E. coli* BL21 (DE3) using a synthetic DNA construct. In this experiment, expression occurred only at a growth temperature of 19° C., and after induction with 0.5 mM IPTG and 1 mM toluic acid.

Example 8: Integration of Fragments Sxt1 to Sxt3 into Sugar Catabolising Operons of *E. coli* DE3(BL21) PPTase The sxt1 construct was integrated into the lac operon of *E. coli* BL21(DE3) PPTase as follows:

The synthetic DNA construct, sxt1, was PCR amplified using 2 μl template DNA, 0.4 μM primers, Phusion DNA polymerase in a 50 μl reaction volume.

The PCR cycles were as follows: 98C for 1 min, 30 cycles: 98C for 5 sec, 72C for 2 min, 72C for 5 min, then hold at 4° C.

The PCR product (8019 bp) was then used for RED ET mediated recombination, after its purification by gel electrophoresis and gel extraction. Prior to recombination, *E. coli* BL21(DE3)

PPTase was transformed with the plasmid pRED (GeneBridges) by electroporation, and transcription of pRED encoded recombinases was induced according to the manufacturer's instructions. Subsequently, the transformed strain was electroporated with the PCR product described above (2.5 kV, 200 Ohm, 25 μF, 150 ng PCR product in 5 μl), followed by recombination into the lac operon.

The electroporated cells were plated onto LB agar with 15 μg/ml kanamycin, and grown overnight at 37° C. Resulting clones were picked and plated onto MacConkey (with lactose) agar with 15 μg/ml kanamycin kanamycin, and grown for at least 24h at 37° C. Resulting white colonies were isolated into pure culture, and tested by PCR and sequencing for correct and mutation-free integration of fragment sxt1 into the lac operon.

Upon confirmation, a clone was chosen to remove the kanamycin resistance cassette by flippase-recombination using plasmid p707, according to the manufacturer's protocol (GeneBridges). Resulting clones were screened for kanamycin resistance, and the successful removal of the kanamycin resistance cassette was verified by PCR. In addition, PCR was used to verify that the remainder of the sxt1 fragment was intact.

The resulting strain was then used for the integration of fragment sxt2 into the maltose operon, using the same approach. The resulting strain, where fragments sxt1 and sxt2 were integrated, and after removal of the kanamycin resistance cassette, was used by the same approach to integrate each of three variants of sxt3 fragment into the xylose operon.

sxt3 variant *E. coli* BL21(DE3) strains

| Strain | Strain Designation | Genes deleted from sxt3 |
|---|---|---|
| T3PPTase sxt1 sxt2 sxt3 v1 | NSX3v1 | none |
| T3PPTase sxt1 sxt2 sxt3 v2 | NSX3v2 | orf24 |
| T3PPTase sxt1 sxt2 sxt3 v3 | NSX3v3 | sxtQ, sxtR, and orf24 |

The 4'-phosphopantetheinyl transferase gene sfp from *Bacillus subtilis* (Pfeifer B A, et al. (2001) Science 291: 1790-2) was then used to replace the T3 PPTase in each of the above strains to produced additional strains.

Figure 9A:
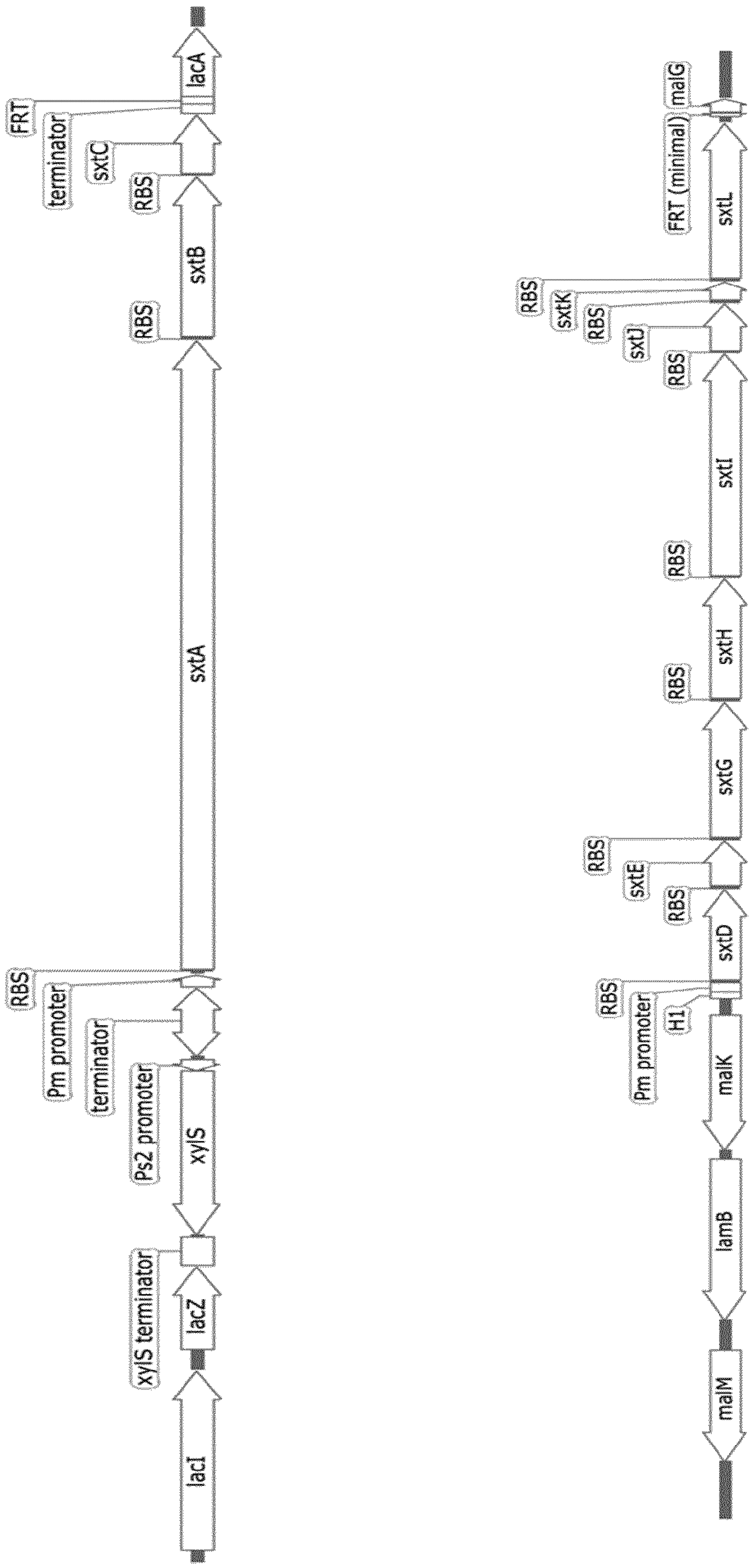
FIGS. 9A and 9B: (a) sxtl integrated into the lactose operon, kanamycin cassette removed by flippase recombination. (b) sxt2 integrated into the maltose operon, kanamycin cassette removed by flippase recombination. (c) sxt3 (all genes) integrated into the xylose operon, kanamycin cassette removed by flippase recombination. (d) sxt4 integrated into the melobiose operon, kanamycin cassette not removed.
Figure 9B:
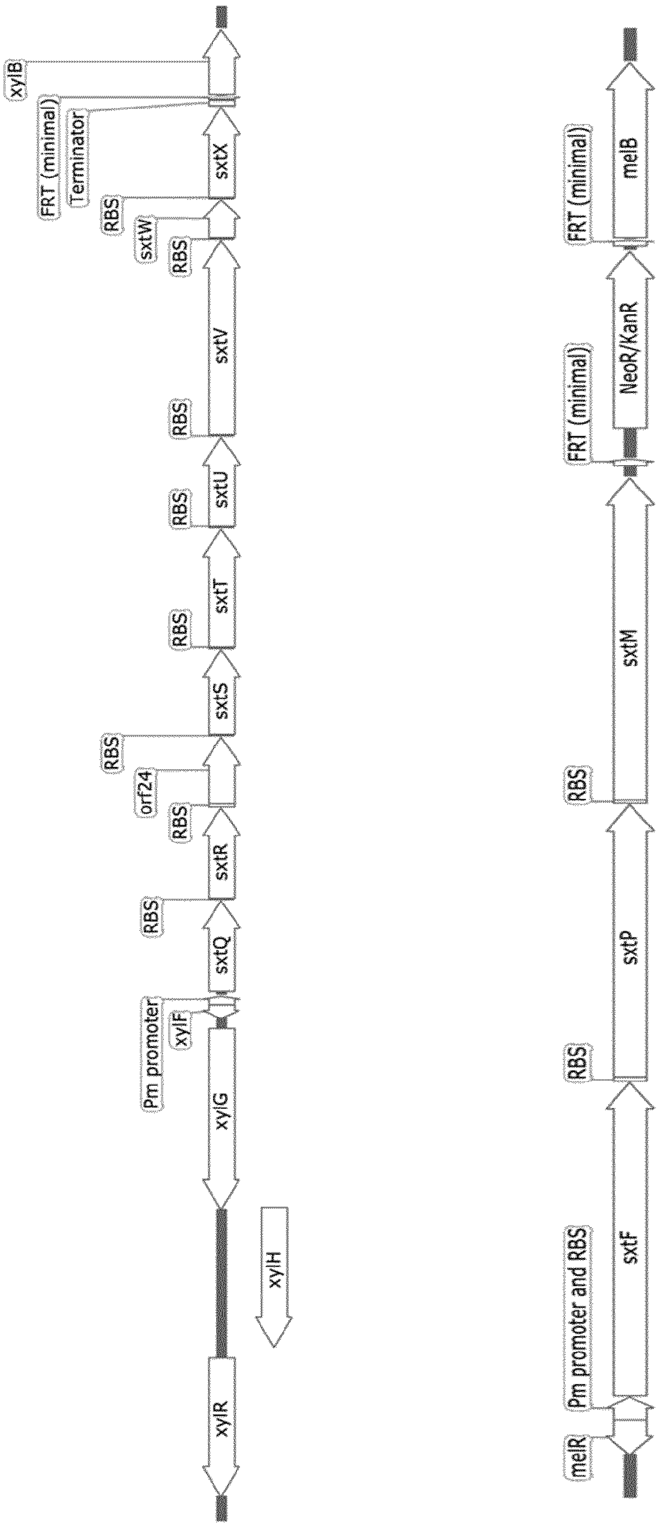

The resulting strains were then used for the integration of fragment sxt4 into the melobiose operon of *E. coli* BL21 (DE3) T3PPTase and *E. coli* BL21(DE3) sfp. The kanamycin cassette was not removed. Diagrams of the sxtl-4 fragments are given in FIG. 9.

Example 9: Creation of Variant Strains of *E. coli* BL21(DE3) Sfp NSX3v3

Strain *E. coli* BL21(DE3) sfp NSX3v3 was used as the parent strain to create the following strains where individual or sets of genes were deleted by homologous recombination methods.

Table of *E. coli* BL21(DE3) strains and what genes they have integrated into dispensable sugar operons

| Strains | Description | Genes |
|---|---|---|
| T3PPTase | T3PPTase | T3PPTase |
| T3PPTase sxt1 | T3PPTase, sxt1 | T3PPTase sxtA, sxtB, sxtC |
| T3PPTase sxt1 sxt2 | T3PPTase, sxt1, sxt2 | T3PPTase sxtA, sxtB, sxtC, sxtD, sxtE, sxtG, sxtH, sxtI, sxtJ, sxtK, sxtL |
| T3PPTase sxt1 sxt2 sxt3 v1 | T3PPTase, sxt1, sxt2, sxt3; all genes of sxt3 present | T3PPTase sxtA, sxtB, sxtC, sxtD, sxtE, sxtG, sxtH, sxtI, sxtJ, sxtK, sxtL, sxtQ, sxtR, ORF24, sxtS, sxtT, sxtU, sxtV, sxtW, sxtX |
| T3PPTase sxt1 sxt2 sxt3 v2 | T3PPTase, sxt1, sxt2, sxt3; orf24 was deleted from sxt3 | T3PPTase sxtA, sxtB, sxtC, sxtD, sxtE, sxtG, sxtH, sxtI, sxtJ, sxtK, sxtL, sxtQ, sxtR, sxtS, sxtT, sxtU, sxtV, sxtW, sxtX |
| T3PPTase sxt1 sxt2 sxt3 v3 | T3PPTase, sxt1, sxt2, sxt3; sxtQ, sxtR and orf24 were deleted from sxt3 | T3PPTase sxtA, sxtB, sxtC, sxtD, sxtE, sxtG, sxtH, sxtI, sxtJ, sxtK, sxtL, sxtS, sxtT, sxtU, sxtV, sxtW, sxtX |
| T3PPTase sxt1 sxt2 sxt3 v3 sxt4 | T3PPTase, sxt1, sxt2, sxt3, sxt4; sxtQ, sxtR and orf24 were deleted from sxt3; kanR present | T3PPTase sxtA, sxtB, sxtC, sxtD, sxtE, sxtG, sxtH, sxtI, sxtJ, sxtK, sxtL, sxtS, sxtT, sxtU, sxtV, sxtW, sxtX, sxtF, sxtP, sxtM |
| sfp sxt123 V1 (NSXv1) | sfp, sxt1, sxt2, sxt3; all genes of sxt3 present | sfp sxtA, sxtB, sxtC, sxtD, sxtE, sxtG, sxtH, sxtI, sxtJ, sxtK, sxtL, sxtQ, sxtR, ORF24, sxtS, sxtT, sxtU, sxtV, sxtW, sxtX |
| sfp sxt 123 V2 (NSXv2) | sfp, sxt1, sxt2, sxt3: orf24 was deleted from sxt3 | sfp sxtA, sxtB, sxtC, sxtD, sxtE, sxtG, sxtH, sxtI, sxtJ, sxtK, sxtL, sxtQ, sxtR, sxtS, sxtT, sxtU, sxtV, sxtW, sxtX |
| sfp sxt 123 V3 (NSXv3) | sfp, sxt1, sxt2, sxt3: sxtQ, sxtR and orf24 were deleted from sxt3 | sfp sxtA, sxtB, sxtC, sxtD, sxtE, sxtG, sxtH, sxtI, sxtJ, sxtK, sxtL, sxtS, sxtT, sxtU, sxtV, sxtW, sxtX |
| sfp sxt 123 V4 (NSXv4) | sfp, sxt1, sxt2, sxt3: sxtQ, sxtR and orf24 were deleted from sxt3; sxtC was deleted from sxt1 | sfp sxtA, sxtB, sxtD, sxtE, sxtG, sxtH, sxtI, sxtJ, sxtK, sxtL, sxtS, sxtT, sxtU, sxtV, sxtW, sxtX |
| sfp sxt 123 V5 (NSXv5) | sfp, sxt1, sxt2, sxt3: sxtQ, sxtR and orf24 were deleted from sxt3; sxtL was deleted from sxt2 | sfp sxtA, sxtB, sxtC, sxtD, sxtE, sxtG, sxtH, sxtI, sxtJ, sxtK, sxtS, sxtT, sxtU, sxtV, sxtW, sxtX |
| sfp sxt 123 V6 (NSXv6) | sfp, sxt1, sxt2, sxt3: sxtQ, sxtR and orf24 were deleted from sxt3; sxtJ, sxtK, sxtL were deleted from sxt2 | sfp sxtA, sxtB, sxtC, sxtD, sxtE, sxtG, sxtH, sxtI, sxtS, sxtT, sxtU, sxtV, sxtW, sxtX |
| sfp sxt 123 V7 (NSXv7) | sfp, sxt1, sxt2, sxt3, sxt4:sxtQ, sxtR and orf24 were deleted from sxt3; kanR present | sfp sxtA, sxtB, sxtC, sxtD, sxtE, sxtG, sxtH, sxtI, sxtJ, sxtK, sxtL, sxtS, sxtT, sxtU, sxtV, sxtW, sxtX, sxtF, sxtP, sxtM |

Example 10: Use of LC-MS to Detect Neosaxitoxin and Intermediates

LC-MS was used to detect neosaxitoxin and intermediates in the production of neosaxitoxin. LC-MS analysis was performed on a ThermoFisher Scientific Q Exative Hybrid Quadrupole mass spectrometer that was fitted with an ESI II ion source, and coupled online to a Dionex 3000 Ultimate RSLC Ultrapressure liquid chromatography instrument.

Mass/charge ratios (m/z) of possible saxitoxin analogues and intermediate metabolites that might by produced by *E. coli* BL21(DE3) NSX3 strains

| Compound | m/z [M + H]+ adduct | Chemical Composition |
|---|---|---|
| Intermediate 1 | 187.15534 | $C_8H_{19}ON_4$ |
| Intermediate 2 | 229.17714 | $C_9H_{21}ON_6$ |
| Intermediate 3 | 211.16657 | $C_9H_{19}N_6$ |
| Intermediate 4 | 209.14584 | $C_9H_{17}N_6$ |
| Intermediate 5 | 207.13527 | $C_9H_{15}N_6$ |
| Intermediate 6 | 223.13019 | $C_9H_{15}ON_6$ |
| Intermediate 7 | 223.13090 | $C_9H_{15}ON_6$ |
| Intermediate 8 | 225.14584 | $C_9H_{17}ON_6$ |
| Intermediate 9 | 268.15165 | $C_{10}H_{18}O_2N_7$ |
| dcSTX | 257.13566 | $C_9H_{17}O_3N_6$ |
| dcneoSTX | 273.13058 | $C_9H_{17}O_4N_6$ |
| STX | 300.14148 | $C_{10}H_{18}O_4N_7$ |
| neoSTX | 316.13639 | $C_{10}H_{18}O_5N_7$ |
| STX-15N4 | 304.12962 | $C_{10}H_{18}O_4N_3{}^{-15}N_4$ |

Example 11: Detection of Intermediate 1 and Intermediate 8 in *E. coli* Extract

*E. coli* BL21(DE3) T3PPtase NSX3v1 was grown in 20 ml LB broth in a 100 ml flask at 19° C. with shaking (200 rpm). The culture was induced with 0.2 mM IPTG, 1 mM toluic acid, when it reached an $OD_{600}$ of 0.9, and grown for 18 hours to an $OD_{600}$=5.

The cells were harvested by centrifugation, and extracted in 800 μl of 0.1 M acetic acid in methanol. The lysate was centrifuged, and the supernatant diluted 1:5 with acetonitrile prior to LC-MS analysis.

Figure 10:
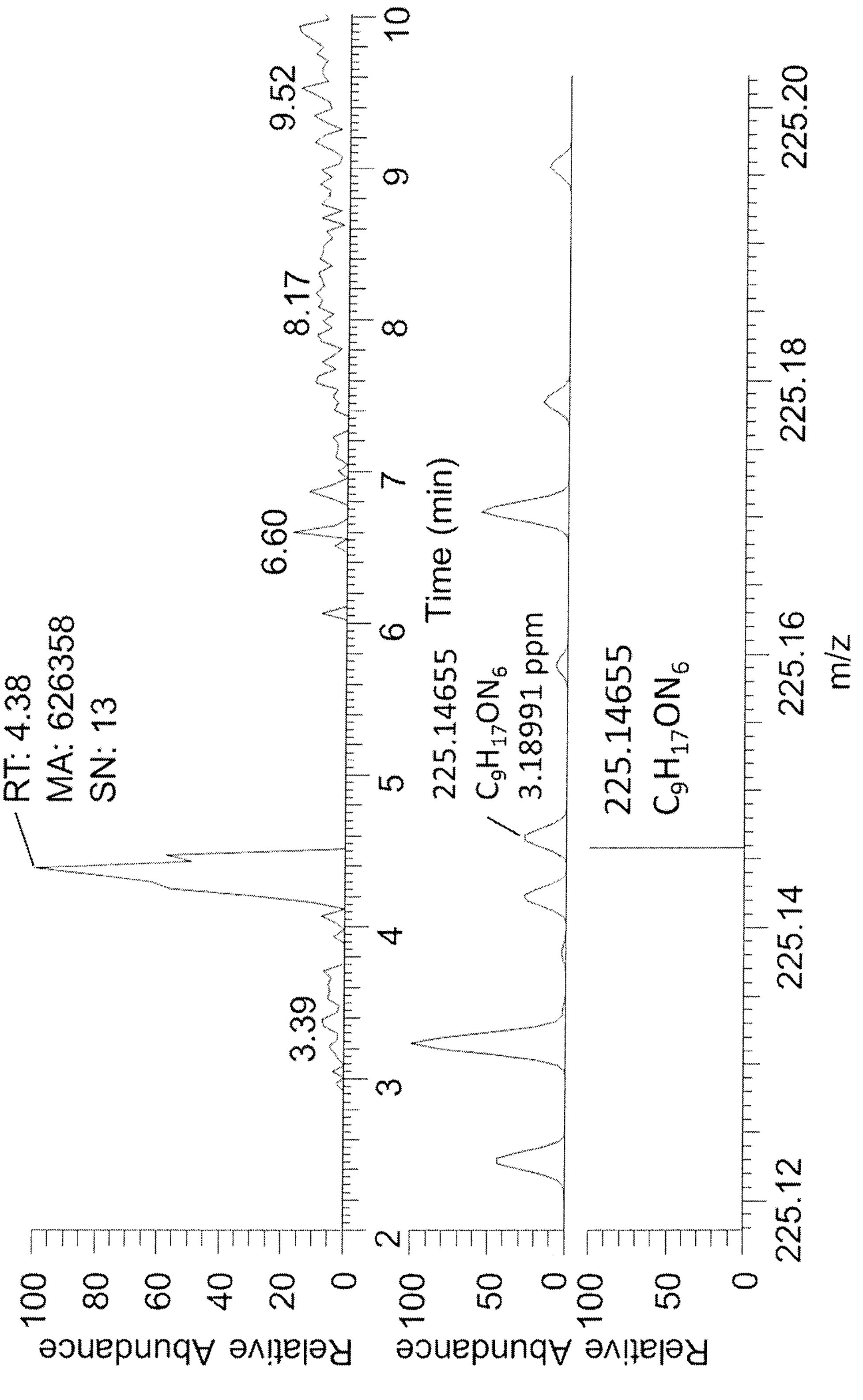
FIG. 10: Detection of intermediate 8 in cell extract of *E. coli* BL21(DE3) T3PPTase NSX3v1.
Figure 11:
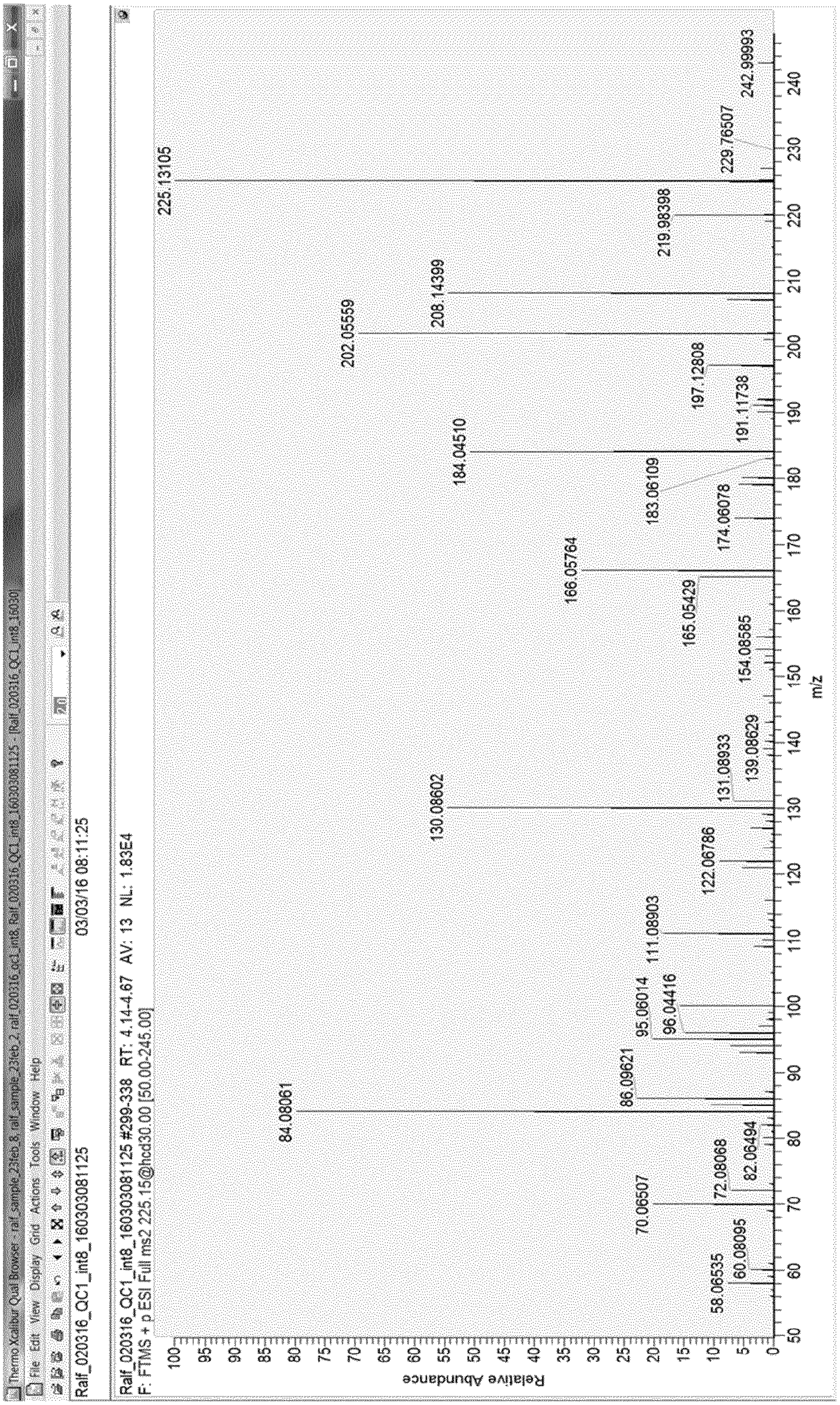
FIG. 11: MS/MS spectra of Intermediate 8 in cell extract of *E. coli* BL21(DE3) T3PPTase NSX3v1.

Intermediates 1 and 8 were detected in the extract. The spectra from Intermediate 8 are shown in FIGS. 10 and 11.

Example 12: Production of Neosaxitoxin

A seed culture of *E. coli* sfp NSX3v3 was prepared in 50 ml Hi YE medium, and incubated overnight at 30° C. (225 rpm). A New Brunswick BioFlo 110 fermentor (2 L volume) equipped a heater sleave, water cooling, a pH and dissolved oxygen probe was set up for a fermentation experiment according to the manufacturer's instructions. The fermentor was filled with 2 L Hi-YE medium base, and autoclaved. Stock solutions of yeast extract, magnesium chloride, glucose and glycerol were aseptically added to the fermenter after autoclavation. In addition, 2 ml sterlie solution of 5% antifoam 204 (Sigma Aldrich) was added to the fermenter. The medium was inoculated with 20 ml overnight seed-culture, which had an $OD_{600}$ of 5.71. The $OD_{600}$ of the starting culture was measured at 0.15. The culture was incubated at 19° C. with an initial agitation at 50 rpm, which was increased to 600 rpm after 26 hours incubation. The culture was purged with pressurised air at a flow-rate of 2 l/hour. The pH and dissolved oxygen levels were continuously monitored, and the growth was measured off-line after taking samples. The pH (pH 7.1) was stable during the entire experiment, as well as the dissolved oxygen level (100%). The culture was induced with 0.5 mM m-toluic acid and 0.2 mM IPTG after 22 hours incubation ($OD_{600}$=10.6), and incubated for a further 22 hours. Sterile glucose solution (400 g/l) was fed to the culture at a flow-rate of 2.9 ml/min between 24 and 26.3 hours of the experiment (total 11.4 g), and 1.8 ml of a sterile 1 M magnesium sulfate solution was added at 26.3 hours of the experiment in an attempt to stimulate growth and production of neoSTX. The experiment was terminated after 45 hours, when the culture was harvested by centrifugation (5000×5, 30 minutes at 4° C.). The cell pellet was washed twice with 50 ml ice-cold MQ water (5.000×g, 10 min, 4° C.), weighed, and stored at −20° C. until analysis. The total biomass obtained was 23.77 g.

Figure 12:
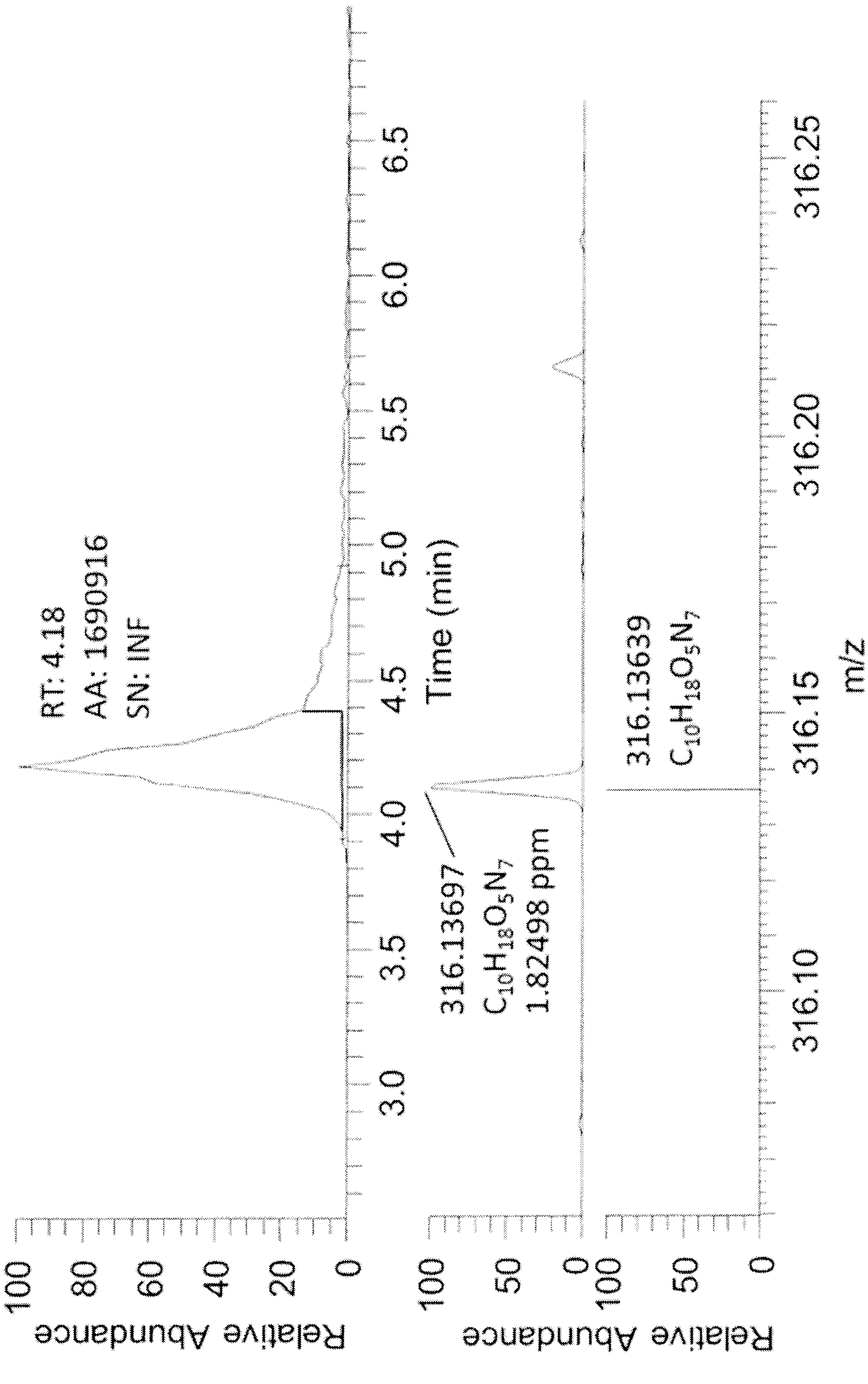
FIG. 12: Accurate mass LC-MS analysis of neosaxitoxin standard solution (100 nM). Selected ion monitoring chromatogram of m/z 316.13639 (400 mmu window) is shown in the upper plot, and MS spectrum across the peak, and theoretic spectrum are shown in the middle and lower plots, respectively. The retention time (RT), manually integrated peak area (MA), signal to noise ratio (SN) is given in the upper plot. The measured mass, chemical composition, and mass error (ppm) is given in the middle and lower plots.
Figure 13:
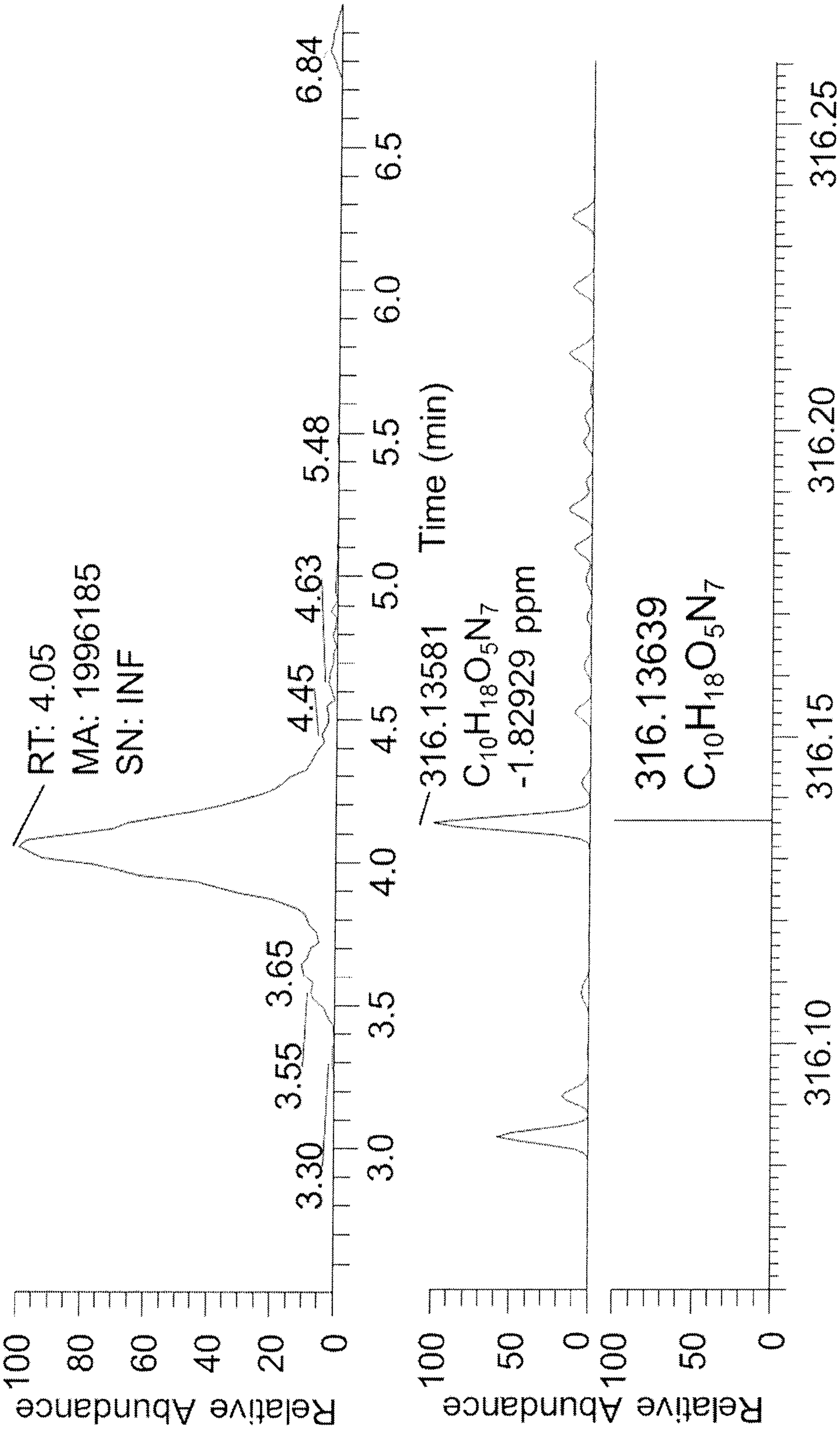
FIG. 13: Accurate mass LC-MS analysis of extract from *E. coli* BL21(DE3) sfp NSX3v3. Selected ion monitoring chromatogram of m/z 316.13639 (400 mmu window) is shown in the upper plot, and MS spectrum across the peak, and theoretic spectrum are shown in the middle and lower plots, respectively. The retention time (RT), manually integrated peak area (MA), signal to noise ratio (SN) is given in the upper plot. The measured mass, chemical composition, and mass error (ppm) is given in the middle and lower plots.

The cells from the fermentation experiments were lysed by boiling in 0.1% formic acid, and the extract was diluted 1:5 with acetonitrile with 0.1% formic acid prior to LC-MS analysis (see FIGS. 12 and 13). The content of neoSTX in the pellet was also analysed by a mouse neuroblastoma assay MS.

Example 13: Optimisation of Cell Lysis to Extract Intermediates

The native genes sxtA, sxtB, sxtC were cloned into pVB vector (Vectrons Biosolutions), and the resulting vector pVB-sxtABC was transformed into *E. coli* BAP1. BAP1 pVB-sxtABC was grown in 10 ml TB medium at 19° C. with shaking at 200 rpm for 24 hours. The cells were harvested by centrifugation, and washed twice with ice-cold MQ water, the pellets were weighed, and stored at −20° C. until analysis.

Figure 14:
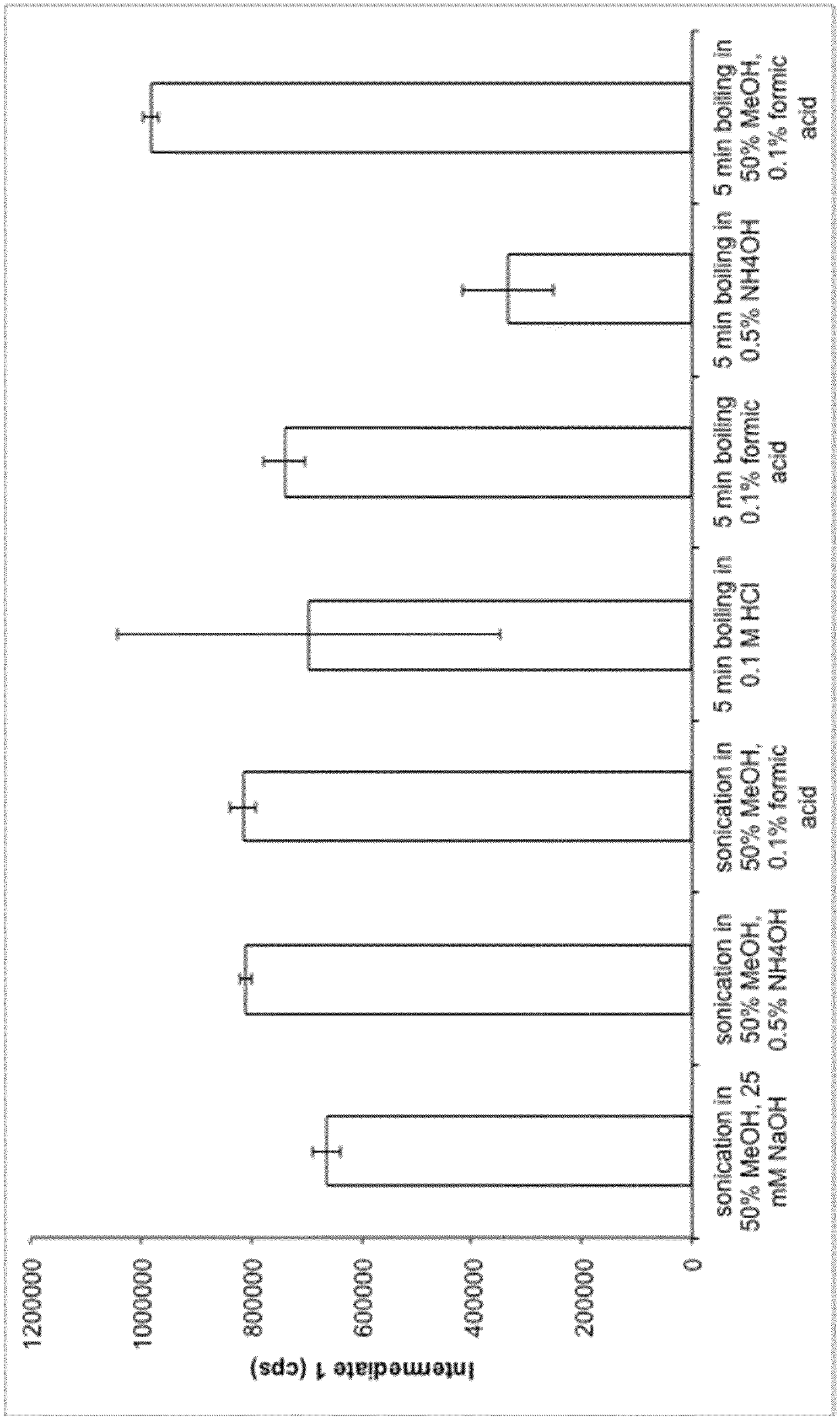
FIG. 14: Recovery of intermediate 1 from *E. coli* BL21 (DE3) pVB-sxtABC by various methods of cell lysis. LC-MS analysis was carried out in SIM mode (m/z 187.15534 with a 400 mmu mass window). The instrument response is given as peak area (counts per second).

The pellets were resuspended (1:3 wet weight:volume) in various lysis solutions:

1. 50% methanol with 25 mM sodium hydroxide
2. 50% methanol with 0.5% ammonium hydroxide
3. 50% methanol with 0.1% formic acid
4. 0.1 mM hydrochloric acid
5. 0.1% formic acid
6. 0.5% ammonium hydroxide Treatments 1, 2 and 3 were sonicated for 2 minutes using a Branson Sonifier 250, equipped with a microprobe (output 2, duty cycle 50%). Treatments 3, to 5 were boiled for 5 minutes in a boiling water batch. The extracts were centrifuged for 10 minutes at 18000×g (4° C.). 250 μl supernatant were mixed with 750 μl acetonitrile with 0.4% formic acid, and centrifuged (10 minutes at 18000×g, 4° C.). The supernatant was transferred to autosampler vials for LC-MS analysis of Intermediate 1 (see FIG. 14).

5 minutes boiling in 0.1% formic acid was regarded as the most suitable method, as it did not cause interference with HILIC LC-MS, and produced a minimal amount of precipitation during extraction.

Example 14: Optimal Strain and Production Levels

Seed-cultures of the *E. coli* strains were prepared in 10 ml LB broth and grown overnight at 30° C. with shaking at 200 rpm. The following strains were compared for neoSTX production levels:

*E. coli* BL21(DE3) sfp
*E. coli* BL21(DE3) T3PPTase sxt1 sxt2
*E. coli* BL21(DE3) T3PPTase NSX3v1
*E. coli* BL21(DE3) sfp NSX3v1
*E. coli* BL21(DE3) sfp NSX3v2
*E. coli* BL21(DE3) sfp NSX3v3
*E. coli* BL21(DE3) sfp NSX3v4

*E. coli* BL21(DE3) sfp NSX3v5
*E. coli* BL21(DE3) sfp NSX3v6
*E. coli* BL21(DE3) sfp NSX3v7

30 ml Terrific Broth (TB) with 0.4% glycerol and buffered to pH 6.8 with 89 mM phosphate buffer were inoculated with 300 μl overnight seed-culture to an approximate $OD_{600}$ of 0.05. Cultures were incubated at 30° C. with shaking at 225 rpm until they reached an $OD_{600}$ of 0.4. The cultures were then transferred to 19° C. (with shaking 225 rpm), and grown to an $OD_{600}$ of 0.5. For induction of sfp and sxt genes, 0.05 mM IPTG (0.05 mM final concentration) and toluic acid (0.5 mM final concentration) were added to the cultures, which incubated at 19° C. with shaking (225 rpm) for a further 48 hours. Each strain was grown in triplicate sub-cultures. 25 ml of each culture was harvested by centrifugation at 3000×g for 10 min at 4° C. Aliquots of 1 ml supernatant was stored at −20° C., and the remaining supernatant discarded. The cell pellets were washed with twice with respectively 25 and 5 ml ice-cold MQ water (3000×g for 10 min at 4° C.). Cell pellets were weighed and stored at −20° C.

Toxin Extraction from Cell Pellets

Bacterial cell pellet was resuspended in 0.1% formic acid at a ratio of 1:4 (wwt:vol) and boiled for 5 minutes. The extract was briefly cooled on ice, centrifuged at 16.000×g for 10 minutes, and the supernatant collected. For LC-MS analysis, the supernatant was diluted with 90% acetonitrile: 10% methanol:0.1% formic acid containing 25 nM saxitoxin-$^{15}N_4$ internal standard at a ratio of 1:5. The sample was centrifuged (16.000×g for 10 minutes, 4° C.) and the supernatant transferred to autosampler vials for LC-MS analysis.

Toxin Extraction from Growth Media

Figure 15:
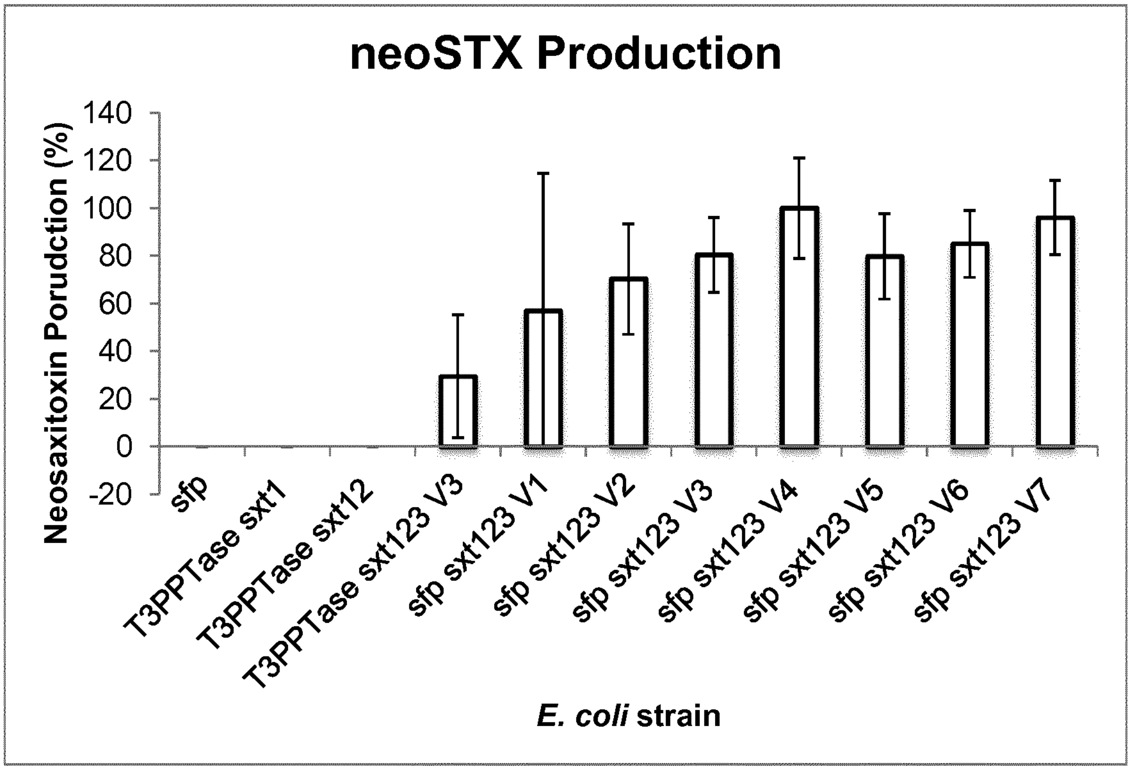
FIG. 15: Production levels of neoSTX in percent relative to *E. coli* sfp NSX3v4 (sfp sxt123 V4). The estimated concentration of neoSTX in the extract of sfp sxt123 V4 was 2.8 nM.

Growth media (200 μl) was acidified with 2 μl 10% formic acid, boiled for 5 minutes, cooled on ice, and centrifuged at 16000×g for 10 minutes at 4° C. The supernatant was transferred to a new tube, and 40 μl internal standard was added (25 nM saxitoxin-$^{15}N_4$ in 10% methanol 90% acetonitrile and 0.1% formic acid). The tube was centrifuged at 16000×g 4° C. for 10 minutes, and the supernatant transferred to an HPLC auto-sampler vial for LC-MS analysis. The results are shown in FIG. 15.

Example 15: Mouse Neuroblastoma Assay (MNBA) for the Detection of Sodium Channel Blocking Toxins

*E. coli* Cultures for MNBA

Seed-cultures of the *E. coli* strains BL21(DE3) sfp and BL21(DE3) sfp NSX3v3 were prepared in 10 ml LB broth and grown overnight at 30° C. with shaking at 200 rpm. 50 ml Terrific Broth (TB) with 0.4% glycerol and buffered to pH 6.8 with 89 mM phosphate buffer were inoculated with 500 μl overnight seed-culture to an approximate $OD_{600}$ of 0.05. Cultures were incubated at 30° C. with shaking at 225 rpm until they reached an $OD_{600}$ of 0.4. The cultures were then transferred to 19° C. (with shaking 225 rpm), and grown to an $OD_{600}$ of 0.5. For induction of sfp and sxt genes, 0.05 mM IPTG (0.05 mM final concentration) and toluic acid (0.5 mM final concentration) were added to the cultures, which incubated at 19° C. with shaking (225 rpm) for a further 48 hours. Each strain was grown in triplicate sub-cultures. Cultures were harvested by centrifugation at 2500×g for 10 min at 4° C. The cell pellets were washed with twice with respectively 25 ice-cold MQ water (2500×g for 10 min at 4° C.). Cell pellets were weighed and stored at −20° C.

Cell Extraction for MNBA

Bacterial cells were extracted by weak cation exchange solid phase extraction (WCX-SPE) for the MNBA, using Accell Plus CM cartridges (360 mg, 1.1 ml, WAT010910, Waters) according to the following protocol.

1.2 g cell pellet was resuspended in 3.6 ml 0.15% formic acid and lysed by boiling for 5 minutes. The cell extract was cleared by centrifugation at 16.000×g for 10 minutes.

Columns were conditioned with 3.6 ml methanol, followed by 3.6 ml 0.15% formic acid. 3 ml sample was loaded, and the column was washed with 1.8 ml MQ water, followed by 1.8 ml acetonitrile. The column was then dried, and the sample eluted in 2×3.6 ml methanol with 5% formic acid. The eluate was dried by vacuum centrifugation, and the sample reconstituted in 200 μl 0.01% formic acid.

Mouse Neuroblastoma Assay for Sodium Channel Blocking Toxins

A mouse neuroblastoma assay was used (as described by Humpage et al. (2007). Environ. Toxicol. Chem. 26:1512-9), using the mouse neuro-2a cell line (CCL131).

Figure 16:
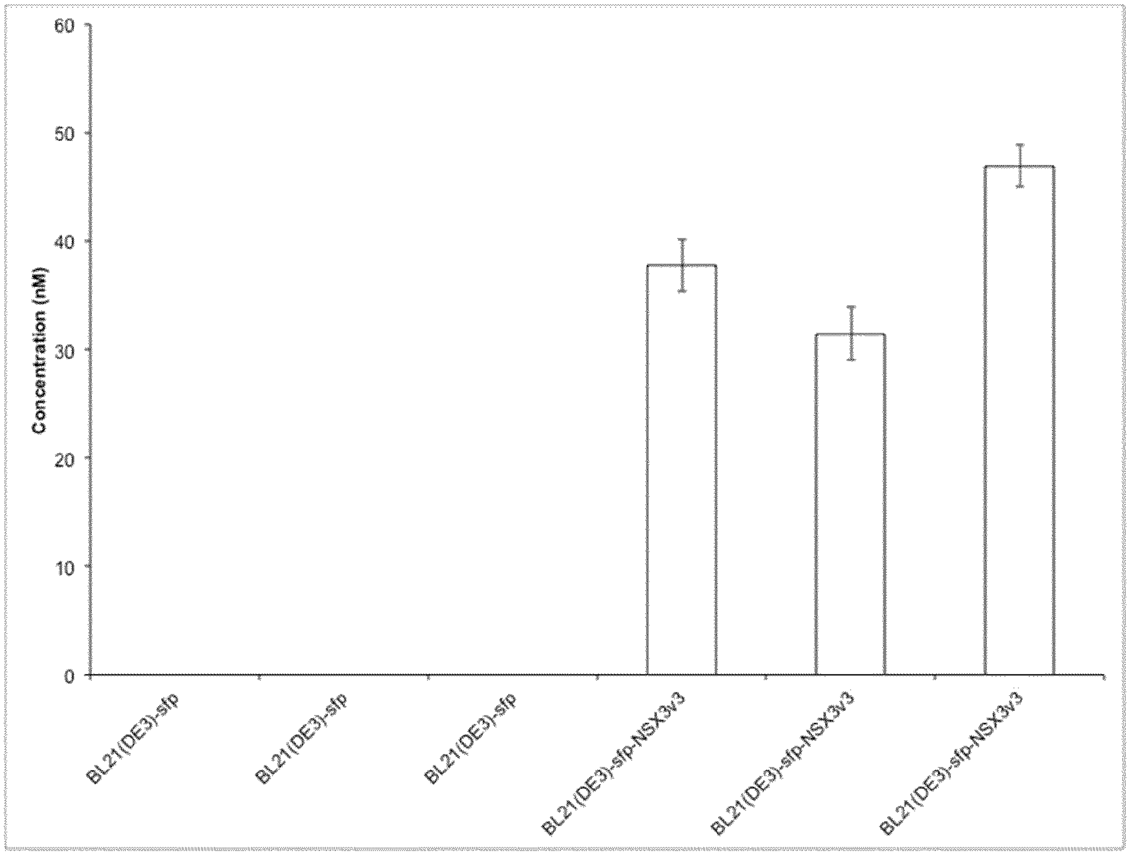
FIG. 16: Concentration the sodium channel blocking toxin neoSTX from *E. coli* BL21(DE3) sfp (negative control strain), and BL21(DE3) sfp NSX3v3 grown in shaker flask cultures in 50 ml TB medium. Each bar represents a biological replicate. Error bars represent the standard deviation of 4 replicates MNBA assays of the same extract. All samples were extracted by weak cation exchange solid phase extraction prior to analysis from a 1.2 g cell pellet. The concentration is given in nmol neoSTX per liter. The average concentration of neoSTX in the extract was 38.74 nM (±7.8 standard deviation).

A calibrator curve for the MNBA assay was prepared with and without biological matrix using a certified reference material for neoSTX (CRM-NEO-c, lot 2009-02-18, 65.6 μM in 3 mM HCl). The results are shown in FIG. 16.

Example 16: Immunochemical Detection of Neosaxitoxin by ELISA

A saxitoxin ELISA Kit (Abraxis PN 52255B, Microtiter Plate 96T) was used to detect neoSTX produced in *E. coli*. The kit employs polyclonal saxitoxin antibodies, which have 1.3% cross-reactivity to neoSTX. Cultures of *E. coli* T3PPTase NSX3v3 were prepared and cell lysates obtained. Samples were extracted by solid phase extraction on SampliQ silica columns (Agilent PN 5982-2211, 1 ml, 100 mg) Jansson D and Astot C (2015) m J Chromatogr A 1417:41-8). Extracted and evaporated samples were dissolved in 100 μl sample buffer provided by the STX ELISA kit. A 1:1000 dilution of *E. coli* T3PPTase NSX3v3 extract in sample buffer was also prepared. The assay was calibrated by a 2 point standard curve using Std 0 as the blank, Std 1 (0.0668 nM STX) and STd 5 (1.3365 nM STX) provided by the kit. The reference sample was used to estimate the accuracy of the STX ELISA kit for neoSTX, whereas the recovery of neoSTX during SPE was estimated based on the ratio of the extracted reference sample versus the reference sample. Results of the assay are shown in the Table below. The estimated accuracy was 119%, whereas the recovery during SPE was 92%. The assay detected an equivalent of 1.16 nM STX in the cell extract of *E. coli* T3PPTase NSX3v3. Converted to neoSTX, this amounts to 89.1 nM, and a yield of approximately 223 pmol neoSTX per liter of *E. coli* culture.

STX ELISA. Std 0, Std 1, and Std 5 were provided by the STX ELISA kit. The ELISA assay was calibrated by 2 points (y=−0.4627+0.7597). The concentration of neoSTX was calculated on the basis of 1.3% cross reactivity of the STX antibody according to the manufacturer. ND: none detected. The recovery of neoSTX by SPE was 92%.

| Sample ID | STX (nM) | neoSTX (nM) | $ABS_{450}$ | Ratio ($ABS_{sample}/ABS_{std0}$) | STX equivalent (nM) | Calculated Conc'n (nM neoSTX) |
|---|---|---|---|---|---|---|
| Std 0 | 0 | | 1.8190 | 1.00000 | ND | |
| Std 1 | 0.067 | | 1.3257 | 0.72879 | 0.067 | |
| Std 5 | 1.337 | | 0.2570 | 0.14129 | 1.337 | |
| Ref | | 100 | 0.0700 | 0.03848 | 1.559 | 119.901 |
| Ref Extract'd | | 100 | 0.1723 | 0.09474 | 1.437 | 110.548 |
| NSX3 cells | | | 0.4070 | 0.22375 | 1.158 | 89.101 |
| NSX3 media | | | 1.8740 | 1.03024 | ND | |
| NSX3 cells 1:1000 diluted | | | 1.8870 | 1.03738 | ND | |

Example 17: Effect of Synthetic v. Native Gene and RBS Spacer

A number of pVB constructs were made using the following elements:

(i) the Pm promoter;

(ii) the sxtA synthetic (codon-optimised for *E. coli*) or the sxt native gene; and (iii) a 8 or 10 bp spacer between the ribosome binding site (RBS) and start codon.

The sequence of the Pm promoter with the 8 bp spacer between RBS and start codon of SxtA is shown below. The RBS and start codon are shown with capital letters, the spacer is underlined:

```
                                   (SEQ ID NO: 100)
agtccagccttgcaagaagcggatacaggagtgcaaaaaatggctatctc

tagaaaggcctaccccttaggctttatgcaacagaaacaataataatGGA

GtcatgaacATG
```

The sequence of the Pm promoter with the 10 bp spacer between RBS and start codon of SxtA is shown below. The RBS and start codon are shown with capital letters, the spacer is underlined:

```
                                   (SEQ ID NO: 101)
agtccagccttgcaagaagcggatacaggagtgcaaaaaatggctatctc

tagaaaggcctaccccttaggctttatgcaacagaaacaataataatGGA

GtcatgaacatATG
```

The four pVB-sxtA plasmids were independently transformed into *E. coli* BL21(DE3) sfp.

Figure 17:
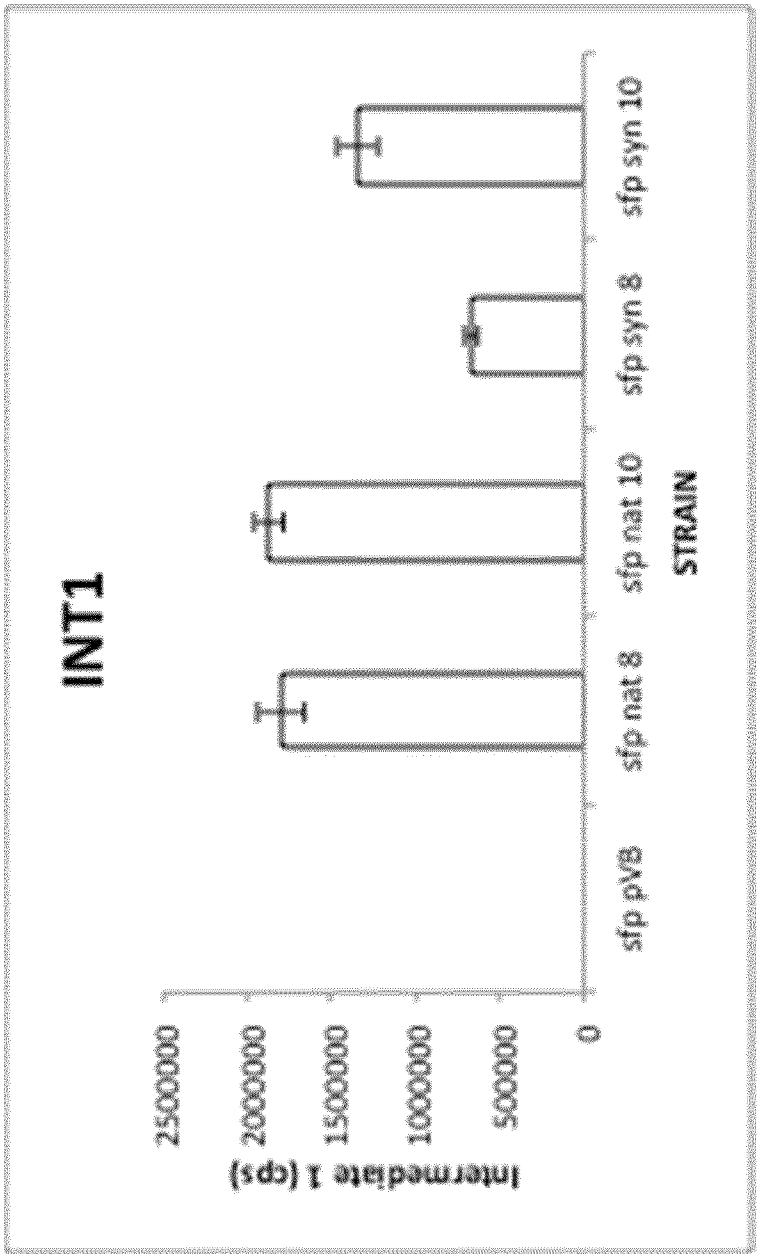
FIG. 17: Production of intermediate 1 by *E. coli* BL21 (DE3) sfp pVB-sxtA. sfp pVB: pVB vector without insert. sfp nat 8: pVB vector with native sxtA codon usage and 8 bp spacer between RBS and start codon. sfp nat 10: pVB vector with native sxtA codon usage and 10 bp spacer between RBS and start codon. sfp syn 8: pVB vector with synthetic sxtA gene that was codon usage-optimised for expression in *E. coli* with and 8 bp spacer between RBS and start codon. sfp syn 10: pVB vector with synthetic sxtA gene that was codon usage-optimised for expression in *E. coli* with and 10 bp spacer between RBS and start codon.

Cultures of each of the four *E. coli* BL21(DE3) sfp with pVB-sxtA variants were prepared and cells were harvested. Cell pellets were extracted and the presence of Intermediate 1 was analysed by LC-MS. The results are shown in FIG. 17. It can be seen that significantly more Intermediate 1 was produced in the synthetic sxtA construct which contained a 10 bp spacer between the RBS and start codon, compared to the synthetic sxtA construct which contained the 8 bp spacer.

Example 18: Production of Intermediate 8 in the Presence of Various PPTases

In this experiment, the following PPTases were compared:

1. T3PPT: *E. coli* BL21(DE3) T3PPTase NSX3v1
2. T3PPT: *E. coli* BL21(DE3) T3PPTase NSX3v1 pET28B-NsPPT (pET vector with phosphopantetheinyl transferase from *Nodularia spumigena*)

3. Ala18T3PPT: *E. coli* BL21(DE3) T3PPTase NSX3v1 pET30b-Ala18T3PPTase (T3PPTase where there first 18 amino acids were removed to increase solubility of expressed protein.)

The strains were cultured for 18 hours in 20 ml LB broth at 19° C. with shaking 200 rpm. Strains with pET vector were grown in the presence of 50 μg/ml kanamycin. Cultures were either grown without inducer, or induced with 0.2 mM IPTG and 1 mM toluic acid at $OD_{600}$ ca. 0.8. There was clear background expression of sxt and PPTase genes in the absence of inducer.

Figure 18:
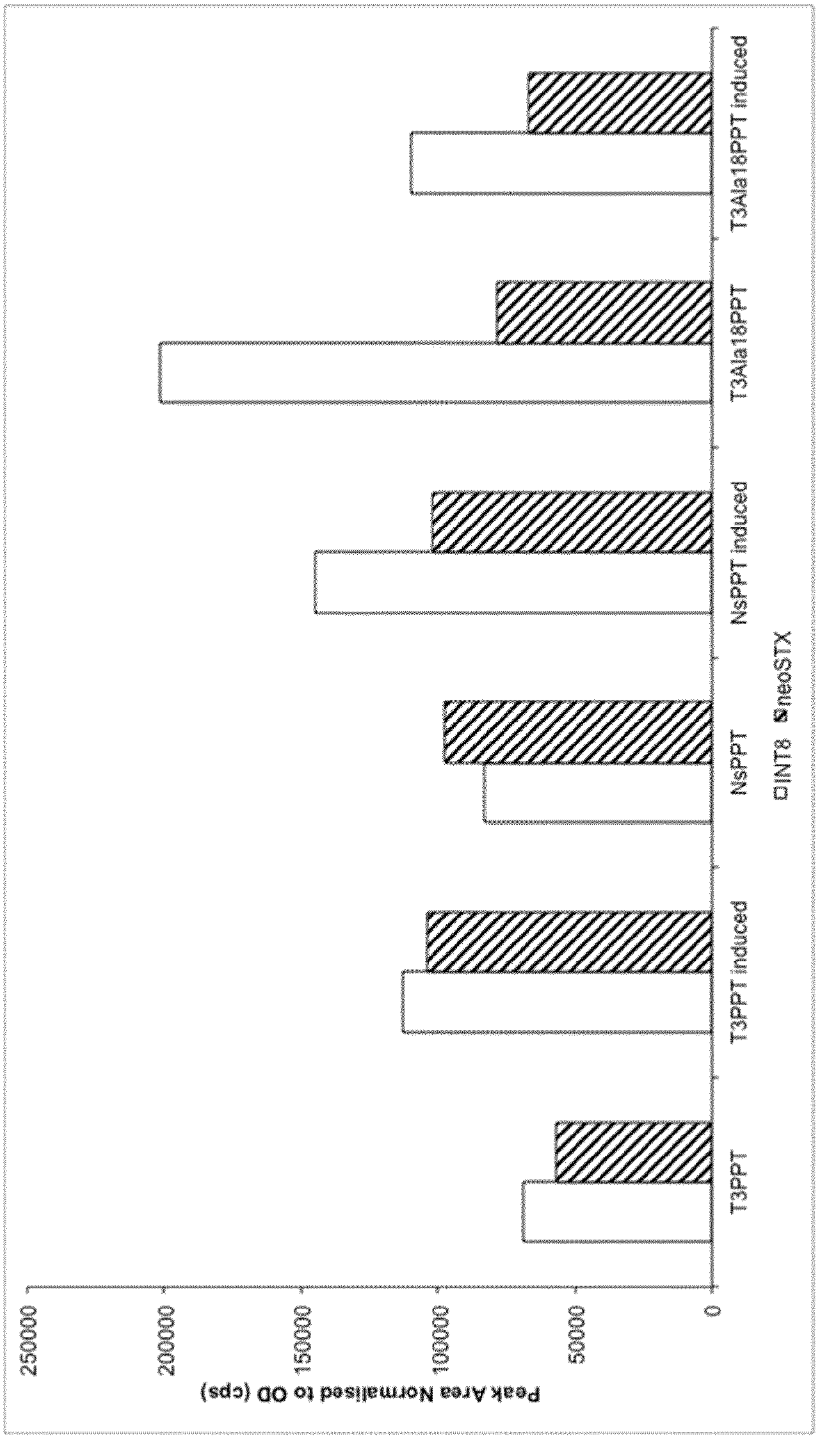
FIG. 18: Production of Intermediate 8 and neoSTX in *E. coli* strains. T3PPT: *E. coli* T3PPTase NSX3V1. NsPPT: *E. coli* T3PPTase NSX3V1 pET28b-NsPPT, coding for the *Nodularia spumigena* phosphopantetheinyl transferase. T3Ala18T3PPTase: *E. coli* T3PPTase NSX3V1 pET30b-Ala18T3PPTase, coding for T3PPTase that had the first 18 N-terminal amino acids removed to improve solubility during expression. Cultures were induced with 0.2 mM IPTG, and 1 mM toluic acid, where indicated.

Intermediate 8 and neoSTX were measured, and used as an indicator for the effectiveness of the PPTase. The results are shown in FIG. 18. The Ala18T3PPT gave the highest levels, but reduced levels after induction. This phenomenon may be due to inhibition of SxtA, when PPTase levels get too high, and occupy the enzyme.

Example 19: Production of Saxitoxin Analogues and Variants

Saxitoxin may be converted to GTX-5 by SxtN (i.e. by sulfonation of the carbamoyl side-chain). Similarly, saxitoxin may be converted 11-hydroxy STX by SxtDIOX. This is a step preceding C-11 sulfonation to convert STX to GTX-2/3 (or neosaxitoxin to GTX-4/1).

sxtN from *Scytonema* cf. *crispum* UCFS15 was cloned into an appropriate expression vector, and placed under the control of the IPTG-inducible T7 promoter, and provided with a hexa-histidine tag on its N- and C-terminus.

sxtO from S. cf. *crispum* UCFS15 was cloned into an appropriate expression vector, and placed under the control of the IPTG-inducible T7 promoter, and provided with a hexa-histidine tag on its N- and C-terminus.

The expression vectors were expressed in *E. coli* and the Sxt proteins were purified using No-NTA resin (Novagen). Purity of the proteins was assessed on SDS gels.

Figure 19:
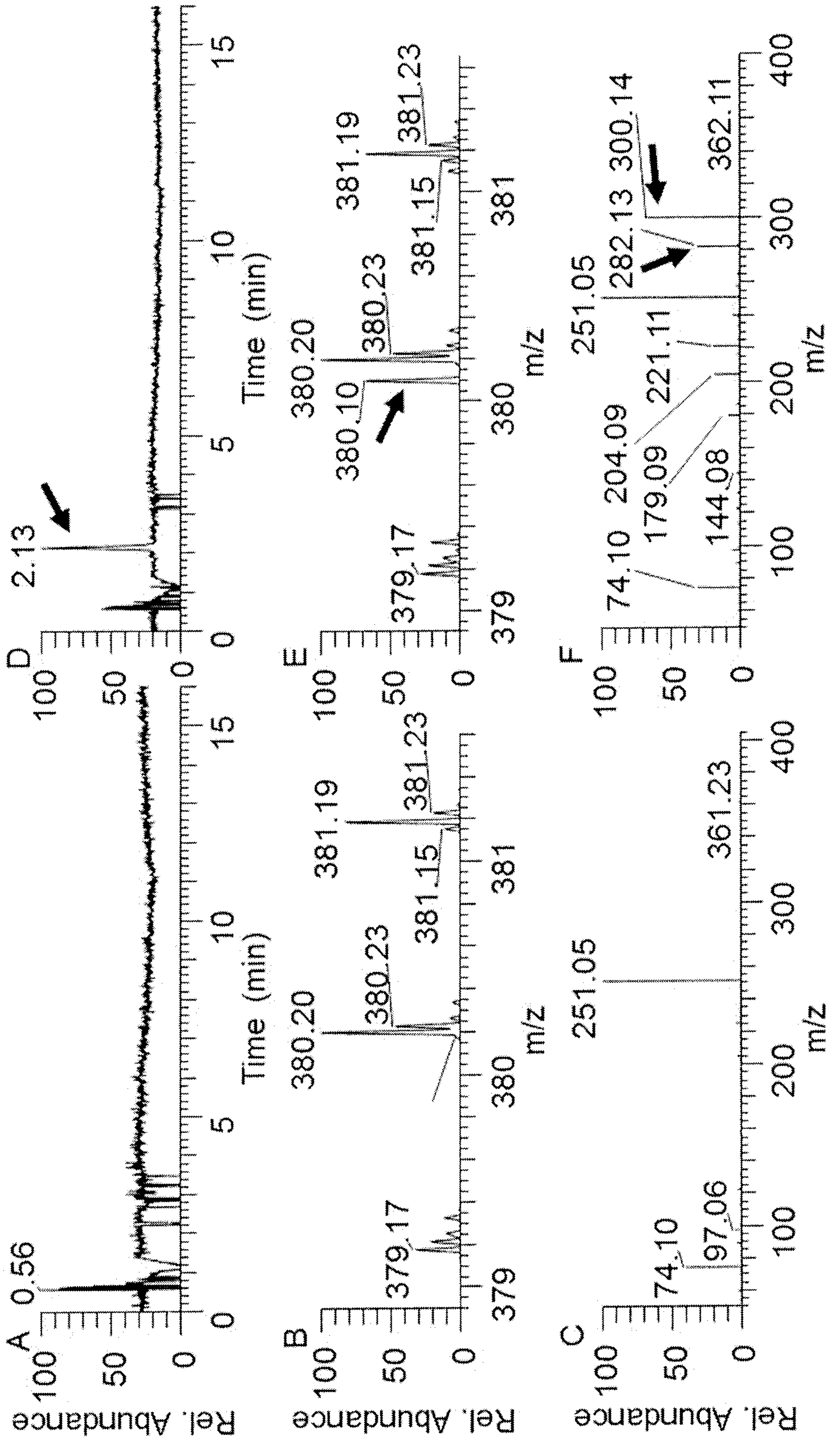
FIG. 19: LC chromatogram, MS spectra, MS/MS fragmentation (from top to bottom) of sulfotransferase assay of SxtN using saxitoxin as a substrate.

The sulfotransferase activity of SxtN was tested using saxitoxin or GTX2. The results were determined using HPLC-MS/MS. Using saxitoxin as substrate, a peak at 2.13 min was identified that was not present in the control. This contained a major peak of m/z 380.10, which fragmented (LC-MS/MS) to m/z of 300.14 and 282.13, proposed to be GTX5 (shown in FIG. 19). In using GTX2 as a substrate, no difference in toxin presence was observed between the samples and the control.

Figure 20:
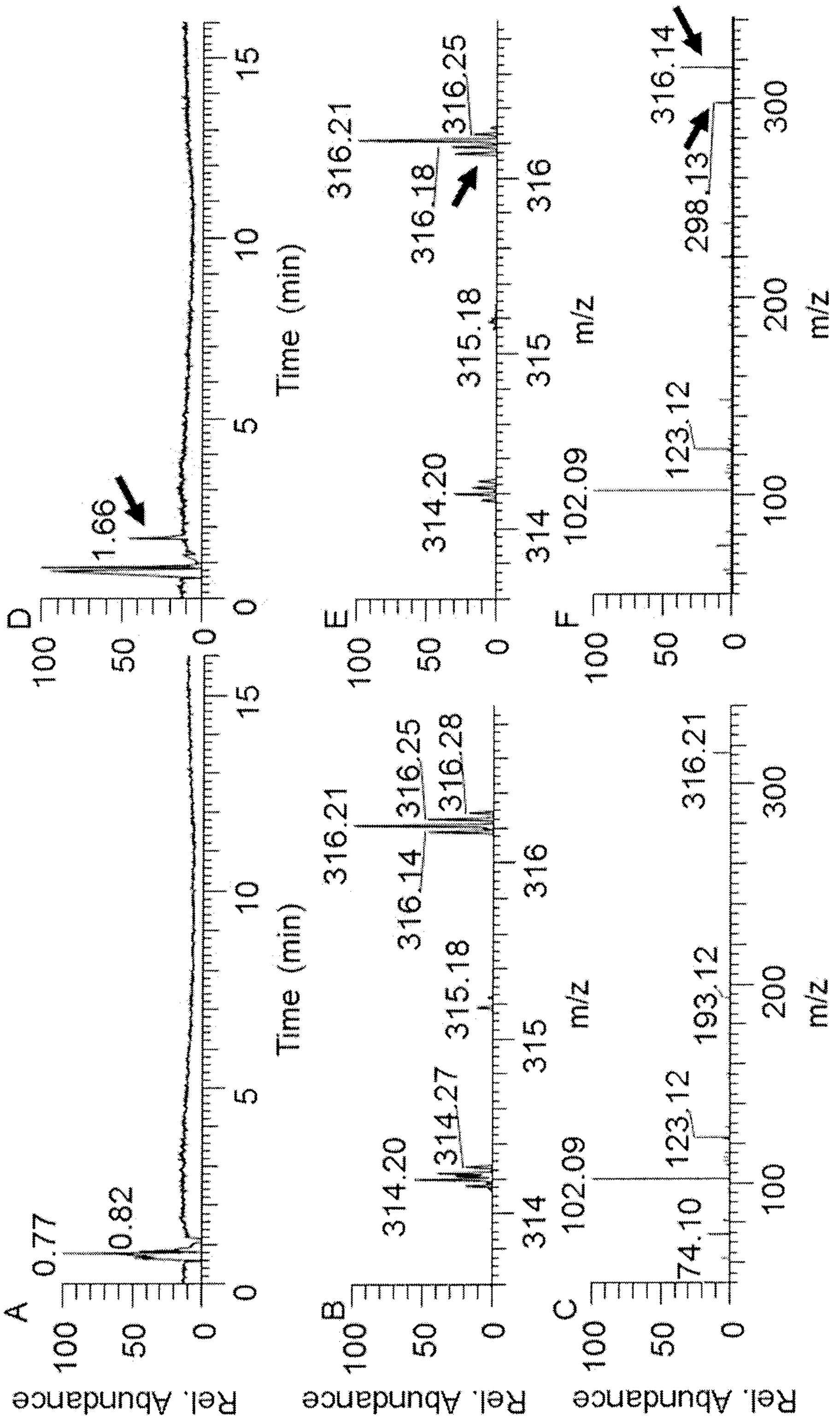
FIG. 20: LC chromatogram, MS spectra, MS/MS fragmentation (from top to bottom) of dioxygenase assay (SxtDIOX) using STX as substrate. Peaks that indicate hydroxy-STX production in the assay (right), not present in the control (left) are indicated by arrows.

The dioxygenase activity of SxtDIOX was tested using saxitoxin. The results were determined using HPLC-MS/MS. The substrate was identified in both the assay and the control. Further, a peak of m/z 316.14>296.13 at 1.66 min that was not present in the control was identified in the assay, suggesting the presence of hydroxylated saxitoxin (FIG. 20).

SEQUENCES

The accompanying Sequence Listing is fully incorporated herein as part of the description.

SEQ ID NO: 91: Sequence of sxt1 fragment after integration into lactose operon. Flanking regions of xylose the operon at integration site are included. Open reading frames of XylS gene and sxt genes (A, B, C) are indicated by upper case letters.

gtttcatctgtggtgcaacgggcgctgggtcggttacggccaggacagtcagtggagatgcccaagggcacttcg ggtcgaggaacccgacctgcattgggacgcggccacggagagcgcgggcaaacgccggcactatagccagtggag tttgtaaaacgctatttcagagcttggagagtgtctaagaaagccgggcgatgccaacccatcccttcttcggct aCGTTCGTAATCAAGCCACTTCCTTTTTGCATTGACGCAGGGTGTCGGAAGGCAACTCGCCGAACGCGCTCCTAT

AGTTTTCAGCGAAGCGTCCCAAATGTAAGAAGCCGTAGTCTAGGGCTATCTCAGTTATACTACGCACATTGGCAC

TGGGATCGTTCAAGCAGGCGCGGATGCTTTCGAGCTTGCGGTTGCGGATGTAGTTCTTCGGCGTGGTGCCGGCAT

GCTTCTCGAACAAATTGTAGAGCGAGCGTGGACTCATCATCGCCAGCTCCGCTAACCGCTCAAGGCTGATATTCC

GTTTGAGATTCTCCTCAATGAATTGAACGACTCGCTCGAAAGACGGGTTACCTTTGCTGAAAATTTCACGGCTGA

CATTGCTGCCCAGCATTTCGAGCAGCTTGGAAGCGATGATCCCCGCATAGTGCTCTTGGACCCGAGGCATCGACT

TTGTATGTTCCGCTTCGTCACAAACTAACCCGAGTAGATTGATAAAGCCATCGAGTTGCTGGAGATTGTGTCGCG

CGGCGAAACGGATACCCTCCCTCGGCTTGTGCCAATTGTTGTCACTGCATGCCCGATCAAGGACCACTGAGGGCA

ATTTAACGATAAATTTCTCGCAATCTTCTGAATAGGTCAGGTCGGCTTGGTCATCCGGATTGAGCAGCAATAGTT

CGCCCGGCGCAAAATAGTGCTCCTGGCCATGGCCACGCCACAGGCAATGGCCTTTGAGTATTATTTGCAGATGAT

AACAGGTCTCTAATCCAGGCGAGATTACCCTCACGCTACCGCCGTAGCTGATTCGACACAGGTCGAGGCATCCGA

AGATTCTGTGGTGCAGCCTGCCTGCCGGGGGCCCGCCCTTGGGCAGGCGAATAGAGTGCGTACCGACATACTGGT

TAACATAATCGGAGACTGCATAGGGCTCGGCGTGGACGAAGATCTGACTTTTCTCGTTCAATAAGCAAAAATCCA

Tagttcacggttctcttattttaatgtgggctgcttggtgtgatgtagaaaggcgccaagtcgatgaaaatgcag gaattaattcgcagatcctggcggatgagagaagattttcagcctgatacagattaaatcagaacgcagaagcgg tctgataaaacagaatttgcctggcggcagtagcgcggtggtcccacctgaccccatgccgaactcagaagtgaa acgccgtagcgccgatggtagtgtggggtctccccatgcgagagtagggaactgccaggcatcaaataaaacgaa aggctcagtcgaaagactgggcctttcgttttatctgttgtttgtcggtgaacgctctcctgagtaggacaaatc cgccgggagcggatttgaacgttgcgaagcaacggcccggagggtggcgggcaggacgcccgccataaactgcca ggcatcaaattaagcagaaggccatcctgacggatggcctttttgcgtagatcccagccttgcaagaagcggata caggagtgcaaaaaatggctatctctagaaaggcctaccccttaggctttatgcaacagaaacaataataatgga gtcatgaacATGCTGCAGAAAATCAATCGTTATACCCATGGTTTTGTTGCCGTTCCGGTTATTCTGGCATGTCGT

GAAAAAGGTGTTTTTGAACTGCTGGCAGATGAAAGTCCGCTGAGCCTGAATCAGATGGTTGAACATCTGGGTGCC

AATAGCGGTCATTTTCAGGTTGCACTGCGTATGCTGGAAAGTCTGCATTGGCTGAGCCGTAATAAAGAACTGAAA

TATAGCCTGACCGCAGAAGCAGCAATTCATAACAAAATTAGCGAAGATATCCTGCAGCTGTATAATCTGCCGATT

CAGAGCTATCTGGAAGGTAAACAGGGCAATCTGCTGGGTCGTTGGATTGAACGTAGCTGTCAGCTGTGGAATCTG

GATAATCCGCTGATGGCAGATTTTCTGGATGGTCTGCTGGTTATTCCGCTGCTGCTGGCACTGCATAAACATAAC

CTGCTGGCCGATTCTGAAGATAAACCGCTGCTGAGCAGCCTGAGCAGTACCGTTCAAGAAGAACTGGGTAAACTG

TTTCTGCATCTGGGTTGGGCAGATCTGACAGCAGGTCGTCTGACCATTACCGAACTGGGTCGCTTTATGGGTGAA

CGTGCACTGAATACCGCAATTGTTGCAAGCTATACCCCGATGCTGAGTCGTATTCATGATGTTCTGTTTGGTAAT

TGCCTGAGCGTTTTTCAGCGTGATGCAAGCGGTCATGAACGTCATATTGATCGTACCCTGAATGTTATTGGTAGC

GGTTTTCAGCACCAGAAATACTTTGCAGATCTGGAAGAAAGCATTCTGAGCGTGTTTAATCAGCTGCCGCTGGAA

GAACAGCCGAAATACATTACCGATATGGGTTGTGGTGATGGCACCCTGCTGAAACGTGTTTGGGAAACCATTCAG

-continued

TTTAAAAGCGCACGTGGTAAAGCACTGGAACAGTATCCGCTGCGTCTGATTGGTGTTGATTATAATGAAGCAAGC

CTGAAAGCAACCACCCGTACCCTGGCAAGCCTGCCGCATCTGGTTCTGCAGGGTGATATTGGTAATCCGGAACAA

ATGGTTCGTAGCCTGGAAGCACATGGCATTCATGATCCGGAAAATATTCTGCATATTCGCAGCTTTCTGGATCAC

GATCGTCTGTTTATTCCGCCTCAGAAACGTAATGAACTGAAAGAACGTGCCCATCTGCCGTATCAGAGTGTTTGT

GTTGATGATCAGGGTGAACTGATTCCTCCGCATGTTATGGTTCAGAGCCTGGTGGAACACCTGGAACGTTGGAGC

CAGGTTGTTAATAAACATGGTCTGATGATTCTGGAAGTGCATTGTCTGGAACCGCGTGTTGTTTATCAGTTTCTG

GATAAAAGCGAAAACCTGCACTTTGATGCATTTCAGGGTTTTAGCCAGCAGTATCTGGTTGAAGCCGAAGTTTTT

CTGATGAGCGCAGCACAGGTTGGTCTGTTTCCGAAACTGGAACTGAGCAAACGTTATCCGAAAACCTTTCCGTTT

ACCCGTATTACCCTGAACTATTTCGAAAAACGTCCGTACAAAATCAGCCATGCATATCTGAGCGATCTGCCTGCA

CTGGTTGACCTGGAAGTTAAATGTTGGCCTGAGAATCTGCGTGCAAGCACCCATGAAATTCGTCGTCGTCTGGAA

CTGAATCCGCAGGGTAACCTGGTTCTGATTATTGAAGATCAGATTATCGGTGCCATTTACAGCCAGACCATTACA

AGCACCGAAGCCCTGGAAAATGTTAAATATGCACAGGTTCCGACCCTGCATACACCGCAGGGTTCAGTGATTCAG

CTGCTGGCCCTGAACATTCTGCCGGAATTTCAGGCACGTGGTCTGGGCAATGAACTGCGTGATTTTTATGCTGTAT

TATTGCACCCTGAAAGGTGGTATTGAAAGCGTTGTTGGTGTTACCCGTTGTCGCAATTATGTGAATTATAGCCAG

ATGCCGATGATGGAATATCTGAAACTGCATAATGAACAGCGTCAACTGCTGGATCCGATTGTTGGTTTTCATGTT

AGCGGTGGTGCAGAAATTCGTGGCATTATTGCAAATTATCGTCCGGAAGATACAGATAATCTGGGTATGGGTATT

CTGATCGAATATAACCTGCGTGATAGCGCACTGCATTCACCGGGTGATCGTAAAGGTCCGTATATCAATAGCGCA

ATTGGTAGCCTGGTTCCGAAAGCGACCAGCGCAACCAAAGAAAACAAAACCGTTGCGGATCTGGTGAAAGAATGT

ATTCTGAAAGTGATGGGTAGCCAGCGTCAGGCAGCATATGCACCGCAGCAGAAACTGCTGGACATGGGTCTGGAT

AGCCTGGATCTGCTGGAACTGCAGACCCTGCTGGAAGAACGTCTGGGTATTAATCTGAGCGGCACCTTTTTTCTG

CAAAAAAACACCCCGACCGCCATCATTACCTATTTTCAGAATCAGGTCGTGCAAGAGAAACAGAGTGATCTGGCA

CCGCCTGTTGATAGCGCCAATGAAATCAATACACTGGAAAACGTTGTGAATCAGCAGAAAATTCCGCAGGTTACA

CGTGTTGTTACCGAACAGCAGGGACGTAAAGTTCTGATTGATGGTCATTGGGTTATTGATTTTGCCAGCTGTAAT

TATCTGGGCCTGGACCTGCATCCGAAAGTTAAAGAAGCAATTCCTCCGGCACTGGATAAATGGGGCACCCATCCG

AGCTGGACCCGTCTGGTTGCAAGTCCGGCAATTTATGAGGAACTGGAAGAGGAACTGTCAAAACTGCTGGGTGTG

CCGGATGTTCTGGTTTTTCCGGCAGTTACACTGCTGCAGATTGGTATTCTGCCTCTGCTGACCGGTAATAATGGT

GTGATTTTTGGCGATATTGCAGCCCATCGTTGTATTTATGAAGCATGTTGTCTGGCCCAGCATAAAGGTGCACAG

TTTATTCAGTATCGTCATAACGACCTGAATGATCTGGCCGAAAAACTGGCCAAATATCCGCCTGAACAGGTTAAA

ATCATTGTGATCGATGGTGTGTATAGCATGAGTGCCGATTTCCCGGACCTGCCTGCATATGTTCATCTGGCAAAA

GAATATAACGCCCTGATCTATATGGATGATGCACATGGCTTTGGCATTCTGGGTGAAAATCCGAGCAGCGATATG

CCGTATGGTTATAAAGGTAATGGCATGGTGAACTACTTTGATCTGCGTTTTGCCGAAGATAACATCATTTATGTT

GCAGGTCTGAGCAAAGCCTATAGCAGCTATGCAGCATTTCTGACCTGTGGTGATCGTCGTATTAAAACCAATTTT

CGTAATGCATGGACCGCGATTTTTAGCGGTCCGAGTCCGGTTGCAAGCCTGGCCAGCGCACTGGCAGGTCTGCAG

GTTAATCGTCAAGAAGGTGAACAGCTGCGCAAACAAATCTATCATCTGACACATAAACTGGTTACCCAGGCTCGT

GCCATTGGTTTTGAAGTTGATAATTATGGTTATGTGCCGATTGTGGGTGTTCTGGTGGGTGATGCACAGCATATG

ATTGATGTGTGCCAACTGCTGTGGGAATATGGTATCCTGATTACCCCTGCAATTTTTCCGATTGTGCCGCTGAAT

AAATCAGCACTGCGTTTTAGCATTACCGCAGCAAATACCGAAGAAGAAATTGATCAGGCCATCAAAAGTCTGAAA

GCAGTTTGGGACCTGCTGCAAAAACGTAAAGCCCTGCCGTGTAAACAAGAAGAAAATATCCTGAAACATTGAgaa ggagatatacatATGACCCATGTTGCCCTGGAACAGGCAATTGCAAAAGTTCCGCGTAGCATTCAGAGCGAACTG

CGTACCATTCTGGCACAGCATGCAGTTATTGATAGCAGCGTTGTGGCAAGCTGGATTGATCGTCTGGGCACCAAT

-continued

ATTAGTACCCTGATGATCCAGCTGCTGCCGGTTGCAGCAACCTATGCACGTGTTCCGATTAGCCAGTTTTATGTT

GGTGCCATTGCACTGGGCAAACCGCAGAGTAAAAATCAGCTGGGTAGCGGCACCCTGTATTTTGGTGCAGATATG

GAATTTGTTGGTCAGGCACTGAGCTTTAGCGTTCATGCAGAACAGAGCGCCACCATTAATGCCTGGCTGCATGGC

GAAACCGGACTGCAGGCACTGGCAATCCATGAAGCACCGTGTGGTTATTGTCGCCAGTTTCTGTATGAAATGGCA

ACCGTGAATCAGAATTTTGTGCTGCTGGTGAAAAGCAATGAAAGCCAGCCGGAACAGACCTATACCAGCAACAAA

CTGCCGCATTTTCTGCCTGAACCGTTTGGTCCAGCCGATCTGGGTCTGACCGGTGGCCTGATGCAGACCGTGTTT

CACGATCTGGAAACCTATAGCACCGATGATGTTGTTCTGGCAGCACTGAGTGCAGCAAATCAGAGTTATGCACCG

TATACCAAAAACTTTGCCGGTGTTGCACTGAAAGATAGTCATGGTAACATTTTTACAGGTCGCTATGCCGAAAAC

GCAGCATTTAATAGCAGCATGAGCCCGATGGAAAGCGCACTGACCTTTATGAATATGAATCGTTATTCACAGAGC

CTGTTCGATATTTGTGATGCAGTTCTGGTAGAAGTGGAAACCGGTATTAGTCAGCGTCCGGTTACCGAAGCCTTT

CTGAGTAGCATTGCACCGAAAGTGAAACTGCGCTATGCACCGGCAACCCCGAGCAGTAACAAACTGTGAgaagga gatatacatATGTTTCAGACCAAAAGCTATTATAGCGTCGTTGGCCTGGAAACCGAACTGATTAAAGGTAAATTC

TTCATGAGCAACGAACTGACCAATGAACAGGTGTTTAAACTGGTGTGCATGGAAGTGATTGAAAAAATGGGTTTT

GCACACTTTCCGCCTATTATCCTGGTTTATGAAATGACCAATTCCGGCTTTGTTGATTGGTGCGAGCAGATGGTT

TTTGTGGATGATAAAGGCAAACTGGATGAGGGCGAAAAATTTCTGCTGGATTGGATGCGTCGTAATGTGGGTAAT

TTTGATCTGATTCGCGAACTGATGCCGGTGGCAGAACGCCTGGAAATGAAAATGCGTAGCTAActcggtaccaaa ttccagaaaagaggcctcccgaaagggggcctttttcgttttggtcccgaagttcctattctctagaaagtat aggaacttcgaccgcctgtctatttctcttacggttccaacatccatataggccgcaatt SEQ ID NO: 92: Sequence of sxt3 fragment version 1 integrated into the xylose operon, which contains all genes. Flanking regions of xylose the operon at integration site are included. sxt open reading frames (Q, R, orf24, S, T, U, V, W, X) are indicated by upper case letters.

ttgcatttccttgagccttatccgacttgtcagtcggataaggcttttactttgtctcaggcagttgagctac gagcctgaagcgttgttggtgcgttttatcatgcctggcgggtaggtcggataaggcgttcacgccgcatccga caaccacgcagcgttacctgatgtgacgccgacaattctcatcatcgctacaacatgacctcgctatttacatc gcgatactcttttggcgtcgtgtcatatgctttttaaaaacagagtagaaatattgcagcgatggataaccgc acatttgcgatatctcattgatcgacaaggtggttgaaatcagcagactgcgcgctttctccagcttctcggca tgaatcatggcatggatggtttcacccacctcttctttaaaacgcttctcaagattggagcgcgagatcccgac cgcatccagtacctgatccactttaatccctttacaggcgtgattacgaatgtaatgcatggcctgaataacgg cgggatcggtcagcgagcgataatctgttgagcgccgttcaatgacgcgaactggtgggaccaaaattcgctgt agcggcatttcttctttatctaataatcgatgcaacagttttgccgcctgatagcccatttgccgcgcgccctg agcgaccgaagaaagggcgacacgcgacagatagcgggtcagttcttcgttatcgatgccaatcacgcataatt tttccggtacgggaatatgtagatgttcacatacttgcagaatatgccgcgctcgggcgtcagtaacggcaata atcccggtttgcggtggtagcgtttgtagccagtctgccagccgattttgcgcgtgttgccagttctctggcgc ggtttctaacccctgataaaccactccgcgatacttttcttcggcgacaagctgacgaaatgcatattcgcgct cagtggcccaacgtttgccgcttgattccggaagaccataaaaagcaaagcggttaacgcctttctcttttaaa tgcaaaaatgcgctttcaaccagcgcatagttatcggtggcaatgtaatgaacgggtgggtaactttctgcaag gtgatacgagccgccaaccccaacaatggggacgtcgacatcagccagcgcttgctcgatctgtttgtcgtcga agtcggcaatgacgccatctcctaaccagtccttgattttatcaatgcgggcgcggaaatcttcttcaatgaaa atatcccattccgattgtgacgcctgtaaatattcccctacgccttctactacctgccggtcataggctttatt ggcattgaacagtaatgtgatgcggtgacgtttagtaaacatggttcttttcctgctgaatcatgcaaaaactc aaaaccggtaatacgtaaccggctttgagaaaatttttatcaaaatcaagaacggcgtttggttgcggagtcca tccatactgccagcaacagaatcgcacctttaacgatatactgccagaaggtcggtacatccatcatactcatg -continued ccgttatccagtgaagccatgataaatgcccccattactgctccggcaacgcttcccacaccgccagccaggct ggtgccgccaatcacgcatgctgcaattgcgtccagttcggcgatatttcccgcagaaggtgaaccagcgccaa gtcgagaactaaggattaatccggcgatggctaccattaatccgttaatcgcgaacacggcaagtttggtgcgt tcaacgttaatcccggagagacgtgctgcttccagattgccgccgatggcataaatgcgtcgtccaaatgccgt ccgcgtttccataaacattccgccgagtaacagcaacgtcagcagcagaacaggagtgggaacgccacggtaat cattcaacagccagattgcgcctaatacgatgatagcggttaaagcctggcgaccgactactgcggtagaggcc ggagactgcaaacccaaagcctgacggcgcattcttccgcgccattgccaaccaacaaaagccattaagccaag cgcgccaatgatgaagccagtgctggcaggtagatagctttgcccaatttgtgacatcgcggcgctggtgggg aaacagtcgtgccgttggtgatgccaatgagtatgccgcgaaatgccaacatgcccgcgagggtgacaataaat gaagggactttgcggtacgcgacccaccatccgttccaggcaccgagaagcagtcccagaaccaacgtcacaat gatggtaagtggcaaaggccagcctaaccagacgtcacaaatcgccgcgacgccacctaatagccccatcattg agccgacggaaaggtcgatttcagcagaaattatgacgaacaccattcctaccgcgaggatgccggtaatcgcg gtctggcgtaacaggttggagacgttacgggcgcttaagtaggcaccatcggtggtccaggtaaagaacagcat gattgcgatgatagctgcaatcatcacgaagacctgcaaattcagtgatttcagcccggagaagctaccggatg tcggtacggccaatttcacttcagacggattgcttttcgacatgatgttcgctcctcaatgcggcttccatcac ctgctcctgagtcaggttatgatttatcaggttggcttttagtttcccttcatgcatcaccagtacacgatcgc taaggccgagcacttcaggtaattcggaagagatgacaataacggcaataccctgctggacgagttggttaatt aatttgtagatctcgtatttcgcgccaatatcgataccccctggtgggttcatcaagaatgagaatgcgcgggtt aagtaacagacagcgagcgaggatcgctttttgctgattgccgccgctcaaacgtccaatagcaaggtcggggg acgacgttttaactttgagttgctggattgattccagaatacatttttgctctgccgcgtcatcaagctggcta atgccaccggtaaatttattgagtcggcgagggtaatatttttaccaaccgccattaccggaacgatgccgtcg cgctttctgtcttcgggtaccatcgcaatcccctgggcgatggcttgctgacagttacgaatatctacctgttt gccatcaatataaatttttccttcccattgtccgggccacacgccaaacaggcactgaatggtctcggtacgtc cggcaccaacgagtccggcaatacccagtatttcgccacgtttcagggaaaacgagacatcattaactcgttta atatgacgattgaccggatgccatgccgtcagatgttcaatacgtaatatttcatctccggtggtatgtggttc attagggtaaagcgcggttaactctcgcccgaccatcatggtgataatatcgtcttcactcattccggcagcat cacgcgtaccaatgtgctgtccgtcgcgaataacgcaaatcgtatcggaaatcgctttgacttcgttgagtttg tgcgaaatataaatacaggcgataccgtgctgttgtagatcgcgaataatatccagtaaaaccgacgtttcctg ctcagttaatgaggctgtcggttcatcgagaattaacaagcgcacctgtttattaagtgccttggcaatttcaa ccagttgttgttgcccaagccctaaatcgccaacgcgggtatcaggtgaaatggataaactgacctgtgcgagc agcttctgacagcgtagcgtcatcaggtcataatccataatgccattgtgggttatttcgttacccaggaagat attttccagcacggtcaattctttcaccagggccaattcctgatgaatgatggcgatacctttgcgttcggtat cgcggatgtgactcgcctgaatctcttctcccgcaaaaataatttcgccttcgtaggagccatggggataaata ccacacagcactttcatcagcgttgatttaccagacccattttccccacaaagtgagacgatttcgccagcatt caaccgcaagcagacgttatcaatcgccttcacactgccgaaggttttggtaatgttcttcatttcaagtagat aaggcataacgactccacctaagccaattcattcacgcggcatggagagaaatcacgcccccgctccgcgccgg gcgtaacgcttacagctcgctctctttgtggaatccgtctttaattaccgtatctttgatgttgtttttattca catcgatcggtgtcaggaggcgggaggggacatctttcaggccattattcagtgaggtccagccttgcaagaag cggatacaggagtgcaaaaaaatggctatctctagaaaggcctaccccttaggctttatgcaacagaaacaataa taatggagtcatgaacatATGGTGATTAAAAACCTGTGTCCGGATGGTGTTACCCCGATTTGGAATAAAAGCCA -continued

GATGGAAAGCAGCCTGCTGGAAGAATGTCTGCCTGCATGGGTTCGTACCAGCTATAGCACCTTTGTTGAAACCA

TTAGCGATAGCGCATTTCCGTGTTTTTGGGGCACCATTGGTGAACAGAAAGGTATGATTCGTTATCTGATTGTT

AGCAGCCTGACCGATCCGATTCTGGTTGAACATACCCTGGAAGGTATCTACAAATATATCGATGAAGTGAACGA

AAACGAACTGCTGCAGCATGAAAATGCAGATCTGCTGACCCTGGTTATCTTTTTTCCGCCTGAACCGACCGTTC

TGACCGTTGAAGAATATGCAGGTCAGGCATTTGATTTTCTGAATGCACTGCATAGCCTGGATGCAGTTAGCTGT

CCGTGTCATTGGAGCGCAGATCCGCAGAGCGCAAATTGGAGCTATAGCCTGGGTGGTTGTGCACTGTTTGTTAG

CGTTAGCACACCGGCAAATCAGAAACGTCGTAGCCGTCATCTGGGTAGCGGTATGACCTTTGTTATTACACCGG

TTGAAGTGCTGCTGAATAAACATGGTGGTGAAAACAGCAGCATTTTTCGTCGTGTTCGTGAATATGATGGTATT

CCGCCTCATCCGAATCTGCTGATTATGCCTGGTAATGGTAAAGTGGGTAATGAACTGACCGTGCAGGTTCTGCC

GGATAATAATGATAGCGAAATCAGCTTCGATTTTCAGTATAAATTCAAAGATTGagaaggagatatacatATGA

CCATCCAGATTGTGCAGCATAACCTGGAATATAGCTTTGTGACCCCGAAAGAAACCAGCGATTTTGTTGAACGT

ACCATGAGCGTTTTTGATCAGGCATATCCGAAATTTCTGATCCATGATGTTTGGGCAGATCCGGCAAGCCTGGC

CCTGTTTGAAATTTATCCGGAATTTCAGTTTGGTCTGGTGGAAGCAACCACCCAGCTGATGATTGCACAGGGTA

ATTGTATTCCGCTGACCTATGAAAGCCGTTTTGATGAACTGCCGGATGAAGGTTGTGATTGGGCACTGGCAAAA

TGGCTGGAAGATCGCGAACAGAATCGTCTGCCGAATGCCCTGTGTGTTGTGAGCATTAGCATCCTGCCGGAATA

TCAGGGTAAAAATCTGAGCCAGTATCTGATCGGCTATATGAAAGAACTGGCACAGTATCATGGTCTGAATAGCC

TGATTATGGCAGCACGTCCGAGCCTGAAATATCTGTATCCGCTGATTCCGATTGAACGCTATATTACCTGGCGT

GATAAAAACGGCCTGATTTTTGATCCGTGGCTGCGTGTTAATGTTAAACATGGCGCAAAAATTGCCGGTATCTG

CTTTAAAAGCACCACCATTAATGATACCATTGATGGTTGGGAGGATCGTGTTGGTATGCGTTTTCCGGAAACCG

GTGATTATATCATTCCGAAAGGTCTGGTTCCGGTGAAAATTGATTATCCGAATAACATGGGCATCTACATCGAA

CCGAATATCTGGCTGTATTATGATCTGGACTGAgaaggagatatacatATGATCAACATCGAACAGTTTCGCCA

AGAAATCGAAGATTGGATTATTAACGTTGTCAGCATTCCGAACCCGCTGACCGGTAATTTTCCTCCGTGTCCGT

ATGCAAAAGCAGCATGGCTGAATAATCGTGTTAGCGTGCGTTGGTTTCATGGTCCGGAACTGCCTGAACTGCTG

ATGGAACAAATTCGTACATGGAACAACGATTTCGAGATGGTGATTTTTGGTTGCGATCCTCAGAATCTGGATGC

ACAGCGTCTGGAACGTTATATCACCAAAGCAAATTATGTGCTGCCCGAATATGACCTGGTTGCACTGGGTAGCC

ATCCGGATAAACAGTATGTTGGTGATGATGCCGAAAATGTGAACAACGTGATTATTACCCATCCGAAATATGTT

CTGGCAAGCGTTCAGAGCTTTAGCCAGCTGCAAGAGGCAAGTGATGAGCTGCTGCGTCTGGGTTATTTCCAGTA

TTGGTCAGCAGAAAAACTGGCCGAAATGAAAAGCGAACGTGCAAGCCATAATCTGAGCAGCATTCAGCGTAAAA

ATAGCTATCGTATTATCCCGACCAACCATTGAgaaggagatatacatATGCTGACCGCAGAACAGAAACAGGCA

TATACCAATGATGGCTATTTTACCGTGGAAGAAGCAGTTCCGAAAGCACTGATTGAAGAAATTCGCCATGAAGT

GGAACTGATCACCGAGCAGAAACGTGGTGGTGTGCTGGCAGGCGATTATGAATGGTGGTCAGAACACACCATTC

CGGATCCGGTTCGTTATCAGAAAATTATCCAGCGTCTGCTGGAACTGCCGACCGTTATGGGTCCGGTTCAGGCC

CTGATTGGTAGCGATATTTTTCTGTTAATTACCGACCTGGCAATTATTCGTGCAGGCACCGGTTATATTGCATG

GCATCAGGATCATGGCTATGTTGTTGAAGTTCTGAACGCCCTGGCAAGCATGAGCAAAAATGAGCTGAATGATG

ATGCACTGCGCCTGCTGGTGCCGGTTGCAAATCAGGCAATGGTGTTTATTACCATCTATCTGCAGGATACCGAT

AACACCATGGGCACCATGCGTGTGATTCCGAGCAGCCATCAGTGGGAACATAGTCTGGATAGCAGCAGCGCCAA

TTCACTGAATGCAGAAATTTGTCTGAGCCTGCCTGGTGGTGCAGCAATGTTTTATACCCCGACCGTTTGGCATA

CCGCAGCAGCAAATACCAGCATTACCGATTATCGTATGCTGACGCTGATCTTCACCAAAAACAACATTAAACCG

CTGCTGGTTGATGCCCTGAAACGTATTATTTGAgaaggagatatacatATGACAACCACCGATCCGATCCTGAT

TAATAACTGGCATGTTGTGGCAAATGTCGAGGATTGTAAACCGGGTAGCATTACCCGTAGCCGTTTACTGGGTG

TTAAACTGGTTCTGTGGCGTAGCTATGAACAGAATAGCCCGATTCAGGTTTGGCTGGATTATTGTCCGCATCGT

-continued

GGTGTTCCGCTGAGCATGGGTGAAATTACCAATAATACCCTGGTTTGTCCGTATCATGGCTGGCGTTATAATGA

AGCAGGTAAATGTATTCAGATTCCGGCACATCCGGGTATGGTTCCGCCTGCAAGCGCAGAAGCACGTACCTATC

ATAGCCAAGAACGTTATGGTCTGGTTTGGGTTTGTCTGGGTGATCCGGTTAATGATATTCCGTCATTTCCGGAA

TGGGATGATCCGAATTATCACAAAACCTACACCAAAAGCTATCTGATTAAAGCAAGCGCCTTTCGCGTTATGGA

TAATTCACTGGATGTTAGCCATTTTCCGTTTATTCATGATGGCTGGCTGGGCGATCGTAACTATACCAAAGTGG

AAGAATTTGAAGTGAAACTGGATAAAGATGGTCTGACGATGGGCAAATATCAGTTTCAGACCAGCCGTATTGTG

AGCCATATTGAAGATGATAGCTGGGTGAATTGGTTTCGTCTGAGCCATCCGCTGTGTCAGTATTGTGTTAGCGA

AAGTCCGGAAATGCGTATTGTTGATCTGATGACCATTACGCCGATTGATGAAGAAAATAGCGTTCTGCGCATGC

TGATCATGTGGAATGGTTATGAAACCCTGGAAAGCAAAATGCTGACAGAGTATGATGAAACGATCGAACAGGAT

ATTCGTATTCTGCATGCCCAGCAGCCGGTGCGTCTGCCGCTGCTGACACCGAAGCAGATTAATACCCAGCTGTT

TAGCCATGAAATTCATGTTCCGAGCGATCGTTGTACCCTGGCATATCGTCGTTGGCTGAAACAACTGGGTGTGA

CCTATGGTGTTTGTTGAgaaggagatatacatATGGCAGGTAAACTGGATGGTAAGGTTGCAATTATTACCGGT

GCAAGCAGCGGTATTGGTGAAGCCACCGCATTTGCACTGGCAGCAGAAGGTGCAAAAGTTGCAATTGCAGCCCG

TCGTGCAGAACTGTTACATGCACTGGCCAAACGTATTGAAGCAAGCGGTGGTCAGGCACTGCCGATTGTTACCG

ATATCACCGATGAAAGCCAGGTTAATCATCTGGTTCAGAAAACCAAAGTTGAACTGGGTCATGTTGATATCCTG

GTGAATAATGCAGGTATTGGCGTTTTTGGTGCAATCGATACCGGTAATCCGGCAGATTGGCGTCGTGCATTTGA

TGTTAATGTGCTGGGTGTTCTGTATGCAATTCATGCAGTTCTGCCTTTACTGAAAGCACAGAAAAGCGGTCATA

TTGTGAATATTAGCAGCGTGGATGGTCGTATTGCACAGAGCGGTGCAGTTGTTTATAGCGCAGCAAAAAGCGGT

GTTAATGCCCTGAGCGAAGCACTGCGTCAAGAAGTGAGCCTGGATAATATTCGTGTGACCATTATTGAACCGGG

TCTGGTAGATACCCCGTTTAATGATCTGATTAGTGATCCGATTACCAAACAGCTGAGCAAAGAACAGCTGTCAA

CCATTACTCCGCTGCAGAGCGAAGATATTGCACGTGCCATTATCTATGCAGTTACCCAGCCGGATCATGTTAAC

GTTAATGAAATTCTGATTCGTCCGACCGCAGAGGATAATTGAgaaggagatatacatATGAACCTGACCCTGAA

CAAAGAAGAAAAACAGCTGCTGACGGCATATAGCGGCACCGAACTGCAGCTGACAGCAGATGTTCTGGTTATTG

GTGGTGGTCCGGCAGCCGCATGGGCAGCTTGGGCAGCAGGCGCACAGGGTGTGAAAGTTATTATTGTGGATAAA

GGTTTTCTGGGCACCAGCGGTGCCGCAGCCGCAAGCGGTAATAGCGTTATGGCACCGTCACCGGAAAATTGGGA

AAAAGATGTGAGCGAATGTTACAGCAAAGGTAATAATCTGGCAAATCTGCGTTGGATTGAACGTGTTATTGAAA

AAGCCTGGCTGTCACTGCCGCTGGTTGAAGATTGGGGTTATCGTTTTCCTAAAGAAAATGGTGAAAGCGTGCGT

CAGAGCTATTATGGTCCTGAATATATGCGTGTTCTGCGGAAAAATCTGCTGCGCGTTGGTGTTCAGATCTTTGA

TCAGTCACCGGCACTGGAATTACTGCTGGCACAGGATGGTAGCGTTGCCGGTGCACGTGGTGTGCAGCGTCAGA

ATCATCGTACATATACCGTTCGTGCCGGTGCCGTTGTTCTGGCCAATGGTGGTTGCGCATTTCTGAGTAAAGCA

CTGGGTTGTAATACCAATACCGGTGATGGTCTGTTAATGGCAGTTGAAGCCGGTGGTGAACTGAGCAGTATGGA

AGCCAGCAGCCATTATACCATTAGCACCGCCTTTAATGCAACCGTTACCCGTGCAGCTCCGTTTTATTGGGCAA

GCTATACCGATGAAGCTGGCAATGATCTGGGTGGCTATATTAACGGTCGTCGTGATCCGAGCTTTCTGCCGAAC

GCACTGCTGAAAGGTCCGGTTTATGCACGTCTGGATCGTGCAACACCGGAAATTCAGGCGCTGGTAGAAAAAAG

CCATTTTATTGCATTTCTGCCGTACAAGAAAGCCGGTATTGATCCGTATACCGAACGTGTTCCGGTTACCCTGG

TGCTGGAAGGCACCGTGCGTGGCACCGGTGGTATTCGCATTGTTAATGATTCATGTGGCACCAAAGTTCCGGGA

CTGTATGCAGCGGGTGATGCAGCAAGCCGTGAATTTCTGGCAGGCATTGCCAGCGGTGGTGATGGACCGAATGC

AGCATGGGCAATTTCAACCGGTCAGTGGGCAGGCGAAGGTGCAGCAGCCTTTGCAAAAAGTCTGGGTGCACATG

TTCATGAACGCGTTGTTCGTCCGGCAGGCCAGGCAGGTCTGCGTAGTCAGTATCCGGGTAGCGAAACCTTTGAT

AGTGAAGCAGTTGTTCGTGGCGTTCAGGCAGAAATGTTTCCGCTGGAAAAAAACTATCTGCGCTGTGAACAGGG

-continued

ACTGCTGGATAGCCTGGCAAAACTGGAAATGCTGTGGCAGCAGGTTCAGGGTAATCCGAAACAGGATACAGTTC

GTGATCTGGAATTTTCACGTCGTGCGGCAGCACTGGTTAGCGTGGCACGTTGGGCATATTTTAGCGCACTGCAT

CGTAAAGAAACCCGTAGCGAACATATCCGTATTGATTACCCGGAAACGGATCCGAATCAACTGTATTATCAGGC

AACCGGTGGCCTGGAACGTCTGTGGGTGCGTCGTGATTGGGTTAAAGATGCAAGCGCCACCCCTCCGGTGCTGA

CCACCTGAgaaggagatatacatATGATTGAACTGGTGAGCCATAAGCTGTGCATTAATTGTAATGTTTGTGTT

CAGGTGTGCCCGACCAATGTTTTTGATGCAGTGCCGAATCAGCCTCCGGCAATTGCACGCCAAGAAGATTGTCA

GACCTGTTTTATTTGTGAAGCATATTGTCCTGCAGATGCGCTGTATGTTGCACCGCAGAGCCATACCAATGTTG

CAGTTAACGAAGATGATTTAATCGACAGCGGCATTATGGGTGAATATCGTCGCATTCTGGGTTGGGGCTATGGT

CGTAAAAACAATAGCGAACTGGATACCGACCATAAACTGCGTCTGTTTGAATGAgaaggagatatacatATGTC

ATTTCAGAAATTTGTGCAAGAAGCAGCCTATAAAGTCGCACCGTTTAAACCGAATCGTTTTGCCAAAATTAGCG

AGCGTGAAGATAAATGTGCAATTCCGGTTCCGGCATGGCGTGCACTGCTGGCCAATCGTGACCTGTTTACCTGG

AAAGGTATTCCGTTTCTGAAAGGTTGTACCGAAATTGCACTGTATAGCATGCTGCTGTATGAACTGCGTCCGAA

AACGATTATTGAAATTGGTGCGCTGAGCGGTGGTAGCGCAATTTGGCTGGCAGATCATCTGGAACTGTTTCAGA

TTGAAGGTTGCGTGTATTGCATTGATATTGATCTGTCTCTGCTGGACGAAAAAGCAAAAACCGATAGCCGTGTT

CATTTTCTGGAAGGTGATTGCAATAATATGGGTGCAATTATGTCAAGCGAGCTGCTGAGTGGTCTGGCACATCC

TTGGCTGATTGTTGAAGATGCACATGCAAATGCCGTTGGTGTGGTTGAATATTTTCACGAAAACGGTCTGAAAA

GTGGCGATTACCTGATCGTGGAAGATACCAATAAAACAATGTGGGAACTGGATCGCGAAGAACTGGACCGTGAT

GACCTGGATGAACAAGAACTGATCGAAAAAGGTGAGCAGAAATTAGCAGAACTGAAAAGCTGGCTGATGCTGCA

TGAGAATGAATATCTGATAGATACCTACTATCAGGATATGTATGGCTATAATGGTAGCCGTAATTGGAACAGCA

TTCTGAAACGTGTGGAAAAGAACTTTTAAtctaactaaaaacaccctaacgggtgtttttcttttctggtctc cccgaagttcctattctctagaaagtataggaacttcgctggattgggccgcgaaattaaccggcctgagcaat gtcccagctttaatcgctgcagctcaacaggctgatgaaagtgccgagccagtttggtttctgccttatctttc cggcgagcgtacgccacacaataatccccaggcgaaggggttttctttggtttgactcatcaacatggcccca atgaactggcgcgagcagtgctggaaggcgtgggttatgcgctggcagatggcatggatgtcgtgcatgcctgc ggtattaaaccgcaaagtgttacgttgattgggggcggggcgcgtagtgagtactggcgtcagatgctggcgga tatcagcggtcagcagctcgattaccgtacgggaggggatgtggggccagcactgggcgcagcaaggctggcgc agatcgcggcgaatccagagaaatcgctcattgaattgttgccgcaactaccgttagaacagtcgcatctacca gatgcgcagcgttatgccgcttatcagccacgacgagaaacgttccgtcgcctctatcagcaacttctgccatt aatggcgtaaacgttatcccctgcctgaccgggtgggggataattcacatctatatatctcagtaattaattaa tatttagtatgaatttattctgaaaatcatttgttaatggcatttttcagttttgtctttcgttggttactcgt aatgtatcgctggtagatatggagatcgtt SEQ ID NO: 93: Sequence of sxt3 fragment version 2 integrated into the xylose operon, which has orf24 deleted. Flanking regions of the xylose operon at integration site are included. sxt open reading frames (Q, R, S, T, U, V, W, X) are indicated by upper case letters.

ggtgtcaggaggcgggaggggacatctttcaggccattattcagtgaggtccagccttgcaagaagcggataca ggagtgcaaaaaatggctatctctagaaaggcctaccccttaggctttatgcaacagaaacaataataatggag tcatgaacatATGGTGATTAAAAACCTGTGTCCGGATGGTGTTACCCCGATTTGGAATAAAAGCCAGATGGAAA

GCAGCCTGCTGGAAGAATGTCTGCCTGCATGGGTTCGTACCAGCTATAGCACCTTTGTTGAAACCATTAGCGAT

AGCGCATTTCCGTGTTTTTGGGGCACCATTGGTGAACAGAAAGGTATGATTCGTTATCTGATTGTTAGCAGCCT

GACCGATCCGATTCTGGTTGAACATACCCTGGAAGGTATCTACAAATATATCGATGAAGTGAACGAAAACGAAC

TGCTGCAGCATGAAAATGCAGATCTGCTGACCCTGGTTATCTTTTTTCCGCCTGAACCGACCGTTCTGACCGTT

GAAGAATATGCAGGTCAGGCATTTGATTTTCTGAATGCACTGCATAGCCTGGATGCAGTTAGCTGTCCGTGTCA

-continued

TTGGAGCGCAGATCCGCAGAGCGCAAATTGGAGCTATAGCCTGGGTGGTTGTGCACTGTTTGTTAGCGTTAGCA

CACCGGCAAATCAGAAACGTCGTAGCCGTCATCTGGGTAGCGGTATGACCTTTGTTATTACACCGGTTGAAGTG

CTGCTGAATAAACATGGTGGTGAAAACAGCAGCATTTTTCGTCGTGTTCGTGAATATGATGGTATTCCGCCTCA

TCCGAATCTGCTGATTATGCCTGGTAATGGTAAAGTGGGTAATGAACTGACCGTGCAGGTTCTGCCGGATAATA

ATGATAGCGAAATCAGCTTCGATTTTCAGTATAAATTCAAAGATTGagaaggagatatacatATGACCATCCAG

ATTGTGCAGCATAACCTGGAATATAGCTTTGTGACCCCGAAAGAAACCAGCGATTTTGTTGAACGTACCATGAG

CGTTTTTGATCAGGCATATCCGAAATTTCTGATCCATGATGTTTGGGCAGATCCGGCAAGCCTGGCCCTGTTTG

AAATTTATCCGGAATTTCAGTTTGGTCTGGTGGAAGCAACCACCCAGCTGATGATTGCACAGGGTAATTGTATT

CCGCTGACCTATGAAAGCCGTTTTGATGAACTGCCGGATGAAGGTTGTGATTGGGCACTGGCAAAATGGCTGGA

AGATCGCGAACAGAATCGTCTGCCGAATGCCCTGTGTGTTGTGAGCATTAGCATCCTGCCGGAATATCAGGGTA

AAAATCTGAGCCAGTATCTGATCGGCTATATGAAAGAACTGGCACAGTATCATGGTCTGAATAGCCTGATTATG

GCAGCACGTCCGAGCCTGAAATATCTGTATCCGCTGATTCCGATTGAACGCTATATTACCTGGCGTGATAAAAA

CGGCCTGATTTTTGATCCGTGGCTGCGTGTTAATGTTAAACATGGCGCAAAAATTGCCGGTATCTGCTTTAAAA

GCACCACCATTAATGATACCATTGATGGTTGGGAGGATCGTGTTGGTATGCGTTTTCCGGAAACCGGTGATTAT

ATCATTCCGAAAGGTCTGGTTCCGGTGAAAATTGATTATCCGAATAACATGGGCATCTACATCGAACCGAATAT

CTGGCTGTATTATGATCTGGACTGAgaaggagatatacatATGCTGACCGCAGAACAGAAACAGGCATATACCA

ATGATGGCTATTTTACCGTGGAAGAAGCAGTTCCGAAAGCACTGATTGAAGAAATTCGCCATGAAGTGGAACTG

ATCACCGAGCAGAAACGTGGTGGTGTGCTGGCAGGCGATTATGAATGGTGGTCAGAACACACCATTCCGGATCC

GGTTCGTTATCAGAAAATTATCCAGCGTCTGCTGGAACTGCCGACCGTTATGGGTCCGGTTCAGGCCCTGATTG

GTAGCGATATTTTTCTGTTAATTACCGACCTGGCAATTATTCGTGCAGGCACCGGTTATATTGCATGGCATCAG

GATCATGGCTATGTTGTTGAAGTTCTGAACGCCCTGGCAAGCATGAGCAAAAATGAGCTGAATGATGATGCACT

GCGCCTGCTGGTGCCGGTTGCAAATCAGGCAATGGTGTTTATTACCATCTATCTGCAGGATACCGATAACACCA

TGGGCACCATGCGTGTGATTCCGAGCAGCCATCAGTGGGAACATAGTCTGGATAGCAGCAGCGCCAATTCACTG

AATGCAGAAATTTGTCTGAGCCTGCCTGGTGGTGCAGCAATGTTTTATACCCCGACCGTTTGGCATACCGCAGC

AGCAAATACCAGCATTACCGATTATCGTATGCTGACGCTGATCTTCACCAAAAACAACATTAAACCGCTGCTGG

TTGATGCCCTGAAACGTATTATTTGAgaaggagatatacatATGACAACCACCGATCCGATCCTGATTAATAAC

TGGCATGTTGTGGCAAATGTCGAGGATTGTAAACCGGGTAGCATTACCCGTAGCCGTTTACTGGGTGTTAAACT

GGTTCTGTGGCGTAGCTATGAACAGAATAGCCCGATTCAGGTTTGGCTGGATTATTGTCCGCATCGTGGTGTTC

CGCTGAGCATGGGTGAAATTACCAATAATACCCTGGTTTGTCCGTATCATGGCTGGCGTTATAATGAAGCAGGT

AAATGTATTCAGATTCCGGCACATCCGGGTATGGTTCCGCCTGCAAGCGCAGAAGCACGTACCTATCATAGCCA

AGAACGTTATGGTCTGGTTTGGGTTTGTCTGGGTGATCCGGTTAATGATATTCCGTCATTTCCGGAATGGGATG

ATCCGAATTATCACAAAACCTACACCAAAAGCTATCTGATTAAAGCAAGCGCCTTTCGCGTTATGGATAATTCA

CTGGATGTTAGCCATTTTCCGTTTATTCATGATGGCTGGCTGGGCGATCGTAACTATACCAAAGTGGAAGAATT

TGAAGTGAAACTGGATAAAGATGGTCTGACGATGGGCAAATATCAGTTTCAGACCAGCCGTATTGTGAGCCATA

TTGAAGATGATAGCTGGGTGAATTGGTTTCGTCTGAGCCATCCGCTGTGTCAGTATTGTGTTAGCGAAAGTCCG

GAAATGCGTATTGTTGATCTGATGACCATTACGCCGATTGATGAAGAAAATAGCGTTCTGCGCATGCTGATCAT

GTGGAATGGTTATGAAACCCTGGAAAGCAAAATGCTGACAGAGTATGATGAAACGATCGAACAGGATATTCGTA

TTCTGCATGCCCAGCAGCCGGTGCGTCTGCCGCTGCTGACACCGAAGCAGATTAATACCCAGCTGTTTAGCCAT

GAAATTCATGTTCCGAGCGATCGTTGTACCCTGGCATATCGTCGTTGGCTGAAACAACTGGGTGTGACCTATGG

TGTTTGTTGAgaaggagatatacatATGGCAGGTAAACTGGATGGTAAGGTTGCAATTATTACCGGTGCAAGCA

-continued

GCGGTATTGGTGAAGCCACCGCATTTGCACTGGCAGCAGAAGGTGCAAAAGTTGCAATTGCAGCCCGTCGTGCA

GAACTGTTACATGCACTGGCCAAACGTATTGAAGCAAGCGGTGGTCAGGCACTGCCGATTGTTACCGATATCAC

CGATGAAAGCCAGGTTAATCATCTGGTTCAGAAAACCAAAGTTGAACTGGGTCATGTTGATATCCTGGTGAATA

ATGCAGGTATTGGCGTTTTTGGTGCAATCGATACCGGTAATCCGGCAGATTGGCGTCGTGCATTTGATGTTAAT

GTGCTGGGTGTTCTGTATGCAATTCATGCAGTTCTGCCTTTACTGAAAGCACAGAAAAGCGGTCATATTGTGAA

TATTAGCAGCGTGGATGGTCGTATTGCACAGAGCGGTGCAGTTGTTTATAGCGCAGCAAAAAGCGGTGTTAATG

CCCTGAGCGAAGCACTGCGTCAAGAAGTGAGCCTGGATAATATTCGTGTGACCATTATTGAACCGGGTCTGGTA

GATACCCCGTTTAATGATCTGATTAGTGATCCGATTACCAAACAGCTGAGCAAAGAACAGCTGTCAACCATTAC

TCCGCTGCAGAGCGAAGATATTGCACGTGCCATTATCTATGCAGTTACCCAGCCGGATCATGTTAACGTTAATG

AAATTCTGATTCGTCCGACCGCAGAGGATAATTGAgaaggagatatacatATGAACCTGACCCTGAACAAAGAA

GAAAAACAGCTGCTGACGGCATATAGCGGCACCGAACTGCAGCTGACAGCAGATGTTCTGGTTATTGGTGGTGG

TCCGGCAGCCGCATGGGCAGCTTGGGCAGCAGGCGCACAGGGTGTGAAAGTTATTATTGTGGATAAAGGTTTTC

TGGGCACCAGCGGTGCCGCAGCCGCAAGCGGTAATAGCGTTATGGCACCGTCACCGGAAAATTGGGAAAAAGAT

GTGAGCGAATGTTACAGCAAAGGTAATAATCTGGCAAATCTGCGTTGGATTGAACGTGTTATTGAAAAAGCCTG

GCTGTCACTGCCGCTGGTTGAAGATTGGGGTTATCGTTTTCCTAAAGAAAATGGTGAAAGCGTGCGTCAGAGCT

ATTATGGTCCTGAATATATGCGTGTTCTGCGGAAAAATCTGCTGCGCGTTGGTGTTCAGATCTTTGATCAGTCA

CCGGCACTGGAATTACTGCTGGCACAGGATGGTAGCGTTGCCGGTGCACGTGGTGTGCAGCGTCAGAATCATCG

TACATATACCGTTCGTGCCGGTGCCGTTGTTCTGGCCAATGGTGGTTGCGCATTTCTGAGTAAAGCACTGGGTT

GTAATACCAATACCGGTGATGGTCTGTTAATGGCAGTTGAAGCCGGTGGTGAACTGAGCAGTATGGAAGCCAGC

AGCCATTATACCATTAGCACCGCCTTTAATGCAACCGTTACCCGTGCAGCTCCGTTTTATTGGGCAAGCTATAC

CGATGAAGCTGGCAATGATCTGGGTGGCTATATTAACGGTCGTCGTGATCCGAGCTTTCTGCCGAACGCACTGC

TGAAAGGTCCGGTTTATGCACGTCTGGATCGTGCAACACCGGAAATTCAGGCGCTGGTAGAAAAAAGCCATTTT

ATTGCATTTCTGCCGTACAAGAAAGCCGGTATTGATCCGTATACCGAACGTGTTCCGGTTACCCTGGTGCTGGA

AGGCACCGTGCGTGGCACCGGTGGTATTCGCATTGTTAATGATTCATGTGGCACCAAAGTTCCGGGACTGTATG

CAGCGGGTGATGCAGCAAGCCGTGAATTTCTGGCAGGCATTGCCAGCGGTGGTGATGGACCGAATGCAGCATGG

GCAATTTCAACCGGTCAGTGGGCAGGCGAAGGTGCAGCAGCCTTTGCAAAAAGTCTGGGTGCACATGTTCATGA

ACGCGTTGTTCGTCCGGCAGGCCAGGCAGGTCTGCGTAGTCAGTATCCGGGTAGCGAAACCTTTGATAGTGAAG

CAGTTGTTCGTGGCGTTCAGGCAGAAATGTTTCCGCTGGAAAAAAACTATCTGCGCTGTGAACAGGGACTGCTG

GATAGCCTGGCAAAACTGGAAATGCTGTGGCAGCAGGTTCAGGGTAATCCGAAACAGGATACAGTTCGTGATCT

GGAATTTTCACGTCGTGCGGCAGCACTGGTTAGCGTGGCACGTTGGGCATATTTTAGCGCACTGCATCGTAAAG

AAACCCGTAGCGAACATATCCGTATTGATTACCCGGAAACGGATCCGAATCAACTGTATTATCAGGCAACCGGT

GGCCTGGAACGTCTGTGGGTGCGTCGTGATTGGGTTAAAGATGCAAGCGCCACCCCTCCGGTGCTGACCACCTG

AgaaggagatatacatATGATTGAACTGGTGAGCCATAAGCTGTGCATTAATTGTAATGTTTGTGTTCAGGTGT

GCCCGACCAATGTTTTTGATGCAGTGCCGAATCAGCCTCCGGCAATTGCACGCCAAGAAGATTGTCAGACCTGT

TTTATTTGTGAAGCATATTGTCCTGCAGATGCGCTGTATGTTGCACCGCAGAGCCATACCAATGTTGCAGTTAA

CGAAGATGATTTAATCGACAGCGGCATTATGGGTGAATATCGTCGCATTCTGGGTTGGGGCTATGGTCGTAAAA

ACAATAGCGAACTGGATACCGACCATAAACTGCGTCTGTTTGAATGAgaaggagatatacatATGTCATTTCAG

AAATTTGTGCAAGAAGCAGCCTATAAAGTCGCACCGTTTAAACCGAATCGTTTTGCCAAAATTAGCGAGCGTGA

AGATAAATGTGCAATTCCGGTTCCGGCATGGCGTGCACTGCTGGCCAATCGTGACCTGTTTACCTGGAAAGGTA

TTCCGTTTCTGAAAGGTTGTACCGAAATTGCACTGTATAGCATGCTGCTGTATGAACTGCGTCCGAAAACGATT

ATTGAAATTGGTGCGCTGAGCGGTGGTAGCGCAATTTGGCTGGCAGATCATCTGGAACTGTTTCAGATTGAAGG

-continued

TTGCGTGTATTGCATTGATATTGATCTGTCTCTGCTGGACGAAAAAGCAAAAACCGATAGCCGTGTTCATTTTC

TGGAAGGTGATTGCAATAATATGGGTGCAATTATGTCAAGCGAGCTGCTGAGTGGTCTGGCACATCCTTGGCTG

ATTGTTGAAGATGCACATGCAAATGCCGTTGGTGTGGTTGAATATTTTCACGAAAACGGTCTGAAAAGTGGCGA

TTACCTGATCGTGGAAGATACCAATAAAACAATGTGGGAACTGGATCGCGAAGAACTGGACCGTGATGACCTGG

ATGAACAAGAACTGATCGAAAAAGGTGAGCAGAAATTAGCAGAACTGAAAAGCTGGCTGATGCTGCATGAGAAT

GAATATCTGATAGATACCTACTATCAGGATATGTATGGCTATAATGGTAGCCGTAATTGGAACAGCATTCTGAA

ACGTGTGGAAAAGAACTTTTAAtctaactaaaaacaccctaacgggtgtttttcttttctggtctccccgaag ttcctattctctagaaagtataggaacttcgctggattgggccgcgaaattaaccggcctgagcaatgtcccag ctttaat SEQ ID NO: 94: Sequence of sxt3 fragment version 3 integrated into the xylose operon, which has sxtQ, sxtR and orf24 deleted. Flanking regions of the xylose operon at integration site are included. sxt open reading frames (S, T, U, V, W, X) are indicated by upper case letters.

ggtgtcaggaggcgggaggggacatctttcaggccattattcagtgaggtCCAGCCTTGCAAGAAGCGGATACA

GGAGTGCAAAAAATGGCTATCTCTAGAAAGGCCTACCCCTTAGGCTTTATGCAACAGAAACAATAATAATGGAG

TCATGAACATGCTGACCGCAGAACAGAAACAGGCATATACCAATGATGGCTATTTTACCGTGGAAGAAGCAGTT

CCGAAAGCACTGATTGAAGAAATTCGCCATGAAGTGGAACTGATCACCGAGCAGAAACGTGGTGGTGTGCTGGC

AGGCGATTATGAATGGTGGTCAGAACACACCATTCCGGATCCGGTTCGTTATCAGAAAATTATCCAGCGTCTGC

TGGAACTGCCGACCGTTATGGGTCCGGTTCAGGCCCTGATTGGTAGCGATATTTTTCTGTTAATTACCGACCTG

GCAATTATTCGTGCAGGCACCGGTTATATTGCATGGCATCAGGATCATGGCTATGTTGTTGAAGTTCTGAACGC

CCTGGCAAGCATGAGCAAAAATGAGCTGAATGATGATGCACTGCGCCTGCTGGTGCCGGTTGCAAATCAGGCAA

TGGTGTTTATTACCATCTATCTGCAGGATACCGATAACACCATGGGCACCATGCGTGTGATTCCGAGCAGCCAT

CAGTGGGAACATAGTCTGGATAGCAGCAGCGCCAATTCACTGAATGCAGAAATTTGTCTGAGCCTGCCTGGTGG

TGCAGCAATGTTTTATACCCCGACCGTTTGGCATACCGCAGCAGCAAATACCAGCATTACCGATTATCGTATGC

TGACGCTGATCTTCACCAAAAACAACATTAAACCGCTGCTGGTTGATGCCCTGAAACGTATTATTTGAGAAGGA

GATATACATATGACAACCACCGATCCGATCCTGATTAATAACTGGCATGTTGTGGCAAATGTCGAGGATTGTAA

ACCGGGTAGCATTACCCGTAGCCGTTTACTGGGTGTTAAACTGGTTCTGTGGCGTAGCTATGAACAGAATAGCC

CGATTCAGGTTTGGCTGGATTATTGTCCGCATCGTGGTGTTCCGCTGAGCATGGGTGAAATTACCAATAATACC

CTGGTTTGTCCGTATCATGGCTGGCGTTATAATGAAGCAGGTAAATGTATTCAGATTCCGGCACATCCGGGTAT

GGTTCCGCCTGCAAGCGCAGAAGCACGTACCTATCATAGCCAAGAACGTTATGGTCTGGTTTGGGTTTGTCTGG

GTGATCCGGTTAATGATATTCCGTCATTTCCGGAATGGGATGATCCGAATTATCACAAAACCTACACCAAAAGC

TATCTGATTAAAGCAAGCGCCTTTCGCGTTATGGATAATTCACTGGATGTTAGCCATTTTCCGTTTATTCATGA

TGGCTGGCTGGGCGATCGTAACTATACCAAAGTGGAAGAATTTGAAGTGAAACTGGATAAAGATGGTCTGACGA

TGGGCAAATATCAGTTTCAGACCAGCCGTATTGTGAGCCATATTGAAGATGATAGCTGGGTGAATTGGTTTCGT

CTGAGCCATCCGCTGTGTCAGTATTGTGTTAGCGAAAGTCCGGAAATGCGTATTGTTGATCTGATGACCATTAC

GCCGATTGATGAAGAAAATAGCGTTCTGCGCATGCTGATCATGTGGAATGGTTATGAAACCCTGGAAAGCAAAA

TGCTGACAGAGTATGATGAAACGATCGAACAGGATATTCGTATTCTGCATGCCCAGCAGCCGGTGCGTCTGCCG

CTGCTGACACCGAAGCAGATTAATACCCAGCTGTTTAGCCATGAAATTCATGTTCCGAGCGATCGTTGTACCCT

GGCATATCGTCGTTGGCTGAAACAACTGGGTGTGACCTATGGTGTTTGTTGAGAAGGAGATATACATATGGCAG

GTAAACTGGATGGTAAGGTTGCAATTATTACCGGTGCAAGCAGCGGTATTGGTGAAGCCACCGCATTTGCACTG

GCAGCAGAAGGTGCAAAAGTTGCAATTGCAGCCCGTCGTGCAGAACTGTTACATGCACTGGCCAAACGTATTGA

AGCAAGCGGTGGTCAGGCACTGCCGATTGTTACCGATATCACCGATGAAAGCCAGGTTAATCATCTGGTTCAGA

-continued

AAACCAAAGTTGAACTGGGTCATGTTGATATCCTGGTGAATAATGCAGGTATTGGCGTTTTTGGTGCAATCGAT

ACCGGTAATCCGGCAGATTGGCGTCGTGCATTTGATGTTAATGTGCTGGGTGTTCTGTATGCAATTCATGCAGT

TCTGCCTTTACTGAAAGCACAGAAAAGCGGTCATATTGTGAATATTAGCAGCGTGGATGGTCGTATTGCACAGA

GCGGTGCAGTTGTTTATAGCGCAGCAAAAAGCGGTGTTAATGCCCTGAGCGAAGCACTGCGTCAAGAAGTGAGC

CTGGATAATATTCGTGTGACCATTATTGAACCGGGTCTGGTAGATACCCCGTTTAATGATCTGATTAGTGATCC

GATTACCAAACAGCTGAGCAAAGAACAGCTGTCAACCATTACTCCGCTGCAGAGCGAAGATATTGCACGTGCCA

TTATCTATGCAGTTACCCAGCCGGATCATGTTAACGTTAATGAAATTCTGATTCGTCCGACCGCAGAGGATAAT

TGAGAAGGAGATATACATATGAACCTGACCCTGAACAAAGAAGAAAAACAGCTGCTGACGGCATATAGCGGCAC

CGAACTGCAGCTGACAGCAGATGTTCTGGTTATTGGTGGTGGTCCGGCAGCCGCATGGGCAGCTTGGGCAGCAG

GCGCACAGGGTGTGAAAGTTATTATTGTGGATAAAGGTTTTCTGGGCACCAGCGGTGCCGCAGCCGCAAGCGGT

AATAGCGTTATGGCACCGTCACCGGAAAATTGGGAAAAAGATGTGAGCGAATGTTACAGCAAAGGTAATAATCT

GGCAAATCTGCGTTGGATTGAACGTGTTATTGAAAAAGCCTGGCTGTCACTGCCGCTGGTTGAAGATTGGGGTT

ATCGTTTTCCTAAAGAAAATGGTGAAAGCGTGCGTCAGAGCTATTATGGTCCTGAATATATGCGTGTTCTGCGG

AAAAATCTGCTGCGCGTTGGTGTTCAGATCTTTGATCAGTCACCGGCACTGGAATTACTGCTGGCACAGGATGG

TAGCGTTGCCGGTGCACGTGGTGTGCAGCGTCAGAATCATCGTACATATACCGTTCGTGCCGGTGCCGTTGTTC

TGGCCAATGGTGGTTGCGCATTTCTGAGTAAAGCACTGGGTTGTAATACCAATACCGGTGATGGTCTGTTAATG

GCAGTTGAAGCCGGTGGTGAACTGAGCAGTATGGAAGCCAGCAGCCATTATACCATTAGCACCGCCTTTAATGC

AACCGTTACCCGTGCAGCTCCGTTTTATTGGGCAAGCTATACCGATGAAGCTGGCAATGATCTGGGTGGCTATA

TTAACGGTCGTCGTGATCCGAGCTTTCTGCCGAACGCACTGCTGAAAGGTCCGGTTTATGCACGTCTGGATCGT

GCAACACCGGAAATTCAGGCGCTGGTAGAAAAAAGCCATTTTATTGCATTTCTGCCGTACAAGAAAGCCGGTAT

TGATCCGTATACCGAACGTGTTCCGGTTACCCTGGTGCTGGAAGGCACCGTGCGTGGCACCGGTGGTATTCGCA

TTGTTAATGATTCATGTGGCACCAAAGTTCCGGGACTGTATGCAGCGGGTGATGCAGCAAGCCGTGAATTTCTG

GCAGGCATTGCCAGCGGTGGTGATGGACCGAATGCAGCATGGGCAATTTCAACCGGTCAGTGGGCAGGCGAAGG

TGCAGCAGCCTTTGCAAAAAGTCTGGGTGCACATGTTCATGAACGCGTTGTTCGTCCGGCAGGCCAGGCAGGTC

TGCGTAGTCAGTATCCGGGTAGCGAAACCTTTGATAGTGAAGCAGTTGTTCGTGGCGTTCAGGCAGAAATGTTT

CCGCTGGAAAAAAACTATCTGCGCTGTGAACAGGGACTGCTGGATAGCCTGGCAAAACTGGAAATGCTGTGGCA

GCAGGTTCAGGGTAATCCGAAACAGGATACAGTTCGTGATCTGGAATTTTCACGTCGTGCGGCAGCACTGGTTA

GCGTGGCACGTTGGGCATATTTTAGCGCACTGCATCGTAAAGAAACCCGTAGCGAACATATCCGTATTGATTAC

CCGGAAACGGATCCGAATCAACTGTATTATCAGGCAACCGGTGGCCTGGAACGTCTGTGGGTGCGTCGTGATTG

GGTTAAAGATGCAAGCGCCACCCCTCCGGTGCTGACCACCTGAGAAGGAGATATACATATGATTGAACTGGTGA

GCCATAAGCTGTGCATTAATTGTAATGTTTGTGTTCAGGTGTGCCCGACCAATGTTTTTGATGCAGTGCCGAAT

CAGCCTCCGGCAATTGCACGCCAAGAAGATTGTCAGACCTGTTTTATTTGTGAAGCATATTGTCCTGCAGATGC

GCTGTATGTTGCACCGCAGAGCCATACCAATGTTGCAGTTAACGAAGATGATTTAATCGACAGCGGCATTATGG

GTGAATATCGTCGCATTCTGGGTTGGGGCTATGGTCGTAAAAACAATAGCGAACTGGATACCGACCATAAACTG

CGTCTGTTTGAATGAGAAGGAGATATACATATGTCATTTCAGAAATTTGTGCAAGAAGCAGCCTATAAAGTCGC

ACCGTTTAAACCGAATCGTTTTGCCAAAATTAGCGAGCGTGAAGATAAATGTGCAATTCCGGTTCCGGCATGGC

GTGCACTGCTGGCCAATCGTGACCTGTTTACCTGGAAAGGTATTCCGTTTCTGAAAGGTTGTACCGAAATTGCA

CTGTATAGCATGCTGCTGTATGAACTGCGTCCGAAAACGATTATTGAAATTGGTGCGCTGAGCGGTGGTAGCGC

AATTTGGCTGGCAGATCATCTGGAACTGTTTCAGATTGAAGGTTGCGTGTATTGCATTGATATTGATCTGTCTC

TGCTGGACGAAAAAGCAAAAACCGATAGCCGTGTTCATTTTCTGGAAGGTGATTGCAATAATATGGGTGCAATT

ATGTCAAGCGAGCTGCTGAGTGGTCTGGCACATCCTTGGCTGATTGTTGAAGATGCACATGCAAATGCCGTTGG

-continued

TGTGGTTGAATATTTTCACGAAAACGGTCTGAAAAGTGGCGATTACCTGATCGTGGAAGATACCAATAAAACAA

TGTGGGAACTGGATCGCGAAGAACTGGACCGTGATGACCTGGATGAACAAGAACTGATCGAAAAAGGTGAGCAG

AAATTAGCAGAACTGAAAAGCTGGCTGATGCTGCATGAGAATGAATATCTGATAGATACCTACTATCAGGATAT

GTATGGCTATAATGGTAGCCGTAATTGGAACAGCATTCTGAAACGTGTGGAAAAGAACTTTTAATCTAACTAAA

AACACCCTAACGGGTGTTTTTTCTTTTCTGGTCTCCCCGAAGTTCCTATTCTCTAGAAAGTATAGGAACTTCGc tggattgggccgcgaaattaaccggcctgagcaatgtcccagctttaat SEQ ID NO: 95: Sequence of sxt1 fragment, integrated into the lactose operon
after seam-less deletion of sxtC. Flanking regions of the lactose operon at
integration site are included. sxt open reading frames are indicated by upper
case letters.

atgaccatgattacggattcactggccgtcgttttacaacgtcgtgactgggaaaaccctggcgttacccaact taatcgccttgcagcacatccccctttcgccagctggcgtaatagcgaagaggcccgcaccgatcgcccttccc aacagttgcgcagcctgaatggcgaatggcgctttgcctggtttccggcaccagaagcggtgccggaaagctgg ctggagtgcgatcttcctgaggccgatactgtcgtcgtcccctcaaactggcagatgcacggttacgatgcgcc catctacaccaacgtgacctatcccattacggtcaatccgccgtttgttcccacggagaatccgacgggttgtt actcgctcacatttaatgttgatgaaagctggctacaggaaggccagacgcgaattatttttgatggcgttaac tcggcgtttcatctgtggtgcaacgggcgctgggtcggttacggccaggacagtcagtggagatgcccaagggc acttcgggtcgaggaacccgacctgcattgggacgcggccacggagagcgcgggcaaacgccggcactatagcc agtggagtttgtaaaacgctatttcagagcttggagagtgtctaagaaagccgggcgatgccaacccatccctt cttcggctacgttcgtaatcaagccacttcctttttgcattgacgcagggtgtcggaaggcaactcgccgaacg cgctcctatagttttcagcgaagcgtcccaaatgtaagaagccgtagtctagggctatctcagttatactacgc acattggcactgggatcgttcaagcaggcgcggatgctttcgagcttgcggttgcggatgtagttcttcggcgt ggtgccggcatgcttctcgaacaaattgtagagcgagcgtggactcatcatcgccagctccgctaaccgctcaa ggctgatattccgtttgagattctcctcaatgaattgaacgactcgctcgaaagacgggttacctttgctgaaa atttcacggctgacattgctgcccagcatttcgagcagcttggaagcgatgatccccgcatagtgctcttggac ccgaggcatcgactttgtatgttccgcttcgtcacaaactaacccgagtagattgataaagccatcgagttgct ggagattgtgtcgcgcggcgaaacggataccctccctcggcttgtgccaattgttgtcactgcatgcccgatca aggaccactgagggcaatttaacgataaatttctcgcaatcttctgaataggtcaggtcggcttggtcatccgg attgagcagcaatagttcgcccggcgcaaaatagtgctcctggccatggccacgccacaggcaatggcctttga gtattatttgcagatgataacaggtctctaatccaggcgagattaccctcacgctaccgccgtagctgattcga cacaggtcgaggcatccgaagattctgtggtgcagcctgcctgccgggggcccgcccttgggcaggcgaataga gtgcgtaccgacatactggttaacataatcggagactgcatagggctcggcgtggacgaagatctgacttttct cgttcaataagcaaaaatccatagttcacggttctcttatttaatgtgggctgcttggtgtgatgtagaaagg cgccaagtcgatgaaaatgcaggaattaattcgcagatcctggcggatgagagaagattttcagcctgatacag attaaatcagaacgcagaagcggtctgataaaacagaatttgcctggcggcagtagcgcggtggtcccacctga ccccatgccgaactcagaagtgaaacgccgtagcgccgatggtagtgtggggtctccccatgcgagagtaggga actgccaggcatcaaataaaacgaaaggctcagtcgaaagactgggcctttcgttttatctgttgtttgtcggt gaacgctctcctgagtaggacaaatccgccgggagcggatttgaacgttgcgaagcaacggcccggagggtggc gggcaggacgcccgccataaactgccaggcatcaaattaagcagaaggccatcctgacggatggcctttttgcg tagatcccagccttgcaagaagcggatacaggagtgcaaaaaatggctatctctagaaaggcctaccccttagg ctttatgcaacagaaacaataataatggagtcatgaacatgctgcagaaaatcaatcgttatacccatggtttt gttgccgttccggttattctggcatgtcgtgaaaaaggtgtttttgaactgctggcagatgaaagtccgctgag -continued cctgaatcagatggttgaacatctgggtgccaatagcggtcattttcaggttgcactgcgtatgctggaaagtc tgcattggctgagccgtaataaagaactgaaatatagcctgaccgcagaagcagcaattcataacaaaattagc gaagatatcctgcagctgtataatctgccgattcagagctatctggaaggtaaacagggcaatctgctgggtcg ttggattgaacgtagctgtcagctgtggaatctggataatccgctgatggcagattttctggatggtctgctgg ttattccgctgctgctggcactgcataaacataacctgctggccgattctgaagataaaccgctgctgagcagc ctgagcagtaccgttcaagaagaactgggtaaactgtttctgcatctgggttgggcagatctgacagcaggtcg tctgaccattaccgaactgggtcgctttatgggtgaacgtgcactgaataccgcaattgttgcaagctataccc cgatgctgagtcgtattcatgatgttctgtttggtaattgcctgagcgtttttcagcgtgatgcaagcggtcat gaacgtcatattgatcgtaccctgaatgttattggtagcggttttcagcaccagaaatactttgcagatctgga agaaagcattctgagcgtgtttaatcagctgccgctggaagaacagccgaaatacattaccgatatgggttgtg gtgatggcaccctgctgaaacgtgtttgggaaaccattcagtttaaaagcgcacgtggtaaagcactggaacag tatccgctgcgtctgattggtgttgattataatgaagcaagcctgaaagcaaccacccgtaccctggcaagcct gccgcatctggttctgcagggtgatattggtaatccggaacaaatggttcgtagcctggaagcacatggcattc atgatccggaaaatattctgcatattcgcagctttctggatcacgatcgtctgtttattccgcctcagaaacgt aatgaactgaaagaacgtgcccatctgccgtatcagagtgtttgtgttgatgatcagggtgaactgattcctcc gcatgttatggttcagagcctggtggaacacctggaacgttggagccaggttgttaataaacatggtctgatga ttctggaagtgcattgtctggaaccgcgtgttgtttatcagtttctggataaaagcgaaaacctgcactttgat gcatttcagggttttagccagcagtatctggttgaagccgaagtttttctgatgagcgcagcacaggttggtct gtttccgaaactggaactgagcaaacgttatccgaaaacctttccgtttacccgtattaccctgaactatttcg aaaaacgtccgtacaaaatcagccatgcatatctgagcgatctgcctgcactggttgacctggaagttaaatgt tggcctgagaatctgcgtgcaagcacccatgaaattcgtcgtcgtctggaactgaatccgcagggtaacctggt tctgattattgaagatcagattatcggtgccatttacagccagaccattacaagcaccgaagccctggaaaatg ttaaatatgcacaggttccgaccctgcatacaccgcagggttcagtgattcagctgctggccctgaacattctg ccggaatttcaggcacgtggtctgggcaatgaactgcgtgattttatgctgtattattgcaccctgaaaggtgg tattgaaagcgttgttggtgttacccgttgtcgcaattatgtgaattatagccagatgccgatgatggaatatc tgaaactgcataatgaacagcgtcaactgctggatccgattgttggttttcatgttagcggtggtgcagaaatt cgtggcattattgcaaattatcgtccggaagatacagataatctgggtatgggtattctgatcgaatataacct gcgtgatagcgcactgcattcaccgggtgatcgtaaaggtccgtatatcaatagcgcaattggtagcctggttc cgaaagcgaccagcgcaaccaaagaaaacaaaaccgttgcggatctggtgaaagaatgtattctgaaagtgatg ggtagccagcgtcaggcagcatatgcaccgcagcagaaactgctggacatgggtctggatagcctggatctgct ggaactgcagaccctgctggaagaacgtctgggtattaatctgagcggcacctttttctgcaaaaaaacaccc cgaccgccatcattacctattttcagaatcaggtcgtgcaagagaaacagagtgatctggcaccgcctgttgat agcgccaatgaaatcaatacactggaaaacgttgtgaatcagcagaaaattccgcaggttacacgtgttgttac cgaacagcagggacgtaaagttctgattgatggtcattgggttattgattttgccagctgtaattatctgggcc tggacctgcatccgaaagttaaagaagcaattcctccggcactggataaatggggcacccatccgagctggacc cgtctggttgcaagtccggcaatttatgaggaactggaagaggaactgtcaaaactgctgggtgtgccggatgt tctggtttttccggcagttacactgctgcagattggtattctgcctctgctgaccggtaataatggtgtgattt ttggcgatattgcagcccatcgttgtatttatgaagcatgttgtctggcccagcataaaggtgcacagtttatt cagtatcgtcataacgacctgaatgatctggccgaaaaactggccaaatatccgcctgaacaggttaaaatcat tgtgatcgatggtgtgtatagcatgagtgccgatttcccggacctgcctgcatatgttcatctggcaaaagaat ataacgccctgatctatatggatgatgcacatggctttggcattctgggtgaaaatccgagcagcgatatgccg -continued tatggttataaaggtaatggcatggtgaactactttgatctgcgttttgccgaagataacatcatttatgttgc aggtctgagcaaagcctatagcagctatgcagcatttctgacctgtggtgatcgtcgtattaaaaccaattttc gtaatgcatggaccgcgatttttagcggtccgagtccggttgcaagcctggccagcgcactggcaggtctgcag gttaatcgtcaagaaggtgaacagctgcgcaaacaaatctatcatctgacacataaactggttacccaggctcg tgccattggttttgaagttgataattatggttatgtgccgattgtgggtgttctggtgggtgatgcacagcata tgattgatgtgtgccaactgctgtgggaatatggtatcctgattacccctgcaatttttccgattgtgccgctg aataaatcagcactgcgttttagcattaccgcagcaaataccgaagaagaaattgatcaggccatcaaaagtct gaaagcagtttgggacctgctgcaaaaacgtaaagccctgccgtgtaaacaagaagaaaatatcctgaaacatt gagaaggagatatacatatgacccatgttgccctggaacaggcaattgcaaaagttccgcgtagcattcagagc gaactgcgtaccattctggcacagcatgcagttattgatagcagcgttgtggcaagctggattgatcgtctggg caccaatattagtaccctgatgatccagctgctgccggttgcagcaacctatgcacgtgttccgattagccagt tttatgttggtgccattgcactgggcaaaccgcagagtaaaaatcagctgggtagcggcaccctgtattttggt gcagatatggaatttgttggtcaggcactgagctttagcgttcatgcagaacagagcgccaccattaatgcctg gctgcatggcgaaaccggactgcaggcactggcaatccatgaagcaccgtgtggttattgtcgccagtttctgt atgaaatggcaaccgtgaatcagaattttgtgctgctggtgaaaagcaatgaaagccagccggaacagacctat accagcaacaaactgccgcattttctgcctgaaccgtttggtccagccgatctgggtctgaccggtggcctgat gcagaccgtgtttcacgatctggaaacctatagcaccgatgatgttgttctggcagcactgagtgcagcaaatc agagttatgcaccgtataccaaaaactttgccggtgttgcactgaaagatagtcatggtaacatttttacaggt cgctatgccgaaaacgcagcatttaatagcagcatgagcccgatggaaagcgcactgacctttatgaatatgaa tcgttattcacagagcctgttcgatatttgtgatgcagttctggtagaagtggaaaccggtattagtcagcgtc cggttaccgaagcctttctgagtagcattgcaccgaaagtgaaactgcgctatgcaccggcaaccccgagcagt aacaaactgtgactcggtaccaaattccagaaaagaggcctcccgaaaggggggccttttttcgttttggtccc gaagttcctattctctagaaagtataggaacttc SEQ ID NO: 96: Sequence of sxt4 fragment integrated into the melobiose operon. Flanking regions of the melobiose operon at integration site are included. sxt open reading frames are indicated by upper case letters.

aagcctgccgtcagggcaatatcgagaatacttttatcggtatcgctcagCCAGCCTTGCAAGAAGCGGATACA

GGAGTGCAAAAAATGGCTATCTCTAGAAAGGCCTACCCCTTAGGCTTTATGCAACAGAAACAATAATAATGGAG

TCATGAACATATGGAAACCACGAGCAAAAAATTCAAAAGCGATCTGATTCTGGAAGCACGTGCAAGCCTGAAAC

TGGGTATTCCGCTGGTTATTAGCCAGATGTGTGAAACCGGTATTTATACCGCAAATGCAGTTATGATGGGTCTG

CTGGGCACCCAGGTTCTGGCAGCCGGTGCTCTGGGTGCACTGGCATTTCTGACCCTGCTGTTTGCATGTCATGG

TATTCTGAGCGTTGGTGGTAGCCTGGCAGCGGAAGCATTTGGTGCAAACAAAATTGATGAAGTTAGCCGTATTG

CAAGCGGTCAGATTTGGCTGGCAGTTACCCTGAGCCTGCCTGCAATGCTGCTGCTGTGGCATGGTGATACCATT

CTGCTGTTATTTGGTCAAGAAGAAAGCAACGTTCTGCTGACCAAAACCTATCTGCATAGCATTCTGTGGGGTTT

TCCGGCAGCACTGAGTATTCTGACACTGCGTGGTATTGCCAGCGCACTGAATGTTCCGCGTCTGATTACCATTA

CCATGCTGACCCAGCTGATTCTGAATACCGCAGCAGATTATGTTCTGATCTTTGGTAAATTTGGTCTGCCGCAG

CTGGGTCTGGCAGGTATTGGTTGGGCAACCGCACTGGGTTTTTGGGTTAGCTTTACCCTGGGTCTGATCCTGCT

GATTTTTAGCCTGAAAGTGCGTGATTATAAACTGTTTCGTTATCTGCACCAGTTCGACAAGCAGATCTTTGTGA

AAATCTTTCAGACCGGTTGGCCGATGGGTTTTCAGTGGGGTGCAGAAACAGCACTGTTTAATGTTACCGCATGG

GTTGCAGGTTATCTGGGCACCGTTACCCTGGCAGCACATGATATTGGTTTTCAGACAGCAGAACTGGCAATGGT

TATCCCGCTGGGTGTTGGTAATGTTGCAATGACCCGTGTTGGTCAGAGCATTGGTGAAAAAAATCCACTGGGTG

CCCGTCGTGTTGCAAGCATTGGTATTACCATTGTTGGTATTTATGCCAGCATTGTTGCCCTGGTTTTTTGGCTG

-continued

TTTCCGTATCAGATTGCAGGCATTTATCTGAACATTAATAACCCGGAAAACATTGAAGCCATCAAAAAAGCCAC
CACCTTTATTCCACTGGCAGGTCTGTTTCAGATGTTTTATAGCATTCAGATCATTATCGTTGGTGCGCTGGTTG
GTCTGCGTGATACCTTTGTTCCGGTTAGCATGAATCTGATTGTTTGGGGTCTGGGTTTAGCAGGTAGCTATTTT
ATGGCAATTATTCTGGGTTGGGGTGGTATTGGTATCTGGCTGGCCATGGTTCTGAGTCCGCTGCTGAGCGCAGT
TATTCTGACCGTTCGTTTTTATCGCGTGATTGATAATCTGCTGGCCAACAGTGATGATATGCTGCAGAATGCAA
GCGTTACCACCCTGGGATGAGAAGGAGATATACATATGAAACGTCTGACGCTGCTGATCATTGCAGGTATTCTG
TCAGTTAGCACCTTTCTGTGTATTACACCGGTTGCACTGGCCAATATTACCGATTATTATCTGAAAAACGAGAA
ACTGAGCGGTCAGTTTAGCGTTCCGGTGAATCTGTCTGTTGGTGTTCGTTTTGCACATCGTAGCAGCTATGCAA
CCGCAATTAACTTTCCGACCGGTCTGGATGCAGATAGCGTTGCAGTTGGTGATTTTAACAGCGATAGCAAACTG
GATCTGGCCGTTACCAATTGGTTTGATAACAATGTTAGCGTGCTGCTGGGTAATGGCAATGGCAGCTTTGGTGC
AGCAACCAATTTTCCGGTTGGCACCAATCCGGTTTTTGTTGTTACCGGTGATGTTAATGGTGACAGTAAACTGG
ATTTAGCCGTGGCAAATTTTAGCAGCAATAATGTTTCAGTTCTGCTGGGAAACGGTAATGGTTCTTTTGGCGCA
GCCACAAACTTTAGCGTTGGTACAAATCCGTATAGCGTGGCCATTGGTGATGTGAATAATGATAGTGAACTGGA
CCTGGCATTTACGAACTGGTTCGATAATAAAGTTCTGGTGCTGTTAGGCAATGGTAATGGCTCGTTTGGTGCCG
CAAGCTCATTTCCGGTGGATACCTATAGCATTAGCGTTGCGATTGCAGATTTCAACTCAGATTCTAAATTAGAC
CTGGCGATCACCAATTGGGTGTCAAATAATGTGAGTGTGTTACTGGGGAATGGTAACGGTAGTTTTGGAGCTGC
GACAAATTTTCCTGTGGGTACAAACCCGATTTTTGTGGCAACCGGTGACGTGAATGGCGATTCTAAGCTGGACT
TAGCAGTTGCAAATACCAGCTCTAATAACGTTAGCGTTCTGTTAGGTAACGGGAACGGCTCATTCGGTGCTGCC
ACGAATTTTCCAGCAGGCACCAACCCGTATAGTGTTGCAATTCGCGACGTTAACGGTGATAGCAAATTAGATTT
AGCGGTGACCAACTATAGCAGCAACAACGTGAGTGTTCTGCCAGGCAACGGTAACGGATCATTTGGTATTGCGA
CCAACTTTCCAGTAGGTACGAATCCGGAAAGCATTGCAATTGCCGATTTTAATGGGGATTCCAAGTTAGATCTG
GCAGTGACAAATAGCGGTAACAATAATGTAAGCATACTGCTGAATAACTTTCAGGGTCTGCCGAAAAACAAGAT
TTGAGAAGGAGATATACATATGACCAATACCGAACGTGGTCTGGCCGAAATTACCAGCACCGGTTATAAAAGCG
AACTGCGTAGCGAAGCCCGTGTTAGCCTGCAGCTGGCAATTCCTCTGGTTCTGGTTGAAATTTGTGGCACCAGC
ATTAATGTTGTTGATGTTGTGATGATGGGTTTACTGGGTACACAAGTGTTAGCAGCGGGTGCCCTGGGAGCAAT
TGCCTTCCTGAGCGTTAGCAATACCTGCTATAATATGCTGCTGAGTGGTGTTGCAAAAGCAAGCGAAGCCTTTG
GAGCCAATAAAATCGATCAGGTTTCACGTATTGCCTCAGGCCAGATTTGGTTAGCCCTGACCCTGTCATTACCA
GCCATGCTGTTACTGTGGTATATGGATACCATCCTGGTTCTGTTTGGTCAGGTTGAAAGCAATACCCTGATTGC
GAAAACATACCTGCATTCAATTGTGTGGGGCTTTCCTGCCGCAGTTGGTATCCTGATTCTGCGTGGCATAGCAA
GTGCAGTTAACGTTCCTCAGCTGGTTACCGTGACCATGCTGGTTGGCCTGGTGCTGAATGCACCGGCTAATTAT
GTGCTGATGTTCGGCAAATTCGGTTTACCGGAATTAGGCCTGGCTGGCATTGGCTGGGCCAGCACACTGGTGTT
TTGGATTAGTTTTCTGGTTGGTGTTGTGCTGCTGATATTTTCACCGAAAGTTCGCGACTACAAACTGTTCCGCT
ATTTACATCAGTTTGATCGTCAGACCGTGGTTGAGATTTTTCAGACGGGCTGGCCTATGGGCTTCCTGCTGGGT
GTGGAAAGCGTTGTTCTGAGCCTGACCGCATGGCTGACCGGCTATCTGGGTACAGTGACCTTAGCAGCCCATGA
AATTGCAATCCAGACTGCCGAACTGGCGATTGTGATTCCGTTAGGTATTGGCAATGTTGCCGTTACCCGTGTGG
GCCAGACAATCGGCGAAAAAAACCCGCTGGGAGCACGCCGTGCAGCCCTGATTGGCATTATGATTGGTGGCATT
TATGCGAGCCTGGTTGCAGTGATTTTTTGGTTATTCCCTTATCAAATCGCAGGCCTGTACCTGAAAATTAACGA
TCCGGAATCAATGGAAGCAGTTAAAACCGCAACAAACTTTCTGTTTTTAGCTGGCCTGTTCCAGTTTTTTCATA
GCGTGCAGATTATTGTTGTGGGTGTTCTGATTGGCCTGCAGGATACCTTTATCCCTCTGCTGATGAATCTGGTG
GGCTGGGGACTGGGCCTGGCGGTTTCCTATTATATGGGTATTATCCTGTGCTGGGGTGGCATGGGCATCTGGTT

-continued

AGGTCTGGTACTGTCACCGCTGCTGTCAGGCCTGATCCTGATGGTGCGCTTTTATCAAGAAATTGCCAATCGCA

TTGCGAATAGCGACGATGGCCAAGAAAGCATTAGCATTGATAATGTTGAAGAACTGAGCTAATAGACCAACCCC

TTGCGGCCTCAATCGGGGGGGATGGGGTTTTTTGTCGAAGTTCCTATTCTCTAGAAAGTATAGGAACTTCGcaa ccgtctgctgaaggaagccatctgacacttaaagccatcgttgcgct SEQ ID NO: 97: Sequence of sxt2 fragment integrated into the maltose operon. Flanking regions of the maltose operon at integration site are included. sxt open reading frames (D, E, G, H, I J, K, L) are indicated by upper case letters.

ctgtgaactaaaccgaggtcatgtaaggaatttcgtgatgttgcttgcaaccagccttgcaagaagcggataca ggagtgcaaaaaatggctatctctagaaaggcctaccccttaggctttatgcaacagaaacaataataatggag tcatgaacatgattgataccattagcgttctgctgcgtgaatggaccgttatttttctgaccggtctggcattt tggctgtgggaaattcgtagtccgctgcatcagattgaatacaaagccaaattttttcaaagaactgggttgggc aggtatcagctttgtttttcgtattgtttatgcctatgttagcgtggccattatcaaactgctgagcagcctgt ttatgggtgaaagcgcaaattttgccggtgttatgtatgttccgctgtggctgcgtattattaccgcatatatt ctgcaggatctgaccgattatctgctgcatcgtaccatgcatagcaatcagtttctgtggctgacccataaatg gcatcatagcaccaaacagagttggtggctgagcggtaataaagatagctttaccggtggtctgctgtataccg ttaccgcactgtggtttccgctgctggatattccgagcgaagttatgagcgttgttgcagttcatcaggtgatt cataacaactggattcacctgaatgtgaaatggaatagctggctgggtattatcgaatggatttatgttacacc gcgtatccataccctgcatcatctggataccggtggtcgtaatctgagcagtatgtttacctttattgatcgtc tgtttggcacctatgtgtttccggaaaactttgatatcgaaaaaagcaaaaaccgcctggatgatcagagcgtt accgttaaaaccattctgggtttctgagaaggagatatacatATGCTGAAAGATTTTAACCAGTTCCTGATTCG

TACCCTGGCATTTGTTTTTGCCTTTGGCATTTTTCTGACAACCGGTGTTGGTATTGCAAAAGCAGATTATCTGG

TGAAAGGTGGCAAAATTACCAATGTTCAGAATACCAGCAGCAACGGTGATAATTATGCAGTTAGCATTAGCGGT

GGTTTTGGTCCGTGTGCAGATCGTGTTATTATTCTGCCGACCAGCGGTGTTATTAATCGTGATATTCACATGCG

TGGTTATGAAGCAGCACTGACCGCACTGAGCAATGGTTTTCTGGTTGATATCTATGATTATACCGGTAGCAGCT

GTAGCAATGGTGGCCAGCTGACCATTACCAATCAGCTGGGTAAACTGATTAGCAATTGAgaaggagatatacat

ATGACCAATCAGAACAACCAAGAGCTGGAAAATGATCTGCCGATTGCAAAACAGCCGTGTCCGGTTAATAGCTA

TAATGAATGGGATACCCTGGAAGAAGTTATTGTTGGTAGCGTTGAAGGTGCAATGCTGCCTGCACTGGAACCGA

TTAACAAATGGACCTTTCCGTTTGAAGAACTGGAAAGCGCACAGAAAATTCTGAGCGAACGTGGTGGTGTTCCG

TATCCGCCTGAAATGATTACCCTGGCACATAAAGAACTGAACGAGTTTATTCATATCCTGGAAGCCGAAGGTGT

TAAAGTTCGTCGTGTTAAACCGGTTGATTTTAGCGTTCCGTTTAGCACACCGGCATGGCAGGTTGGTAGCGGTT

TTTGTGCAGCAAATCCGCGTGATGTTTTTCTGGTTATTGGCAACGAAATTATCGAAGCACCGATGGCAGATCGT

AATCGTTATTTTGAAACCTGGGCATATCGCGAAATGCTGAAAGAATATTTTCAGGCAGGCGCAAAATGGACCGC

AGCACCGAAACCGCAGCTGTTTGATGCACAGTATGATTTCAATTTTCAGTTTCCGCAGCTGGGTGAACCGCCTC

GTTTTGTTGTTACCGAATTTGAACCGACCTTTGATGCAGCCGATTTTGTTCGTTGTGGTCGTGATATTTTTGGC

CAGAAAAGCCATGTTACCAATGGTCTGGGTATTGAATGGCTGCAGCGTCATCTGGAAGATGAATATCGCATTCA

TATCATCGAAAGCCATTGTCCGGAAGCACTGCATATTGATACCACCCTGATGCCGCTGGCACCGGGTAAAATTC

TGGTTAATCCGGAATTTGTGGACGTGAATAAACTGCCGAAAATTCTGAAAAGCTGGGATATTCTGGTTGCACCG

TATCCGAATCATATTCCGCAGAATCAGCTGCGTCTGGTTAGCGAATGGGCAGGTCTGAATGTTCTGATGCTGGA

TGAAGAACGTGTGATCGTGGAAAAAAAATCAAGAGCAGATGATCAAAGCCCTGAAAGATTGGGGTTTTAAACCGA

TTGTTTGCCACTTCGAAAGCTATTATCCGTTTCTGGGTAGCTTTCATTGTGCAACCCTGGATGTTCGTCGTCGT

GGCACCCTGCAGAGCTATTTTTGAgaaggagatatacatATGACGACCGCAGATCTGATTCTGATCAATAATTG

GTATGTTGTGGCCAAGGTGGAAGATTGTAAACCGGGTAGCATTACCACCGCACTGCTGCTGGGTGTTAAACTGG

-continued

TTCTGTGGCGTAGCCGTGAACAGAATAGCCCGATTCAGATTTGGCAGGATTATTGTCCGCATCGTGGTGTTGCA

CTGAGCATGGGTGAAATTGTGAATAATACCCTGGTTTGTCCGTATCATGGTTGGCGTTATAATCAGGCAGGTAA

ATGTGTTCATATTCCGGCACATCCGGATATGACCCCTCCGGCAAGCGCACAGGCAAAAATCTATCATTGTCAAG

AACGTTATGGTCTGGTTTGGGTTTGTCTGGGTGATCCGGTTAATGATATTCCGAGTCTGCCGGAATGGGATGAT

CCGAATTATCATAATACCTGCACCAAGAGCTACTTTATCCAGGCAAGCGCATTTCGTGTGATGGATAACTTTAT

TGATGTGAGCCATTTTCCGTTTGTGCATGATGGTGGTCTGGGCGATCGTAATCATGCACAGATTGAAGAATTTG

AGGTGAAAGTGGATAAAGACGGTATTAGCATTGGCAATCTGAAACTGCAGATGCCTCGTTTTAATAGCAGCAAT

GAAGATGATAGCTGGACCCTGTATCAGCGTATTAGCCATCCGCTGTGTCAGTATTATATCACCGAAAGCAGCGA

AATTCGTACAGCAGATCTGATGCTGGTTACCCCGATTGATGAAGATAATTCACTGGTTCGTATGCTGGTGACCT

GGAATCGTAGCGAAATTCTGGAAAGCACCGTTCTGGAAGAATTTGATGAAACCATTGAACAGGATATCCCGATT

ATTCATAGCCAGCAGCCTGCACGTCTGCCGCTGCTGCCGAGCAAGCAGATTAATATGCAGTGGCTGAGCCAAGA

AATTCATGTTCCGAGCGATCGTTGTACCGTTGCATATCGTCGTTGGCTGAAAGAACTGGGCGTTACCTATGGTG

TTTGTTGAgaaggagatatacatATGCAGATTCTGGGTATCAGCGCCTATTATCATGATAGCGCAGCAGCAATG

GTTATTGATGGTGAAATTGTTGCAGCAGCACAAGAAGAACGTTTTAGCCGTCGTAAACATGATGCAGGTTTTCC

GACCGGTGCAATTACCTATTGTCTGAAACAGGTTGGCACCAAACTGCAGTATATTGATCAGATCGTGTTCTATG

ATAAACCGCTGGTGAAATTTGAACGTCTGCTGGAAACCTATCTGGCCTATGCACCGAAAGGTTTTGGTAGTTTT

ATTACCGCAATGCCGGTGTGGCTGAAAGAGAAACTGTATCTGAAAACCCTGCTGAAAAAAGAACTGGCACTGCT

GGGTGAATGTAAAGCAAGCCAGCTGCCTCCGCTGCTGTTTACCAGCCATCATCAGGCACATGCAGCAGCAGCAT

TTTTTCCGAGCCCGTTTCAGCGTGCAGCAGTTCTGTGTCTGGATGGTGTTGGTGAATGGGCAACCACCAGTGTT

TGGCTGGGTGAAGGTAATAAACTGACACCGCAGTGGGAAATTGATTTTCCGCATAGCCTGGGCCTGCTGTATAG

CGCATTTACCTATTATACCGGCTTTAAAGTGAACAGCGGTGAGTATAAACTGATGGGTCTGGCACCGTATGGTG

AACCGAAATATGTTGATCAGATTCTGAAACATCTGCTGGATCTGAAAGAAGATGGCACCTTTCGTCTGAACATG

GATTATTTCAATTATACCGTTGGTCTGACCATGACCAACCATAAATTTCATAGCATGTTTGGTGGTCCGCCTCG

TCAGGCAGAAGGTAAAATTAGCCAGCGTGATATGGATCTGGCAAGCAGCATTCAGAAAGTTACCGAAGAAGTGA

TTCTGCGTCTGGCACGTACCATTAAGAAAGAATTAGGTGTTGAATACCTGTGTCTGGCAGGCGGTGTTGGTCTG

AATTGTGTTGCAAATGGTCGTATTCTGCGTGAGAGCGATTTTAAAGATATTTGGATTCAGCCTGCAGCCGGTGA

TGCAGGTAGCGCAGTTGGTGCAGCACTGGCAATTTGGCATGAATATCATAAAAAACCGCGTACCAGCACCGCAG

GCGATCGTATGAAAGGTAGCTATCTGGGTCCGAGCTTTAGCGAAGCAGAAATTCTGCAGTTTCTGAACAGCGTG

AATATTCCGTATCATCGTTGTGTGGATAATGAACTGATGGCACGTCTGGCGGAAATTCTGGATCAGGGTAATGT

TGTTGGTTGGTTTAGCGGTCGTATGGAATTTGGTCCGCGTGCACTGGGTGGTCGTAGCATTATTGGTGATAGCC

GTAGCCCGAAAATGCAGAGCGTTATGAATCTGAAAATCAAATATCGCGAAAGCTTCCGTCCGTTTGCACCGAGC

GTTCTGGCAGAACGTGTTAGCGATTATTTTGATCTGGATCGTCCGAGCCCGTATATGCTGCTGGTTGCACAGGT

TAAAGAAAATCTGCATATTCCGATGACCCAAGAACAGCATGAACTGTTTGGTATCGAAAAACTGAATGTTCCGC

GTAGCCAGATTCCGGCAGTTACCCATGTTGATTATAGCGCACGTATTCAGACCGTTCATAAAGAAACCAATCCG

CGTTATTATGAACTGATCCGTCATTTTGAAGCACGTACCGGTTGTGCAGTTCTGGTTAATACCAGCTTTAATGT

TCGTGGTGAACCGATTGTGTGTACACCGGAAGATGCATATCGTTGTTTTATGCGTACCGAGATGGATTACCTGG

TGATGGAAAATTTTCTGCTGGTGAAAAGCGAACAGCCTCGTGGTAATAGTGATGAAAGCTGGCAGAAAGAATTT

GAGCTGGATTGAgaaggagatatacatATGGAACAAATTAAAGAACTGGATAAGAAAGGCCTGCGTGAATTTGG

TCTGATTGGTGGTAGCATTGTTGCCGTTCTGTTTGGTTTTCTGCTGCCGGTTATTCGTCATCATAGCCTGAGCG

TTATTCCGTGGGTTGTTGCAGGTTTTCTGTGGATTTGGGCAATTATTGCACCGACCACCCTGAGCTTTATCTAT

-continued

CAGATTTGGATGCGTATTGGTCTGGTGCTGGGTTGGATTCAGACCCGTATTATTCTGGGTGTTCTGTTCTATAT

TATGATTACCCCGATCGGTTTTATTCGTCGTCTGCTGAATCAGGATCCGATGACCCGTATTTTTGAACCGGAAC

TGCCGACCTATCGTCAGCTGAGCAAAAGCCGTACCACCCAGAGCATGGAAAAACCGTTCTGAgaaggagatata catATGTTAAAAGACACCTGGGATTTTATCAAGGATATCGCAGGCTTTATCAAAGAACAGAAAAACTATCTGCT

GATTCCGCTGATTATTACCCTGGTTAGCCTGGGTGCACTGATTGTTTTTGCACAGAGCAGCGCAATTGCACCGT

TTATCTATACCCTGTTTTGAgaaggagatatacatATGAGCAACTTCAAAGGCAGCGTTAAAATTGCACTGATG

GGCATTCTGATTTTTTGCGGTCTGATTTTTGGTGTGGCCTTTGTTGAAATTGGTCTGCGTATTGCAGGCATTGA

ACATATTGCCTTTCATAGCATTGATGAACATCGTGGTTGGGTTGGTCGTCCGCATGTTAGCGGTTGGTATCGTA

CCGAAGGTGAAGCACATATTCAGATGAATAGTGATGGTTTTCGTGATCGCAACACATTAAAGTGAAACCGGAA

AATACCTTTCGTATTGCCCTGCTGGGTGATAGCTTTGTTGAAAGCATGCAGGTTCCGCTGGAACAGAATCTGGC

AGCAGTTATTGAAGGCGAAATTAGCAGCTGTATTGCACTGGCAGGTCGTAAAGCCGAAGTTATTAACTTTGGTG

TTACCGGTTATGGCACCGATCAAGAACTGATTACCCTGCGTGAAAAAGTGTGGGATTATAGTCCGGATATTGTT

GTGCTGGATTTCTATACCGGTAACGATATTGTTGATAATAGCCGTGCACTGTCCCAGAAATTCTATCCGAATGA

ACTGGGTAGCCTGAAACCGTTTTTTATCCTGCGTGATGGTAATCTGGTTGTTGATGCAAGCTTTATCAACACCG

ATAACTATCGTAGCAAACTGACCTGGTGGGGTAAAACCTATATGAAAATCAAAGATCATAGCCGCATTCTGCAG

GTCCTGAATATGGTTCGTGATGCACTGAATAATAGCAGCCGTGGTTTTAGCAGCCAGGCAATTGAAGAACCGCT

GTTTAGTGATGGTAAACAGGATACCAAACTGAGCGGCTTCTTCGATATCTATAAACCGCCTACCGATCCGGAAT

GGCAGCAGGCCTGGCAGGTTACCGAAAAACTGATTAGTAGCATGCAGCATGAAGTGACCGCCAAAAAAGCCGAT

TTTCTGGTTGTTACCTTTGGCGGTCCGTTTCAGCGCGAACCGCTGGTTCGTCAGAAAGAAATGCAAGAACTGGG

TCTGACCGATTGGTTTTATCCGGAAAAACGTATTACCCGTCTGGGTGAAGATGAAGGTTTTAGCGTGCTGAATC

TGAGCCCGAATCTGCAGGTTTATAGCGAACAGAATAATGCCTGTCTGTATGGTTTTGATGATACCCAGGGTTGT

GTTGGTCATTGGAATGCACTGGGTCATCAGGTTGCAGGTAAAATGATTGCAAGCAAAATTTGTCAGCAGCAGAT

GCGTGAAAGCATTCTGCCGCATAAACATGATCCGAGCAGCCAGAGCAGCCCGATTACCCAGAGCGTTATTCAGT

AAtactctaaccccatcggccgtcttaggggttttttgtcgaagttcctattctctagaaagtataggaacttc gacctgtggggtgactttgccgccgctgccgtgatgtctgcattaccgatc SEQ ID NO: 98: Sequence of sxt2 fragment integrated into the maltose operon
after deletetion of sxtL. Flanking regions of the maltose operon at
integration site are included. sxt open reading frames are indicated by upper
case letters.

ctgtgaactaaaccgaggtcatgtaaggaatttcgtgatgttgcttgcaaccagccttgcaagaagcggataca ggagtgcaaaaaatggctatctctagaaaggcctaccccttaggctttatgcaacagaaacaataataatggag tcatgaacATGATTGATACCATTAGCGTTCTGCTGCGTGAATGGACCGTTATTTTTCTGACCGGTCTGGCATTT

TGGCTGTGGGAAATTCGTAGTCCGCTGCATCAGATTGAATACAAAGCCAAATTTTTCAAAGAACTGGGTTGGGC

AGGTATCAGCTTTGTTTTTCGTATTGTTTATGCCTATGTTAGCGTGGCCATTATCAAACTGCTGAGCAGCCTGT

TTATGGGTGAAAGCGCAAATTTTGCCGGTGTTATGTATGTTCCGCTGTGGCTGCGTATTATTACCGCATATATT

CTGCAGGATCTGACCGATTATCTGCTGCATCGTACCATGCATAGCAATCAGTTTCTGTGGCTGACCCATAAATG

GCATCATAGCACCAAACAGAGTTGGTGGCTGAGCGGTAATAAAGATAGCTTTACCGGTGGTCTGCTGTATACCG

TTACCGCACTGTGGTTTCCGCTGCTGGATATTCCGAGCGAAGTTATGAGCGTTGTTGCAGTTCATCAGGTGATT

CATAACAACTGGATTCACCTGAATGTGAAATGGAATAGCTGGCTGGGTATTATCGAATGGATTTATGTTACACC

GCGTATCCATACCCTGCATCATCTGGATACCGGTGGTCGTAATCTGAGCAGTATGTTTACCTTTATTGATCGTC

TGTTTGGCACCTATGTGTTTCCGGAAAACTTTGATATCGAAAAAAGCAAAAACCGCCTGGATGATCAGAGCGTT

ACCGTTAAAACCATTCTGGGTTTCTGAgaaggagatatacatATGCTGAAAGATTTTAACCAGTTCCTGATTCG

TACCCTGGCATTTGTTTTTGCCTTTGGCATTTTTCTGACAACCGGTGTTGGTATTGCAAAAGCAGATTATCTGG

-continued

TGAAAGGTGGCAAAATTACCAATGTTCAGAATACCAGCAGCAACGGTGATAATTATGCAGTTAGCATTAGCGGT

GGTTTTGGTCCGTGTGCAGATCGTGTTATTATTCTGCCGACCAGCGGTGTTATTAATCGTGATATTCACATGCG

TGGTTATGAAGCAGCACTGACCGCACTGAGCAATGGTTTTCTGGTTGATATCTATGATTATACCGGTAGCAGCT

GTAGCAATGGTGGCCAGCTGACCATTACCAATCAGCTGGGTAAACTGATTAGCAATTGAgaaggagatatacat

ATGACCAATCAGAACAACCAAGAGCTGGAAAATGATCTGCCGATTGCAAAACAGCCGTGTCCGGTTAATAGCTA

TAATGAATGGGATACCCTGGAAGAAGTTATTGTTGGTAGCGTTGAAGGTGCAATGCTGCCTGCACTGGAACCGA

TTAACAAATGGACCTTTCCGTTTGAAGAACTGGAAAGCGCACAGAAAATTCTGAGCGAACGTGGTGGTGTTCCG

TATCCGCCTGAAATGATTACCCTGGCACATAAAGAACTGAACGAGTTTATTCATATCCTGGAAGCCGAAGGTGT

TAAAGTTCGTCGTGTTAAACCGGTTGATTTTAGCGTTCCGTTTAGCACACCGGCATGGCAGGTTGGTAGCGGTT

TTTGTGCAGCAAATCCGCGTGATGTTTTTCTGGTTATTGGCAACGAAATTATCGAAGCACCGATGGCAGATCGT

AATCGTTATTTTGAAACCTGGGCATATCGCGAAATGCTGAAAGAATATTTTCAGGCAGGCGCAAAATGGACCGC

AGCACCGAAACCGCAGCTGTTTGATGCACAGTATGATTTCAATTTTCAGTTTCCGCAGCTGGGTGAACCGCCTC

GTTTTGTTGTTACCGAATTTGAACCGACCTTTGATGCAGCCGATTTTGTTCGTTGTGGTCGTGATATTTTTGGC

CAGAAAAGCCATGTTACCAATGGTCTGGGTATTGAATGGCTGCAGCGTCATCTGGAAGATGAATATCGCATTCA

TATCATCGAAAGCCATTGTCCGGAAGCACTGCATATTGATACCACCCTGATGCCGCTGGCACCGGGTAAAATTC

TGGTTAATCCGGAATTTGTGGACGTGAATAAACTGCCGAAAATTCTGAAAAGCTGGGATATTCTGGTTGCACCG

TATCCGAATCATATTCCGCAGAATCAGCTGCGTCTGGTTAGCGAATGGGCAGGTCTGAATGTTCTGATGCTGGA

TGAAGAACGTGTGATCGTGGAAAAAAATCAAGAGCAGATGATCAAAGCCCTGAAAGATTGGGGTTTTAAACCGA

TTGTTTGCCACTTCGAAAGCTATTATCCGTTTCTGGGTAGCTTTCATTGTGCAACCCTGGATGTTCGTCGTCGT

GGCACCCTGCAGAGCTATTTTTGAgaaggagatatacatATGACGACCGCAGATCTGATTCTGATCAATAATTG

GTATGTTGTGGCCAAGGTGGAAGATTGTAAACCGGGTAGCATTACCACCGCACTGCTGCTGGGTGTTAAACTGG

TTCTGTGGCGTAGCCGTGAACAGAATAGCCCGATTCAGATTTGGCAGGATTATTGTCCGCATCGTGGTGTTGCA

CTGAGCATGGGTGAAATTGTGAATAATACCCTGGTTTGTCCGTATCATGGTTGGCGTTATAATCAGGCAGGTAA

ATGTGTTCATATTCCGGCACATCCGGATATGACCCCTCCGGCAAGCGCACAGGCAAAAATCTATCATTGTCAAG

AACGTTATGGTCTGGTTTGGGTTTGTCTGGGTGATCCGGTTAATGATATTCCGAGTCTGCCGGAATGGGATGAT

CCGAATTATCATAATACCTGCACCAAGAGCTACTTTATCCAGGCAAGCGCATTTCGTGTGATGGATAACTTTAT

TGATGTGAGCCATTTTCCGTTTGTGCATGATGGTGGTCTGGGCGATCGTAATCATGCACAGATTGAAGAATTTG

AGGTGAAAGTGGATAAAGACGGTATTAGCATTGGCAATCTGAAACTGCAGATGCCTCGTTTTAATAGCAGCAAT

GAAGATGATAGCTGGACCCTGTATCAGCGTATTAGCCATCCGCTGTGTCAGTATTATATCACCGAAAGCAGCGA

AATTCGTACAGCAGATCTGATGCTGGTTACCCCGATTGATGAAGATAATTCACTGGTTCGTATGCTGGTGACCT

GGAATCGTAGCGAAATTCTGGAAAGCACCGTTCTGGAAGAATTTGATGAAACCATTGAACAGGATATCCCGATT

ATTCATAGCCAGCAGCCTGCACGTCTGCCGCTGCTGCCGAGCAAGCAGATTAATATGCAGTGGCTGAGCCAAGA

AATTCATGTTCCGAGCGATCGTTGTACCGTTGCATATCGTCGTTGGCTGAAAGAACTGGGCGTTACCTATGGTG

TTTGTTGAgaaggagatatacatATGCAGATTCTGGGTATCAGCGCCTATTATCATGATAGCGCAGCAGCAATG

GTTATTGATGGTGAAATTGTTGCAGCAGCACAAGAAGAACGTTTTAGCCGTCGTAAACATGATGCAGGTTTTCC

GACCGGTGCAATTACCTATTGTCTGAAACAGGTTGGCACCAAACTGCAGTATATTGATCAGATCGTGTTCTATG

ATAAACCGCTGGTGAAATTTGAACGTCTGCTGGAAACCTATCTGGCCTATGCACCGAAAGGTTTTGGTAGTTTT

ATTACCGCAATGCCGGTGTGGCTGAAAGAGAAACTGTATCTGAAAACCCTGCTGAAAAAAGAACTGGCACTGCT

GGGTGAATGTAAAGCAAGCCAGCTGCCTCCGCTGCTGTTTACCAGCCATCATCAGGCACATGCAGCAGCAGCAT

TTTTTCCGAGCCCGTTTCAGCGTGCAGCAGTTCTGTGTCTGGATGGTGTTGGTGAATGGGCAACCACCAGTGTT

-continued

TGGCTGGGTGAAGGTAATAAACTGACACCGCAGTGGGAAATTGATTTTCCGCATAGCCTGGGCCTGCTGTATAG

CGCATTTACCTATTATACCGGCTTTAAAGTGAACAGCGGTGAGTATAAACTGATGGGTCTGGCACCGTATGGTG

AACCGAAATATGTTGATCAGATTCTGAAACATCTGCTGGATCTGAAAGAAGATGGCACCTTTCGTCTGAACATG

GATTATTTCAATTATACCGTTGGTCTGACCATGACCAACCATAAATTTCATAGCATGTTTGGTGGTCCGCCTCG

TCAGGCAGAAGGTAAAATTAGCCAGCGTGATATGGATCTGGCAAGCAGCATTCAGAAAGTTACCGAAGAAGTGA

TTCTGCGTCTGGCACGTACCATTAAGAAAGAATTAGGTGTTGAATACCTGTGTCTGGCAGGCGGTGTTGGTCTG

AATTGTGTTGCAAATGGTCGTATTCTGCGTGAGAGCGATTTTAAAGATATTTGGATTCAGCCTGCAGCCGGTGA

TGCAGGTAGCGCAGTTGGTGCAGCACTGGCAATTTGGCATGAATATCATAAAAAACCGCGTACCAGCACCGCAG

GCGATCGTATGAAAGGTAGCTATCTGGGTCCGAGCTTTAGCGAAGCAGAAATTCTGCAGTTTCTGAACAGCGTG

AATATTCCGTATCATCGTTGTGTGGATAATGAACTGATGGCACGTCTGGCGGAAATTCTGGATCAGGGTAATGT

TGTTGGTTGGTTTAGCGGTCGTATGGAATTTGGTCCGCGTGCACTGGGTGGTCGTAGCATTATTGGTGATAGCC

GTAGCCCGAAAATGCAGAGCGTTATGAATCTGAAAATCAAATATCGCGAAAGCTTCCGTCCGTTTGCACCGAGC

GTTCTGGCAGAACGTGTTAGCGATTATTTTGATCTGGATCGTCCGAGCCCGTATATGCTGCTGGTTGCACAGGT

TAAAGAAAATCTGCATATTCCGATGACCCAAGAACAGCATGAACTGTTTGGTATCGAAAAACTGAATGTTCCGC

GTAGCCAGATTCCGGCAGTTACCCATGTTGATTATAGCGCACGTATTCAGACCGTTCATAAAGAAACCAATCCG

CGTTATTATGAACTGATCCGTCATTTTGAAGCACGTACCGGTTGTGCAGTTCTGGTTAATACCAGCTTTAATGT

TCGTGGTGAACCGATTGTGTGTACACCGGAAGATGCATATCGTTGTTTTATGCGTACCGAGATGGATTACCTGG

TGATGGAAAATTTTCTGCTGGTGAAAAGCGAACAGCCTCGTGGTAATAGTGATGAAAGCTGGCAGAAAGAATTT

GAGCTGGATTGAgaaggagatatacatATGGAACAAATTAAAGAACTGGATAAGAAAGGCCTGCGTGAATTTGG

TCTGATTGGTGGTAGCATTGTTGCCGTTCTGTTTGGTTTTCTGCTGCCGGTTATTCGTCATCATAGCCTGAGCG

TTATTCCGTGGGTTGTTGCAGGTTTTCTGTGGATTTGGGCAATTATTGCACCGACCACCCTGAGCTTTATCTAT

CAGATTTGGATGCGTATTGGTCTGGTGCTGGGTTGGATTCAGACCCGTATTATTCTGGGTGTTCTGTTCTATAT

TATGATTACCCCGATCGGTTTTATTCGTCGTCTGCTGAATCAGGATCCGATGACCCGTATTTTTGAACCGGAAC

TGCCGACCTATCGTCAGCTGAGCAAAAGCCGTACCACCCAGAGCATGGAAAAACCGTTCTGAgaaggagatata catATGTTAAAAGACACCTGGGATTTTATCAAGGATATCGCAGGCTTTATCAAAGAACAGAAAAACTATCTGCT

GATTCCGCTGATTATTACCCTGGTTAGCCTGGGTGCACTGATTGTTTTTGCACAGAGCAGCGCAATTGCACCGT

TTATCTATACCCTGTTTTGAtactctaaccccatcggccgtcttaggggtttttttgtcgaagttcctattctct agaaagtataggaacttcacctgtggggtgactttgccgccgctgccgtgatgtctgcattaccgatc SEQ ID NO: 99: Sequence of sxt2 fragment integrated into the maltose operon after deletetion of sxtJ, sxtK and sxtL. Flanking regions of the maltose operon at integration site are included. sxt open reading frames are indicated by upper case letters.

ctgtgaactaaaccgaggtcatgtaaggaatttcgtgatgttgcttgcaaccagccttgcaagaagcggataca ggagtgcaaaaaatggctatctctagaaaggcctaccccttaggctttatgcaacagaaacaataataatggag tcatgaacATGATTGATACCATTAGCGTTCTGCTGCGTGAATGGACCGTTATTTTTCTGACCGGTCTGGCATTT

TGGCTGTGGGAAATTCGTAGTCCGCTGCATCAGATTGAATACAAAGCCAAATTTTTCAAAGAACTGGGTTGGGC

AGGTATCAGCTTTGTTTTTCGTATTGTTTATGCCTATGTTAGCGTGGCCATTATCAAACTGCTGAGCAGCCTGT

TTATGGGTGAAAGCGCAAATTTTGCCGGTGTTATGTATGTTCCGCTGTGGCTGCGTATTATTACCGCATATATT

CTGCAGGATCTGACCGATTATCTGCTGCATCGTACCATGCATAGCAATCAGTTTCTGTGGCTGACCCATAAATG

GCATCATAGCACCAAACAGAGTTGGTGGCTGAGCGGTAATAAAGATAGCTTTACCGGTGGTCTGCTGTATACCG

TTACCGCACTGTGGTTTCCGCTGCTGGATATTCCGAGCGAAGTTATGAGCGTTGTTGCAGTTCATCAGGTGATT

CATAACAACTGGATTCACCTGAATGTGAAATGGAATAGCTGGCTGGGTATTATCGAATGGATTTATGTTACACC

GCGTATCCATACCCTGCATCATCTGGATACCGGTGGTCGTAATCTGAGCAGTATGTTTACCTTTATTGATCGTC

-continued

TGTTTGGCACCTATGTGTTTCCGGAAAACTTTGATATCGAAAAAAGCAAAAACCGCCTGGATGATCAGAGCGTT
ACCGTTAAAACCATTCTGGGTTTCTGAgaaggagatatacatATGCTGAAAGATTTTAACCAGTTCCTGATTCG
TACCCTGGCATTTGTTTTTGCCTTTGGCATTTTTCTGACAACCGGTGTTGGTATTGCAAAAGCAGATTATCTGG
TGAAAGGTGGCAAAATTACCAATGTTCAGAATACCAGCAGCAACGGTGATAATTATGCAGTTAGCATTAGCGGT
GGTTTTGGTCCGTGTGCAGATCGTGTTATTATTCTGCCGACCAGCGGTGTTATTAATCGTGATATTCACATGCG
TGGTTATGAAGCAGCACTGACCGCACTGAGCAATGGTTTTCTGGTTGATATCTATGATTATACCGGTAGCAGCT
GTAGCAATGGTGGCCAGCTGACCATTACCAATCAGCTGGGTAAACTGATTAGCAATTGAgaaggagatatacat
ATGACCAATCAGAACAACCAAGAGCTGGAAAATGATCTGCCGATTGCAAAACAGCCGTGTCCGGTTAATAGCTA
TAATGAATGGGATACCCTGGAAGAAGTTATTGTTGGTAGCGTTGAAGGTGCAATGCTGCCTGCACTGGAACCGA
TTAACAAATGGACCTTTCCGTTTGAAGAACTGGAAAGCGCACAGAAAATTCTGAGCGAACGTGGTGGTGTTCCG
TATCCGCCTGAAATGATTACCCTGGCACATAAAGAACTGAACGAGTTTATTCATATCCTGGAAGCCGAAGGTGT
TAAAGTTCGTCGTGTTAAACCGGTTGATTTTAGCGTTCCGTTTAGCACACCGGCATGGCAGGTTGGTAGCGGTT
TTTGTGCAGCAAATCCGCGTGATGTTTTTCTGGTTATTGGCAACGAAATTATCGAAGCACCGATGGCAGATCGT
AATCGTTATTTTGAAACCTGGGCATATCGCGAAATGCTGAAAGAATATTTTCAGGCAGGCGCAAAATGGACCGC
AGCACCGAAACCGCAGCTGTTTGATGCACAGTATGATTTCAATTTTCAGTTTCCGCAGCTGGGTGAACCGCCTC
GTTTTGTTGTTACCGAATTTGAACCGACCTTTGATGCAGCCGATTTTGTTCGTTGTGGTCGTGATATTTTTGGC
CAGAAAAGCCATGTTACCAATGGTCTGGGTATTGAATGGCTGCAGCGTCATCTGGAAGATGAATATCGCATTCA
TATCATCGAAAGCCATTGTCCGGAAGCACTGCATATTGATACCACCCTGATGCCGCTGGCACCGGGTAAAATTC
TGGTTAATCCGGAATTTGTGGACGTGAATAAACTGCCGAAAATTCTGAAAAGCTGGGATATTCTGGTTGCACCG
TATCCGAATCATATTCCGCAGAATCAGCTGCGTCTGGTTAGCGAATGGGCAGGTCTGAATGTTCTGATGCTGGA
TGAAGAACGTGTGATCGTGGAAAAAAATCAAGAGCAGATGATCAAAGCCCTGAAAGATTGGGGTTTTAAACCGA
TTGTTTGCCACTTCGAAAGCTATTATCCGTTTCTGGGTAGCTTTCATTGTGCAACCCTGGATGTTCGTCGTCGT
GGCACCCTGCAGAGCTATTTTTGAgaaggagatatacatATGACGACCGCAGATCTGATTCTGATCAATAATTG
GTATGTTGTGGCCAAGGTGGAAGATTGTAAACCGGGTAGCATTACCACCGCACTGCTGCTGGGTGTTAAACTGG
TTCTGTGGCGTAGCCGTGAACAGAATAGCCCGATTCAGATTTGGCAGGATTATTGTCCGCATCGTGGTGTTGCA
CTGAGCATGGGTGAAATTGTGAATAATACCCTGGTTTGTCCGTATCATGGTTGGCGTTATAATCAGGCAGGTAA
ATGTGTTCATATTCCGGCACATCCGGATATGACCCCTCCGGCAAGCGCACAGGCAAAAATCTATCATTGTCAAG
AACGTTATGGTCTGGTTTGGGTTTGTCTGGGTGATCCGGTTAATGATATTCCGAGTCTGCCGGAATGGGATGAT
CCGAATTATCATAATACCTGCACCAAGAGCTACTTTATCCAGGCAAGCGCATTTCGTGTGATGGATAACTTTAT
TGATGTGAGCCATTTTCCGTTTGTGCATGATGGTGGTCTGGGCGATCGTAATCATGCACAGATTGAAGAATTTG
AGGTGAAAGTGGATAAAGACGGTATTAGCATTGGCAATCTGAAACTGCAGATGCCTCGTTTTAATAGCAGCAAT
GAAGATGATAGCTGGACCCTGTATCAGCGTATTAGCCATCCGCTGTGTCAGTATTATATCACCGAAAGCAGCGA
AATTCGTACAGCAGATCTGATGCTGGTTACCCCGATTGATGAAGATAATTCACTGGTTCGTATGCTGGTGACCT
GGAATCGTAGCGAAATTCTGGAAAGCACCGTTCTGGAAGAATTTGATGAAACCATTGAACAGGATATCCCGATT
ATTCATAGCCAGCAGCCTGCACGTCTGCCGCTGCTGCCGAGCAAGCAGATTAATATGCAGTGGCTGAGCCAAGA
AATTCATGTTCCGAGCGATCGTTGTACCGTTGCATATCGTCGTTGGCTGAAAGAACTGGGCGTTACCTATGGTG
TTTGTTGAgaaggagatatacatATGCAGATTCTGGGTATCAGCGCCTATTATCATGATAGCGCAGCAGCAATG
GTTATTGATGGTGAAATTGTTGCAGCAGCACAAGAAGAACGTTTTAGCCGTCGTAAACATGATGCAGGTTTTCC
GACCGGTGCAATTACCTATTGTCTGAAACAGGTTGGCACCAAACTGCAGTATATTGATCAGATCGTGTTCTATG
ATAAACCGCTGGTGAAATTTGAACGTCTGCTGGAAACCTATCTGGCCTATGCACCGAAAGGTTTTGGTAGTTTT -continued

ATTACCGCAATGCCGGTGTGGCTGAAAGAGAAACTGTATCTGAAAACCCTGCTGAAAAAGAACTGGCACTGCT

GGGTGAATGTAAAGCAAGCCAGCTGCCTCCGCTGCTGTTTACCAGCCATCATCAGGCACATGCAGCAGCAGCAT

TTTTTCCGAGCCCGTTTCAGCGTGCAGCAGTTCTGTGTCTGGATGGTGTTGGTGAATGGGCAACCACCAGTGTT

TGGCTGGGTGAAGGTAATAAACTGACACCGCAGTGGGAAATTGATTTTCCGCATAGCCTGGGCCTGCTGTATAG

CGCATTTACCTATTATACCGGCTTTAAAGTGAACAGCGGTGAGTATAAACTGATGGGTCTGGCACCGTATGGTG

AACCGAAATATGTTGATCAGATTCTGAAACATCTGCTGGATCTGAAAGAAGATGGCACCTTTCGTCTGAACATG

GATTATTTCAATTATACCGTTGGTCTGACCATGACCAACCATAAATTTCATAGCATGTTTGGTGGTCCGCCTCG

TCAGGCAGAAGGTAAAATTAGCCAGCGTGATATGGATCTGGCAAGCAGCATTCAGAAAGTTACCGAAGAAGTGA

TTCTGCGTCTGGCACGTACCATTAAGAAAGAATTAGGTGTTGAATACCTGTGTCTGGCAGGCGGTGTTGGTCTG

AATTGTGTTGCAAATGGTCGTATTCTGCGTGAGAGCGATTTTAAAGATATTTGGATTCAGCCTGCAGCCGGTGA

TGCAGGTAGCGCAGTTGGTGCAGCACTGGCAATTTGGCATGAATATCATAAAAAACCGCGTACCAGCACCGCAG

GCGATCGTATGAAAGGTAGCTATCTGGGTCCGAGCTTTAGCGAAGCAGAAATTCTGCAGTTTCTGAACAGCGTG

AATATTCCGTATCATCGTTGTGTGGATAATGAACTGATGGCACGTCTGGCGGAAATTCTGGATCAGGGTAATGT

TGTTGGTTGGTTTAGCGGTCGTATGGAATTTGGTCCGCGTGCACTGGGTGGTCGTAGCATTATTGGTGATAGCC

GTAGCCCGAAAATGCAGAGCGTTATGAATCTGAAAATCAAATATCGCGAAAGCTTCCGTCCGTTTGCACCGAGC

GTTCTGGCAGAACGTGTTAGCGATTATTTTGATCTGGATCGTCCGAGCCCGTATATGCTGCTGGTTGCACAGGT

TAAAGAAAATCTGCATATTCCGATGACCCAAGAACAGCATGAACTGTTTGGTATCGAAAAACTGAATGTTCCGC

GTAGCCAGATTCCGGCAGTTACCCATGTTGATTATAGCGCACGTATTCAGACCGTTCATAAAGAAACCAATCCG

CGTTATTATGAACTGATCCGTCATTTTGAAGCACGTACCGGTTGTGCAGTTCTGGTTAATACCAGCTTTAATGT

TCGTGGTGAACCGATTGTGTGTACACCGGAAGATGCATATCGTTGTTTTATGCGTACCGAGATGGATTACCTGG

TGATGGAAAATTTTCTGCTGGTGAAAAGCGAACAGCCTCGTGGTAATAGTGATGAAAGCTGGCAGAAAGAATTT

GAGCTGGATTGAtactctaaccccatcggccgtcttaggggtttttttgtcgaagttcctattctctagaaagta taggaacttcacctgtggggtgactttgccgccgctgccgtgatgtctgcattaccgatc

SEQUENCE LISTING FREE TEXT

SEQ ID NO: 91
Sequence of sxt1 fragment after integration into *E. coli* lactose operon.

SEQ ID NO: 92
Sequence of sxt3 fragment version 1 integrated into the *E. coli* xylose operon.

SEQ ID NO: 93
Sequence of sxt3 fragment version 2 integrated into the *E. coli* xylose operon.

SEQ ID NO: 94
Sequence of sxt3 fragment version 3 integrated into the *E. coli* xylose operon.

SEQ ID NO: 95
Sequence of sxt1 fragment, integrated into the *E. coli* lactose operon.

SEQ ID NO: 96
Sequence of sxt4 fragment integrated into the *E. coli* melobiose operon.

SEQ ID NO: 97
Sequence of sxt2 fragment integrated into the *E. coli* maltose operon.

SEQ ID NO: 98
Sequence of sxt2 fragment integrated into the maltose operon after deletion of sxtL.

SEQ ID NO: 99
Sequence of sxt2 fragment integrated into the maltose operon.

The invention claimed is:

1. A process for producing neosaxitoxin in a host cell, the process comprising the steps:

(A) culturing a host cell which comprises nucleic acid molecules encoding a phosphopantetheinyltransferase (PPTase) and encoding the Sxt polypeptides A, B, D, G, H, I, S, T, U, V, W and X in a culture medium in the presence of the substrates:

(i) S-adenosylmethionine, (ii) arginine (iii) acetyl-CoA, malony-CoA or propionyl-CoA, and (iv) carbamoyl phosphate, wherein the host cell is a recombinant prokaryotic cell or a recombinant yeast cell, and wherein the host cell does not comprise nucleic acid molecules encoding the Sxt polypeptides C, F, J, K, L, M, P, Q, R and ORF24, under conditions which are suitable for the production of neosaxitoxin; and optionally (B) isolating and/or purifying neosaxitoxin from the host cells or from the culture medium.

2. A process for producing neosaxitoxin or an analogue or variant thereof, the process comprising the steps:

(A) contacting the substrates:

(i) S-adenosylmethionine, (ii) arginine (iii) acetyl-CoA, malony-CoA or propionyl-CoA, and (iv) carbamoyl phosphate, with Sxt A, B, D, G, H, I, S, T, U, V, W and X polypeptides, in a reaction medium, and optionally (B) isolating and/or purifying neosaxitoxin or an analogue or variant thereof from the reaction medium.

3. A process as claimed in claim 2, wherein the reaction medium additionally comprises a PPTase.

4. A process for producing neosaxitoxin or an analogue or variant thereof in a host cell, the process comprising the steps:

(A) culturing a host cell which comprises nucleic acid molecules encoding the Sxt polypeptides A, B, D, G, H, I, S, T, U, V, W and X in a culture medium in the presence of the substrates:

(i) S-adenosylmethionine, (ii) arginine (iii) acetyl-CoA, malony-CoA or propionyl-CoA, and (iv) carbamoyl phosphate, wherein the host cell is a recombinant prokaryotic cell or a recombinant yeast cell, and wherein the host cells do not comprise nucleic acid molecules encoding one or more or all of Sxt polypeptides Q, R and ORF24, under conditions which are suitable for the production of neosaxitoxin or an analogue or variant thereof; and optionally (B) isolating and/or purifying neosaxitoxin or an analogue or variant thereof from the host cells or from the culture medium.

5. A process as claimed in claim 4, wherein the host cell additionally comprises a nucleic acid molecule encoding a PPTase.

6. A process as claimed in claim 4, wherein the host cells do not comprise nucleic acid molecules encoding one or more or all of the Sxt polypeptides C, J and K.

7. A process as claimed in claim 4, wherein the host cells do not comprise nucleic acid molecules encoding any of the Sxt polypeptides in one or more of (a)-(c)

(a) C, Q, R and ORF24;

(b) L, Q, R and ORF 24

(c) J, K, L, Q, R and ORF 24.

8. A process as claimed in claim 4, wherein the host cells do not comprise nucleic acid molecules encoding one or more or all of Sxt polypeptides F, M and P.

9. A process as claimed in claim 4, wherein the host cell additionally comprises nucleic acid molecules encoding one or more of Sxt polypeptides C, E, J, K, and L (preferably C and/or E).

10. A process as claimed in claim 4, wherein the host cells do not comprise nucleic acid molecules encoding one or more or all of Sxt polypeptides F, M, N, O, P, Y, Z, ORF3, ORF4, ORF29, ORF34, OMPR or HISA.

11. A process as claimed in claim 4, wherein the host cell is a bacterial cell, or an *E. coli* cell.

12. A process as claimed in claim 4, wherein the host cell is a heterotroph.

13. A process as claimed in claim 4, wherein the neosaxitoxin or analogue or variant thereof, or a pharmaceutically acceptable salt thereof, is formulated into a pharmaceutical composition.

14. A process as claimed in claim 13, wherein the formulating step comprises admixing isolated or purified neosaxitoxin or an analogue or variant thereof with one or more pharmaceutically-acceptable carriers, adjuvants and/or excipients.

15. A host cell which comprises nucleic acid molecules coding for the Sxt polypeptides A, B, D, G, H, I, S, T, U, V, W and X, wherein the host cell does not comprise nucleic acid molecules coding for:

(i) one or more or all of the Sxt polypeptides C, J or K;
(ii) one or more or all of the Sxt polypeptides Q, R and ORF24;
(iii) one or more or all of the Sxt polypeptides C, Q, R and ORF24;
(iv) one or more or all of the Sxt polypeptides L, Q, R and ORF 24;
(v) one or more or all of the Sxt polypeptides J, K, L, Q, R and ORF 24; or
(vi) one or more or all of the Sxt polypeptides F, M and P, wherein the host cell is a recombinant prokaryotic cell or a recombinant yeast cell.

16. A host cell as claimed in claim 15, wherein the host cell additionally comprises nucleic acid molecules coding for one or more Sxt polypeptides selected from the group consisting of Sxt C, E, J, K, L, and/or R (preferably C and/or E).

17. A host cell as claimed in claim 15, wherein the host cell does not comprise nucleic acid molecules coding for one or more or all of the Sxt polypeptides selected from the group consisting of F, M, N, O, P, Y, Z, ORF3, ORF4, ORF29, ORF34, OMPR or HISA.

18. A host cell as claimed in claim 15, wherein the host cell is a bacterial cell, or an *E. coli* cell.

* * * * *